US006673545B2

(12) United States Patent
Faris et al.

(10) Patent No.: US 6,673,545 B2
(45) Date of Patent: Jan. 6, 2004

(54) PROSTATE CANCER MARKERS

(75) Inventors: Mary Faris, Los Angeles, CA (US); Christopher M. Turner, Stanford, CA (US)

(73) Assignee: Incyte Corporation, Palo Alto, CA (US)

( * ) Notice: Subject to any disclaimer, the term of this patent is extended or adjusted under 35 U.S.C. 154(b) by 0 days.

(21) Appl. No.: 09/919,172

(22) Filed: Jul. 30, 2001

(65) Prior Publication Data

US 2002/0119463 A1 Aug. 29, 2002

Related U.S. Application Data

(60) Provisional application No. 60/222,469, filed on Jul. 28, 2000.

(51) Int. Cl.[7] .................................................. C12Q 1/68

(52) U.S. Cl. ......................... 435/6; 435/7.1; 435/287.2; 536/23.1

(58) Field of Search ............................ 536/23.1; 435/6, 435/287.2, 7.1

(56) References Cited

U.S. PATENT DOCUMENTS 5,968,784 A * 10/1999 Spinella et al. ............ 435/91.1

FOREIGN PATENT DOCUMENTS

WO WO 0064479 11/2000 .................... 514/2

OTHER PUBLICATIONS

AF005258, GENBANK, Nov. 21, 1997.*

AF047855, GENBANK, Feb. 25, 1998.*

Gerhold et al., It's the genes! EST access to human genome content. 1996, BioEssays, vol. 18, No. 12, pp. 973–981.*

Wells et al., The chemokine information source: identification and characterization of novel chemokines using the WorldWideWeb and Expressed Sequence Tag Databases. 1997, Journal of Leukocyte Biology, vol. 61, No. 5, pp. 545–550.*

Russell et al., Structural Features can be Unconserved in Proteins with Similar Folds. 1994, Journal of Molecular Biology, vol. 244, pp. 332–350.*

Lopez et al., Whole–genome sequence annotation: 'Going wrong with confidence.' 1999, Molecular Microbiology, vol. 32, pp. 881–891.*

Attwood, The Babel of Bioinformatics. 2000, Science, vol. 290, No. 5491, pp. 471–473.*

Lin, J., et al., "The Phosphatidylinositol 3'–kinase Pathway is a Dominant Growth Factor–Activated Cell Survival Pathway in LNCaP Human Prostate Carcinoma Cells", *Cancer Res*;59(12):2891–2897, (Jun. 15, 1999).

Putz T., et al., Epideral Growth Factor (EGF) Receptor Blockade Inhibits the Action of EGF, Insulin–like Growth Factor I, and a Protein Kinase A Activator on the Mitogen–activated Protein Kinase Pathway in Prostate Cancer Cell Lines[1], Cancer Res 59: 227–233 (1999).

Gold, L.I., "The Role for Transforming Growth Factor–β (TGF–β)in Human Cancer", Crit Rev Oncog 10(4):303–360 (1999).

Chung T.D., et al., "Characterization of the Role of IL–6 in the Progression of Prostate Cancer", Prostate 38: 199–207 (1999).

Hubert, R.S., et al., "STEAP: A prostate–specific cell–surface antigen highly expressed in human prostate tumors", PNAS, vol. 96, No. 25, 14523–14528 (Dec. 7, 1999).

* cited by examiner

*Primary Examiner*—Ardin H. Marschel
*Assistant Examiner*—Carolyn L Smith
(74) *Attorney, Agent, or Firm*—Incyte Corporation

(57) ABSTRACT

The present invention relates to a composition comprising a plurality of cDNAs which are differentially expressed in prostate cancer and which may be used in their entirety or in part as to diagnose, to stage to treat or to monitor the treatment of a subject with prostate cancer.

9 Claims, No Drawings

SEQUENCE LISTING

<160> NUMBER OF SEQ ID NOS: 102

<210> SEQ ID NO 1
<211> LENGTH: 1645
<212> TYPE: DNA
<213> ORGANISM: Homo sapiens
<220> FEATURE:
<221> NAME/KEY: misc_feature
<223> OTHER INFORMATION: Incyte ID No: 1382961.3

<400> SEQUENCE: 1
cctttccaat ttacccgagc accttctctt cactcagcca actgctcgct cgctcacctc 60
cctcctctgc accatgacta cctgcagccg ccagttcacc tcctccagct ccatgaaggg 120
ctcctgcggc atcgggggcg gcatcggggg cggctccagc cgcatctcct ccgtcctggc 180
cggagggtcc tgccgcgccc ccagcaccta cgggggcggc ctgtctgtct catcctcccg 240
cttctcctct gggggagcct atgggttggg gggcggctat ggcggtggct tcagcagcag 300
aaccagcagc tttggtagtg gctttggggg aggatatggt ggtggccttg gtgctggctt 360
gggtggtggc tttggtggtg gctttgctgg tggtgatggg cttctggtgg gcagtgagaa 420

-continued

```
ggtgaccatg cagaacctca acgaccgcct ggcctcctac ctggacaagg tgcgtgctct    480

ggaggaggcc aacgccgacc tggaagtgaa gatccgtgac tggtaccaga ggcagcggcc    540

tgctgagatc aaagactaca gtccctactt caagaccatt gaggacctga ggaacaagat    600

tctcacagcc acagtggaca atgccaatgt ccttctgcag attgacaatg cccgtctggc    660

cgcggatgac ttccgcacca agtatgagac agagttgaac ctgcgcatga gtgtggaagc    720

cgacatcaat ggcctgcgca gggtgctgga cgaactgacc ctggccagag ctgacctgga    780

gatgcagatt gagagcctga aggaggagct ggcctacctg aagaagaacc acgaggagga    840

gatgaatgcc ctgagaggcc aggtgggtgg agatgtcaat gtggagatgg acgctgcacc    900

tggcgtggac ctgagccgca ttctgaacga gatgcgtgac cagtatgaga agatggcaga    960

gaagaaccgc aaggatgccg aggaatggtt cttcaccaag acagaggagc tgaaccgcga   1020

ggtggccacc aacagcgagc tggtgcagag cggcaagagc gagatctcgg agctccggcg   1080

caccatgcag aacctggaga ttgagctgca gtcccagctc agcatgaaag catccctgga   1140

gaacagcctg gaggagacca aaggtcgcta ctgcatgcag ctggcccaga tccaggagat   1200

gattggcagc gtggaggagc agctggccca gctccgctgc gagatggagc agcagaacca   1260

ggagtacaag atcctgctgg acgtgaagac gcggctggag caggagatcg ccacctaccg   1320

ccgcctgctg gagggcgagg acgcccacct ctcctcctcc cagttctcct ctggatcgca   1380

gtcatccaga gatgtgacct cctccagccg ccaaatccgc accaaggtca tggatgtgca   1440

cgatggcaag gtggtgtcca cccacgagca ggtccttcgc accaagaact gaggctgccc   1500

agccccgctc aggcctagga ggcccccgt gtggacacag atcccactgg aagatcccct   1560

ctcctgccca agcacttcac agctggaccc tgcttcaccc tcacccctc ctggcaatca   1620

atacagcttc attatctgag ttgca                                          1645
```

```
<210> SEQ ID NO 2
<211> LENGTH: 1051
<212> TYPE: DNA
<213> ORGANISM: Homo sapiens
<220> FEATURE:
<221> NAME/KEY: misc_feature
<223> OTHER INFORMATION: Incyte ID No: 1382961.5

<400> SEQUENCE: 2

agcaaatgcc ttctccctgc atgctccctg caaggcctcc tcgctatctc cacacacctg     60

actcatccca ttttacagga gcagttgatc ccaggaagag cattggagcc tccagcaggg    120

gctgttgggg cctgtctgag gagataggat gcgtcaggca gccccagaca cgatcacatt    180

cctctcaaca tgcctgccgg gccgggtatc catcccctgc agcagcaggc ttcctctacg    240

tggatgttaa aggcccattc agttcatgga gagctagcag gtgcgtgctc tggaggaggc    300

caacgccgac ctggaagtga agatccgtga ctggtaccag aggcagcggc ctgctgagat    360

caaagactac agtccctact tcaagaccat tgaggacctg aggaacaaga ttctcacagc    420

cacagtggac aatgccaatg tccttctgca gattgacaat gcccgtctgg ccgcggatga    480

cttccgcacc aagtatgaga cagagttgaa cctgcgcatg agtgtggaag ccgaccatca    540

atggcctgcg cagggtgctg gacgaactga cctggccaga gctgacctgg agatgcagat    600

tgagagcctg aaggaggagc tggcctacct gaagaagaac cacgaggagg agatgaatgc    660

cctgagaggc caggtgggtg gagatgtcaa tgtggagatg gacgctgcac ctggcgtgga    720

cctgagccgc attctgaacg agatgcgtga ccagtatgag aagatggcag agaagaaccg    780
```

-continued

```
caaggatgcc gaggaatggt tcttcaccaa gacagaggag ctgaaccgcg aggtggccac    840

caacagcgag ctggtgcaga gcggcaagag cgagatctcg gagctccggc gcaccatgca    900

gaacctggag atgattggca gcgtggagga gcagctggcc cagctccgct gcgagatgga    960

gcagcagaac caggagtaca agatcctgct ggacgtgaag acgcggctgg agcaggagat   1020

cgccacctac cgccgcctgc tggagggcga g                                  1051


<210> SEQ ID NO 3
<211> LENGTH: 1930
<212> TYPE: DNA
<213> ORGANISM: Homo sapiens
<220> FEATURE:
<221> NAME/KEY: misc_feature
<223> OTHER INFORMATION: Incyte ID No: 2852561CB1

<400> SEQUENCE: 3

ccttaagggg cgggccgggg cggggctccg ctgccccttc ccagaggccg cgcctgctgc     60

tgagcagatg cagtagccga aactgcgcgg aggcacagag gccgggggaga gcgttctggg   120

tccgagggtc caggtagggg ttgagccacc atctgaccgc aagctgcgtc gtgtcgccgg    180

ttctgcaggc accatgagcc aggacaccga ggtggatatg aaggaggtgg agctgaatga    240

gttagagccc gagaagcagc cgatgaacgc ggcgtctggg gcggccatgt ccctggcggg    300

agccgagaag aatggtctgg tgaagatcaa ggtggcggaa gacgaggcgg aggcggcagc    360

cgcggctaag ttcacgggcc tgtccaagga ggagctgctg aaggtggcag gcagccccgg    420

ctgggtacgc acccgctggg cactgctgct gctcttctgg ctcggctggc tcggcatgct    480

tgctggtgcc gtggtcataa tcgtgcgagc gccgcgttgt cgcgagctac cggcgcagaa    540

gtggtggcac acgggcgccc tctaccgcat cggcgacctt caggccttcc agggccacgg    600

cgcgggcaac ctggcgggtc tgaaggggcg tctcgattac ctgagctctc tgaaggtgaa    660

gggccttgtg ctgggtccaa ttcacaagaa ccagaaggat gatgtcgctc agactgactt    720

gctgcagatc gaccccaatt ttggctccaa ggaagatttt gacagtctct tgcaatcggc    780

taaaaaaaag agcatccgtg tcattctgga ccttactccc aactaccggg gtgagaactc    840

gtggttctcc actcaggttg acactgtggc caccaaggtg aaggatgctc tggagttttg    900

gctgcaagct ggcgtggatg ggttccaggt tcgggacata gagaatctga aggatgcatc    960

ctcattcttg gctgagtggc aaaatatcac caagggcttc agtgaagaca ggctcttgat   1020

tgcggggact aactcctccg accttcagca gatcctgagc ctactcgaat ccaacaaaga   1080

cttgctgttg actagctcat acctgtctga ttctggttct actggggagc atacaaaatc   1140

cctagtcaca cagtatttga atgccactgg caatcgctgg tgcagctgga gtttgtctca   1200

ggcaaggctc ctgacttcct tcttgccggc tcaacttctc cgactctacc agctgatgct   1260

cttcaccctg ccagggaccc ctgttttcag ctacggggat gagattggcc tggatgcagc   1320

tgcccttcct ggacagccta tggaggctcc agtcatgctg tgggatgagt ccagcttccc   1380

tgacatccca ggggctgtaa gtgccaacat gactgtgaag ggccagagtg aagaccctgg   1440

ctccctcctt tccttgttcc ggcggctgag tgaccagcgg agtaaggagc gctccctact   1500

gcatggggac ttccacgcgt tctccgctgg gcctggactc ttctcctata tccgccactg   1560

ggaccagaat gagcgttttc tggtagtgct taactttggg gatgtgggcc tctcggctgg   1620

actgcaggcc tccgacctgc ctgccagcgc cagcctgcca gccaaggctg acctcctgct   1680

cagcacccag ccaggccgtg aggagggctc ccctcttgag ctggaacgcc tgaaactgga   1740
```

-continued

```
gcctcacgaa gggctgctgc tccgcttccc ctacgcggcc tgacttcagc ctgacatgga   1800

cccactaccc ttctcctttc cttcccaggc cctttggctt ctgatttttc tctttttttaa   1860

aaacaaacaa acaaactgtt gcagattatg agtgaacccc caaataggtg tttctgcctt   1920

caaataagaa                                                          1930


<210> SEQ ID NO 4
<211> LENGTH: 529
<212> TYPE: PRT
<213> ORGANISM: Homo sapiens
<220> FEATURE:
<221> NAME/KEY: misc_feature
<223> OTHER INFORMATION: Incyte ID No: 2852561CD1

<400> SEQUENCE: 4

Met Ser Gln Asp Thr Glu Val Asp Met Lys Glu Val Glu Leu Asn
  1               5                  10                  15

Glu Leu Glu Pro Glu Lys Gln Pro Met Asn Ala Ala Ser Gly Ala
                 20                  25                  30

Ala Met Ser Leu Ala Gly Ala Glu Lys Asn Gly Leu Val Lys Ile
                 35                  40                  45

Lys Val Ala Glu Asp Glu Ala Glu Ala Ala Ala Ala Ala Lys Phe
                 50                  55                  60

Thr Gly Leu Ser Lys Glu Glu Leu Leu Lys Val Ala Gly Ser Pro
                 65                  70                  75

Gly Trp Val Arg Thr Arg Trp Ala Leu Leu Leu Leu Phe Trp Leu
                 80                  85                  90

Gly Trp Leu Gly Met Leu Ala Gly Ala Val Val Ile Ile Val Arg
                 95                 100                 105

Ala Pro Arg Cys Arg Glu Leu Pro Ala Gln Lys Trp Trp His Thr
                110                 115                 120

Gly Ala Leu Tyr Arg Ile Gly Asp Leu Gln Ala Phe Gln Gly His
                125                 130                 135

Gly Ala Gly Asn Leu Ala Gly Leu Lys Gly Arg Leu Asp Tyr Leu
                140                 145                 150

Ser Ser Leu Lys Val Lys Gly Leu Val Leu Gly Pro Ile His Lys
                155                 160                 165

Asn Gln Lys Asp Asp Val Ala Gln Thr Asp Leu Leu Gln Ile Asp
                170                 175                 180

Pro Asn Phe Gly Ser Lys Glu Asp Phe Asp Ser Leu Leu Gln Ser
                185                 190                 195

Ala Lys Lys Lys Ser Ile Arg Val Ile Leu Asp Leu Thr Pro Asn
                200                 205                 210

Tyr Arg Gly Glu Asn Ser Trp Phe Ser Thr Gln Val Asp Thr Val
                215                 220                 225

Ala Thr Lys Val Lys Asp Ala Leu Glu Phe Trp Leu Gln Ala Gly
                230                 235                 240

Val Asp Gly Phe Gln Val Arg Asp Ile Glu Asn Leu Lys Asp Ala
                245                 250                 255

Ser Ser Phe Leu Ala Glu Trp Gln Asn Ile Thr Lys Gly Phe Ser
                260                 265                 270

Glu Asp Arg Leu Leu Ile Ala Gly Thr Asn Ser Ser Asp Leu Gln
                275                 280                 285

Gln Ile Leu Ser Leu Leu Glu Ser Asn Lys Asp Leu Leu Leu Thr
                290                 295                 300
```

-continued

```
Ser Ser Tyr Leu Ser Asp Ser Gly Ser Thr Gly Glu His Thr Lys
                305                 310                 315

Ser Leu Val Thr Gln Tyr Leu Asn Ala Thr Gly Asn Arg Trp Cys
                320                 325                 330

Ser Trp Ser Leu Ser Gln Ala Arg Leu Leu Thr Ser Phe Leu Pro
                335                 340                 345

Ala Gln Leu Leu Arg Leu Tyr Gln Leu Met Leu Phe Thr Leu Pro
                350                 355                 360

Gly Thr Pro Val Phe Ser Tyr Gly Asp Glu Ile Gly Leu Asp Ala
                365                 370                 375

Ala Ala Leu Pro Gly Gln Pro Met Glu Ala Pro Val Met Leu Trp
                380                 385                 390

Asp Glu Ser Ser Phe Pro Asp Ile Pro Gly Ala Val Ser Ala Asn
                395                 400                 405

Met Thr Val Lys Gly Gln Ser Glu Asp Pro Gly Ser Leu Leu Ser
                410                 415                 420

Leu Phe Arg Arg Leu Ser Asp Gln Arg Ser Lys Glu Arg Ser Leu
                425                 430                 435

Leu His Gly Asp Phe His Ala Phe Ser Ala Gly Pro Gly Leu Phe
                440                 445                 450

Ser Tyr Ile Arg His Trp Asp Gln Asn Glu Arg Phe Leu Val Val
                455                 460                 465

Leu Asn Phe Gly Asp Val Gly Leu Ser Ala Gly Leu Gln Ala Ser
                470                 475                 480

Asp Leu Pro Ala Ser Ala Ser Leu Pro Ala Lys Ala Asp Leu Leu
                485                 490                 495

Leu Ser Thr Gln Pro Gly Arg Glu Glu Gly Ser Pro Leu Glu Leu
                500                 505                 510

Glu Arg Leu Lys Leu Glu Pro His Glu Gly Leu Leu Leu Arg Phe
                515                 520                 525

Pro Tyr Ala Ala
```

<210> SEQ ID NO 5
<211> LENGTH: 664
<212> TYPE: DNA
<213> ORGANISM: Homo sapiens
<220> FEATURE:
<221> NAME/KEY: misc_feature
<223> OTHER INFORMATION: Incyte ID No: 335942.2

<400> SEQUENCE: 5

```
ccaaaatgga gggaataata cctaagcctt cctgccgcaa cagtttttta tgctaatcag     60

ggaggtcatt ttggtaaaat acttcttgaa gccgagcctc aagatgaagg caaagcacga    120

aatgttattt tttaattatt atttatatat gtatttataa atatatttaa gataattata    180

atatactata tttatgggaa ccccttcatc ctctgagtgt gaccaggcat cctccacaat    240

agcagacagt gttttctggg ataagtaagt ttgatttcat taatacaggg cattttggtc    300

caagttgtgc ttatcccata gccaggaaac tctgcattct agtacttggg agacctgtaa    360

tcatataata aatgtacatt aattaccttg agccagtaat tggtccgatc tttgactctt    420

ttgccattaa acttacctgg gcattcttgt ttcaattcca cctgcaatca agtcctacaa    480

gctaaaatta gatgaactca actttgacaa ccatgagacc actgttatca aaactttctt    540

ttctggaatg taatcaatgt ttcttctagg ttctaaaaat tgtgatcaga ccataatgtt    600

acattattat caacaatagt gattgataga gtgttatcag tcataactaa ataaagcttg    660
```

-continued

```
caac                                                                 664

<210> SEQ ID NO 6
<211> LENGTH: 1667
<212> TYPE: DNA
<213> ORGANISM: Homo sapiens
<220> FEATURE:
<221> NAME/KEY: misc_feature
<223> OTHER INFORMATION: Incyte ID No: 2483854CB1

<400> SEQUENCE: 6

gtcatttcat tggcgtttga gtcagcaaag aagtcaagat ggccaaagtt ccagacatgt     60

ttgaagacct gaagaactgt tacagtgaaa atgaagaaga cagttcctcc attgatcatc    120

tgtctctgaa tcagaaatcc ttctatcatg taagctatgg cccactccat gaaggctgca    180

tggatcaatc tgtgtctctg agtatctctg aaacctctaa aacatccaag cttaccttca    240

aggagagcat ggtggtagta gcaaccaacg ggaaggttct gaagaagaga cggttgagtt    300

taagccaatc catcactgat gatgacctgg aggccatcgc caatgactca gaggaagaaa    360

tcatcaagcc taggtcagca ccttttagct tcctgagcaa tgtgaaatac aactttatga    420

ggatcatcaa atacgaattc atcctgaatg acgccctcaa tcaaagtata attcgagcca    480

atgatcagta cctcacggct gctgcattac ataatctgga tgaagcagtg aaatttgaca    540

tgggtgctta taagtcatca aaggatgatg ctaaaattac cgtgattcta agaatctcaa    600

aaactcaatt gtatgtgact gcccaagatg aagaccaacc agtgctgctg aaggagatgc    660

ctgagatacc caaaaccatc acaggtagtg agaccaacct cctcttcttc tgggaaactc    720

acggcactaa gaactatttc acatcagttg cccatccaaa cttgtttatt gccacaaagc    780

aagactactg ggtgtgcttg gcagggggc caccctctat cactgacttt cagatactgg    840

aaaaccaggc gtaggtctgg agtctcactt gtctcacttg tgcagtgttg acagttcata    900

tgtaccatgt acatgaagaa gctaaatcct ttactgttag tcatttgctg agcatgtact    960

gagccttgta attctaaatg aatgtttaca ctctttgtaa gagtggaacc aacactaaca   1020

tataatgttg ttatttaaag aacaccctat attttgcata gtaccaatca ttttaattat   1080

tattcttcat aacaatttta ggaggaccag agctactgac tatggctacc aaaaagactc   1140

tacccatatt acagatgggc aaattaaggc ataagaaaac taagaaatat gcacaatagc   1200

agttgaaaca agaagccaca gacctaggat ttcatgattt catttcaact gtttgccttc   1260

tacttttaag ttgctgatga actcttaatc aaatagcata agtttctggg acctcagttt   1320

tatcattttc aaaatggagg gaataatacc taagccttcc tgccgcaaca gttttttatg   1380

ctaatcaggg agggcatttt ggtaaaatac ttcttgaagc cgagcctcaa gatgaaggca   1440

aagcacgaaa tgttattttt taattattat ttatatatgt atttataaat atatttcaga   1500

taattataat atacctatat tgatgggaac ccttcatcct ctgaggtgtg accagggcat   1560

cctccacaat tagccgacag tggtttcctg ggataggta aggtttggtt tccattaata   1620

ccagggcatt ttgggtccaa gttgtgctta atcccataag ccaggga                1667

<210> SEQ ID NO 7
<211> LENGTH: 271
<212> TYPE: PRT
<213> ORGANISM: Homo sapiens
<220> FEATURE:
<221> NAME/KEY: misc_feature
<223> OTHER INFORMATION: Incyte ID No: 2483854CD1
```

<400> SEQUENCE: 7

```
Met Ala Lys Val Pro Asp Met Phe Glu Asp Leu Lys Asn Cys Tyr
  1               5                  10                  15

Ser Glu Asn Glu Glu Asp Ser Ser Ser Ile Asp His Leu Ser Leu
                 20                  25                  30

Asn Gln Lys Ser Phe Tyr His Val Ser Tyr Gly Pro Leu His Glu
                 35                  40                  45

Gly Cys Met Asp Gln Ser Val Ser Leu Ser Ile Ser Glu Thr Ser
                 50                  55                  60

Lys Thr Ser Lys Leu Thr Phe Lys Glu Ser Met Val Val Val Ala
                 65                  70                  75

Thr Asn Gly Lys Val Leu Lys Lys Arg Arg Leu Ser Leu Ser Gln
                 80                  85                  90

Ser Ile Thr Asp Asp Asp Leu Glu Ala Ile Ala Asn Asp Ser Glu
                 95                 100                 105

Glu Glu Ile Ile Lys Pro Arg Ser Ala Pro Phe Ser Phe Leu Ser
                110                 115                 120

Asn Val Lys Tyr Asn Phe Met Arg Ile Ile Lys Tyr Glu Phe Ile
                125                 130                 135

Leu Asn Asp Ala Leu Asn Gln Ser Ile Ile Arg Ala Asn Asp Gln
                140                 145                 150

Tyr Leu Thr Ala Ala Ala Leu His Asn Leu Asp Glu Ala Val Lys
                155                 160                 165

Phe Asp Met Gly Ala Tyr Lys Ser Ser Lys Asp Asp Ala Lys Ile
                170                 175                 180

Thr Val Ile Leu Arg Ile Ser Lys Thr Gln Leu Tyr Val Thr Ala
                185                 190                 195

Gln Asp Glu Asp Gln Pro Val Leu Leu Lys Glu Met Pro Glu Ile
                200                 205                 210

Pro Lys Thr Ile Thr Gly Ser Glu Thr Asn Leu Leu Phe Phe Trp
                215                 220                 225

Glu Thr His Gly Thr Lys Asn Tyr Phe Thr Ser Val Ala His Pro
                230                 235                 240

Asn Leu Phe Ile Ala Thr Lys Gln Asp Tyr Trp Val Cys Leu Ala
                245                 250                 255

Gly Gly Pro Pro Ser Ile Thr Asp Phe Gln Ile Leu Glu Asn Gln
                260                 265                 270

Ala
```

<210> SEQ ID NO 8
<211> LENGTH: 1511
<212> TYPE: DNA
<213> ORGANISM: Homo sapiens
<220> FEATURE:
<221> NAME/KEY: misc_feature
<223> OTHER INFORMATION: Incyte ID No: 1454852CB1

<400> SEQUENCE: 8

```
cccctctcct ccccagccct tctcctgtgt gcctgcctcc tgctgccctc accatgacca     60

cctccatccg ccagttcacc tcctccagct ccatcaaggg ctcctccggc ctgggggggcg    120

gctcgtcccg cacctcctgc cggctgtctg gcggcctggg tgccggctcc tgcaggctgg    180

gatctgctgg cggcctgggc agcaccctcg ggggtagcag ctactccagc tgctacagct    240

ttggctctgg tggtggctat ggcagcagct ttgggggtgt tgatgggctg ctggctggag    300
```

-continued

```
gtgagaaggc caccatgcag aacctcaatg accgcctggc ctcctacctg gacaaggtgc    360

gtgccctgga ggaggccaac actgagctgg aggtgaagat ccgtgactgg taccagaggc    420

aggccccggg gcccgcccgt gactacagcc agtactacag gacaattgag gagctgcaga    480

acaagatcct cacagccacc gtggacaatg ccaacatcct gctacagatt gacaatgccc    540

gtctggctgc tgatgacttc cgcaccaagt ttgagacaga gcaggccctg cgcctgagtg    600

tggaggccga catcaatggc ctgcgcaggg tgctggatga gctgaccctg gccagagccg    660

acctggagat gcagattgag aacctcaagg aggagctggc ctacctgaag aagaaccacg    720

aggaggagat gaacgccctg cgaggccagg tgggtggtga gatcaatgtg gagatggacg    780

ctgccccagg cgtggacctg agccgcatcc tcaacgagat gcgtgaccag tatgagaaga    840

tggcagagaa gaaccgcaag gatgccgagg attggttctt cagcaagaca gaggaactga    900

accgcgaggt ggccaccaac agtgagctgg tgcagagtgg caagagtgag atctcggagc    960

tccggcgcac catgcaggcc ttggagatag agctgcagtc ccagctcagc atgaaagcat   1020

ccctggaggg caacctggcg gagacagaga accgctactg cgtgcagctg tcccagatcc   1080

aggggctgat tggcagcgtg gaggagcagc tggcccagct tcgctgcgag atggagcagc   1140

agaaccagga atacaaaatc ctgctggatg tgaagacgcg gctggagcag gagattgcca   1200

cctaccgccg cctgctggag ggagaggatg cccacctgac tcagtacaag aaagaaccgg   1260

tgaccacccg tcaggtgcgt accattgtgg aagaggtcca ggatggcaag gtcatctcct   1320

cccgcgagca ggtccaccag accacccgct gaggactcag ctaccccggc cggccaccca   1380

ggaggcaggg aggcagccgc cccatctgcc ccacagtctc cggcctctcc agcctcagcc   1440

ccctgcttca gtcccttccc catgcttcct tgcctgatga caataaagct tgttgactca   1500

gctaaaaaaa a                                                        1511
```

<210> SEQ ID NO 9
<211> LENGTH: 432
<212> TYPE: PRT
<213> ORGANISM: Homo sapiens
<220> FEATURE:
<221> NAME/KEY: misc_feature
<223> OTHER INFORMATION: Incyte ID No: 1454852CD1

<400> SEQUENCE: 9

```
Met Thr Thr Ser Ile Arg Gln Phe Thr Ser Ser Ser Ser Ile Lys
  1               5                  10                  15

Gly Ser Ser Gly Leu Gly Gly Gly Ser Ser Arg Thr Ser Cys Arg
                 20                  25                  30

Leu Ser Gly Gly Leu Gly Ala Gly Ser Cys Arg Leu Gly Ser Ala
                 35                  40                  45

Gly Gly Leu Gly Ser Thr Leu Gly Gly Ser Ser Tyr Ser Ser Cys
                 50                  55                  60

Tyr Ser Phe Gly Ser Gly Gly Gly Tyr Gly Ser Ser Phe Gly Gly
                 65                  70                  75

Val Asp Gly Leu Leu Ala Gly Gly Glu Lys Ala Thr Met Gln Asn
                 80                  85                  90

Leu Asn Asp Arg Leu Ala Ser Tyr Leu Asp Lys Val Arg Ala Leu
                 95                 100                 105

Glu Glu Ala Asn Thr Glu Leu Glu Val Lys Ile Arg Asp Trp Tyr
                110                 115                 120

Gln Arg Gln Ala Pro Gly Pro Ala Arg Asp Tyr Ser Gln Tyr Tyr
                125                 130                 135
```

```
Arg Thr Ile Glu Glu Leu Gln Asn Lys Ile Leu Thr Ala Thr Val
                140                 145                 150

Asp Asn Ala Asn Ile Leu Leu Gln Ile Asp Asn Ala Arg Leu Ala
                155                 160                 165

Ala Asp Asp Phe Arg Thr Lys Phe Glu Thr Glu Gln Ala Leu Arg
                170                 175                 180

Leu Ser Val Glu Ala Asp Ile Asn Gly Leu Arg Arg Val Leu Asp
                185                 190                 195

Glu Leu Thr Leu Ala Arg Ala Asp Leu Glu Met Gln Ile Glu Asn
                200                 205                 210

Leu Lys Glu Glu Leu Ala Tyr Leu Lys Lys Asn His Glu Glu Glu
                215                 220                 225

Met Asn Ala Leu Arg Gly Gln Val Gly Gly Glu Ile Asn Val Glu
                230                 235                 240

Met Asp Ala Ala Pro Gly Val Asp Leu Ser Arg Ile Leu Asn Glu
                245                 250                 255

Met Arg Asp Gln Tyr Glu Lys Met Ala Glu Lys Asn Arg Lys Asp
                260                 265                 270

Ala Glu Asp Trp Phe Phe Ser Lys Thr Glu Glu Leu Asn Arg Glu
                275                 280                 285

Val Ala Thr Asn Ser Glu Leu Val Gln Ser Gly Lys Ser Glu Ile
                290                 295                 300

Ser Glu Leu Arg Arg Thr Met Gln Ala Leu Glu Ile Glu Leu Gln
                305                 310                 315

Ser Gln Leu Ser Met Lys Ala Ser Leu Glu Gly Asn Leu Ala Glu
                320                 325                 330

Thr Glu Asn Arg Tyr Cys Val Gln Leu Ser Gln Ile Gln Gly Leu
                335                 340                 345

Ile Gly Ser Val Glu Glu Gln Leu Ala Gln Leu Arg Cys Glu Met
                350                 355                 360

Glu Gln Gln Asn Gln Glu Tyr Lys Ile Leu Leu Asp Val Lys Thr
                365                 370                 375

Arg Leu Glu Gln Glu Ile Ala Thr Tyr Arg Arg Leu Leu Glu Gly
                380                 385                 390

Glu Asp Ala His Leu Thr Gln Tyr Lys Lys Glu Pro Val Thr Thr
                395                 400                 405

Arg Gln Val Arg Thr Ile Val Glu Glu Val Gln Asp Gly Lys Val
                410                 415                 420

Ile Ser Ser Arg Glu Gln Val His Gln Thr Thr Arg
                425                 430
```

<210> SEQ ID NO 10
<211> LENGTH: 309
<212> TYPE: DNA
<213> ORGANISM: Homo sapiens
<220> FEATURE:
<221> NAME/KEY: misc_feature
<223> OTHER INFORMATION: Incyte ID No: 353005.1
<221> NAME/KEY: unsure
<222> LOCATION: 6, 10, 18, 24-25, 67, 76, 83, 98, 159, 290
<223> OTHER INFORMATION: a, t, c, g, or other

<400> SEQUENCE: 10

```
ggtggntggn accatggnac tgtnnatctc cccctcttcc tcttggcctc tgtggacggt     60

gcctttncat ctgctnccac ttnaatcctc tgtctctnga ggaactaggc tccaacacgg    120
```

```
ggatccaggt tttcaatcag attgtgaagt cgaggcctna tgacaacatc gtgatctctc    180

cccatgggat tgcgtcggtc ctggggatgc ttcagctggg ggcggacggc aggaccagaa    240

gcagctcgcc atggtgatga gatacggcgt aaatgatatg attgacaatn tgctgtcccc    300

agatcttat                                                            309


<210> SEQ ID NO 11
<211> LENGTH: 176
<212> TYPE: DNA
<213> ORGANISM: Homo sapiens
<220> FEATURE:
<221> NAME/KEY: misc_feature
<223> OTHER INFORMATION: Incyte ID No: 378497.1
<221> NAME/KEY: unsure
<222> LOCATION: 18, 30, 35, 39, 44, 52, 87, 93, 108, 112, 114, 151,
      166, 168, 170
<223> OTHER INFORMATION: a, t, c, g, or other

<400> SEQUENCE: 11

gcccaacgtc atcgggcngc agtgcacccn ctgtncaana ggancactac gnattcccac     60

gctgcaaccg tgcagctgtg gtcggcncct ttntgaagag atgacggngc antnccggct    120

tcccttcccc gcacggtcag gccccagtgt naggtgtgtg agacanantn cattca        176


<210> SEQ ID NO 12
<211> LENGTH: 3544
<212> TYPE: DNA
<213> ORGANISM: Homo sapiens
<220> FEATURE:
<221> NAME/KEY: misc_feature
<223> OTHER INFORMATION: Incyte ID No: 994684.9

<400> SEQUENCE: 12

cagcgtcaaa tttgtctcca ccacctcctc ctcccggaag agcttcaaga gctaagaacc     60

tgctgcaagt cactgccttc caagtgcagc aacccagccc atggagattg cctcttctag    120

gcagttgctc aagccatgtt ttatcctttt ctggatagca tcatcgctga ggtcaaggcc    180

cagtatgagg agattgccaa ccgcagccgg acagaagccg agtcctggta tcagaccaag    240

tatgaggagc tgcagcagac agctggccgg catggcgatg acctccgcaa caccaagcat    300

gagatctctg agatgaaccg gatgatccag aggctgagag ccgagattga caatgtcaag    360

aaacagtgcg ccaatctgca gaacgccatt gcggatgccg agcagcgtgg ggagctggcc    420

ctcaaggatg ccaggaacaa gctggccgag ctggaggagg ccctgcagaa ggccaagcag    480

gacatggccc ggctgctgcg tgagtaccag gagctcatga acaccaagct ggccctggac    540

gtggagatcg ccacttaccg caagctgctg gagggcgagg aatgcagact cagtggagaa    600

ggagttggac cagtcaacat ctgtaagtag ctttgaacag acattaacaa cgacaataat    660

atgggatata tttagtgcca actcagaatt ctgctgtttc tagatccaaa cttttcccat    720

cccagcatat ggttatttat aataatacac ttagtaagtt gtgggtggtg gaggggaagg    780

acagattggg acaggaagca atgtggctta tgtctcatct cttaaagggt aagccatgca    840

tcctatgctt cttggaccct gtcccctgcc ttgtccctag tacctagctc cccccagtac    900

ctagctcctc ccctcagtac ctagctcccc tcagtaccta gctccctgta gtacctagct    960

cccctcagta cctagctcct ctcagtacct agcaccttgc ctcttacact cacccacttt   1020

tttagggacc ttaattaaat gacagttctt ccgggccttg tttgctactc tgtaaagggg   1080

gtccagtaga gtgctccaac accagcagat caaataaatg ggccatgcag gatcagcctg   1140

gcagatggtc tcactgagtc ctccctcctt tccctgcagc tgttgtcaca agcagtgttt   1200
```

-continued

```
cctctggata tggcagtggc agtggctatg gcggtggcct cggtggaggt cttggcggcg   1260
gcctcggtgg aggtcttgcc ggaggtagca gtggaagcta ctactccagc agcagtgggg   1320
gtgtcggcct aggtggtggg ctcagtgtgg ggggctctgg cttcagtgca agcagtggcc   1380
gagggctggg ggtgggcttt ggcagtggcg gggtagcag ctccagcgtc aaatttgtct    1440
ccaccacctc ctcctcccgg aagagcttca agagctaaga acctgctgca agtcactgcc   1500
ttccaagtgc agcaacccag cccatggaga ttgcctcttc taggcagagt cagccttgcg   1560
ggtgcttgtg gagtgggtgg ctatggcagc cggagcctct acaacctggg gggctccaag   1620
aggatatcca tcagcactag tggtggcagc ttcaggaacc ggtttggtgc tggtgctgga   1680
ggcggctatg gctttggagg tggtgccggt agtggatttg gtttcggcgg tggagctggt   1740
ggtggctttg ggctcggtgg cggagctggc tttggaggtg gcttcggtgg ccctggcttt   1800
cctgtctgcc ctcctggagg tatccaagag gtcactgtca accagagtct cctgactccc   1860
ctcaacctgc aaatcgaccc cagcatccag agggtgagga ccgaggagcg cgagcagatc   1920
aagaccctca acaataagtt tgcctccttc atcgacaagg tgcggttcct ggagcagcag   1980
aacaaggttc tggaaacaaa gtggaccctg ctgcaggagc agggcaccaa gactgtgagg   2040
cagaacctgg agccgttgtt cgagcagtac atcaacaacc tcaggaggca gctggacagc   2100
atcgtggggg aacggggccg cctggactca gagctgagaa acatgcagga cctggtggaa   2160
gacttcaaga acaagtatga ggatgaaatc aacaagcgta ccactgctga gaatgagttt   2220
gtgatgctga agaaggatgt agatgctgcc tacatgaaca aggtggagct ggaggccaag   2280
gttgatgcac tgatggatga gattaacttc atgaagatgt tctttgatgc ggagctgtcc   2340
cagatgcaga cgcatgtctc tgacacctca gtggtcctct ccatggacaa caaccgcaac   2400
ctggacctgg atagcatcat cgctgaggtc aaggcccagt atgaggagat tgccaaccgc   2460
agccggaccg aagccgagtc ctggtatcag accaagtatg aggagctgca gcagacagct   2520
ggccggcatg gcgatgacct ccgcaacacc aagcatgaga tctctgagat gaaccggatg   2580
atccagaggc tgagagccga gattgacaat gtcaagaaac agtgcgccaa tctggcagaa   2640
cgccattgcg gatgccgagc agcgtgggga gctggccctc aaggatgcca ggaacaagct   2700
ggccgagctg gaggaggccc tgcagaaggc caagcaggac atgggcccgg ctgctgcgtg   2760
agtaccagga gctcatgaac accaagctgg ccctggacgt ggagatcgcc acttaccgca   2820
agctgctgga gggcgaggaa tgcagactca gtggagaagg agttggacca gtcaacatct   2880
ctgttgtcac aagcagtgtt tcctctggat atggcagtgg cagtggctat ggcggtggcc   2940
tcggtggagg tcttggcggc ggcctcggtg gaggtcttgc cggaggtagc agtggaagct   3000
actactccag cagcagtggg ggtgtcggcc taggtggtgg gctcagtgtg gggggctctg   3060
gcttcagtgc aagcagtggc cgagggctgg gggtgggctt tggcagtggc gggggtagca   3120
gctccagcgt caaatttgtc tccaccacct cctcctcccg gaagagcttc aagagctaag   3180
aacctgctgc aagtcactgc cttccaagtg cagcaaccca gcccatggag attgcctctt   3240
ctaggcagtt gctcaagcca tgttttatcc ttttctggag agtagtctag accaagccaa   3300
ttgcagaacc acattctttg gttcccagga gagccccatt cccagcccct ggtctcccgt   3360
gccgcagttc tatattctgc ttcaaatcag ccttcaggtt tcccacagca tggcccctgc   3420
tgacacgaga acccaaagtt ttcccaaatc taaatcatca aaacagaatc cccaccccaa   3480
tcccaaattt tgttttggtt ctaactacct ccagaatgtg ttcaataaaa tgcttttata   3540
```

-continued

```
ttat                                                                3544

<210> SEQ ID NO 13
<211> LENGTH: 3000
<212> TYPE: DNA
<213> ORGANISM: Homo sapiens
<220> FEATURE:
<221> NAME/KEY: misc_feature
<223> OTHER INFORMATION: Incyte ID No: 995610.1

<400> SEQUENCE: 13

ggagtttatt cataacgcgc tctccaagta tacgtggcaa tgcgttgctg ggttatttta     60

atcattctag gcatcgtttt cctccttatg cctctatcat tcctccctat ctacactaac    120

atcccacgct ctgaacgcgc gcccattaat acccttcttt cctccactct ccctgggact    180

cttgatcaaa gcgcggccct ttccccagcc ttagcgaggc gccctgcagc ctggtacgcg    240

cgtggcgtgg cggtgggcgc gcagtgcgtt ctcggtgtgg agggcagctg ttccgcctgc    300

gatgatttat actcacagga caaggatgcg gtttgtcaaa cagtactgct acggaggagc    360

agcagagaaa gggagagggt ttgagaggga gcaaaagaaa atggtaggcg cgcgtagtta    420

attcatgcgg ctctcttact ctgtttacat cctagagcta gagtgctcgg ctgcccggct    480

gagtctcctc cccaccttcc ccaccctccc caccctcccc ataagcgccc tcccgggttc    540

ccaaagcaga gggcgtgggg gaaaagaaaa aagatcctct ctcgctaatc tccgcccacc    600

ggccctttat aatgcgaggg tctggacggc tgaggacccc cgagctgtgc tgctcgcggc    660

cgccaccgcc gggccccggc cgtccctggc tcccctcctg cctcgagaag ggcagggctt    720

ctcagaggct tggcgggaaa aagaacggag ggagggatcg cgctgagtat aaaagccggt    780

tttcggggct ttatctaact cgctgtagta attccagcga gaggcagagg gagcgagcgg    840

gcggccggct agggtggaag agccgggcga gcagagctgc gctgcgggcg tcctgggaag    900

ggagatccgg agcgaatagg gggcttcgcc tctggcccag ccctcccgct gatcccccag    960

ccagcggtcc gcaacccttg ccgcatccac gaaactttgc ccatagcagc gggcgggcac   1020

tttgcactgg aacttacaac acccgagcaa ggacgcgact ctcccgacgc ggggaggcta   1080

ttctgcccat ttggggacac ttccccgccg ctgccaggac ccgcttctct gaaaggctct   1140

ccttgcagct gcttagacgc tggatttttt tcgggtagtg gaaaaccagc agcctcccgc   1200

gacgatgccc ctcaacgtta gcttcaccaa caggaactat gacctcgact acgactcggt   1260

gcagccgtat ttctactgcg acgaggagga gaacttctac cagcagcagc agcagagcga   1320

ggctgcagcc cccggcgccc agcgaggata tctggaagaa attcgagctg ctgcccaccc   1380

cgcccctgtc ccctagccgc cgctccgggc tctgctcgcc ctcctacgtt gcggtcacac   1440

ccttctccct tcggggagac aacgacggcg gtggcgggag cttctccacg gccgaccagc   1500

tggagatggt gaccgagctg ctgggaggag acatggtgaa ccagagtttc atctgcgacc   1560

cggacgacga gaccttcatc aaaaacatca tcatccagga ctgtatgtgg agcggcttct   1620

cggccgccgc caagctcgtc tcagagaagc tggcctccta ccaggctgcg cgcaaagaca   1680

gcggcagccc gaaccccgcc cgcggccaca gcgtctgctc cacctccagc ttgtacctgc   1740

aggatctgag cgccgccgcc tcagagtgca tcgacccctc ggtggtcttc ccctaccctc   1800

tcaacgacag cagctcgccc aagtcctgcg cctcgcaaga ctccagcgcc ttctctccgt   1860

cctcggattc tctgctctcc tcgacggagt cctccccgca gggcagcccc gagcccctgg   1920

tgctccatga ggagacaccg cccaccacca gcagcgactc tgaggaggaa caagaagatg   1980
```

-continued

```
aggaagaaat cgatgttgtt tctgtggaaa agaggcaggc tcctggcaaa aggtcagagt   2040

ctggatcacc ttctgctgga ggccacagca aacctcctca cagcccactg gtcctcaaga   2100

ggtgccacgt ctccacacat cagcacaact acgcagcgcc tccctccact cggaaggact   2160

atcctgctgc caagagggtc aagttggaca gtgtcagagt cctgagacag atcagcaaca   2220

accgaaaatg caccagcccc aggtcctcgg acaccgagga gaatgtcaag aggcgaacac   2280

acaacgtctt ggagcgccag aggaggaacg agctaaaacg gagctttttt gccctgcgtg   2340

accagatccc ggagttggaa aacaatgaaa aggcccccaa ggtagttatc cttaaaaaag   2400

ccacagcata catcctgtcc gtccaagcag aggagcaaaa gctcatttct gaagaggact   2460

tgttgcggaa acgacgagaa cagttgaaac acaaacttga acagctacgg aactcttgtg   2520

cgtaaggaaa agtaaggaaa acgattcctt ctaacagaaa tgtcctgagc aatcacctat   2580

gaacttgttt caaatgcatg atcaaatgca acctcacaac cttggctgag tcttgagact   2640

gaaagattta gccataatgt aaactgcctc aaattggact ttgggcataa aagaactttt   2700

ttatgcttac catctttttt ttttctttaa cagatttgta tttaagaatt gtttttaaaa   2760

aattttaaga tttacacaat gtttctctgt aaatattgcc attaaatgta aataacttta   2820

ataaaacgtt tatagcagtt acacagaatt tcaatcctag tatatagtac ctagtattat   2880

aggtactata aaccctaatt ttttttattt aagtacattt tgctttttaa agttgatttt   2940

tttctattgt ttttagaaaa aataaaataa ctggcaaata tatcattgag ccaaaaaaaa   3000
```

<210> SEQ ID NO 14
<211> LENGTH: 427
<212> TYPE: DNA
<213> ORGANISM: Homo sapiens
<220> FEATURE:
<221> NAME/KEY: misc_feature
<223> OTHER INFORMATION: Incyte ID No: 417119.1

<400> SEQUENCE: 14

```
aaaacaaaga aggctggaaa ccaaagcaat catctcttta gtggaaacta ttcttaaaga     60

agatcttgat ggctactgac atttgcaact ccctcactct ttctcagggg cctttcactt    120

acattgtcac cagaggttcg taacctccct gtgggctagt gttatgacca tcaccatttt    180

acctaagtag ctctgttgct cggccacagt gagcagtaat agacctgaag ctggaaccca    240

tgtctaatag tgtcaggtcc agtgttctta gccaccccac tcccagcttc atccctactg    300

gtgttgtcat cagactttga ccgtatatgc tcaggtgtcc tccaagaaat caaattttgc    360

cacctcgcct tcacgaggcc tgcccttctg gatttatacc taacaacatg tgctccacat    420

ttcagaa                                                              427
```

<210> SEQ ID NO 15
<211> LENGTH: 4108
<212> TYPE: DNA
<213> ORGANISM: Homo sapiens
<220> FEATURE:
<221> NAME/KEY: misc_feature
<223> OTHER INFORMATION: Incyte ID No: 3615080CB1

<400> SEQUENCE: 15

```
tgccagattc ctgagacccg cctgcggtgg ggctacaccc agccagggag tctccagagg     60

tgaggctgtt gtttaaaaac ctggagccgg gaggggagac ccccacattc aagaggagct    120

ttcaggcgat ctggagaaag aacggcagaa cacacagcaa ggaaaggtcc tttctgggga    180

tcaccccatt ggctgaagat gagaccattc ttcctcttgt gttttgccct gcctggcctc    240
```

-continued

```
ctgcatgccc aacaagcctg ctcccgtggg gcctgctatc cacctgttgg ggacctgctt    300
gttgggagga cccggtttct ccgagcttca tctacctgtg gactgaccaa gcctgagacc    360
tactgcaccc agtatggcga gtggcagatg aaatgctgca agtgtgactc caggcagcct    420
cacaactact acagtcaccg agtagagaat gtggcttcat cctccggccc catgcgctgg    480
tggcagtcac agaatgatgt gaaccctgtc tctctgcagc tggacctgga caggagattc    540
cagcttcaag aagtcatgat ggagttccag gggcccatgc ccgccggcat gctgattgag    600
cgctcctcag acttcggtaa gacctggcga gtgtaccagt acctggctgc cgactgcacc    660
tccaccttcc ctcgggtccg ccagggtcgg cctcagagct ggcaggatgt tcggtgccag    720
tccctgcctc agaggcctga tgcacgccta aatgggggga aggtccaact taaccttatg    780
gatttagtgt ctgggattcc agcaactcaa agtcaaaaaa ttcaagaggt gggggagatc    840
acaaacttga gagtcaattt caccaggctg gcccctgtgc cccaaagggg ctaccaccct    900
cccagcgcct actatgctgt gtcccagctc cgtctgcagg ggagctgctt ctgtcacggc    960
catgctgatc gctgcgcacc caagcctggg gcctctgcag gcccctccac cgctgtgcag   1020
gtccacgatg tctgtgtctg ccagcacaac actgccggcc caaattgtga gcgctgtgca   1080
cccttctaca acaaccggcc ctggagaccg gcggagggcc aggacgccca tgaatgccaa   1140
aggtgcgact gcaatgggca ctcagagaca tgtcactttg accccgctgt gtttgccgcc   1200
agccaggggg catatggagg tgtgtgtgac aattgccggg accacaccga aggcaagaac   1260
tgtgagcggt gtcagctgca ctatttccgg aaccggcgcc cgggagcttc cattcaggag   1320
acctgcatct cctgcgagtg tgatccggat ggggcagtgc caggggctcc ctgtgaccca   1380
gtgaccgggc agtgtgtgtg caaggagcat gtgcagggag agcgctgtga cctatgcaag   1440
ccgggcttca ctggactcac ctacgccaac ccgcagggct gccaccgctg tgactgcaac   1500
atcctggggt cccggaggga catgccgtgt gacgaggaga gtgggcgctg cctttgtctg   1560
cccaacgtgg tgggtcccaa atgtgaccag tgtgctccct accactggaa gctggccagt   1620
ggccagggct gtgaaccgtg tgcctgcgac ccgcacaact ccctcagccc acagtgcaac   1680
cagttcacag ggcagtgccc ctgtcgggaa ggctttggtg gcctgatgtg cagcgctgca   1740
gccatccgcc agtgtccaga ccggacctat ggagacgtgg ccacaggatg ccgagcctgt   1800
gactgtgatt tccggggaac agagggcccg ggctgcgaca aggcatcagg ccgctgcctc   1860
tgccgccctg gcttgaccgg gccccgctgt gaccagtgcc agcgaggcta ctgcaatcgc   1920
tacccggtgt gcgtggcctg ccacccttgc ttccagacct atgatgcgga cctccgggag   1980
caggccctgc gctttggtag actccgcaat gccaccgcca gcctgtggtc agggcctggg   2040
ctggaggacc gtggcctggc ctcccggatc ctagatgcaa agagtaagat tgagcagatc   2100
cgagcagttc tcagcagccc cgcagtcaca gagcaggagg tggctcaggt ggccagtgcc   2160
atcctctccc tcaggcgaac tctccagggc ctgcagctgg atctgcccct ggaggaggag   2220
acgttgtccc ttccgagaga cctggagagt cttgacagaa gcttcaatgg tctccttact   2280
atgtatcaga ggaagaggga gcagtttgaa aaaataagca gtgctgatcc ttcaggagcc   2340
ttccggatgc tgagcacagc ctacgagcag tcagcccagg ctgctcagca ggtctccgac   2400
agctcgcgcc ttttggacca gctcagggac agccggagag aggcagagag gctggtgcgg   2460
caggcgggag gaggaggagg caccggcagc cccaagcttg tggccctgag gctggagatg   2520
tcttcgttgc ctgacctgac acccaccttc aacaagctct gtggcaactc caggcagatg   2580
```

-continued

```
gcttgcaccc caatatcatg ccctggtgag ctatgtcccc aagacaatgg cacagcctgt   2640

ggctcccgct gcaggggtgt ccttcccagg gccggtgggg ccttcttgat ggcggggcag   2700

gtggctgagc agctgcgggg cttcaatgcc cagctccagc ggaccaggca gatgattagg   2760

gcagccgagg aatctgcctc acagattcaa tccagtgccc agcgcttgga gacccaggtg   2820

agcgccagcc gctcccagat ggaggaagat gtcagacgca cacggctcct aatccagcag   2880

gtccgggact tcctaacaga ccccgacact gatgcagcca ctatccagga ggtcagcgag   2940

gccgtgctgg ccctgtggct gcccacagac tcagatactg ttctgcagaa gatgaatgag   3000

atccaggcca ttgcagccag gctccccaac gtggacttgg tgctgtccca gaccaagcag   3060

gacattgcgc gtgcccgccg gttgcaggct gaggctgagg aagccaggag ccgagcccat   3120

gcagtggagg gccaggtgga agatgtggtt gggaacctgc ggcaggggac agtggcactg   3180

caggaagctc aggacaccat gcaaggcacc agccgctccc ttcggcttat ccaggacagg   3240

gttgctgagg ttcagcaggt actgcggcca gcagaaaagc tggtgacaag catgaccaag   3300

cagctgggtg acttctggac acggatggag gagctccgcc accaagcccg gcagcagggg   3360

gcagaggcag tccaggccca gcagcttgcg gaaggtgcca gcgagcaggc attgagtgcc   3420

caagagggat ttgagagaat aaaacaaaag tatgctgagt tgaaggaccg gttgggtcag   3480

agttccatgc tgggtgagca gggtgcccgg atccagagtg tgaagacaga ggcagaggag   3540

ctgtttgggg agaccatgga gatgatggac aggatgaaag acatggagtt ggagctgctg   3600

cggggcagcc aggccatcat gctgcgctca gcggacctga caggactgga gaagcgtgtg   3660

gagcagatcc gtgaccacat caatgggcgc gtgctctact atgccacctg caagtgatgc   3720

tacagcttcc agcccgttgc cccactcatc tgccgccttt gcttttggtt gggggcagat   3780

tgggttggaa tgctttccat ctccaggaga ctttcatgta gcctaaagta cagcctggac   3840

cacccctggt gtgtagctag taagattacc ctgagctgca gctgagcctg agccaatggg   3900

acagttacac ttgacagaca aagatggtgg agattggcat gccattgaaa ctaagagctc   3960

tcaagtcaag gaagctgggc tgggcagtat cccccgcctt tagttctcca ctggggagga   4020

atcctggacc aagcacaaaa acttaacaaa agtgatgtaa aaatgaaaag ccaaataaaa   4080

atctttggaa aagaaaaaaa aaaaaaaa                                      4108
```

<210> SEQ ID NO 16
<211> LENGTH: 1172
<212> TYPE: PRT
<213> ORGANISM: Homo sapiens
<220> FEATURE:
<221> NAME/KEY: misc_feature
<223> OTHER INFORMATION: Incyte ID No: 3615080CD1

<400> SEQUENCE: 16

```
Met Arg Pro Phe Phe Leu Leu Cys Phe Ala Leu Pro Gly Leu Leu
  1               5                  10                  15

His Ala Gln Gln Ala Cys Ser Arg Gly Ala Cys Tyr Pro Pro Val
                 20                  25                  30

Gly Asp Leu Leu Val Gly Arg Thr Arg Phe Leu Arg Ala Ser Ser
                 35                  40                  45

Thr Cys Gly Leu Thr Lys Pro Glu Thr Tyr Cys Thr Gln Tyr Gly
                 50                  55                  60

Glu Trp Gln Met Lys Cys Cys Lys Cys Asp Ser Arg Gln Pro His
                 65                  70                  75

Asn Tyr Tyr Ser His Arg Val Glu Asn Val Ala Ser Ser Ser Gly
```

-continued

```
                80                  85                  90

Pro Met Arg Trp Trp Gln Ser Gln Asn Asp Val Asn Pro Val Ser
                95                  100                 105

Leu Gln Leu Asp Leu Asp Arg Arg Phe Gln Leu Gln Glu Val Met
                110                 115                 120

Met Glu Phe Gln Gly Pro Met Pro Ala Gly Met Leu Ile Glu Arg
                125                 130                 135

Ser Ser Asp Phe Gly Lys Thr Trp Arg Val Tyr Gln Tyr Leu Ala
                140                 145                 150

Ala Asp Cys Thr Ser Thr Phe Pro Arg Val Arg Gln Gly Arg Pro
                155                 160                 165

Gln Ser Trp Gln Asp Val Arg Cys Gln Ser Leu Pro Gln Arg Pro
                170                 175                 180

Asp Ala Arg Leu Asn Gly Gly Lys Val Gln Leu Asn Leu Met Asp
                185                 190                 195

Leu Val Ser Gly Ile Pro Ala Thr Gln Ser Gln Lys Ile Gln Glu
                200                 205                 210

Val Gly Glu Ile Thr Asn Leu Arg Val Asn Phe Thr Arg Leu Ala
                215                 220                 225

Pro Val Pro Gln Arg Gly Tyr His Pro Pro Ser Ala Tyr Tyr Ala
                230                 235                 240

Val Ser Gln Leu Arg Leu Gln Gly Ser Cys Phe Cys His Gly His
                245                 250                 255

Ala Asp Arg Cys Ala Pro Lys Pro Gly Ala Ser Ala Gly Pro Ser
                260                 265                 270

Thr Ala Val Gln Val His Asp Val Cys Val Cys Gln His Asn Thr
                275                 280                 285

Ala Gly Pro Asn Cys Glu Arg Cys Ala Pro Phe Tyr Asn Asn Arg
                290                 295                 300

Pro Trp Arg Pro Ala Glu Gly Gln Asp Ala His Glu Cys Gln Arg
                305                 310                 315

Cys Asp Cys Asn Gly His Ser Glu Thr Cys His Phe Asp Pro Ala
                320                 325                 330

Val Phe Ala Ala Ser Gln Gly Ala Tyr Gly Gly Val Cys Asp Asn
                335                 340                 345

Cys Arg Asp His Thr Glu Gly Lys Asn Cys Glu Arg Cys Gln Leu
                350                 355                 360

His Tyr Phe Arg Asn Arg Arg Pro Gly Ala Ser Ile Gln Glu Thr
                365                 370                 375

Cys Ile Ser Cys Glu Cys Asp Pro Asp Gly Ala Val Pro Gly Ala
                380                 385                 390

Pro Cys Asp Pro Val Thr Gly Gln Cys Val Cys Lys Glu His Val
                395                 400                 405

Gln Gly Glu Arg Cys Asp Leu Cys Lys Pro Gly Phe Thr Gly Leu
                410                 415                 420

Thr Tyr Ala Asn Pro Gln Gly Cys His Arg Cys Asp Cys Asn Ile
                425                 430                 435

Leu Gly Ser Arg Arg Asp Met Pro Cys Asp Glu Glu Ser Gly Arg
                440                 445                 450

Cys Leu Cys Leu Pro Asn Val Val Gly Pro Lys Cys Asp Gln Cys
                455                 460                 465

Ala Pro Tyr His Trp Lys Leu Ala Ser Gly Gln Gly Cys Glu Pro
                470                 475                 480
```

-continued

```
Cys Ala Cys Asp Pro His Asn Ser Leu Ser Pro Gln Cys Asn Gln
                485                 490                 495

Phe Thr Gly Gln Cys Pro Cys Arg Glu Gly Phe Gly Gly Leu Met
                500                 505                 510

Cys Ser Ala Ala Ala Ile Arg Gln Cys Pro Asp Arg Thr Tyr Gly
                515                 520                 525

Asp Val Ala Thr Gly Cys Arg Ala Cys Asp Cys Asp Phe Arg Gly
                530                 535                 540

Thr Glu Gly Pro Gly Cys Asp Lys Ala Ser Gly Arg Cys Leu Cys
                545                 550                 555

Arg Pro Gly Leu Thr Gly Pro Arg Cys Asp Gln Cys Gln Arg Gly
                560                 565                 570

Tyr Cys Asn Arg Tyr Pro Val Cys Val Ala Cys His Pro Cys Phe
                575                 580                 585

Gln Thr Tyr Asp Ala Asp Leu Arg Glu Gln Ala Leu Arg Phe Gly
                590                 595                 600

Arg Leu Arg Asn Ala Thr Ala Ser Leu Trp Ser Gly Pro Gly Leu
                605                 610                 615

Glu Asp Arg Gly Leu Ala Ser Arg Ile Leu Asp Ala Lys Ser Lys
                620                 625                 630

Ile Glu Gln Ile Arg Ala Val Leu Ser Ser Pro Ala Val Thr Glu
                635                 640                 645

Gln Glu Val Ala Gln Val Ala Ser Ala Ile Leu Ser Leu Arg Arg
                650                 655                 660

Thr Leu Gln Gly Leu Gln Leu Asp Leu Pro Leu Glu Glu Glu Thr
                665                 670                 675

Leu Ser Leu Pro Arg Asp Leu Glu Ser Leu Asp Arg Ser Phe Asn
                680                 685                 690

Gly Leu Leu Thr Met Tyr Gln Arg Lys Arg Glu Gln Phe Glu Lys
                695                 700                 705

Ile Ser Ser Ala Asp Pro Ser Gly Ala Phe Arg Met Leu Ser Thr
                710                 715                 720

Ala Tyr Glu Gln Ser Ala Gln Ala Ala Gln Gln Val Ser Asp Ser
                725                 730                 735

Ser Arg Leu Leu Asp Gln Leu Arg Asp Ser Arg Arg Glu Ala Glu
                740                 745                 750

Arg Leu Val Arg Gln Ala Gly Gly Gly Gly Gly Thr Gly Ser Pro
                755                 760                 765

Lys Leu Val Ala Leu Arg Leu Glu Met Ser Ser Leu Pro Asp Leu
                770                 775                 780

Thr Pro Thr Phe Asn Lys Leu Cys Gly Asn Ser Arg Gln Met Ala
                785                 790                 795

Cys Thr Pro Ile Ser Cys Pro Gly Glu Leu Cys Pro Gln Asp Asn
                800                 805                 810

Gly Thr Ala Cys Gly Ser Arg Cys Arg Gly Val Leu Pro Arg Ala
                815                 820                 825

Gly Gly Ala Phe Leu Met Ala Gly Gln Val Ala Glu Gln Leu Arg
                830                 835                 840

Gly Phe Asn Ala Gln Leu Gln Arg Thr Arg Gln Met Ile Arg Ala
                845                 850                 855

Ala Glu Glu Ser Ala Ser Gln Ile Gln Ser Ser Ala Gln Arg Leu
                860                 865                 870
```

-continued

```
Glu Thr Gln Val Ser Ala Ser Arg Ser Gln Met Glu Glu Asp Val
            875                 880                 885

Arg Arg Thr Arg Leu Leu Ile Gln Gln Val Arg Asp Phe Leu Thr
            890                 895                 900

Asp Pro Asp Thr Asp Ala Ala Thr Ile Gln Glu Val Ser Glu Ala
            905                 910                 915

Val Leu Ala Leu Trp Leu Pro Thr Asp Ser Asp Thr Val Leu Gln
            920                 925                 930

Lys Met Asn Glu Ile Gln Ala Ile Ala Ala Arg Leu Pro Asn Val
            935                 940                 945

Asp Leu Val Leu Ser Gln Thr Lys Gln Asp Ile Ala Arg Ala Arg
            950                 955                 960

Arg Leu Gln Ala Glu Ala Glu Glu Ala Arg Ser Arg Ala His Ala
            965                 970                 975

Val Glu Gly Gln Val Glu Asp Val Val Gly Asn Leu Arg Gln Gly
            980                 985                 990

Thr Val Ala Leu Gln Glu Ala Gln Asp Thr Met Gln Gly Thr Ser
            995                 1000                1005

Arg Ser Leu Arg Leu Ile Gln Asp Arg Val Ala Glu Val Gln Gln
            1010                1015                1020

Val Leu Arg Pro Ala Glu Lys Leu Val Thr Ser Met Thr Lys Gln
            1025                1030                1035

Leu Gly Asp Phe Trp Thr Arg Met Glu Glu Leu Arg His Gln Ala
            1040                1045                1050

Arg Gln Gln Gly Ala Glu Ala Val Gln Ala Gln Gln Leu Ala Glu
            1055                1060                1065

Gly Ala Ser Glu Gln Ala Leu Ser Ala Gln Glu Gly Phe Glu Arg
            1070                1075                1080

Ile Lys Gln Lys Tyr Ala Glu Leu Lys Asp Arg Leu Gly Gln Ser
            1085                1090                1095

Ser Met Leu Gly Glu Gln Gly Ala Arg Ile Gln Ser Val Lys Thr
            1100                1105                1110

Glu Ala Glu Glu Leu Phe Gly Glu Thr Met Glu Met Met Asp Arg
            1115                1120                1125

Met Lys Asp Met Glu Leu Glu Leu Leu Arg Gly Ser Gln Ala Ile
            1130                1135                1140

Met Leu Arg Ser Ala Asp Leu Thr Gly Leu Glu Lys Arg Val Glu
            1145                1150                1155

Gln Ile Arg Asp His Ile Asn Gly Arg Val Leu Tyr Tyr Ala Thr
            1160                1165                1170

Cys Lys
```

<210> SEQ ID NO 17
<211> LENGTH: 795
<212> TYPE: DNA
<213> ORGANISM: Homo sapiens
<220> FEATURE:
<221> NAME/KEY: misc_feature
<223> OTHER INFORMATION: Incyte ID No: 331749.3

<400> SEQUENCE: 17

```
attttacata cactgtatgt tatagaactt catggatcag atctggggca gcaccctata     60

aatcaccacc ttaatatgct gcaacaaaat gtagaatatt cagacaaaat ggatacataa    120

agactaagta gcccataagg ggtcaaattt tgctgccaaa tgcgtatgcc accaacttac    180
```

-continued

```
aaaaacactt cgttcgcaga gcttttcaga ttgtggaatg ttggataagg aattatagac    240

ctctagtagc tgaaatgcaa gaccccaaga ggaagttcag atcttaatat aaattcactt    300

tcatttttga tagctgtccc atctggtcat ttggttggca ctagactggt ggcaggggct    360

tctagctgac tcgcacaggg attctcacaa tagccgatat cagaatttgt gttgaaggaa    420

cttgtctctt catctaatat gatagcggga aaaggagagg aaactactgc ctttagaaaa    480

tataagtaaa gtgattaaag tgctcacgtt accttgacac atagtttttc agtctatggg    540

tttagttact ttagatggca agcatgtaac ttatattaat agtaatttgt aaagttggtt    600

ggataagcta tccatgttgc aggttcatgg attacttctc tataaaaaat atgtatttac    660

caaaaaattt tgtgacattc cttctcccat ctcttccttg acatgcattg taaataggtt    720

cttcttgttc tgagattcaa tattgaattt ctcctatgct attgacaata aaatattatt    780

gaactacaaa aaaaa                                                     795


<210> SEQ ID NO 18
<211> LENGTH: 2538
<212> TYPE: DNA
<213> ORGANISM: Homo sapiens
<220> FEATURE:
<221> NAME/KEY: misc_feature
<223> OTHER INFORMATION: Incyte ID No: 979243.1
<221> NAME/KEY: unsure
<222> LOCATION: 1479-1784, 1933-2000, 2002
<223> OTHER INFORMATION: a, t, c, g, or other

<400> SEQUENCE: 18

cgccaggaca tgcagcccac catgaagttc gtgatggaca catctaaata ctggtttaag     60

ccaaacatca cccgagagca agcaatcgag ctgctgagga aggaggagcc aggggctttg    120

tcataaggga cagctcttca taccgaggct ccttcggcct ggccctgaag gtgcaggagg    180

ttcccgcgtc tgctcagaat cgaccaggtg aggacagcaa tgacctcatc cgacacttcc    240

tcatcgagtc gtctgccaaa ggagtgcatc tcaaaggagc agatgaggag ccctactttg    300

aactgggagg tgcagatggg gcctcggact ctacagacag cccagcctcc tgccagaaga    360

aatctgcggg ctgccacacc ctgtacctga gctcagtgag cgtggagacc ctgactggag    420

ccctggccgt gcagaaagcc atctccacca cctttgagag ggacatcctc cccacgccca    480

ccgtggtcca cttcaaagtc acagagcagg gcatcactct gactgatgtc cagaggaagg    540

tgtttttccg gcgccattac ccactcacca ccctccgctt ctgtggtatg gaccctgagc    600

aacggaagtg gcagaagtac tgcaaaccct cctggatctt tgggtttgtg gccaagagcc    660

agacagagcc tcaggagaac gtatgccacc tctttgcgga gtatgacatg gtccagccag    720

cctcgcaggt catcggcctg gtgactgctc tgctgcagga cgcagaaagg atgtagggga    780

gagactgcct gtgcacctaa ccaacacctc caggggctcg ctaaggagcc cccctccacc    840

ccctgaatgg gtgtggcttg tggccatatt gacagaccaa tctatgggac taggggggatt    900

ggcatcaagt tgacaccctt gaacctgcta tggccttcag cagtcaccat catccagacc    960

ccccgggcct cagtttcctc aatcatagaa gaagaccaat agacaagatc agctgttctt   1020

agatgctggt gggcatttga acatgctcct ccatgattct gaagcatgca cacctctgaa   1080

gacccctgca tgaaaataac ctccaaggac cctctgaccc catcgacctg ggccctgccc   1140

acacaacagt ctgagcaaga gacctgcagc ccctgtttcg tggcagacag caggtgcctg   1200

gcggtgaccc acggggctcc tggcttgcag ctggtgatgg tcaagaactg actacaaaac   1260

aggaatggat agactctatt tccttccata tctgttcctc tgttcctttt cccactttct   1320
```

-continued

```
gggtggcttt ttgggtccac ccagccagga tgctgcaggc caagctgggt gtggtattta   1380

gggcagctca gcagggggaa cttgtcccca tggtcagagg agacccagct gtcctgcacc   1440

cccttgcaga tgagtatcac cccatctttt ctttccacnn nnnnnnnnnn nnnnnnnnnn   1500

nnnnnnnnnn nnnnnnnnnn nnnnnnnnnn nnnnnnnnnn nnnnnnnnnn nnnnnnnnnn   1560

nnnnnnnnnn nnnnnnnnnn nnnnnnnnnn nnnnnnnnnn nnnnnnnnnn nnnnnnnnnn   1620

nnnnnnnnnn nnnnnnnnnn nnnnnnnnnn nnnnnnnnnn nnnnnnnnnn nnnnnnnnnn   1680

nnnnnnnnnn nnnnnnnnnn nnnnnnnnnn nnnnnnnnnn nnnnnnnnnn nnnnnnnnnn   1740

nnnnnnnnnn nnnnnnnnnn nnnnnnnnnn nnnnnnnnnn nnnnccattc cttgataggc   1800

gagtattcca aagctggtat cgtagctgcc ctaatgttgc atattaggcg gcgggggcag   1860

agataagggc catctctctg tgattctgcc tcagctcctg tcttgctgag ccctccccca   1920

acccacgctc cannnnnnnn nnnnnnnnnn nnnnnnnnnn nnnnnnnnnn nnnnnnnnnn   1980

nnnnnnnnnn nnnnnnnnnn gnccctctac tgctatgtgg cttcaaccag cctcacagcc   2040

acacggggga agcagagagt caagaatgca aagaggccgc ttccctaaga ggcttggagg   2100

agctgggctc tatcccacac ccacccccac cccaccccca cccagcctcc agaagctgga   2160

accatttctc ccgcaggcct gagttcctaa ggaaaccacc ctaccggggt ggaagggagg   2220

gtcagggaag aaacccactc ttgctctacg aggagcaagt gcctgccccc tcccagcagc   2280

cagccctgcc aaagttgcat tatctttggc caaggctggg cctgacggtt atgatttcag   2340

ccctgggcct gcaggagagg ctgagaccag cccacccagc cagtggtcga gcactgcccc   2400

gccgccaaag tctgcagaat gtgagatgag gttctcaagg tcacaggccc cagtcccagc   2460

ctgggggctg gcagaggccc ccatatactc tgctacagct cctatcatga aaaataaaat   2520

gtttgtcttt gcaaaaca                                                 2538
```

<210> SEQ ID NO 19
<211> LENGTH: 1730
<212> TYPE: DNA
<213> ORGANISM: Homo sapiens
<220> FEATURE:
<221> NAME/KEY: misc_feature
<223> OTHER INFORMATION: Incyte ID No: 3189059CB1

<400> SEQUENCE: 19

```
gcggccgcgc ggtatcccac ccagcccacc ccgccccggc cgacggctga cagctgacct     60

ggatccttcg agcgcccgcc gaccgccagc gatcttccct catcttccgg gctggtttct    120

gctgcgcgag gagcgtgccc tcgccgcccc tctcgccgga cccccggccc ccgatggctc    180

ggatggggct tgcgggcgcc gctggacgct ggtggggact cgctctcggc ttgaccgcat    240

tcttcctccc aggcgtccac tcccaggtgg tccaggtgaa cgactccatg tatggcttca    300

tcggcacaga cgtggttctg cactgcagct ttgccaaccc gcttcccagc gtgaagatca    360

cccaggtcac atggcagaag tccaccaatg gctccaagca gaacgtggcc atctacaacc    420

catccatggg cgtgtccgtg ctggctccct accgcgagcg tgtggaattc ctgcggccct    480

ccttcaccga tggcactatc cgcctctccc gcctggagct ggaggatgag ggtgtctaca    540

tctgcgagtt tgctaccttc cctacgggca atcgagaaag ccagctcaat ctcacggtga    600

tggccaaacc caccaattgg atagagggta cccaggcagt gcttcgagcc aagaaggggc    660

aggatgacaa ggtcctggtg gccacctgca cctcagccaa tgggaagcct cccagtgtgg    720

tatcctggga aactcggtta aaaggtgagg ccagagtacc aggagactcc ggaaccccaa    780
```

-continued

```
tggcaccagt gacggtcatc agccgctacc gcctggtgcc cagcagggaa gcccaccagc    840
agtccttggc ctgcatcgtc aactaccaca tggaccgctt caaggaaagc ctcactctca    900
acgtgcagta tgagcctgag gtaaccattg aggggtttga tggcaactgg tacctgcagc    960
ggatggacgt gaagctcacc tgcaaagctg atgctaaccc cccagccact gagtaccact   1020
ggaccacgct aaatggctct ctccccaagg gtgtggaggc ccagaacaga accctcttct   1080
tcaagggacc catcaactac agcctggcag ggacctacat ctgtgaggcc accaacccca   1140
tcggtacacg ctcaggccag gtggaggtca atatcacaga attcccctac accccgtctc   1200
ctcccgaaca tgggcggcgc gccgggccgg tgcccacggc catcattggg ggcgtggcgg   1260
ggagcatcct gctggtgttg attgtggtcg gcgggatcgt ggtcgccctg cgtcggcgcc   1320
ggcacacctt caagggtgac tacagcacca agaagcacgt gtatggcaac ggctacagca   1380
aggcaggcat cccccagcac cacccaccaa tggcacagaa cctgcagtac cccgacgact   1440
cagacgacga gaagaaggcc ggcccactgg gtggaagcag ctatgaggag gaggaggagg   1500
aggaggaggg cggtggaggg ggcgagcgca aggtgggcgg cccccacccc aaatatgacg   1560
aggacgccaa gcggccctac ttcaccgtgg atgaggccga ggcccgtcag gacggctacg   1620
gggaccggac tctgggctac cagtacgacc ctgagcagct ggacttggct gagaacatgg   1680
tttctcagaa cgacgggtct ttcatttcca agaaggagtg gtacgtgtag              1730
```

<210> SEQ ID NO 20
<211> LENGTH: 518
<212> TYPE: PRT
<213> ORGANISM: Homo sapiens
<220> FEATURE:
<221> NAME/KEY: misc_feature
<223> OTHER INFORMATION: Incyte ID No: 3189059CD1

<400> SEQUENCE: 20

```
Met Ala Arg Met Gly Leu Ala Gly Ala Ala Gly Arg Trp Trp Gly
  1               5                  10                  15

Leu Ala Leu Gly Leu Thr Ala Phe Phe Leu Pro Gly Val His Ser
                 20                  25                  30

Gln Val Val Gln Val Asn Asp Ser Met Tyr Gly Phe Ile Gly Thr
                 35                  40                  45

Asp Val Val Leu His Cys Ser Phe Ala Asn Pro Leu Pro Ser Val
                 50                  55                  60

Lys Ile Thr Gln Val Thr Trp Gln Lys Ser Thr Asn Gly Ser Lys
                 65                  70                  75

Gln Asn Val Ala Ile Tyr Asn Pro Ser Met Gly Val Ser Val Leu
                 80                  85                  90

Ala Pro Tyr Arg Glu Arg Val Glu Phe Leu Arg Pro Ser Phe Thr
                 95                 100                 105

Asp Gly Thr Ile Arg Leu Ser Arg Leu Glu Leu Glu Asp Glu Gly
                110                 115                 120

Val Tyr Ile Cys Glu Phe Ala Thr Phe Pro Thr Gly Asn Arg Glu
                125                 130                 135

Ser Gln Leu Asn Leu Thr Val Met Ala Lys Pro Thr Asn Trp Ile
                140                 145                 150

Glu Gly Thr Gln Ala Val Leu Arg Ala Lys Lys Gly Gln Asp Asp
                155                 160                 165

Lys Val Leu Val Ala Thr Cys Thr Ser Ala Asn Gly Lys Pro Pro
                170                 175                 180
```

-continued

```
Ser Val Val Ser Trp Glu Thr Arg Leu Lys Gly Glu Ala Arg Val
                185                 190                 195

Pro Gly Asp Ser Gly Thr Pro Met Ala Pro Val Thr Val Ile Ser
                200                 205                 210

Arg Tyr Arg Leu Val Pro Ser Arg Glu Ala His Gln Gln Ser Leu
                215                 220                 225

Ala Cys Ile Val Asn Tyr His Met Asp Arg Phe Lys Glu Ser Leu
                230                 235                 240

Thr Leu Asn Val Gln Tyr Glu Pro Glu Val Thr Ile Glu Gly Phe
                245                 250                 255

Asp Gly Asn Trp Tyr Leu Gln Arg Met Asp Val Lys Leu Thr Cys
                260                 265                 270

Lys Ala Asp Ala Asn Pro Pro Ala Thr Glu Tyr His Trp Thr Thr
                275                 280                 285

Leu Asn Gly Ser Leu Pro Lys Gly Val Glu Ala Gln Asn Arg Thr
                290                 295                 300

Leu Phe Phe Lys Gly Pro Ile Asn Tyr Ser Leu Ala Gly Thr Tyr
                305                 310                 315

Ile Cys Glu Ala Thr Asn Pro Ile Gly Thr Arg Ser Gly Gln Val
                320                 325                 330

Glu Val Asn Ile Thr Glu Phe Pro Tyr Thr Pro Ser Pro Pro Glu
                335                 340                 345

His Gly Arg Arg Ala Gly Pro Val Pro Thr Ala Ile Ile Gly Gly
                350                 355                 360

Val Ala Gly Ser Ile Leu Leu Val Leu Ile Val Val Gly Gly Ile
                365                 370                 375

Val Val Ala Leu Arg Arg Arg Arg His Thr Phe Lys Gly Asp Tyr
                380                 385                 390

Ser Thr Lys Lys His Val Tyr Gly Asn Gly Tyr Ser Lys Ala Gly
                395                 400                 405

Ile Pro Gln His His Pro Pro Met Ala Gln Asn Leu Gln Tyr Pro
                410                 415                 420

Asp Asp Ser Asp Asp Glu Lys Lys Ala Gly Pro Leu Gly Gly Ser
                425                 430                 435

Ser Tyr Glu Glu Glu Glu Glu Glu Glu Glu Gly Gly Gly Gly Gly
                440                 445                 450

Glu Arg Lys Val Gly Gly Pro His Pro Lys Tyr Asp Glu Asp Ala
                455                 460                 465

Lys Arg Pro Tyr Phe Thr Val Asp Glu Ala Glu Ala Arg Gln Asp
                470                 475                 480

Gly Tyr Gly Asp Arg Thr Leu Gly Tyr Gln Tyr Asp Pro Glu Gln
                485                 490                 495

Leu Asp Leu Ala Glu Asn Met Val Ser Gln Asn Asp Gly Ser Phe
                500                 505                 510

Ile Ser Lys Lys Glu Trp Tyr Val
                515
```

<210> SEQ ID NO 21
<211> LENGTH: 1444
<212> TYPE: DNA
<213> ORGANISM: Homo sapiens
<220> FEATURE:
<221> NAME/KEY: misc_feature
<223> OTHER INFORMATION: Incyte ID No: 1650519CB1

<400> SEQUENCE: 21

```
ggagaatttg aaagggtgcc ccaaaggaca atctctaaag gggtaagggg gatacctacc      60
ttgtctggta ggggagatgt ttcgttttca tgctttacca gaaaatccac ttccctgccg     120
accttagttt caaagcttat tcttaattag agacaagaaa cctgtttcaa cttgaagaca     180
ccgtatgagg tgaatggaca gccagccacc acaatgaaag aaatcaaacc aggaataacc     240
tatgctgaac ccacgcctca atcgtcccca agtgtttcct gacacgcatc tttgcttaca     300
gtgcatcaca actgaagaat ggggttcaac ttgacgcttg caaaattacc aaataacgag     360
ctgcacggcc aagagagtca caattcaggc aacaggagcg acgggccagg aaagaacacc     420
acccttcaca atgaatttga cacaattgtc ttgccggtgc tttatctcat tatatttgtg     480
gcaagcatct tgctgaatgg tttagcagtg tggatcttct tccacattag gaataaaacc     540
agcttcatat tctatctcaa aaacatagtg gttgcagacc tcataatgac gctgacattt     600
ccatttcgaa tagtccatga tgcaggattt ggaccttggt acttcaagtt tattctctgc     660
agatacactt cagttttgtt ttatgcaaac atgtatactt ccatcgtgtt ccttgggctg     720
ataagcattg atcgctatct gaaggtggtc aagccatttg ggactctcgg gatgtacagc     780
ataaccttca cgaaggtttt atctgtttgt gtttgggtga tcatggctgt tttgtctttg     840
ccaaacatca tcctgacaaa tggtcagcca acagaggaca atatccatga ctgctcaaaa     900
cttaaaagtc ctttgggggt caaatggcat acggcagtca cctatgtgaa cagctgcttg     960
tttgtggccg tgctggtgat tctgatcgga tgttacatag ccatatccag gtacatccac    1020
aaatccagca ggcaattcat aagtcagtca agccgaaagc gaaaacataa ccagagcatc    1080
agggttgttg tggctgtgta ttttacctgc tttctaccat atcacttgtg cagaatgcct    1140
tctactttta gtcacttaga caggctttta gatgaatctg cacaaaaaat cctatattac    1200
tgcaaagaaa ttacactttt cttgtctgcg tgtaatgttt gcctggatcc aataatttac    1260
tttttcatgt gtaggtcatt ttcaagatgg ctgttcaaaa aatcaaatat cagacccagg    1320
agtgaaagca tcagatcact gcaaagtgtg agaagatcgg aagttcgcat atattatgat    1380
tacactgatg tgtaggcctt ttattgtttg ttggaatcga tatgtacaaa gtgtaataca    1440
tcag                                                                 1444
```

<210> SEQ ID NO 22
<211> LENGTH: 358
<212> TYPE: PRT
<213> ORGANISM: Homo sapiens
<220> FEATURE:
<221> NAME/KEY: misc_feature
<223> OTHER INFORMATION: Incyte ID No: 1650519CD1

<400> SEQUENCE: 22

```
Met Gly Phe Asn Leu Thr Leu Ala Lys Leu Pro Asn Asn Glu Leu
  1               5                  10                  15

His Gly Gln Glu Ser His Asn Ser Gly Asn Arg Ser Asp Gly Pro
                 20                  25                  30

Gly Lys Asn Thr Thr Leu His Asn Glu Phe Asp Thr Ile Val Leu
                 35                  40                  45

Pro Val Leu Tyr Leu Ile Ile Phe Val Ala Ser Ile Leu Leu Asn
                 50                  55                  60

Gly Leu Ala Val Trp Ile Phe Phe His Ile Arg Asn Lys Thr Ser
                 65                  70                  75

Phe Ile Phe Tyr Leu Lys Asn Ile Val Val Ala Asp Leu Ile Met
```

-continued

```
                 80                  85                  90

Thr Leu Thr Phe Pro Phe Arg Ile Val His Asp Ala Gly Phe Gly
                 95                 100                 105

Pro Trp Tyr Phe Lys Phe Ile Leu Cys Arg Tyr Thr Ser Val Leu
                110                 115                 120

Phe Tyr Ala Asn Met Tyr Thr Ser Ile Val Phe Leu Gly Leu Ile
                125                 130                 135

Ser Ile Asp Arg Tyr Leu Lys Val Val Lys Pro Phe Gly Asp Ser
                140                 145                 150

Arg Met Tyr Ser Ile Thr Phe Thr Lys Val Leu Ser Val Cys Val
                155                 160                 165

Trp Val Ile Met Ala Val Leu Ser Leu Pro Asn Ile Ile Leu Thr
                170                 175                 180

Asn Gly Gln Pro Thr Glu Asp Asn Ile His Asp Cys Ser Lys Leu
                185                 190                 195

Lys Ser Pro Leu Gly Val Lys Trp His Thr Ala Val Thr Tyr Val
                200                 205                 210

Asn Ser Cys Leu Phe Val Ala Val Leu Val Ile Leu Ile Gly Cys
                215                 220                 225

Tyr Ile Ala Ile Ser Arg Tyr Ile His Lys Ser Ser Arg Gln Phe
                230                 235                 240

Ile Ser Gln Ser Ser Arg Lys Arg Lys His Asn Gln Ser Ile Arg
                245                 250                 255

Val Val Val Ala Val Tyr Phe Thr Cys Phe Leu Pro Tyr His Leu
                260                 265                 270

Cys Arg Met Pro Ser Thr Phe Ser His Leu Asp Arg Leu Leu Asp
                275                 280                 285

Glu Ser Ala Gln Lys Ile Leu Tyr Tyr Cys Lys Glu Ile Thr Leu
                290                 295                 300

Phe Leu Ser Ala Cys Asn Val Cys Leu Asp Pro Ile Ile Tyr Phe
                305                 310                 315

Phe Met Cys Arg Ser Phe Ser Arg Trp Leu Phe Lys Lys Ser Asn
                320                 325                 330

Ile Arg Pro Arg Ser Glu Ser Ile Arg Ser Leu Gln Ser Val Arg
                335                 340                 345

Arg Ser Glu Val Arg Ile Tyr Tyr Asp Tyr Thr Asp Val
                350                 355

<210> SEQ ID NO 23
<211> LENGTH: 5933
<212> TYPE: DNA
<213> ORGANISM: Homo sapiens
<220> FEATURE:
<221> NAME/KEY: misc_feature
<223> OTHER INFORMATION: Incyte ID No: 474630.4
<221> NAME/KEY: unsure
<222> LOCATION: 2373-2407
<223> OTHER INFORMATION: a, t, c, g, or other

<400> SEQUENCE: 23

caggacgggc gcacagcagc agccgaggct ggccgggaga gggaggaaga ggatggcagg     60

gccacgcccc agcccatggg ccaggctgct cctggcagcc ttgatcagcg tcagcctctc    120

tgggaccttg gcaactgacc actgcccacc ttcagggctg gaaaacttga ggctccaagc    180

tcttcagcct agagaagctt gagccctgac cacggggcct gagaatagga gcgaaggagg    240

ctgtgtctag aggaaagagg agacacccac ccaggactga ggcacccaga ggatgcactg    300
```

-continued

```
aggccccaga gcaaaccgct gcaagaaggc cccagtgaag agctgcacgg agtgtgtccg    360
tgtggataag gactgcgcct actgcacaga cgagatgttc agggaccggc gctgcaacac    420
ccaggcggag ctgctggccg cgggctgcca gcgggagagc atcgtggtca tggagagcag    480
cttccaaatc acagaggaga cccagattga caccaccctg cggcgcagcc agatgtcccc    540
ccaaggcctg cgggtccgtc tgcggcccgg tgaggagcgg cattttgagc tggaggtgtt    600
tgagccactg gagagccccg tggacctgta catcctcatg gacttctcca actccatgtc    660
cgatgatctg gacaacctca agaagatggg gcagaacctg gctcgggtcc tgagccagct    720
caccagcgac tacactattg gatttggcaa gtttgtggac aaagtcagcg tcccgcagac    780
ggacatgagg cctgagaagc tgaaggagcc ttggcccaac agtgaccccc ccttctcctt    840
caagaacgtc atcagcctga cagaagatgt ggatgagttc cggaataaac tgcagggaga    900
gcggatctca ggcaacctgg atgctcctga gggcggcttc gatgccatcc tgcagacagc    960
tgtgtgcacg agggacattg gctggcgccc ggacagcacc cacctgctgg tcttctccac   1020
cgagtcagcc ttccactatg aggctgatgg cgccaacgtg ctggctggca tcatgagccg   1080
caacgatgaa cggtgccacc tggacaccac gggcacctac acccagtaca ggacacagga   1140
ctacccgtcg gtgcccaccc tggtgcgcct gctcgccaag cacaacatca tccccatctt   1200
tgcttgtcac caactactcc tatagctact acgagaagct tcacacctat ttccctgtct   1260
cctcactggg ggtgctgcag gaggactcgt ccaacatcgt ggagctgctg gaggaggcct   1320
tcaatcggat ccgctccaac ctggacatcc gggccctaga cagcccccga ggccttcgga   1380
cagaggtcac ctccaagatg ttccagaaga cgaggactgg gtcctttcac atccggcggg   1440
gggaagtggg tatataccag gtgcagctgc gggcccttga gcacgtggat gggacgcacg   1500
tgtgccagct gccggaggac cagaagggca acatccatct gaaaccttcc ttctccgacg   1560
gcctcaagat ggacgcgggc atcatctgtg atgtgtgcac ctgcgagctg caaaaagagg   1620
tgcggtcagc tcgctgcagc ttcaacggag acttcgtgtg cggacagtgt gtgtgcagcg   1680
agggctggag tggccagacc tgcaactgct ccaccggctc tctgagtgac attcagccct   1740
gcctgcggga gggcgaggac aagccgtgct ccggccgtgg ggagtgccag tgcgggcact   1800
gtgtgtgcta cggcgaaggc cgctacgagg gtcagttctg cgagtatgac aacttccagt   1860
gtccccgcac ttccgggttc ctgtgcaatg accgaggacg ctgctccatg ggccagtgtg   1920
tgtgtgagcc tggttggaca ggcccaagct gtgactgtcc cctcagcaat gccacctgca   1980
tcgacagcaa tgggggcatc tgtaatggac gtggccactg tgagtgtggc cgctgccact   2040
gccaccagca gtcgctctac acggacacca tctgcgagat caactactcg gcgatccacc   2100
cgggcctctg cgaggaccta cgctcctgcg tgcagtgcca ggcgtggggc accggcgaga   2160
agaaggggcg cacgtgtgag gaatgcaact tcaaggtcaa gatggtggac gagcttaaga   2220
gagccgagga ggtggtggtg cgctgctcct tccgggacga ggatgacgac tgcacctaca   2280
gctacaccat ggaaggtgac ggcgcccctg ggcccaacag cactgtcctg gtgcacaaga   2340
agaaggactg ccctccgggc tccttctggt ggnnnnnnnn nnnnnnnnnn nnnnnnnnnn   2400
nnnnnnnggc cctgctactg ctgctatgct ggaagtactg tgcctgctgc aaggcctgcc   2460
tggcacttct cccgtgctgc aaccgaggtc acatggtggg ctttaaggaa gaccactaca   2520
tgctgcggga gaacctgatg gcctctgacc acttggacac gcccatgctg cgcagcggga   2580
acctcaaggg ccgtgacgtg gtccgctgga aggtcaccaa caacatgcag cggcctggct   2640
```

-continued

```
ttgccactca tgccgccagc atcaacccca cagagctggt gccctacggg ctgtccttgc   2700
gcctggcccg cctttgcacc gagaacctgc tgaagcctga cactcgggag tgcgcccagc   2760
tgcgccagga ggtggaggag aacctgaacg aggtctacag gcagatctcc ggtgtacaca   2820
agctccagca gaccaagttc cggcagcagc ccaatgccgg gaaaaagcaa gaccacacca   2880
ttgtggacac agtgctgatg gcgccccgct cggccaagcc ggccctgctg aagcttacag   2940
agaagcaggt ggaacagagg gccttccacg acctcaaggt ggcccccggc tactacaccc   3000
tcactgcaga ccaggacgcc cggggcatgg tggagttcca ggagggcgtg gagctggtgg   3060
acgtacgggt gcccctcttt atccggcctg aggatgacga cgagaagcag ctgctggtgg   3120
aggccatcga cgtgcccgca ggcactgcca ccctcggccg ccgcctggta aacatcacca   3180
tcatcaagga gcaagccaga gacgtggtgt cctttgagca gcctgagttc tcggtcagcc   3240
gcggggacca ggtggcccgc atccctgtca tccggcgtgt cctggacggc gggaagtccc   3300
aggtctccta ccgcacacag gatggcaccg cgcagggcaa ccgggactac atccccgtgg   3360
agggtgagct gctgttccag cctggggagg cctggaaaga gctgcaggtg aagctcctgg   3420
agctgcaaga agttgactcc ctcctgcggg gccgccaggt ccgccgtttc cacgtccagc   3480
tcagcaaccc taagtttggg gcccacctgg gccagcccca ctccaccacc atcatcatca   3540
gggacccaga tgaactggac cggagcttca cgagtcagat gttgtcatca cagccacccc   3600
ctcacggcga cctgggcgcc ccgcagaacc ccaatgctaa ggccgctggg tccaggaaga   3660
tccatttcaa ctggctgccc ccttctggca agccaatggg gtacagggta aagtactgga   3720
ttcagggtga ctccgaatcc gaagcccacc tgctcgacag caaggtgccc tcagtggagc   3780
tcaccaacct gtacccgtat tgcgactatg agatgaaggt gtgcgcctac ggggctcagg   3840
gcgagggacc ctacagctcc ctggtgtcct gccgcaccca ccaggaagtg cccagcgagc   3900
cagggcgtct ggccttcaat gtcgtctcct ccacggtgac ccagctgagc tgggctgagc   3960
cggctgagac caacggtgag atcacagcct acgaggtctg ctatggcctg gtcaacgatg   4020
acaaccgacc tattgggccc atgaagaaag tgctggttga caaccctaag aaccggatgc   4080
tgcttattga gaaccttcgg gagtcccagc cctaccgcta cacggtgaag gcgcgcaacg   4140
gggccggctg gggcctgag cgggaggcca tcatcaacct ggccacccag cccaagaggc   4200
ccatgtccat ccccatcatc cctgacatcc ctatcgtgga cgcccagagc ggggaggact   4260
acgacagctt ccttatgtac agcgatgacg ttctacgctc tccatcgggc agccagaggc   4320
ccagcgtctc cgatgacact gagcacctgg tgaatggccg gatggacttt gccttcccgg   4380
gcagcaccaa ctccctgcac aggatgacca cgaccagtgc tgctgcctat ggcacccacc   4440
tgagcccaca cgtgccccac cgcgtgctaa gcacatcctc caccctcaca cgggactaca   4500
actcactgac ccgctcagaa cactcacact cgaccacact gcccagggac tactccaccc   4560
tcacctccgt ctcctcccac ggcctccctc ccatctggga acacgggagg agcaggcttc   4620
cgctgtcctg ggccctgggg tcccggagtc gggctcagat gaaagggttc ccccttcca    4680
ggggcccacg agactctata atcctggctg ggaggccagc agcgccctcc tggggcccag   4740
actctcgcct gactgctggt gtgcccgaca cgcccacccg cctggtgttc tctgccctgg   4800
ggcccacatc tctcagagtg agctggcagg agccgcggtg cgagcggccg ctgcagggct   4860
acagtgtgga gtaccagctg ctgaacggcg gtgagctgca tcggctcaac atccccaacc   4920
ctgcccagac ctcggtggtg gtggaagacc tcctgcccaa ccactcctac gtgttccgcg   4980
tgcgggccca gagccaggaa ggctggggcc gagagcgtga gggtgtcatc accattgaat   5040
```

-continued

```
cccaggtgca cccgcagagc ccactgtgtc ccctgccagg ctccgccttc actttgagca   5100

ctcccagtgc cccaggcccg ctggtgttca ctgccctgag cccagactcg ctgcagctga   5160

gctgggagcg gccacggagg cccaatgggg atatcgtcgg ctacctggtg acctgtgaga   5220

tggcccaagg aggagggcca gccaccgcat tccgggtgga tggagacagc cccgagagcc   5280

ggctgaccgt gccgggcctc agcgagaacg tgccctacaa gttcaaggtg caggccagga   5340

ccactgaggg cttcgggcca gagcgcgagg gcatcatcac catagagtcc caggatggag   5400

gacccttccc gcagctgggc agccgtgccg ggctcttcca gcacccgctg caaagcgagt   5460

acagcagcat caccaccacc cacaccagcg ccaccgagcc cttcctagtg gatgggccga   5520

ccctgggggc ccagcacctg gaggcaggcg gctccctcac ccggcatgtg acccaggagt   5580

ttgtgagccg gacactgacc accagcggaa cccttagcac ccacatggac caacagttct   5640

tccaaacttg accgcaccct gccccacccc cgccatgtcc cactaggcgt cctcccgact   5700

cctctcccgg agcctcctca gctactccat ccttgcaccc ctgggggccc agcccacccg   5760

catgcacaga gcaggggcta ggtgtctcct gggaggcatg aaggggggcaa ggtccgtcct  5820

ctgtgggccc aaacctattt gtaaccaaag agctgggagc agcacaagga cccagccttt   5880

gttctgcact taataaatgg ttttgctact gctaaaaaaa aaaaaaaaagc ggc          5933
```

```
<210> SEQ ID NO 24
<211> LENGTH: 573
<212> TYPE: DNA
<213> ORGANISM: Homo sapiens
<220> FEATURE:
<221> NAME/KEY: misc_feature
<223> OTHER INFORMATION: Incyte ID No: 093496.1

<400> SEQUENCE: 24

aaaagaaaag gaaaagaaaa gtgtggactt ggatgaaatc ttcaggtcca acatttggga     60

ttctaagttc caaagaccag gttggaatca tttctaagaa ggttctggtg gttacacatt    120

cctggagtcc tctactcccc actccctgcc aagctgggcc tgtggataga tgtgatccct    180

cagcctccca gcttcaaaca cctgccaatg gttgacgtga acaacatggg ctcagtctca    240

gctaggatca cacccaaagc ccagcaccca gtaaggtgca ggagccatcc atttccctga    300

gcagagcaga ttaggctgag gaaagcagca gccatgcctt tgcacaatgc atttctaggg    360

cattcttccc acacataatc tcctctgctc attgtcctgt gaagaaactg tggcctggag    420

aggttgagcc actgtgccaa ggccaccaat gcaggtggta tgtgggtggg tgggggcctg    480

gggtggggag cacggcccag gcagggtctg tgctgaccgc ccttgtgttt ggaacctaga    540

catcccccct tgcctggatc tgagctgacc gaa                                 573
```

```
<210> SEQ ID NO 25
<211> LENGTH: 269
<212> TYPE: DNA
<213> ORGANISM: Homo sapiens
<220> FEATURE:
<221> NAME/KEY: misc_feature
<223> OTHER INFORMATION: Incyte ID No: 1231633.4

<400> SEQUENCE: 25

accactgaag atcctggtgt cgccatgggc cgccgccccg cccgttgtta ccggtattgt     60

aagaacaagc cgtacccaaa gtctcgcttc tgccgaggtg tccctgccct ggaggctgcc    120

cgaatttgtg ccaataagta catggtaaaa agttgtggca aagatggctt ccatatccgg    180
```

-continued

```
gtgcggctcc accccttcca cgtcatccgc atcaacaaga tgttgtcctg tgctggggct    240

gacaggctcc aaacaggcat gcgaggtgc                                      269


<210> SEQ ID NO 26
<211> LENGTH: 1743
<212> TYPE: DNA
<213> ORGANISM: Homo sapiens
<220> FEATURE:
<221> NAME/KEY: misc_feature
<223> OTHER INFORMATION: Incyte ID No: 988891.1
<221> NAME/KEY: unsure
<222> LOCATION: 1562
<223> OTHER INFORMATION: a, t, c, g, or other

<400> SEQUENCE: 26

ggtattcaac agagaaattt ctcagcctcc tacttctgct tttgaaagct ataaaaacag     60

cgagggagaa actggcagat accaaacctc ttcgaggcac aagggcacaa caggctgctc    120

tgggattctc ttcagccaat cttcattgct caagtgtctg aagcagccat ggcagaagta    180

cctgagctcg ccagtgaaat gatggcttat tacagtggca atgaggatga cttgttcttt    240

gaagctgatg gccctaaaca gatgaagtgc tccttccagg acctggacct ctgccctctg    300

gatggcggca tccagctacg aatctccgac caccactaca gcaagggctt caggcaggcc    360

gcgtcagttg ttgtggccat ggacaagctg aggaagatgc tggttccctg cccacagacc    420

ttccaggaga atgacctgag caccttcttt cccttcatct ttgaagaaga acctatcttc    480

ttcgacacat gggataacga ggcttatgtg cacgatgcac ctgtacgatc actgaactgc    540

acgctccggg actcacagca aaaaagcttg gtgatgtctg gtccatatga actgaaagct    600

ctccacctcc agggacagga tatggagcaa caagtggtgt tctccatgtc ctttgtacaa    660

ggagaagaaa gtaatgacaa aatacctgtg gccttgggcc tcaaggaaaa gaatctgtac    720

ctgtcctgcg tgttgaaaga tgataagccc actctacagc tggagagtgt agatcccaaa    780

aattacccaa agaagaagat ggaaaagcga tttgtcttca acaagataga aatcaataac    840

aagctggaat ttgagtctgc ccagttcccc aactggtaca tcagcacctc tcaagcagaa    900

aacatgcccg tcttcctggg agggaccaaa ggcggccagg atataactga cttcaccatg    960

caatttgtgt cttcctaaag agagctgtac ccagagagtc ctgtgctgaa tgtggactca   1020

atccctaggg ctggcagaaa gggaacagaa aggtttttga gtacggctat agcctggact   1080

ttcctgttgt ctacaccaat gcccaactgc ctgccttagg gtagtgctaa gaggatctcc   1140

tgtccatcag ccaggacagt cagctctctc ctttcagggc caatccccag cccttttgtt   1200

gagccaggcc tctctcacct ctcctactca cttaaagccc gcctgacaga aaccacggcc   1260

acatttggtt ctaagaaacc ctctgtcatt cgctcccaca ttctgatgag caaccgcttc   1320

cctatttatt tatttatttg tttgtttgtt ttattcattg gtctaattta ttcaaagggg   1380

gcaagaagta gcagtgtctg taaaagagcc tagtttttaa tagctatgga atcaattcaa   1440

tttggactgg tgtgctctct ttaaatcaag tcctttaatt aagactgaaa atatataagc   1500

tcagattatt taaatgggaa tatttataaa tgagcaaata tcatactgtt caatggttct   1560

gngcttatat attttcagtc ttaattaaag gactggtgtg ctctctttaa atcaagtcct   1620

ttaattaaga ctgaaaatat ataagctcag attatttaaa tgggaatatt tataaatgag   1680

caaatatcat actgttcaat ggttcttcag tgaagtttat ttcagaaaaa aaaaaaaaag   1740

ggg                                                                 1743
```

-continued

<210> SEQ ID NO 27
<211> LENGTH: 391
<212> TYPE: DNA
<213> ORGANISM: Homo sapiens
<220> FEATURE:
<221> NAME/KEY: misc_feature
<223> OTHER INFORMATION: Incyte ID No: 988891.15
<221> NAME/KEY: unsure
<222> LOCATION: 14
<223> OTHER INFORMATION: a, t, c, g, or other

<400> SEQUENCE: 27
attttgctag agantgttct aaaaccattg cactttactt acaactcctg tccggaaggt 60
gcgaggcaac aagtttttac agccttcaca gaggagtttc tggcagcacc tgtacgatca 120
ctgaactgca cgctccggga ctcacagcaa aaaagcttgg tgatgtctgg tccatatgaa 180
ctgaaagctc tccacctcca gggacaggat atggagcaac aagtggtgtt ctccatgtcc 240
tttgtacaag gagaagaaag taatgacaaa atacctgtgg ccttgggcct tcaaggaaaa 300
gaatctgtac ctgtcctgcg tgttgaaaga tggataaagc ccacttctac agctgggaga 360
gtgttaggat ccccaaaaaa atttacccca a 391

<210> SEQ ID NO 28
<211> LENGTH: 7045
<212> TYPE: DNA
<213> ORGANISM: Homo sapiens
<220> FEATURE:
<221> NAME/KEY: misc_feature
<223> OTHER INFORMATION: Incyte ID No: 3774181CB1
<221> NAME/KEY: unsure
<222> LOCATION: 103, 6960
<223> OTHER INFORMATION: a, t, c, g, or other

<400> SEQUENCE: 28
agtttgctcg gaattcggct cgagcagcac ataaaggaga acacagcgta tttcgagttt 60
ttcaatgatg ccaaagaagc tactgattac ttaaggaatc tanaagatgc cattcagcgg 120
aagtacagct gtgatagatc aagcagcatt cacaagctag aagaccttgt tcaggaatca 180
atggaagaga aagaagaact tctgcagtac aaaagcacta tagcaaacct aatgggaaaa 240 gcaaaaaacaa taattcaact gaagccaagg aattctgact gtccactcaa aacttctatt 300
ccgatcaaag ctatctgtga ctacagacaa attgagataa ccatttacaa agacgatgaa 360
tgtgttttgg cgaataactc tcatcgtgct aaatggaagg tcattagtcc tactgggaat 420
gaggctatgg tcccatctgt gtgcttcacc gttcctccac caaacaaaga agcggtggac 480
cttgccaaca gaattgagca acagtatcag aatgtcctga ctctttggca tgagtctcac 540
ataaacatga agagtgtagt atcctggcat tatctcatca atgaaattga tagaattcga 600
gctagcaatg tggcttcaat aaagacaatg ctacctggtg aacatcagca agttctaagt 660
aatctacaat ctcgttttga agattttctg gaagatagcc aggaatccca agtcttttca 720
ggctcagata taacacaact ggaaaaggag gttaatgtat gtaagcagta ttatcaagaa 780
cttcttaaat ctgcagaaag agaggagcaa gaggaatcag tttataatct ctacatctct 840
gaagttcgaa acattagact tcggttagag aactgtgaag atcggctgat tagacagatt 900
cgaactcccc tggaaagaga tgatttgcat gaaagtgtgt tcagaatcac agaacaggag 960
aaactaaaga aagagctgga acgacttaaa gatgatttgg gaacaatcac aaataagtgt 1020
gaggagtttt tcagtcaagc agcagcctct tcatcagtcc ctaccctacg atcagagctt 1080
aatgtggtcc ttcagaacat gaaccaagtc tattctatgt cttccactta catagataag 1140

-continued

```
ttgaaaactg ttaacttggt gttaaaaaac actcaagctg cagaagccct cgtaaaactc   1200
tatgaaacta aactgtgtga agaagaagca gttatagctg acaagaataa tattgagaat   1260
ctaataagta ctttaaagca atggagatct gaagtagatg aaaagagaca ggtattccat   1320
gccttagagg atgagttgca gaaagctaaa gccatcagtg atgaaatgtt taaaacgtat   1380
aaagaacggg accttgattt tgactggcac aaagaaaaag cagatcaatt agttgaaagg   1440
tggcaaaatg ttcatgtgca gattgacaac aggttacggg acttagaggg cattggcaaa   1500
tcactgaagt actacagaga cacttaccat cctttagatg attggatcca gcaggttgaa   1560
actactcaga gaaagattca ggaaaatcag cctgaaaata gtaaaaccct agccacacag   1620
ttgaatcaac agaagatgct ggtgtccgaa atagaaatga aacagagcaa aatggacgag   1680
tgtcaaaaat atgcagaaca gtactcagct acagtgaagg actatgaatt acaaacaatg   1740
acctaccggg ccatggtaga ttcacaacaa aaatctccag tgaaacgccg aagaatgcag   1800
agttcagcag atctcattat tcaagagttc atggacctaa ggactcgata tactgccctg   1860
gtcactctca tgacacaata tattaaattt gctggtgatt cattgaagag gctggaagag   1920
gaggagatta aaaggtgtaa ggagacttct gaacatgggg catattcaga tctgcttcag   1980
cgtcagaagg caacagtgct tgagaatagc aaacttacag gaaagataag tgagttggaa   2040
agaatggtag ctgaactaaa gaaacaaaag tcccgagtag aggaagaact tccgaaggtc   2100
agggaggctg cagaaaatga attgagaaag cagcagagaa atgtagaaga tatctctctg   2160
cagaagataa gggctgaaag tgaagccaag cagtaccgca gggaacttga aaccattgtg   2220
agagagaagg aagccgctga aagagaactg gagcgggtga ggcagctcac catagaggcc   2280
gaggctaaaa gagctgccgt ggaagagaac ctcctgaatt ttcgcaatca gttggaggaa   2340
aacaccttta ccagacgaac actggaagat catcttaaaa gaaaagattt aagtctcaat   2400
gatttggagc aacaaaaaaa taaattaatg gaagaattaa gaagaaagag agacaatgag   2460
gaagaactct tgaagctgat aaagcagatg gaaaaagacc ttgcatttca gaaacaggta   2520
gcagagaaac agttgaaaga aaagcagaaa attgaattgg aagcaagaag aaaaataact   2580
gaaattcagt atacatgtag agaaaatgca ttgccagtgt gtccgatcac acaggctaca   2640
tcatgcaggg cagtaacggg tctccagcaa gaacatgaca agcagaaagc agaagaactc   2700
aaacagcagg tagatgaact aacagctgcc aatagaaagg ctgaacaaga catgagagag   2760
ctgacatatg aacttaatgc cctccagctt gaaaaaacgt catctgagga aaaggctcgt   2820
ttgctaaaag ataaactaga tgaaacaaat aatacactca gatgccttaa gttggagctg   2880
gaaaggaagg atcaggcgga gaaagggtat tctcaacaac tcagagagct tggtaggcaa   2940
ttgaatcaaa ccacaggtaa agctgaagaa gccatgcaag aagctagtga tctcaagaaa   3000
ataaagcgca attatcagtt agaattagaa tctcttaatc atgaaaaagg gaaactacaa   3060
agagaagtag acagaatcac aagggcacat gctgtagctg agaagaatat tcagcattta   3120
aattcacaaa ttcattcttt tcgagatgag aaagaattag aaagactaca aatctgccag   3180
agaaaatcag atcatctaaa agaacaattt gagaaaagcc atgagcagtt gcttcaaaat   3240
atcaaagctg aaaaagaaaa taatgataaa atccaaaggc tcaatgaaga attggagaaa   3300
agtaatgagt gtgcagagat gctaaaacaa aaagtagagg agcttactag gcagaataat   3360
gaaaccaaat taatgatgca gagaattcag gcagaatcag agaatatagt tttagagaaa   3420
caaactatcc agcaaagatg tgaagcactg aaaattcagg cagatggttt taaagatcag   3480
ctacgcagca caaatgaaca cttgcataaa cagacaaaaa cagagcagga ttttcaaaga   3540
```

-continued

```
aaaattaaat gcctagaaga agacctggcg aaaagtcaaa atttggtaag tgaatttaag   3600
caaaagtgtg accaacagaa cattatcatc cagaatacca agaaagaagt tagaaatctg   3660
aatgcggaac tgaatgcttc caaagaagag aagcgacgcg gggagcagaa agttcagcta   3720
caacaagctc aggtgcaaga gttaaataac aggttgaaaa aagtacaaga cgaattacac   3780
ttaaagacca tagaggagca gatgacccac agaaagatgg ttctgtttca ggaagaatct   3840
ggtaaattca aacaatcagc agaggagttt cggaagaaga tggaaaaatt aatggagtcc   3900
aaagtcatca ctgaaaatga tatttcaggc attaggcttg actttgtgtc tcttcaacaa   3960
gaaaactcta gagcccaaga aaatgctaag ctttgtgaaa caaacattaa agaacttgaa   4020
agacagcttc aacagtatcg tgaacaaatg cagcaagggc agcacatgga agcaaatcat   4080
taccaaaaat gtcagaaact tgaggatgag ctgatagccc agaagcgtga ggttgaaaac   4140
ctgaagcaaa aaatggacca acagatcaaa gagcatgaac atcaattagt tttgctccag   4200
tgtgaaattc aaaaaaagag cacagccaaa gactgtacct tcaaaccaga ttttgagatg   4260
acagtgaagg agtgccagca ctctggagag ctgtcctcta gaaacactgg acaccttcac   4320
ccaacaccca gatcccctct gttgagatgg actcaagaac cacagccatt ggaagagaag   4380
tggcagcatc gggttgttga acagataccc aaagaagtcc aattccagcc accaggggct   4440
ccactcgaga aagagaaaag ccagcagtgt tactctgagt acttttctca gacaagcacc   4500
gagttacaga taacttttga tgagacaaac cccattacaa gactgtctga aattgagaag   4560
ataagagacc aagccctgaa caattctaga ccacctgtta ggtatcaaga taacgcatgt   4620
gaaatggaac tggtgaaggt tttgacaccc ttagagatag ctaagaacaa gcagtatgat   4680
atgcatacag aagtcacaac attaaaacaa gaaaagaacc cagttcccag tgctgaagaa   4740
tggatgcttg aagggtgcag agcatctggt ggactcaaga aaggggattt ccttaagaag   4800
ggcttagaac cagagacctt ccagaacttt gatggtgatc atgcatgttc agtcagggat   4860
gatgaattta aattccaagg gcttaggcac actgtgactg ccaggcagtt ggtggaagct   4920
aagcttctgg acatgagaac aattgagcag ctgcgactcg gtcttaagac tgttgaagaa   4980
gttcagaaaa ctcttaacaa gtttctgacg aaagccacct caattgcagg gctttaccta   5040
gaatctacaa aagaaaagat ttcatttgcc tcagcggccg agagaatcat aatagacaaa   5100
atggtggctt tggcattttt agaagctcag gctgcaacag gttttataat tgatcccatt   5160
tcaggtcaga catattctgt tgaagatgca gttcttaaag gagttgttga ccccgaattc   5220
agaattaggc ttcttgaggc agagaaggca gctgtgggat attcttattc ttctaagaca   5280
ttgtcagtgt ttcaagctat ggaaaataga atgcttgaca gacaaaaagg taaacatatc   5340
ttggaagccc agattgccag tgggggtgtc attgaccctg tgagaggcat tcgtgttcct   5400
ccagaaattg ctctgcagca ggggttgttg aataatgcca tcttacagtt tttacatgag   5460
ccatccagca acacaagagt tttccctaat cccaataaca agcaagctct gtattactca   5520
gaattactgc gaatgtgtgt atttgatgta gagtcccaat gctttctgtt tccatttggg   5580
gagaggaaca tttccaatct caatgtcaag aaaacacata gaatttctgt agtagatact   5640
aaaacaggat cagaattgac cgtgtatgag gctttccaga gaaacctgat tgagaaaagt   5700
atatatcttg aactttcagg gcagcaatat cagtggaagg aagctatgtt ttttgaatcc   5760
tatgggcatt cttctcatat gctgactgat actaaaacag gattacactt caatattaat   5820
gaggctatag agcagggaac aattgacaaa gccttggtca aaaagtatca ggaaggcctc   5880
```

-continued

```
atcacactta cagaacttgc tgattctttg ctgagccggt tagtccccaa gaaagatttg   5940

cacagtcctg ttgcagggta ttggctgact gctagtgggg aaaggatctc tgtactaaaa   6000

gcctcccgta gaaatttggt tgatcggatt actgccctcc gatgccttga agcccaagtc   6060

agtacagggg gcataattga tcctcttact ggcaaaaagt accgggtggc cgaagctttg   6120

catagaggcc tggttgatga ggggtttgcc cagcagctgc gacagtgtga attagtaatc   6180

acagggattg gccatcccat cactaacaaa atgatgtcag tggtggaagc tgtgaatgca   6240

aatattataa ataaggaaat gggaatccga tgtttggaat ttcagtactt gacaggaggg   6300

ttgatagagc cacaggttca ctctcggtta tcaatagaag aggctctcca agtaggtatt   6360

atagatgtcc tcattgccac aaaactcaaa gatcaaaagt catatgtcag aaatataata   6420

tgccctcaga caaaaagaaa gttgacatat aaagaagcct tagaaaaagc tgattttgat   6480

ttccacacag gacttaaact gttagaagta tctgagcccc tgatgacagg aatttctagc   6540

ctctactatt cttcctaatg ggacatgttt aaataactgt gcaaggggtg atgcaggctg   6600

gttcatgcca ctttttcaga gtatgatgat atcggctaca tatgcagtct gtgaattatg   6660

taacatactc tatttcttga gggctgcaaa ttgctaagtg ctcaaaatag agtaagtttt   6720

aaattgaaaa ttacataaga tttaatgccc ttcaaatggt ttcatttagc cttgagaatg   6780

gtttttttgaa acttggccac actaaaatgt tttttttttt ttacgtagaa tgtgggataa   6840

acttgatgaa ctccaagttc acagtgtcat ttcttcagaa ctccccttca ttgaatagtg   6900

atcatttatt aaatgataaa ttgcactcgc tgaaagagca cagtcatgag gcacctggan   6960

atccaagggg aaggtataaa ttccgttcca acggccttca ggtggcgtgt tttgggttgc   7020

ttccaaaatg gaaagttttg ccttt                                          7045
```

```
<210> SEQ ID NO 29
<211> LENGTH: 2125
<212> TYPE: PRT
<213> ORGANISM: Homo sapiens
<220> FEATURE:
<221> NAME/KEY: misc_feature
<223> OTHER INFORMATION: Incyte ID No: 3774181CD1

<400> SEQUENCE: 29

Met Glu Glu Lys Glu Glu Leu Leu Gln Tyr Lys Ser Thr Ile Ala
  1               5                  10                  15

Asn Leu Met Gly Lys Ala Lys Thr Ile Ile Gln Leu Lys Pro Arg
                 20                  25                  30

Asn Ser Asp Cys Pro Leu Lys Thr Ser Ile Pro Ile Lys Ala Ile
                 35                  40                  45

Cys Asp Tyr Arg Gln Ile Glu Ile Thr Ile Tyr Lys Asp Asp Glu
                 50                  55                  60

Cys Val Leu Ala Asn Asn Ser His Arg Ala Lys Trp Lys Val Ile
                 65                  70                  75

Ser Pro Thr Gly Asn Glu Ala Met Val Pro Ser Val Cys Phe Thr
                 80                  85                  90

Val Pro Pro Pro Asn Lys Glu Ala Val Asp Leu Ala Asn Arg Ile
                 95                 100                 105

Glu Gln Gln Tyr Gln Asn Val Leu Thr Leu Trp His Glu Ser His
                110                 115                 120

Ile Asn Met Lys Ser Val Val Ser Trp His Tyr Leu Ile Asn Glu
                125                 130                 135

Ile Asp Arg Ile Arg Ala Ser Asn Val Ala Ser Ile Lys Thr Met
```

-continued

```
                140                 145                 150

Leu Pro Gly Glu His Gln Gln Val Leu Ser Asn Leu Gln Ser Arg
                155                 160                 165

Phe Glu Asp Phe Leu Glu Asp Ser Gln Glu Ser Gln Val Phe Ser
                170                 175                 180

Gly Ser Asp Ile Thr Gln Leu Glu Lys Glu Val Asn Val Cys Lys
                185                 190                 195

Gln Tyr Tyr Gln Glu Leu Leu Lys Ser Ala Glu Arg Glu Glu Gln
                200                 205                 210

Glu Glu Ser Val Tyr Asn Leu Tyr Ile Ser Glu Val Arg Asn Ile
                215                 220                 225

Arg Leu Arg Leu Glu Asn Cys Glu Asp Arg Leu Ile Arg Gln Ile
                230                 235                 240

Arg Thr Pro Leu Glu Arg Asp Asp Leu His Glu Ser Val Phe Arg
                245                 250                 255

Ile Thr Glu Gln Glu Lys Leu Lys Lys Glu Leu Glu Arg Leu Lys
                260                 265                 270

Asp Asp Leu Gly Thr Ile Thr Asn Lys Cys Glu Glu Phe Phe Ser
                275                 280                 285

Gln Ala Ala Ala Ser Ser Ser Val Pro Thr Leu Arg Ser Glu Leu
                290                 295                 300

Asn Val Val Leu Gln Asn Met Asn Gln Val Tyr Ser Met Ser Ser
                305                 310                 315

Thr Tyr Ile Asp Lys Leu Lys Thr Val Asn Leu Val Leu Lys Asn
                320                 325                 330

Thr Gln Ala Ala Glu Ala Leu Val Lys Leu Tyr Glu Thr Lys Leu
                335                 340                 345

Cys Glu Glu Glu Ala Val Ile Ala Asp Lys Asn Asn Ile Glu Asn
                350                 355                 360

Leu Ile Ser Thr Leu Lys Gln Trp Arg Ser Glu Val Asp Glu Lys
                365                 370                 375

Arg Gln Val Phe His Ala Leu Glu Asp Glu Leu Gln Lys Ala Lys
                380                 385                 390

Ala Ile Ser Asp Glu Met Phe Lys Thr Tyr Lys Glu Arg Asp Leu
                395                 400                 405

Asp Phe Asp Trp His Lys Glu Lys Ala Asp Gln Leu Val Glu Arg
                410                 415                 420

Trp Gln Asn Val His Val Gln Ile Asp Asn Arg Leu Arg Asp Leu
                425                 430                 435

Glu Gly Ile Gly Lys Ser Leu Lys Tyr Tyr Arg Asp Thr Tyr His
                440                 445                 450

Pro Leu Asp Asp Trp Ile Gln Gln Val Glu Thr Thr Gln Arg Lys
                455                 460                 465

Ile Gln Glu Asn Gln Pro Glu Asn Ser Lys Thr Leu Ala Thr Gln
                470                 475                 480

Leu Asn Gln Gln Lys Met Leu Val Ser Glu Ile Glu Met Lys Gln
                485                 490                 495

Ser Lys Met Asp Glu Cys Gln Lys Tyr Ala Glu Gln Tyr Ser Ala
                500                 505                 510

Thr Val Lys Asp Tyr Glu Leu Gln Thr Met Thr Tyr Arg Ala Met
                515                 520                 525

Val Asp Ser Gln Gln Lys Ser Pro Val Lys Arg Arg Arg Met Gln
                530                 535                 540
```

-continued

```
Ser Ser Ala Asp Leu Ile Ile Gln Glu Phe Met Asp Leu Arg Thr
                545                 550                 555

Arg Tyr Thr Ala Leu Val Thr Leu Met Thr Gln Tyr Ile Lys Phe
                560                 565                 570

Ala Gly Asp Ser Leu Lys Arg Leu Glu Glu Glu Glu Ile Lys Arg
                575                 580                 585

Cys Lys Glu Thr Ser Glu His Gly Ala Tyr Ser Asp Leu Leu Gln
                590                 595                 600

Arg Gln Lys Ala Thr Val Leu Glu Asn Ser Lys Leu Thr Gly Lys
                605                 610                 615

Ile Ser Glu Leu Glu Arg Met Val Ala Glu Leu Lys Lys Gln Lys
                620                 625                 630

Ser Arg Val Glu Glu Glu Leu Pro Lys Val Arg Glu Ala Ala Glu
                635                 640                 645

Asn Glu Leu Arg Lys Gln Gln Arg Asn Val Glu Asp Ile Ser Leu
                650                 655                 660

Gln Lys Ile Arg Ala Glu Ser Glu Ala Lys Gln Tyr Arg Arg Glu
                665                 670                 675

Leu Glu Thr Ile Val Arg Glu Lys Glu Ala Ala Glu Arg Glu Leu
                680                 685                 690

Glu Arg Val Arg Gln Leu Thr Ile Glu Ala Glu Ala Lys Arg Ala
                695                 700                 705

Ala Val Glu Glu Asn Leu Leu Asn Phe Arg Asn Gln Leu Glu Glu
                710                 715                 720

Asn Thr Phe Thr Arg Arg Thr Leu Glu Asp His Leu Lys Arg Lys
                725                 730                 735

Asp Leu Ser Leu Asn Asp Leu Glu Gln Gln Lys Asn Lys Leu Met
                740                 745                 750

Glu Glu Leu Arg Arg Lys Arg Asp Asn Glu Glu Glu Leu Leu Lys
                755                 760                 765

Leu Ile Lys Gln Met Glu Lys Asp Leu Ala Phe Gln Lys Gln Val
                770                 775                 780

Ala Glu Lys Gln Leu Lys Glu Lys Gln Lys Ile Glu Leu Glu Ala
                785                 790                 795

Arg Arg Lys Ile Thr Glu Ile Gln Tyr Thr Cys Arg Glu Asn Ala
                800                 805                 810

Leu Pro Val Cys Pro Ile Thr Gln Ala Thr Ser Cys Arg Ala Val
                815                 820                 825

Thr Gly Leu Gln Gln Glu His Asp Lys Gln Lys Ala Glu Glu Leu
                830                 835                 840

Lys Gln Gln Val Asp Glu Leu Thr Ala Ala Asn Arg Lys Ala Glu
                845                 850                 855

Gln Asp Met Arg Glu Leu Thr Tyr Glu Leu Asn Ala Leu Gln Leu
                860                 865                 870

Glu Lys Thr Ser Ser Glu Glu Lys Ala Arg Leu Leu Lys Asp Lys
                875                 880                 885

Leu Asp Glu Thr Asn Asn Thr Leu Arg Cys Leu Lys Leu Glu Leu
                890                 895                 900

Glu Arg Lys Asp Gln Ala Glu Lys Gly Tyr Ser Gln Gln Leu Arg
                905                 910                 915

Glu Leu Gly Arg Gln Leu Asn Gln Thr Thr Gly Lys Ala Glu Glu
                920                 925                 930
```

-continued

```
Ala Met Gln Glu Ala Ser Asp Leu Lys Lys Ile Lys Arg Asn Tyr
                935                 940                 945

Gln Leu Glu Leu Glu Ser Leu Asn His Glu Lys Gly Lys Leu Gln
                950                 955                 960

Arg Glu Val Asp Arg Ile Thr Arg Ala His Ala Val Ala Glu Lys
                965                 970                 975

Asn Ile Gln His Leu Asn Ser Gln Ile His Ser Phe Arg Asp Glu
                980                 985                 990

Lys Glu Leu Glu Arg Leu Gln Ile Cys Gln Arg Lys Ser Asp His
                995                 1000                1005

Leu Lys Glu Gln Phe Glu Lys Ser His Glu Gln Leu Leu Gln Asn
                1010                1015                1020

Ile Lys Ala Glu Lys Glu Asn Asn Asp Lys Ile Gln Arg Leu Asn
                1025                1030                1035

Glu Glu Leu Glu Lys Ser Asn Glu Cys Ala Glu Met Leu Lys Gln
                1040                1045                1050

Lys Val Glu Glu Leu Thr Arg Gln Asn Asn Glu Thr Lys Leu Met
                1055                1060                1065

Met Gln Arg Ile Gln Ala Glu Ser Glu Asn Ile Val Leu Glu Lys
                1070                1075                1080

Gln Thr Ile Gln Gln Arg Cys Glu Ala Leu Lys Ile Gln Ala Asp
                1085                1090                1095

Gly Phe Lys Asp Gln Leu Arg Ser Thr Asn Glu His Leu His Lys
                1100                1105                1110

Gln Thr Lys Thr Glu Gln Asp Phe Gln Arg Lys Ile Lys Cys Leu
                1115                1120                1125

Glu Glu Asp Leu Ala Lys Ser Gln Asn Leu Val Ser Glu Phe Lys
                1130                1135                1140

Gln Lys Cys Asp Gln Gln Asn Ile Ile Ile Gln Asn Thr Lys Lys
                1145                1150                1155

Glu Val Arg Asn Leu Asn Ala Glu Leu Asn Ala Ser Lys Glu Glu
                1160                1165                1170

Lys Arg Arg Gly Glu Gln Lys Val Gln Leu Gln Gln Ala Gln Val
                1175                1180                1185

Gln Glu Leu Asn Asn Arg Leu Lys Lys Val Gln Asp Glu Leu His
                1190                1195                1200

Leu Lys Thr Ile Glu Glu Gln Met Thr His Arg Lys Met Val Leu
                1205                1210                1215

Phe Gln Glu Glu Ser Gly Lys Phe Lys Gln Ser Ala Glu Glu Phe
                1220                1225                1230

Arg Lys Lys Met Glu Lys Leu Met Glu Ser Lys Val Ile Thr Glu
                1235                1240                1245

Asn Asp Ile Ser Gly Ile Arg Leu Asp Phe Val Ser Leu Gln Gln
                1250                1255                1260

Glu Asn Ser Arg Ala Gln Glu Asn Ala Lys Leu Cys Glu Thr Asn
                1265                1270                1275

Ile Lys Glu Leu Glu Arg Gln Leu Gln Gln Tyr Arg Glu Gln Met
                1280                1285                1290

Gln Gln Gly Gln His Met Glu Ala Asn His Tyr Gln Lys Cys Gln
                1295                1300                1305

Lys Leu Glu Asp Glu Leu Ile Ala Gln Lys Arg Glu Val Glu Asn
                1310                1315                1320

Leu Lys Gln Lys Met Asp Gln Gln Ile Lys Glu His Glu His Gln
```

-continued

```
            1325                1330                1335

Leu Val Leu Leu Gln Cys Glu Ile Gln Lys Lys Ser Thr Ala Lys
            1340                1345                1350

Asp Cys Thr Phe Lys Pro Asp Phe Glu Met Thr Val Lys Glu Cys
            1355                1360                1365

Gln His Ser Gly Glu Leu Ser Ser Arg Asn Thr Gly His Leu His
            1370                1375                1380

Pro Thr Pro Arg Ser Pro Leu Leu Arg Trp Thr Gln Glu Pro Gln
            1385                1390                1395

Pro Leu Glu Glu Lys Trp Gln His Arg Val Val Glu Gln Ile Pro
            1400                1405                1410

Lys Glu Val Gln Phe Gln Pro Pro Gly Ala Pro Leu Glu Lys Glu
            1415                1420                1425

Lys Ser Gln Gln Cys Tyr Ser Glu Tyr Phe Ser Gln Thr Ser Thr
            1430                1435                1440

Glu Leu Gln Ile Thr Phe Asp Glu Thr Asn Pro Ile Thr Arg Leu
            1445                1450                1455

Ser Glu Ile Glu Lys Ile Arg Asp Gln Ala Leu Asn Asn Ser Arg
            1460                1465                1470

Pro Pro Val Arg Tyr Gln Asp Asn Ala Cys Glu Met Glu Leu Val
            1475                1480                1485

Lys Val Leu Thr Pro Leu Glu Ile Ala Lys Asn Lys Gln Tyr Asp
            1490                1495                1500

Met His Thr Glu Val Thr Thr Leu Lys Gln Glu Lys Asn Pro Val
            1505                1510                1515

Pro Ser Ala Glu Glu Trp Met Leu Glu Gly Cys Arg Ala Ser Gly
            1520                1525                1530

Gly Leu Lys Lys Gly Asp Phe Leu Lys Lys Gly Leu Glu Pro Glu
            1535                1540                1545

Thr Phe Gln Asn Phe Asp Gly Asp His Ala Cys Ser Val Arg Asp
            1550                1555                1560

Asp Glu Phe Lys Phe Gln Gly Leu Arg His Thr Val Thr Ala Arg
            1565                1570                1575

Gln Leu Val Glu Ala Lys Leu Leu Asp Met Arg Thr Ile Glu Gln
            1580                1585                1590

Leu Arg Leu Gly Leu Lys Thr Val Glu Glu Val Gln Lys Thr Leu
            1595                1600                1605

Asn Lys Phe Leu Thr Lys Ala Thr Ser Ile Ala Gly Leu Tyr Leu
            1610                1615                1620

Glu Ser Thr Lys Glu Lys Ile Ser Phe Ala Ser Ala Ala Glu Arg
            1625                1630                1635

Ile Ile Ile Asp Lys Met Val Ala Leu Ala Phe Leu Glu Ala Gln
            1640                1645                1650

Ala Ala Thr Gly Phe Ile Ile Asp Pro Ile Ser Gly Gln Thr Tyr
            1655                1660                1665

Ser Val Glu Asp Ala Val Leu Lys Gly Val Val Asp Pro Glu Phe
            1670                1675                1680

Arg Ile Arg Leu Leu Glu Ala Glu Lys Ala Ala Val Gly Tyr Ser
            1685                1690                1695

Tyr Ser Ser Lys Thr Leu Ser Val Phe Gln Ala Met Glu Asn Arg
            1700                1705                1710

Met Leu Asp Arg Gln Lys Gly Lys His Ile Leu Glu Ala Gln Ile
            1715                1720                1725
```

-continued

```
Ala Ser Gly Gly Val Ile Asp Pro Val Arg Gly Ile Arg Val Pro
            1730                1735                1740

Pro Glu Ile Ala Leu Gln Gln Gly Leu Leu Asn Asn Ala Ile Leu
            1745                1750                1755

Gln Phe Leu His Glu Pro Ser Ser Asn Thr Arg Val Phe Pro Asn
            1760                1765                1770

Pro Asn Asn Lys Gln Ala Leu Tyr Tyr Ser Glu Leu Leu Arg Met
            1775                1780                1785

Cys Val Phe Asp Val Glu Ser Gln Cys Phe Leu Phe Pro Phe Gly
            1790                1795                1800

Glu Arg Asn Ile Ser Asn Leu Asn Val Lys Lys Thr His Arg Ile
            1805                1810                1815

Ser Val Val Asp Thr Lys Thr Gly Ser Glu Leu Thr Val Tyr Glu
            1820                1825                1830

Ala Phe Gln Arg Asn Leu Ile Glu Lys Ser Ile Tyr Leu Glu Leu
            1835                1840                1845

Ser Gly Gln Gln Tyr Gln Trp Lys Glu Ala Met Phe Phe Glu Ser
            1850                1855                1860

Tyr Gly His Ser Ser His Met Leu Thr Asp Thr Lys Thr Gly Leu
            1865                1870                1875

His Phe Asn Ile Asn Glu Ala Ile Glu Gln Gly Thr Ile Asp Lys
            1880                1885                1890

Ala Leu Val Lys Lys Tyr Gln Glu Gly Leu Ile Thr Leu Thr Glu
            1895                1900                1905

Leu Ala Asp Ser Leu Leu Ser Arg Leu Val Pro Lys Lys Asp Leu
            1910                1915                1920

His Ser Pro Val Ala Gly Tyr Trp Leu Thr Ala Ser Gly Glu Arg
            1925                1930                1935

Ile Ser Val Leu Lys Ala Ser Arg Arg Asn Leu Val Asp Arg Ile
            1940                1945                1950

Thr Ala Leu Arg Cys Leu Glu Ala Gln Val Ser Thr Gly Gly Ile
            1955                1960                1965

Ile Asp Pro Leu Thr Gly Lys Lys Tyr Arg Val Ala Glu Ala Leu
            1970                1975                1980

His Arg Gly Leu Val Asp Glu Gly Phe Ala Gln Gln Leu Arg Gln
            1985                1990                1995

Cys Glu Leu Val Ile Thr Gly Ile Gly His Pro Ile Thr Asn Lys
            2000                2005                2010

Met Met Ser Val Val Glu Ala Val Asn Ala Asn Ile Ile Asn Lys
            2015                2020                2025

Glu Met Gly Ile Arg Cys Leu Glu Phe Gln Tyr Leu Thr Gly Gly
            2030                2035                2040

Leu Ile Glu Pro Gln Val His Ser Arg Leu Ser Ile Glu Glu Ala
            2045                2050                2055

Leu Gln Val Gly Ile Ile Asp Val Leu Ile Ala Thr Lys Leu Lys
            2060                2065                2070

Asp Gln Lys Ser Tyr Val Arg Asn Ile Ile Cys Pro Gln Thr Lys
            2075                2080                2085

Arg Lys Leu Thr Tyr Lys Glu Ala Leu Glu Lys Ala Asp Phe Asp
            2090                2095                2100

Phe His Thr Gly Leu Lys Leu Leu Glu Val Ser Glu Pro Leu Met
            2105                2110                2115
```

-continued

```
Thr Gly Ile Ser Ser Leu Tyr Tyr Ser Ser
               2120                2125


<210> SEQ ID NO 30
<211> LENGTH: 1708
<212> TYPE: DNA
<213> ORGANISM: Homo sapiens
<220> FEATURE:
<221> NAME/KEY: misc_feature
<223> OTHER INFORMATION: Incyte ID No: 1709387CB1

<400> SEQUENCE: 30

cctgccagca tctcttgggt ttgctgagaa ctcacgggct ccagctacct ggccatgacc     60

accacatttc tgcaaacttc ttcctccacc tttgggggtg gctcaacccg agggggttcc    120

ctcctggctg gggaggtgg ctttggtggg gggagtctct ctgggggagg tggaagccga    180

agtatctcag cttcttctgc taggtttgtc tcttcagggt caggaggagg atatgggggt    240

ggcatgaggg tctgtggctt tggtggaggg gctggtagtg ttttcggtgg aggctttgga    300

gggggcgttg gtgggggttt tggtggtggc tttggtggtg gcgatggtgg tctcctctct    360

ggcaatgaga aaattaccat gcagaacctc aatgaccgcc tggcctccta cctggacaag    420

gtacgtgccc tggaggaggc caatgctgac ctggaggtga agatccatga ctggtaccag    480

aagcagaccc cagccagccc agaatgcgac tacagccaat acttcaagac cattgaagag    540

ctccgggaca agatcatggc caccaccatc gacaactccc gggtcatcct ggagatcgac    600

aatgccaggc tggctgcgga cgacttcagg ctcaagtatg agaatgagct ggccctgcgc    660

cagggcgttg aggctgacat caacggcttg cgccgagtcc tggatgagct gaccctggcc    720

aggactgacc tggagatgca gatcgagggc ctgaatgagg agctagccta cctgaagaag    780

aaccacgaag aggagatgaa ggagttcagc agccagctgg ccggccaggt caatgtggag    840

atggacgcag caccgggtgt ggacctgacc cgtgtgctgg cagagatgag ggagcagtac    900

gaggccatgg cggagaagaa ccgccgggat gtcgaggcct ggttcttcag caagactgag    960

gagctgaaca aagaggtggc ctccaacaca gaaatgatcc agaccagcaa gacggagatc   1020

acagacctga gacgcacgat gcaggagctg gagatcgagc tgcagtccca gctcagcatg   1080

aaagctgggc tggagaactc actggccgag acagagtgcc gctatgccac gcagctgcag   1140

cagatccagg ggctcattgg tggcctggag gcccagctga gtgagctccg atgcgagatg   1200

gaggctcaga accaggagta caagatgctg cttgacataa agacacggct ggagcaggag   1260

atcgctactt accgcagcct gctcgagggc caggatgcca agatggctgg cattggcatc   1320

agggaagcct cttcaggagg tggtggtagc agcagcaatt tccacatcaa tgtagaagag   1380

tcagtggatg gacaggtggt ttcttcccac aagagagaaa tctaagtgtc tattgcagga   1440

gaaacgtccc ttgccactcc ccactctcat caggccaagt ggaggactgg ccagagggcc   1500

tgcacatgca aactccagtc cctgccttca gagagctgaa aagggtccct cggtctttta   1560

tttcagggct ttgcatgcgc tctattcccc ctctgcctct ccccaccttc tttggagcaa   1620

ggagatgcag ctgtattgtg taacaagctc atttgtacag tgtctgttca tgtaataaag   1680

aattactttt ccttttgcaa aaaaaaaa                                       1708


<210> SEQ ID NO 31
<211> LENGTH: 456
<212> TYPE: PRT
<213> ORGANISM: Homo sapiens
<220> FEATURE:
<221> NAME/KEY: misc_feature
```

-continued

<223> OTHER INFORMATION: Incyte ID No: 1709387CD1

<400> SEQUENCE: 31

```
Met Thr Thr Thr Phe Leu Gln Thr Ser Ser Ser Thr Phe Gly Gly
  1               5                  10                  15

Gly Ser Thr Arg Gly Gly Ser Leu Leu Ala Gly Gly Gly Gly Phe
                 20                  25                  30

Gly Gly Gly Ser Leu Ser Gly Gly Gly Gly Ser Arg Ser Ile Ser
                 35                  40                  45

Ala Ser Ser Ala Arg Phe Val Ser Ser Gly Ser Gly Gly Gly Tyr
                 50                  55                  60

Gly Gly Gly Met Arg Val Cys Gly Phe Gly Gly Gly Ala Gly Ser
                 65                  70                  75

Val Phe Gly Gly Gly Phe Gly Gly Gly Val Gly Gly Gly Phe Gly
                 80                  85                  90

Gly Gly Phe Gly Gly Gly Asp Gly Gly Leu Leu Ser Gly Asn Glu
                 95                 100                 105

Lys Ile Thr Met Gln Asn Leu Asn Asp Arg Leu Ala Ser Tyr Leu
                110                 115                 120

Asp Lys Val Arg Ala Leu Glu Glu Ala Asn Ala Asp Leu Glu Val
                125                 130                 135

Lys Ile His Asp Trp Tyr Gln Lys Gln Thr Pro Ala Ser Pro Glu
                140                 145                 150

Cys Asp Tyr Ser Gln Tyr Phe Lys Thr Ile Glu Glu Leu Arg Asp
                155                 160                 165

Lys Ile Met Ala Thr Thr Ile Asp Asn Ser Arg Val Ile Leu Glu
                170                 175                 180

Ile Asp Asn Ala Arg Leu Ala Ala Asp Asp Phe Arg Leu Lys Tyr
                185                 190                 195

Glu Asn Glu Leu Ala Leu Arg Gln Gly Val Glu Ala Asp Ile Asn
                200                 205                 210

Gly Leu Arg Arg Val Leu Asp Glu Leu Thr Leu Ala Arg Thr Asp
                215                 220                 225

Leu Glu Met Gln Ile Glu Gly Leu Asn Glu Glu Leu Ala Tyr Leu
                230                 235                 240

Lys Lys Asn His Glu Glu Glu Met Lys Glu Phe Ser Ser Gln Leu
                245                 250                 255

Ala Gly Gln Val Asn Val Glu Met Asp Ala Ala Pro Gly Val Asp
                260                 265                 270

Leu Thr Arg Val Leu Ala Glu Met Arg Glu Gln Tyr Glu Ala Met
                275                 280                 285

Ala Glu Lys Asn Arg Arg Asp Val Glu Ala Trp Phe Phe Ser Lys
                290                 295                 300

Thr Glu Glu Leu Asn Lys Glu Val Ala Ser Asn Thr Glu Met Ile
                305                 310                 315

Gln Thr Ser Lys Thr Glu Ile Thr Asp Leu Arg Arg Thr Met Gln
                320                 325                 330

Glu Leu Glu Ile Glu Leu Gln Ser Gln Leu Ser Met Lys Ala Gly
                335                 340                 345

Leu Glu Asn Ser Leu Ala Glu Thr Glu Cys Arg Tyr Ala Thr Gln
                350                 355                 360

Leu Gln Gln Ile Gln Gly Leu Ile Gly Gly Leu Glu Ala Gln Leu
                365                 370                 375
```

-continued

```
Ser Glu Leu Arg Cys Glu Met Glu Ala Gln Asn Gln Glu Tyr Lys
                380                 385                 390

Met Leu Leu Asp Ile Lys Thr Arg Leu Glu Gln Glu Ile Ala Thr
                395                 400                 405

Tyr Arg Ser Leu Leu Glu Gly Gln Asp Ala Lys Met Ala Gly Ile
                410                 415                 420

Gly Ile Arg Glu Ala Ser Ser Gly Gly Gly Gly Ser Ser Ser Asn
                425                 430                 435

Phe His Ile Asn Val Glu Glu Ser Val Asp Gly Gln Val Val Ser
                440                 445                 450

Ser His Lys Arg Glu Ile
                455


<210> SEQ ID NO 32
<211> LENGTH: 1393
<212> TYPE: DNA
<213> ORGANISM: Homo sapiens
<220> FEATURE:
<221> NAME/KEY: misc_feature
<223> OTHER INFORMATION: Incyte ID No: 1709118CB1

<400> SEQUENCE: 32

ggacagggct ggagatcgag ttcccagttc gtgaaaagga aaaccccctg aagctgtgcc     60

aagatgtgtg acgacgagga gaccaccgcc ctggtgtgcg acaacggctc tgggctggtg    120

aaggccggct ttgcgggcga tgacgcgccc cgcgctgtct tcccgtccat cgtgggccgc    180

ccgcggcacc agggagttat ggtgggtatg ggtcagaagg actcctacgt aggtgatgaa    240

gcccagagca agagaggcat cctgaccctg aagtatccca tcgagcatgg tatcatcacc    300

aactgggacg acatggagaa gatctggcac cacaccttct acaatgagct ccgtgtggct    360

cccgaggagc accccaccct gctcacagag gccccgctga accccaaggc caaccgggag    420

aagatgactc agatcatgtt tgagaccttc aatgtccctg ccatgtacgt ggccatccag    480

gcagtgctat ccctgtatgc ttctggccgt accacaggca ttgttctgga ctctggggat    540

ggtgtaactc acaatgtccc catctatgag ggctacgctt tgccccatgc catcatgcgt    600

ctggttctgg ctggtcggga cctcactgac tacctcatga agatcctcac tgagcgtggc    660

tactcctttg tcaccactgc tgaacgtgaa attgtccgtg acattaaaga gaagctgtgc    720

tatgtcgccc tggattttga gaatgagatg gccacagctg cctcttcctc ctccctggag    780

aagagctatg aactgcctga tggccaagtc atcactattg gcaatgagcg cttccgctgt    840

cctgagacac tcttccagcc ctccttcatt ggtatggaat ctgctggcat ccatgaaaca    900

acttacaata gcatcatgaa gtgtgacatt gatatccgca aggacctgta tgccaacaat    960

gtcttatctg gaggcaccac tatgtaccct ggtattgctg atcgtatgca gaaggaaatc   1020

actgctctgg ctcctagcac catgaagatt aagattattg ctcccccctga gcgtaaatac   1080

tctgtctgga ttgggggctc catcctggcc tctctgtcca ccttccagca aatgtggatt   1140

agcaagcaag agtacgatga ggcaggccca tccattgtcc accgcaaatg cttctaagat   1200

gccttctctc tccatctacc ttccagtcag gatgacggta ttatgcttct tggagtcttc   1260

caaaccacct tccctcatct ttcatcaatc attgtacagt ttgtttacac acgtgcaatt   1320

tgtttgtgct tctaatattt attgctttat aaataaacca gaccaggact tgcaacctaa   1380

aaaaaaaaaa aaa                                                      1393


<210> SEQ ID NO 33
```

<211> LENGTH: 377
<212> TYPE: PRT
<213> ORGANISM: Homo sapiens
<220> FEATURE:
<221> NAME/KEY: misc_feature
<223> OTHER INFORMATION: Incyte ID No: 1709118CD1

<400> SEQUENCE: 33

```
Met Cys Asp Asp Glu Glu Thr Thr Ala Leu Val Cys Asp Asn Gly
  1               5                  10                  15

Ser Gly Leu Val Lys Ala Gly Phe Ala Gly Asp Asp Ala Pro Arg
                 20                  25                  30

Ala Val Phe Pro Ser Ile Val Gly Arg Pro Arg His Gln Gly Val
                 35                  40                  45

Met Val Gly Met Gly Gln Lys Asp Ser Tyr Val Gly Asp Glu Ala
                 50                  55                  60

Gln Ser Lys Arg Gly Ile Leu Thr Leu Lys Tyr Pro Ile Glu His
                 65                  70                  75

Gly Ile Ile Thr Asn Trp Asp Asp Met Glu Lys Ile Trp His His
                 80                  85                  90

Thr Phe Tyr Asn Glu Leu Arg Val Ala Pro Glu Glu His Pro Thr
                 95                 100                 105

Leu Leu Thr Glu Ala Pro Leu Asn Pro Lys Ala Asn Arg Glu Lys
                110                 115                 120

Met Thr Gln Ile Met Phe Glu Thr Phe Asn Val Pro Ala Met Tyr
                125                 130                 135

Val Ala Ile Gln Ala Val Leu Ser Leu Tyr Ala Ser Gly Arg Thr
                140                 145                 150

Thr Gly Ile Val Leu Asp Ser Gly Asp Gly Val Thr His Asn Val
                155                 160                 165

Pro Ile Tyr Glu Gly Tyr Ala Leu Pro His Ala Ile Met Arg Leu
                170                 175                 180

Val Leu Ala Gly Arg Asp Leu Thr Asp Tyr Leu Met Lys Ile Leu
                185                 190                 195

Thr Glu Arg Gly Tyr Ser Phe Val Thr Thr Ala Glu Arg Glu Ile
                200                 205                 210

Val Arg Asp Ile Lys Glu Lys Leu Cys Tyr Val Ala Leu Asp Phe
                215                 220                 225

Glu Asn Glu Met Ala Thr Ala Ala Ser Ser Ser Ser Leu Glu Lys
                230                 235                 240

Ser Tyr Glu Leu Pro Asp Gly Gln Val Ile Thr Ile Gly Asn Glu
                245                 250                 255

Arg Phe Arg Cys Pro Glu Thr Leu Phe Gln Pro Ser Phe Ile Gly
                260                 265                 270

Met Glu Ser Ala Gly Ile His Glu Thr Thr Tyr Asn Ser Ile Met
                275                 280                 285

Lys Cys Asp Ile Asp Ile Arg Lys Asp Leu Tyr Ala Asn Asn Val
                290                 295                 300

Leu Ser Gly Gly Thr Thr Met Tyr Pro Gly Ile Ala Asp Arg Met
                305                 310                 315

Gln Lys Glu Ile Thr Ala Leu Ala Pro Ser Thr Met Lys Ile Lys
                320                 325                 330

Ile Ile Ala Pro Pro Glu Arg Lys Tyr Ser Val Trp Ile Gly Gly
                335                 340                 345

Ser Ile Leu Ala Ser Leu Ser Thr Phe Gln Gln Met Trp Ile Ser
```

-continued

```
                350                 355                 360

Lys Gln Glu Tyr Asp Glu Ala Gly Pro Ser Ile Val His Arg Lys
                365                 370                 375

Cys Phe


<210> SEQ ID NO 34
<211> LENGTH: 2310
<212> TYPE: DNA
<213> ORGANISM: Homo sapiens
<220> FEATURE:
<221> NAME/KEY: misc_feature
<223> OTHER INFORMATION: Incyte ID No: 008513.49
<221> NAME/KEY: unsure
<222> LOCATION: 2307
<223> OTHER INFORMATION: a, t, c, g, or other

<400> SEQUENCE: 34

cttccctctc tcctccagcc tctcacactc tcctcagctc tctcatctcc tggaaccatg     60

gccagcacat ccaccaccat caggagccac agcagcagcc gccggggttt cagtgccaac    120

ttcagccagg ctccctgggg tcagccgctc tggcttcagc agcgtctccg tgtcccgctc    180

caggggcagt ggtggcctgg gtggtgcatg tggaggagct ggctttggca gccgcagtct    240

gtatggcctg gggggctcca agaggatctc cattggaggg ggcagctgtg ccatcagtgg    300

cggctatggc agcagagccg gaggcagcta tggctttggt ggcgccggga gtggatttgg    360

tttcggtggt ggagccggca ttggctttgg tctgggtggt ggagccggcc ttgctggtgg    420

ctttgggggc cctggcttcc ctgtgtgccc ccctggaggc atccaagagg tcaccgtcaa    480

ccagagtctc ctgactcccc tcaacctgca aatcgatccc accatccagc gggtgcgggc    540

cgaggagcgt gagcagatca agaccctcaa caacaagttt gcctccttca tcgacaaggt    600

gcggttcctg gagcagcaga acaaggttct ggaaacaaag tggaccctgc tgcaggagca    660

gggcaccaag actgtgaggc agaacctgga gccgttgttc gagcagtaca tcaacaacct    720

caggaggcag ctggacagca ttgtcgggga acggggccgc ctggactcag agctcagagg    780

catgcaggac ctggtggagg acttcaagaa caaatatgag gatgaaatca acaagcgcac    840

agcagcagag aatgaatttg tgactctgaa gaaggatgtg gatgctgcct acatgaacaa    900

ggttgaactg caagccaagg cagacactct cacagacgag atcaacttcc tgagagcctt    960

gtatgatgca gagctgtccc agatgcagac ccacatctca gacacatctg tggtgctgtc   1020

catggacaac aaccgcaacc tggacctgga cagcatcatc gctgaggtca aggcccaata   1080

tgaggagatt gctcagagaa gccgggctga ggctgagtcc tggtaccaga ccaagtacga   1140

ggagctgcag gtcacagcag gcagacatgg ggacgacctg cgcaacacca agcaggagat   1200

tgctgagatc aaccgcatga tccagaggct gagatctgag atcgaccacg tcaagaagca   1260

gtgcgccaac ctgcaggccg ccattgctga tgctgagcag cgtggggaga tggccctcaa   1320

ggatgccaag aacaagctgg aagggctgga ggatgccctg cagaaggcca agcaggacct   1380

ggcccggctg ctgaaggagt accaggagct gatgaatgtc aagctggccc tggacgtgga   1440

gatcgccacc taccgcaagc tgctggaggg tgaggagtgc aggctgaatg gcgaaggcgt   1500

tggacaagtc aacatctctg tggtgcagtc caccgtctcc agtggctatg gcggtgccag   1560

tggtgtcggc agtggcttag gcctgggtgg aggaagcagc tactcctatg gcagtggtct   1620

tggcgttgga ggtggcttca gttccagcag tggcagagcc attgggggtg gcctcagctc   1680

tgttggaggc ggcagttcca ccatcaagta caccaccacc tcctcctcca gcaggaagag   1740
```

-continued

```
ctataagcac taaagtgcgt ctgctagctc tcggtcccac agtcctcagg cccctctctg   1800

gctgcagagc cctctcctca ggttgccttt cctctcctgg cctccagtct cccctgctgt   1860

cccaggtaga gctgggtatg gatgcttagt gccctcactt cttctctctc tctctatacc   1920

atctgagcac ccattgctca ccatcagatc aacctctgat tttacatcat gatgtaatca   1980

ccactggagc ttcactgtta ctaaattatt aatttcttgc ctccagtgtt ctatctctga   2040

ggctgagcat tataagaaaa tgacctctgc tccttttcat tgcagaaaat tgccaggggc   2100

ttatttcaga acaacttcca cttactttcc actggctctc aaactctcta acttataagt   2160

gttgtgaacc cccacccagg cagtatccat gaaagcacaa gtgactagtc ctatgatgta   2220

caaagcctgt atctctgtga tgatttctgt gctcttcgct gtttgcaatt gctaaataaa   2280

gcagatttat aatacaaaaa aaaaaanggg                                    2310
```

<210> SEQ ID NO 35
<211> LENGTH: 493
<212> TYPE: DNA
<213> ORGANISM: Homo sapiens
<220> FEATURE:
<221> NAME/KEY: misc_feature
<223> OTHER INFORMATION: Incyte ID No: 047568.1

<400> SEQUENCE: 35

```
cttaacctta attttataag agacaaatac atgttataat aatacttaag ctctttatag     60

aatttgtagg gctattgaga gacattatag ggaagccctt gttctggaag gtgtatggtt    120

gtggccatgg gtttctctgc cactaaatct gtacctggtt gttatttgaa gttttctgtc    180

ctaaaatgta atctttggag aagctgcaca accgccatct gggaactcat gagaaattta    240

cgttttatgc ctaagtaact ctaatgagca atggctatag gaatgactaa taaaatatca    300

acaaggagat gggaattttc aaggaaatat gatatggtaa caatgtcctt tttagaaagt    360

catttttact tatctatatt cacagcataa aatgttccaa aatctatgaa atattaaata    420

ttatacttca aaataaagta atattttgga gataaaagag tactgttcta caattcaaaa    480

ttgaaatagt tca                                                       493
```

<210> SEQ ID NO 36
<211> LENGTH: 1983
<212> TYPE: DNA
<213> ORGANISM: Homo sapiens
<220> FEATURE:
<221> NAME/KEY: misc_feature
<223> OTHER INFORMATION: Incyte ID No: 3120070CB1

<400> SEQUENCE: 36

```
ggaaccgcct ccccgcggcc tcttcgcttt tgtggcggcg cccgcgctcg caggccactc     60

tctgctgtcg cccgtcccgc gcgctcctcc gacccgctcc gctccgctcc gctcggcccc    120

gcgccgcccg tcaacatgat ccgctgcggc ctggcctgcg agcgctgccg ctggatcctg    180

cccctgctcc tactcagcgc catcgccttc gacatcatcg cgctggccgg ccgcggctgg    240

ttgcagtcta gcgaccacgg ccagacgtcc tcgctgtggt ggaaatgctc ccaagagggc    300

ggcggcagcg ggtcctacga ggagggctgt cagagcctca tggagtacgc gtggggtaga    360

gcagcggctg ccatgctctt ctgtggcttc atcatcctgg tgatctgttt catcctctcc    420

ttcttcgccc tctgtggacc ccagatgctt gtcttcctga gagtgattgg aggtctcctt    480

gccttggctg ctgtgttcca gatcatctcc ctggtaattt accccgtgaa gtacacccag    540

accttcaccc ttcatgccaa ccctgctgtc acttacatct ataactgggc ctacggcttt    600
```

```
gggtgggcag ccacgattat cctgattggc tgtgccttct tcttctgctg cctccccaac    660
tacgaagatg accttctggg caatgccaag cccaggtact tctacacatc tgcctaactt    720
gggaatgaat gtgggagaaa atcgctgctg ctgagatgga ctccagaaga agaaactgtt    780
tctccaggcg actttgaacc catttttttgg cagtgttcat attattaaac tagtcaaaaa    840
tgctaaaata atttgggaga aaatattttt taagtagtgt tatagtttca tgtttatctt    900
ttattatgtt ttgtgaagtt gtgtcttttc actaattacc tatactatgc caatatttcc    960
ttatatctat ccataacatt tatactacat ttgtaagaga atatgcacgt gaaacttaac   1020
actttataag gtaaaaatga ggtttccaag atttaataat ctgatcaagt tcttgttatt   1080
tccaaataga atggactcgg tctgttaagg gctaaggaga agaggaagat aaggttaaaa   1140
gttgttaatg accaaacatt ctaaaagaaa tgcaaaaaaa aagtttattt tcaagccttc   1200
gaactattta aggaaagcaa aatcatttcc taaatgcata tcatttgtga gaatttctca   1260
ttaatatcct gaatcattca tttcagctaa ggcttcatgt tgactcgata tgtcatctag   1320
gaaagtacta tttcatggtc caaacctgtt gccatagttg gtaaggcttt cctttaagtg   1380
tgaaatattt agatgaaatt ttctctttta aagttcttta tagggttagg gtgtgggaaa   1440
atgctatatt aataaatctg tagtgttttg tgtttatatg ttcagaacca gagtagactg   1500
gattgaaaga tggactgggt ctaatttatc atgactgata gatctggtta agttgtgtag   1560
taaagcatta gggtcattcc tgtcacaaaa gtgccactaa aacagcctca ggagaataaa   1620
tgacttgctt ttctaaatct caggtttatc tgggctctat catatagaca ggcttctgat   1680
agtttgcaac tgtaagcaga aacctacata tagttaaaat cctggtcttt cttggtaaac   1740
agattttaaa tgtctgatat aaaacatgcc acaggagaat tcggggattt gagtttctct   1800
gaatagcata tatatgatgc atcggatagg tcattatgat tttttaccat ttcgacttac   1860
ataatgaaaa ccaattcatt ttaaatatca gattattatt ttgtaagttg tggaaaaagc   1920
taattgtagt tttcattatg aagttttccc aataaaccag gtattctaaa cttgaaaaaa   1980
aaa                                                                  1983
```

```
<210> SEQ ID NO 37
<211> LENGTH: 193
<212> TYPE: PRT
<213> ORGANISM: Homo sapiens
<220> FEATURE:
<221> NAME/KEY: misc_feature
<223> OTHER INFORMATION: Incyte ID No: 3120070CD1

<400> SEQUENCE: 37

Met Ile Arg Cys Gly Leu Ala Cys Glu Arg Cys Arg Trp Ile Leu
  1               5                  10                  15

Pro Leu Leu Leu Leu Ser Ala Ile Ala Phe Asp Ile Ile Ala Leu
                 20                  25                  30

Ala Gly Arg Gly Trp Leu Gln Ser Ser Asp His Gly Gln Thr Ser
                 35                  40                  45

Ser Leu Trp Trp Lys Cys Ser Gln Glu Gly Gly Gly Ser Gly Ser
                 50                  55                  60

Tyr Glu Glu Gly Cys Gln Ser Leu Met Glu Tyr Ala Trp Gly Arg
                 65                  70                  75

Ala Ala Ala Ala Met Leu Phe Cys Gly Phe Ile Ile Leu Val Ile
                 80                  85                  90

Cys Phe Ile Leu Ser Phe Phe Ala Leu Cys Gly Pro Gln Met Leu
```

-continued

```
                95                  100                 105

Val Phe Leu Arg Val Ile Gly Gly Leu Leu Ala Leu Ala Ala Val
                110                 115                 120

Phe Gln Ile Ile Ser Leu Val Ile Tyr Pro Val Lys Tyr Thr Gln
                125                 130                 135

Thr Phe Thr Leu His Ala Asn Pro Ala Val Thr Tyr Ile Tyr Asn
                140                 145                 150

Trp Ala Tyr Gly Phe Gly Trp Ala Ala Thr Ile Ile Leu Ile Gly
                155                 160                 165

Cys Ala Phe Phe Phe Cys Cys Leu Pro Asn Tyr Glu Asp Asp Leu
                170                 175                 180

Leu Gly Asn Ala Lys Pro Arg Tyr Phe Tyr Thr Ser Ala
                185                 190
```

```
<210> SEQ ID NO 38
<211> LENGTH: 1516
<212> TYPE: DNA
<213> ORGANISM: Homo sapiens
<220> FEATURE:
<221> NAME/KEY: misc_feature
<223> OTHER INFORMATION: Incyte ID No: 1303785CB1
<221> NAME/KEY: unsure
<222> LOCATION: 1512
<223> OTHER INFORMATION: a, t, c, g, or other

<400> SEQUENCE: 38

ctttgttttt ggacatagct gagccatgta cttcaaacag aaggcagcca attactaact     60

tctggttgct aggtgtggct tcctttaaaa tcctataaaa tcagaagccc aagtctccac    120

tgccagtgtg aaatcttcag agaagaattt ctctttagtt ctttgcaaga aggtagagat    180

aaagacactt tttcaaaaat ggcaatggta tcagaattcc tcaagcaggc ctggtttatt    240

gaaaatgaag agcaggaata tgttcaaact gtgaagtcat ccaaaggtgg tcccggatca    300

gcggtgagcc cctatcctac cttcaatcca tcctcggatg tcgctgcctt gcataaggcc    360

ataatggtta aaggtgtgga tgaagcaacc atcattgaca ttctaactaa gcgaaacaat    420

gcacagcgtc aacagatcaa agcagcatat ctccaggaaa caggaaagcc cctggatgaa    480

acactgaaga aagcccttac aggtcacctt gaggaggttg ttttagctct gctaaaaact    540

ccagcgcaat ttgatgctga tgaacttcgt gctgccatga agggccttgg aactgatgaa    600

gatactctaa ttgagatttt ggcatcaaga actaacaaag aaatcagaga cattaacagg    660

gtctacagag aggaactgaa gagagatctg gccaaagaca taacctcaga cacatctgga    720

gattttcgga acgctttgct ttctcttgct aagggtgacc gatctgagga ctttggtgtg    780

aatgaagact tggctgattc agatgccagg gccttgtatg aagcaggaga aaggagaaag    840

gggacagacg taaacgtgtt caataccatc cttaccacca gaagctatcc acaacttcgc    900

agagtgtttc agaaatacac caagtacagt aagcatgaca tgaacaaagt tctggacctg    960

gagttgaaag gtgacattga gaaatgcctc acagctatcg tgaagtgcgc cacaagcaaa   1020

ccagctttct ttgcagagaa gcttcatcaa gccatgaaag gtgttggaac tcgccataag   1080

gcattgatca ggattatggt ttcccgttct gaaattgaca tgaatgatat caaagcattc   1140

tatcagaaga tgtatggtat ctccctttgc caagccatcc tggatgaaac caaaggagag   1200

tatgagaaaa tcctggtggc tctttgtgga ggaaactaaa cattcccttg atggtctcaa   1260

gctatgatca gaagacttta attatatatt ttcatcctat aagcttaaat aggaaagttt   1320

cttcaacagg attacagtgt agctacctac atgctgaaaa atatagcctt taaatcattt   1380
```

-continued

```
ttatattata actctgtata atagagataa gtccattttt taaaaatgtt ttccccaaac   1440

cataaaaccc tatacaagtt gttctagtaa caatacatga gaaagatgtc tatgtagctg   1500

aaaataaaat gncgtc                                                   1516


<210> SEQ ID NO 39
<211> LENGTH: 346
<212> TYPE: PRT
<213> ORGANISM: Homo sapiens
<220> FEATURE:
<221> NAME/KEY: misc_feature
<223> OTHER INFORMATION: Incyte ID No: 1303785CD1

<400> SEQUENCE: 39

Met Ala Met Val Ser Glu Phe Leu Lys Gln Ala Trp Phe Ile Glu
  1               5                  10                  15

Asn Glu Glu Gln Glu Tyr Val Gln Thr Val Lys Ser Ser Lys Gly
                 20                  25                  30

Gly Pro Gly Ser Ala Val Ser Pro Tyr Pro Thr Phe Asn Pro Ser
                 35                  40                  45

Ser Asp Val Ala Ala Leu His Lys Ala Ile Met Val Lys Gly Val
                 50                  55                  60

Asp Glu Ala Thr Ile Ile Asp Ile Leu Thr Lys Arg Asn Asn Ala
                 65                  70                  75

Gln Arg Gln Gln Ile Lys Ala Ala Tyr Leu Gln Glu Thr Gly Lys
                 80                  85                  90

Pro Leu Asp Glu Thr Leu Lys Lys Ala Leu Thr Gly His Leu Glu
                 95                 100                 105

Glu Val Val Leu Ala Leu Leu Lys Thr Pro Ala Gln Phe Asp Ala
                110                 115                 120

Asp Glu Leu Arg Ala Ala Met Lys Gly Leu Gly Thr Asp Glu Asp
                125                 130                 135

Thr Leu Ile Glu Ile Leu Ala Ser Arg Thr Asn Lys Glu Ile Arg
                140                 145                 150

Asp Ile Asn Arg Val Tyr Arg Glu Glu Leu Lys Arg Asp Leu Ala
                155                 160                 165

Lys Asp Ile Thr Ser Asp Thr Ser Gly Asp Phe Arg Asn Ala Leu
                170                 175                 180

Leu Ser Leu Ala Lys Gly Asp Arg Ser Glu Asp Phe Gly Val Asn
                185                 190                 195

Glu Asp Leu Ala Asp Ser Asp Ala Arg Ala Leu Tyr Glu Ala Gly
                200                 205                 210

Glu Arg Arg Lys Gly Thr Asp Val Asn Val Phe Asn Thr Ile Leu
                215                 220                 225

Thr Thr Arg Ser Tyr Pro Gln Leu Arg Arg Val Phe Gln Lys Tyr
                230                 235                 240

Thr Lys Tyr Ser Lys His Asp Met Asn Lys Val Leu Asp Leu Glu
                245                 250                 255

Leu Lys Gly Asp Ile Glu Lys Cys Leu Thr Ala Ile Val Lys Cys
                260                 265                 270

Ala Thr Ser Lys Pro Ala Phe Phe Ala Glu Lys Leu His Gln Ala
                275                 280                 285

Met Lys Gly Val Gly Thr Arg His Lys Ala Leu Ile Arg Ile Met
                290                 295                 300

Val Ser Arg Ser Glu Ile Asp Met Asn Asp Ile Lys Ala Phe Tyr
```

-continued

```
                305                 310                 315

Gln Lys Met Tyr Gly Ile Ser Leu Cys Gln Ala Ile Leu Asp Glu
                320                 325                 330

Thr Lys Gly Glu Tyr Glu Lys Ile Leu Val Ala Leu Cys Gly Gly
                335                 340                 345

Asn


<210> SEQ ID NO 40
<211> LENGTH: 2712
<212> TYPE: DNA
<213> ORGANISM: Homo sapiens
<220> FEATURE:
<221> NAME/KEY: misc_feature
<223> OTHER INFORMATION: Incyte ID No: 1798379CB1

<400> SEQUENCE: 40

ccagccttga ctcttctcaa gagcctgtga ctttcctccc tggacaaagg catcatgagt     60

tgtcagatct cttgcaaatc tcgaggaaga ggaggaggtg gaggaggatt ccggggcttc    120

agcagcggct cagctgtggt gtctggtgga agccggagat caacttccag cttctcctgc    180

ttgagccgcc atggtggtgg tggtggggc ttcggtggag gcggctttgg cagtcggagt    240

cttgttggcc ttggagggac caagagcatc tccattagtg tggctggagg aggtggtggc    300

tttggcgccg ctggtggatt tggtggcaga ggaggtggtt ttggaggcgg cagcggcttt    360

ggaggcggca gcggctttgg aggtggcagc ggcttcagtg gtggtggttt cggtggaggc    420

ggctttggtg gaggccgctt tggaggtttt gggggccctg gtggtgttgg aggtttaggg    480

ggtcctggtg gctttgggcc tggaggatac cctggtggca tccacgaagt ctctgtcaac    540

cagagcctcc tgcagcctct caacgtgaaa gttgacccag agatccagaa tgtgaaggcc    600

caagagcgtg agcagatcaa aactctcaac aacaaatttg cctccttcat tgacaaggtg    660

cggttcttgg agcagcagaa ccaggtgtta cagaccaaat gggagctgct acaacaaatg    720

aatgttggca cccgccccat caacctggag cccatcttcc aggggtatat cgacagcctc    780

aagagatatc tggatgggct cactgcagaa agaacatcac agaattcaga gctgaataac    840

atgcaggatc ttgtggagga ttataagaag aagtatgagg atgaaatcaa taagcgcaca    900

gctgctgaga atgattttgt gacgcttaaa aaggacgtgg acaatgccta catgataaag    960

gtggagttgc agtccaaggt ggacctgctg aaccaggaaa ttgagtttct gaaagttctc   1020

tatgatgcgg agatatccca gatacatcag agtgtcactg acaccaacgt catcctctcc   1080

atggacaaca gccgcaacct ggacttggat agcatcatcg ccgaggtcaa ggcccagtat   1140

gaggagatcg cccagaggag caaggaagaa gcggaggccc tgtaccacag caagtatgag   1200

gagctccagg tgactgtcgg gagacatgga gacagcctga aagagatcaa gatagagatc   1260

agcgagctga accgcgtgat ccagaggctg caggggggaga tcgcacatgt gaagaagcag   1320

tgtaagaatg tgcaagatgc catcgcagat gccgagcagc gtggggagca tgccctcaag   1380

gatgccagga acaagttgaa tgacctggag gaggccctgc agcaggccaa ggaggacttg   1440

gcgcggctgc tgcgtgacta ccaggagctg atgaacgtga agctggccct agatgtggag   1500

atcgccacct accgcaaact gctggagggc gaggagtgca ggatgtctgg agacctcagc   1560

agcaatgtga ctgtgtctgt gacaagcagc accatttcat caaatgtggc atccaaggct   1620

gcctttggag gttctggagg tagagggtcc agttccggag gaggatacag ctctggaagc   1680

agcagttatg gctctggagg ccgacagtct ggctccagag gcggtagtgg aggaggaggt   1740
```

-continued

```
tctatctctg gaggaggata tggctctggc ggtggttctg gaggaagata cggatctggt   1800

ggtggctcta agggagggtc catctctgga ggaggatatg gctctggagg tggaaaacac   1860

agctctggag gtggctctag aggaggctcc agctctggag gaggatatgg ctctggaggt   1920

gggggttcta gctctgtaaa gggtagctca ggtgaagctt ttggttccag cgtgaccttc   1980

tcttttagat aaagatgagc cccaccacc accgactctc ccaacccaga ctctcccact   2040

ccagaatgta gaagcctgtc tctgtacctc taactggcag caagttaaat ttttgtcatt   2100

tatctctgat ggcactttga gggaaaagaa tgtccacata cagtttttga aagatcttct   2160

ctccaaacca gttagttaga gccagtgacg cctctgtgtt ctggggcgga atctgtgctg   2220

tctaggtttg tgcttctagc catgcccatt cccgccccca ccatgcctct ttgcattgcc   2280

cattttccag atgtgtattc tgttgaggac ccaggcccat ccagggattt catctctaag   2340

cctggcagtg ctgggggaa atgtgtttct gtgtatatag ctcctcttgt ccactctgct   2400

ttcggaagtg ctgtggtctg gggtcttca taatataaac ctcatttggc aattcaaaaa   2460

aaaaaaaag gggggccccc ccacttattt aggggttcc cgacctccaa attcgcgaac   2520

cagggaaaaa ccggtttccc ggtggaaaaa ttgtaacccg cacaaaattt ccccaaaaat   2580

attggccccg gaacctaaaa ggtaaaaact cgggggcccc aaagagtttg gcaaacccca   2640

ataatttggg tgggcacaag gcccgtttcc catgggggaa acttttgtgc cacggcttta   2700

ataataggcc cc                                                       2712
```

```
<210> SEQ ID NO 41
<211> LENGTH: 645
<212> TYPE: PRT
<213> ORGANISM: Homo sapiens
<220> FEATURE:
<221> NAME/KEY: misc_feature
<223> OTHER INFORMATION: Incyte ID No: 1798379CD1

<400> SEQUENCE: 41

Met Ser Cys Gln Ile Ser Cys Lys Ser Arg Gly Arg Gly Gly Gly
  1               5                  10                  15

Gly Gly Gly Phe Arg Gly Phe Ser Ser Gly Ser Ala Val Val Ser
                 20                  25                  30

Gly Gly Ser Arg Arg Ser Thr Ser Ser Phe Ser Cys Leu Ser Arg
                 35                  40                  45

His Gly Gly Gly Gly Gly Gly Phe Gly Gly Gly Gly Phe Gly Ser
                 50                  55                  60

Arg Ser Leu Val Gly Leu Gly Gly Thr Lys Ser Ile Ser Ile Ser
                 65                  70                  75

Val Ala Gly Gly Gly Gly Gly Phe Gly Ala Ala Gly Gly Phe Gly
                 80                  85                  90

Gly Arg Gly Gly Gly Phe Gly Gly Gly Ser Gly Phe Gly Gly Gly
                 95                 100                 105

Ser Gly Phe Gly Gly Gly Ser Gly Phe Ser Gly Gly Gly Phe Gly
                110                 115                 120

Gly Gly Gly Phe Gly Gly Gly Arg Phe Gly Gly Phe Gly Gly Pro
                125                 130                 135

Gly Gly Val Gly Gly Leu Gly Gly Pro Gly Gly Phe Gly Pro Gly
                140                 145                 150

Gly Tyr Pro Gly Gly Ile His Glu Val Ser Val Asn Gln Ser Leu
                155                 160                 165

Leu Gln Pro Leu Asn Val Lys Val Asp Pro Glu Ile Gln Asn Val
```

-continued

```
                170                 175                 180

Lys Ala Gln Glu Arg Glu Gln Ile Lys Thr Leu Asn Asn Lys Phe
                185                 190                 195

Ala Ser Phe Ile Asp Lys Val Arg Phe Leu Glu Gln Gln Asn Gln
                200                 205                 210

Val Leu Gln Thr Lys Trp Glu Leu Leu Gln Gln Met Asn Val Gly
                215                 220                 225

Thr Arg Pro Ile Asn Leu Glu Pro Ile Phe Gln Gly Tyr Ile Asp
                230                 235                 240

Ser Leu Lys Arg Tyr Leu Asp Gly Leu Thr Ala Glu Arg Thr Ser
                245                 250                 255

Gln Asn Ser Glu Leu Asn Asn Met Gln Asp Leu Val Glu Asp Tyr
                260                 265                 270

Lys Lys Lys Tyr Glu Asp Glu Ile Asn Lys Arg Thr Ala Ala Glu
                275                 280                 285

Asn Asp Phe Val Thr Leu Lys Lys Asp Val Asp Asn Ala Tyr Met
                290                 295                 300

Ile Lys Val Glu Leu Gln Ser Lys Val Asp Leu Leu Asn Gln Glu
                305                 310                 315

Ile Glu Phe Leu Lys Val Leu Tyr Asp Ala Glu Ile Ser Gln Ile
                320                 325                 330

His Gln Ser Val Thr Asp Thr Asn Val Ile Leu Ser Met Asp Asn
                335                 340                 345

Ser Arg Asn Leu Asp Leu Asp Ser Ile Ile Ala Glu Val Lys Ala
                350                 355                 360

Gln Tyr Glu Glu Ile Ala Gln Arg Ser Lys Glu Glu Ala Glu Ala
                365                 370                 375

Leu Tyr His Ser Lys Tyr Glu Glu Leu Gln Val Thr Val Gly Arg
                380                 385                 390

His Gly Asp Ser Leu Lys Glu Ile Lys Ile Glu Ile Ser Glu Leu
                395                 400                 405

Asn Arg Val Ile Gln Arg Leu Gln Gly Glu Ile Ala His Val Lys
                410                 415                 420

Lys Gln Cys Lys Asn Val Gln Asp Ala Ile Ala Asp Ala Glu Gln
                425                 430                 435

Arg Gly Glu His Ala Leu Lys Asp Ala Arg Asn Lys Leu Asn Asp
                440                 445                 450

Leu Glu Glu Ala Leu Gln Gln Ala Lys Glu Asp Leu Ala Arg Leu
                455                 460                 465

Leu Arg Asp Tyr Gln Glu Leu Met Asn Val Lys Leu Ala Leu Asp
                470                 475                 480

Val Glu Ile Ala Thr Tyr Arg Lys Leu Leu Glu Gly Glu Glu Cys
                485                 490                 495

Arg Met Ser Gly Asp Leu Ser Ser Asn Val Thr Val Ser Val Thr
                500                 505                 510

Ser Ser Thr Ile Ser Ser Asn Val Ala Ser Lys Ala Ala Phe Gly
                515                 520                 525

Gly Ser Gly Gly Arg Gly Ser Ser Ser Gly Gly Gly Tyr Ser Ser
                530                 535                 540

Gly Ser Ser Ser Tyr Gly Ser Gly Gly Arg Gln Ser Gly Ser Arg
                545                 550                 555

Gly Gly Ser Gly Gly Gly Gly Ser Ile Ser Gly Gly Gly Tyr Gly
                560                 565                 570
```

```
Ser Gly Gly Gly Ser Gly Gly Arg Tyr Gly Ser Gly Gly Gly Ser
                575                 580                 585

Lys Gly Gly Ser Ile Ser Gly Gly Gly Tyr Gly Ser Gly Gly Gly
                590                 595                 600

Lys His Ser Ser Gly Gly Gly Ser Arg Gly Gly Ser Ser Ser Gly
                605                 610                 615

Gly Gly Tyr Gly Ser Gly Gly Gly Gly Ser Ser Ser Val Lys Gly
                620                 625                 630

Ser Ser Gly Glu Ala Phe Gly Ser Ser Val Thr Phe Ser Phe Arg
                635                 640                 645
```

<210> SEQ ID NO 42
<211> LENGTH: 663
<212> TYPE: DNA
<213> ORGANISM: Homo sapiens
<220> FEATURE:
<221> NAME/KEY: misc_feature
<223> OTHER INFORMATION: Incyte ID No: 350650.1

<400> SEQUENCE: 42

```
ctgggccatg aaaagctccc tggagggaac cctggctgac acagaagctg gctacgtggc     60

tcagctgtca gaaattcaaa cgcagatcag tgccctggag gaggagatct gccagatctg    120

gggtgagact aaatgccaga acgcagagta caagcaattg ctggacatca agacacgcct    180

ggaggtggag atcgagacct accgccgcct gctcgatgga gagggaggtg gttctagttt    240

tgcagaattt ggtggtagaa actccaggat ctgtaaacat ggggatccca gggatctggg    300

tatctggtga ctcaagatct ggaagctgtt ctggtcaagg acgagattca agcaagacta    360

gagtgactaa gactatcgta gaggagttgg tggatggcaa ggttgtctcg tctcaagtca    420

gcagtatttc tgaggtgaaa gttaaataag gaacttccag atcaacaaaa gtgtctttca    480

aagaaaaaaa aatcaagaag gacacaagcg aagaaatggc atcaatctag gcatctttct    540

ggataatttc aggaaaagct tcagtccaga aatggatgac tagccaactt ttctgcatct    600

tcttatttcc tcattagaat gctcttgaaa tagctgaatt aacaactttg ctttaattgt    660

ttg                                                                  663
```

<210> SEQ ID NO 43
<211> LENGTH: 809
<212> TYPE: DNA
<213> ORGANISM: Homo sapiens
<220> FEATURE:
<221> NAME/KEY: misc_feature
<223> OTHER INFORMATION: Incyte ID No: 474630.24
<221> NAME/KEY: unsure
<222> LOCATION: 511
<223> OTHER INFORMATION: a, t, c, g, or other

<400> SEQUENCE: 43

```
ccgggagctg gagacgggct cccctcgcag agcctacggc cttcccccgc ctggccctgc     60

tcggcccggc gccccccggc ggtgccaacg cggcccttcg ttgttcccaa tggctgcggc    120

tggaagttcg agcccctgct gggggaggag ctggacctgc ggcgcgtcac gtggcggctg    180

cccccggagc tcatcccgcg cctgtcggcc agcagcgggc gctcctccga cgccgaggcg    240

ccccacgggc ccccggacga cggcggcgcg ggcgggaagg gcggcagcct gccccgcagt    300

gcgacacccg ggccccccgg aggtgacagg ctcacccgcc gccccccgat ccgcgcccac    360

ccagcctcac tcgcgcctga gggccctggg gtgggcgtct gcgctgcctc gggggcccca    420
```

-continued

```
gtctcagcca ggcacgggcc ttggcggctg ggagcacagc tgctcagagg cagggcccag    480

tgccagggga cgcgtgaggc aggcgcttgg ncccttatgg tgcctgcctg gccagggggt    540

gcaaattcag aagtctgccc gggaagcgga ccctggcacc caagtagacc cctcaggggc    600

ctcaaaggac aggagggaag gcttggggat ctccccaggg cagagctgac tgcagacgca    660

gcaaaccccc gccactgcca gggtcagcag tgctcacacc gatagagtgg ccggccagag    720

gatatgggct gtggaagcct gggtggccct tgggctcctg ctaggacaga gggcctctgt    780

ccctagtggt ttgagggaaa ctggttgta                                      809


<210> SEQ ID NO 44
<211> LENGTH: 295
<212> TYPE: DNA
<213> ORGANISM: Homo sapiens
<220> FEATURE:
<221> NAME/KEY: misc_feature
<223> OTHER INFORMATION: Incyte ID No: 108089.1

<400> SEQUENCE: 44

gggaactagg tcttggccct ttctacagct tttctcctgc aaagggtcca gccttttcct     60

gctccccacg ttgtccttac ggctgtgtgg ggtagggcag ggtccacact ccttcccatc    120

cattttagag gaggaagctg gagtctggga agggatggga ttttcccagg gcaccctgtg    180

agtcacatgc cacttgagac aagggtctag agctccagca ttttccaagc tacaaatgta    240

tctgctgctc caagtgtccg ccagggtcgg cctcagagct ggcaggagtt cggtg         295


<210> SEQ ID NO 45
<211> LENGTH: 1744
<212> TYPE: DNA
<213> ORGANISM: Homo sapiens
<220> FEATURE:
<221> NAME/KEY: misc_feature
<223> OTHER INFORMATION: Incyte ID No: 3346307CB1

<400> SEQUENCE: 45

ccaaggggga ggtgcgagcg tggacctggg acgggtctgg gcggctctcg gtggttggca     60

cgggttcgca cacccattca agcggcagga cgcacttgtc ttagcagttc tcgctgaccg    120

cgctagctgc ggcttctacg ctccggcact ctgagttcat cagcaaacgc cctggcgtct    180

gtcctcacca tgcctagcct ttgggaccgc ttctcgtcgt cgtccacctc ctcttcgccc    240

tcgtccttgc cccgaactcc caccccagat cggccgccgc gctcagcctg gggtcggcg     300

acccgggagg aggggtttga ccgctccacg agcctggaga gctcggactg cgagtccctg    360

gacagcagca acagtggctt cgggccggag gaagacacgg cttacctgga tggggtgtcg    420

ttgcccgact tcgagctgct cagtgaccct gaggatgaac acttgtgtgc caacctgatg    480

cagctgctgc aggagagcct ggcccaggcg cggctgggct ctcgacgccc tgcgcgcctg    540

ctgatgccta gccagttggt aagccaggtg ggcaaagaac tactgcgcct ggcctacagc    600

gagccgtgcg gcctgcgggg ggcgctgctg gacgtctgcg tggagcaggg caagagctgc    660

cacagcgtgg gccagctggc actcgacccc agcctggtgc ccaccttcca gctgaccctc    720

gtgctgcgcc tggactcacg actctggccc aagatccagg ggctgtttag ctccgccaac    780

tctcccttcc tccctggctt cagccagtcc ctgacgctga gcactggctt ccgagtcatc    840

aagaagaagc tgtacagctc ggaacagctg ctcattgagg agtgttgaac ttcaacctga    900

gggggccgac agtgccctcc aagacagaga cgactgaact tttggggtgg agactagagg    960

caggagctga gggactgatt ccagtggttg gaaaactgag gcagccacct aaggtggagg   1020
```

-continued

```
tgggggaata gtgtttccca ggaagctcat tgagttgtgt gcgggtggct gtgcattggg   1080

gacacatacc cctcagtact gtagcatgaa acaaaggctt aggggccaac aaggcttcca   1140

gctggatgtg tgtgtagcat gtaccttatt atttttgtta ctgacagtta acagtggtgt   1200

gacatccaga gagcagctgg gctgctcccg ccccagcccg gcccagggtg aaggaagagg   1260

cacgtgctcc tcagagcagc cggagggagg ggggaggtcg gaggtcgtgg aggtggtttg   1320

tgtatcttac tggtctgaag ggaccaagtg tgtttgttgt ttgttttgta tcttgttttt   1380

ctgatcggag catcactact gacctgttgt aggcagctat cttacagacg catgaatgta   1440

agagtaggaa ggggtgggtg tcagggatca cttgggatct ttgacacttg aaaaattaca   1500

cctggcagct gcgtttaagc cttcccccat cgtgtactgc agagttgagc tggcagggga   1560

ggggctgaga gggtgggggc tggaacccct ccccgggagg agtgccatct gggtcttcca   1620

tctagaactg tttacatgaa gataagatac tcactgttca tgaatacact tgatgttcaa   1680

gtattaagac ctatgcaata ttttttactt ttctaataaa catgtttgtt aaaacaaaaa   1740

aaaa                                                                1744
```

<210> SEQ ID NO 46
<211> LENGTH: 232
<212> TYPE: PRT
<213> ORGANISM: Homo sapiens
<220> FEATURE:
<221> NAME/KEY: misc_feature
<223> OTHER INFORMATION: Incyte ID No: 3346307CD1

<400> SEQUENCE: 46

```
Met Pro Ser Leu Trp Asp Arg Phe Ser Ser Ser Ser Thr Ser Ser
  1               5                  10                  15

Ser Pro Ser Ser Leu Pro Arg Thr Pro Thr Pro Asp Arg Pro Pro
                 20                  25                  30

Arg Ser Ala Trp Gly Ser Ala Thr Arg Glu Glu Gly Phe Asp Arg
                 35                  40                  45

Ser Thr Ser Leu Glu Ser Ser Asp Cys Glu Ser Leu Asp Ser Ser
                 50                  55                  60

Asn Ser Gly Phe Gly Pro Glu Glu Asp Thr Ala Tyr Leu Asp Gly
                 65                  70                  75

Val Ser Leu Pro Asp Phe Glu Leu Leu Ser Asp Pro Glu Asp Glu
                 80                  85                  90

His Leu Cys Ala Asn Leu Met Gln Leu Leu Gln Glu Ser Leu Ala
                 95                 100                 105

Gln Ala Arg Leu Gly Ser Arg Arg Pro Ala Arg Leu Leu Met Pro
                110                 115                 120

Ser Gln Leu Val Ser Gln Val Gly Lys Glu Leu Leu Arg Leu Ala
                125                 130                 135

Tyr Ser Glu Pro Cys Gly Leu Arg Gly Ala Leu Leu Asp Val Cys
                140                 145                 150

Val Glu Gln Gly Lys Ser Cys His Ser Val Gly Gln Leu Ala Leu
                155                 160                 165

Asp Pro Ser Leu Val Pro Thr Phe Gln Leu Thr Leu Val Leu Arg
                170                 175                 180

Leu Asp Ser Arg Leu Trp Pro Lys Ile Gln Gly Leu Phe Ser Ser
                185                 190                 195

Ala Asn Ser Pro Phe Leu Pro Gly Phe Ser Gln Ser Leu Thr Leu
                200                 205                 210
```

```
Ser Thr Gly Phe Arg Val Ile Lys Lys Lys Leu Tyr Ser Ser Glu
            215                 220                 225

Gln Leu Leu Ile Glu Glu Cys
            230


<210> SEQ ID NO 47
<211> LENGTH: 897
<212> TYPE: DNA
<213> ORGANISM: Homo sapiens
<220> FEATURE:
<221> NAME/KEY: misc_feature
<223> OTHER INFORMATION: Incyte ID No: 200143.25

<400> SEQUENCE: 47

ccccagggca gggagcaggt tatgaccagg actaaggtcc cagagtcccc accctgaccc      60

ctccctgctg ttccagccgc tccctcatat ccacccctgc cccatctcct gactttggtc     120

acgctagcat cttctgctga tcctgaaatt gtaccagcgg caagatgtgg cctggaaggg     180

gactttaagt tctccacaac tgccagcaat ccttccacca ggcaaaacac atcatctaag     240

gaaaagaagt gaggtcggaa caccaacgca tcatctcact gcatggccct ggaggctctg     300

ccgtttaaag accccagaac cttccccatt caaggtcctc tcctgggcac aggagattgg     360

agaaagctcc tcccttaatt ccagggaccg agttccagcc catccaattc tccgtctcac     420

ctgaggctgc tgtggtcctg gtgaccccag ggagcaacct gccgcccatg gctggggagg     480

gggtgaagct gtctctttaa gagcaggaat ggagcccctg ggcctcaggg catctgactt     540

gttttctacc tgcccaggtt tgcttagggc gtggcagctt cggataaacg caggactccg     600

cctggcagcc cgatttctcc cggaacctct gctcagcctg gtgaaccaca caggtgagca     660

gctggggccc cttcctccaa gccctccttg tctctgcccc taaattagga agtatctacc     720

tgccccctga ccctgcccca tagaagcttt tatgttaaag cgcctaaaat cttgtgaaat     780

gcttttctgg agccaggaga taaacggaag tcccttcccc taatgtccct ttccccacca     840

ttctcctctc agggacttgt tgaaccagct gaggccagcg ctctgacatg cagaagg        897


<210> SEQ ID NO 48
<211> LENGTH: 1827
<212> TYPE: DNA
<213> ORGANISM: Homo sapiens
<220> FEATURE:
<221> NAME/KEY: misc_feature
<223> OTHER INFORMATION: Incyte ID No: 001929.1

<400> SEQUENCE: 48

ccttgacaat ctgtctgtcc gtctgcagct gcgtgactgt ctgtctctgc catgtctctc      60

tccccatgcc gggcccagag gggcttcagc gctcgctcag cctgttctgc tcgctcaagg     120

ggccgcagca ggggaggctt cagcagcagg ggcggcttca gcagcaggag ccttaattcc     180

tttgggggt gcctggaagg ctctcgtggg agtacctggg ggtcaggggg taggctgggg     240

gtgcggtttg gggagtggag tggtgggcct gggctctccc tgtgccctcc ggggggcatc     300

caagaagtga ccatcaacca gaatccgctg accccactga agattgagat cgatccccag     360

ttccaggtgg tgcggacgca ggagacccag gagatcagaa ccctcaacaa ccagtttgct     420

tccttcattg acaaggtgcg gttcctggag cagcagaaca aggtcctgga gacgaagtgg     480

catctgctgc agcaacaggg gttgagtggc agccagcagg gcctggagcc tgtctttgag     540

gcctgcctgg atcagctcag gaagcagctg gagcagctcc agggagaacg aggggctctg     600
```

```
gatgctgagt tgaaggcctg ccgggaccag gaggaggagt ataagtccaa gtatgaggag    660

gaggcccaca ggcgtgccac acttgagaac gactttgtgg tcctcaagaa ggatgtggat    720

ggggttttcc tgagcaagat ggagttggag ggcaagctgg aggctctgag agagtacctc    780

tacttcttga agcatctgaa tgaagaagag ctgggccagc tccagaccca ggccagcgac    840

acgtctgtgg tgctgtccat ggacaacaac cgctacctgg acttcagcag catcatcact    900

gaggtccgcg cccggtacga ggagatcgcc cggagcagca aggctgaggc tgaggccttg    960

taccagacca agtaccagga acttcaggtg tctgcccagc ttcatgggga caggatgcag   1020

gaaacgaaag tccagatctc tcagctacac caagagattc agaggctgca gagtcagact   1080

gagaacctca agaagcagaa cgccagcctg caggccgcca tcactgatgc tgagcagcgt   1140

ggggagctgg ccctcaagga cgctcaggcc aaggtggacg agctggaggc tgctctgagg   1200

atggccaagc agaacctggc ccggctgctg tgcgagtacc aggagctgac gagcacgaag   1260

ctttccctgg atgtggagat tgccacttac cgcaggctgc tggagggcga ggagtgcagg   1320

atgtctgggg agtgcaccag ccaggtcact atctcctcgg tgggaggcag cgctgtcatg   1380

tctggaggag ttggtggagg cttggggagc acttgtggac tcggtagtgg gaaaggcagc   1440

cctgggtcct gctgcaccag cattgtgact ggaggctcca acatcattct gggctctggg   1500

aaggaccctg ttttggattc ctgctctgtg tctggctcca gcgctggctc cagctgccac   1560

accatcctga agaagacagt tgagtcgagt ctgaagacat ccatcaccta ctgagcgacc   1620

cagcagccac ctccttcctg aacacatttg gcccactccc cccatcagcc ggctctgcaa   1680

ggccaactcc gtgtccgctg cccacagccc aagccagccc acagcggatg ctgcaaaaat   1740

caataaagtc tcccctcctg ctgttctgaa tgctctaagt gcttgcacac ctcacccagc   1800

aaaacaaaag ctgtgtgact ccccagc                                       1827
```

<210> SEQ ID NO 49
<211> LENGTH: 3936
<212> TYPE: DNA
<213> ORGANISM: Homo sapiens
<220> FEATURE:
<221> NAME/KEY: misc_feature
<223> OTHER INFORMATION: Incyte ID No: 1088524.8
<221> NAME/KEY: unsure
<222> LOCATION: 2060-2170, 3796, 3799, 3816
<223> OTHER INFORMATION: a, t, c, g, or other

<400> SEQUENCE: 49

```
taaacacagc tgcgatgacg aaccctttca cgggaaggaa catgcgagcc cagaaaagtc     60

tctcctggtc ttgggatgga ggtcacacga agcctccgca aggcaaggac ttttgcggct    120

tctgcaacca agcgggtctt acccccggtc ctccgcgtct ccagtcctcg cacctggaac    180

cccaacgtcc ccgagagtcc ccgaatcccc gctcccaggc tacctaagag gatgagcggt    240

gctccgacgg ccggggcagc cctgatgctc tgcgccgcca ccgccgtgct actgagcgct    300

cagggcggac ccgtgcagtc caagtcgccg cgctttgcgt cctgggacga gatgaatgtc    360

ctggcgcacg gactcctgca gctcggccag gggctgcgcg aacacgcgga gcgcacccgc    420

agtcagctga gcgcgctgga gcggcgcctg agcgcgtgcg ggtccgcctg tcagggaacc    480

gaggggtcca ccgacctccc gttagcccct gagagccggg tggaccctga ggtccttcac    540

agcctgcaga cacaactcaa ggctcagaac agcaggatcc agcaactctt ccacaaggtg    600

gcccagcagc agcggcacct ggagaagcag cacctgcgaa ttcagcatct gcaaagccag    660

tttggcctcc tggaccacaa gcacctagac catgaggtgg ccaagcctgc ccgaagaaag    720
```

-continued

```
aggctgcccg agatggccca gccagttgac ccggctcaca atgtcagccg cctgcaccgg    780
ctgcccaggg attgccagga gctgttccag gttggggaga ggcagagtgg actatttgaa    840
atccagcctc aggggtctcc gccatttttg gtgaactgca agatgacctc agatggaggc    900
tggacagtaa ttcagaggcg ccacgatggc tcagtggact tcaaccggcc ctgggaagcc    960
tacaaggcgg ggtttgggga tccccacggc gagttctggc tgggtctgga gaaggtgcat   1020
agcatcaccg gggaccgcaa acagccgcct ggccgtgcag ctgcgggact gggatggcaa   1080
cgccgagttg ctgcagttct ccgtgcacct gggtggcgag gacacggcct atagcctgca   1140
gctcactgca cccgtggccg gccagctggg cgccaccacc gtcccaccca gcggcctctc   1200
cgtacccttc tccacttggg accaggatca cgacctccgc agggacaaga actgcgccaa   1260
gagcctctct ggaggctggt ggtttggcac ctgcagccat tccaacctca acggccagta   1320
cttccgctcc atcccacagc agcggcagaa gcttaagaag ggaatcttct ggaagacctg   1380
gcggggccgc tactacccgc tgcaggccac caccatgttg atccagccca tggcagcaga   1440
ggcagcctcc tagcgtcctg gctgggcctg gtcccaggcc cacgaaagac ggtgactctt   1500
ggctctgccc gaggatgtgg ccgttccctg cctgggcagg ggctccaagg aggggccatc   1560
tggaaacttg tggacagaga agaagaccac gactggagaa gccccctttc tgagtgcagg   1620
ggggctgcat gcgttgcctc ctgagatcga ggctgcagga tatgctcaga ctctagaggc   1680
gtggaccaag ggcatggag cttcactcct tgctggccag ggagttgggg actcagaggg   1740
accacttggg gccagccaga ctggcctcaa tggcggactc agtcacattg actgacgggg   1800
accagggctt gtgtgggtcg agagcgccct catggtgctg gtgctgttgt gtgtaggtcc   1860
cctggggaca caagcaggcg ccaatggtat ctgggcggag ctcacagagt tcttggaata   1920
aaagcaacct cagaacactt tgttctttgt tcttgtttgt tttctttctt ttttttctct   1980
ttctttagtt cacagatcta gtaagttacc ctcagtttgt tttaaaaagt gaacaaagtc   2040
catgtaaaca tgttcccagn nnnnnnnnnn nnnnnnnnnn nnnnnnnnnn nnnnnnnnnn   2100
nnnnnnnnnn nnnnnnnnnn nnnnnnnnnn nnnnnnnnnn nnnnnnnnnn nnnnnnnnnn   2160
nnnnnnnnnn catctcgcaa gggtccatgg cttcattctt gaagtcagtg agaccaagaa   2220
ccccccaatt ccggacacag tgccactgca ctccagccca ggcaacagag cgagattctg   2280
tctggacgta gccccatttc tcttcccgga caggtcctct gatagtcggg taggttctca   2340
atcaagcctc tcattagtta tttggtctgt caatccattt cattcctgca gtcttccgcc   2400
ccgccctctt gagctcgccc ctgataggct ggcgcgtccg tcacttcaaa aaggtccgca   2460
ttccttccgc ctttctccag gacaccgagg gcgaggaggg tggtaccaag cggcgcccac   2520
cctcagagca ctacttccat ctctgattgg cttcgctggg tgcccgtcgc tactccactc   2580
gccgatcccg ccggaagcgc caggacaatg ggacccgggg acgacgagta cgactaccta   2640
ttcaaagtgg tgctcatcgg ggactcaggc gtgggcaaga gcaacctgct gtcgcgcttc   2700
acccgcaacg agttcaacct ggagagcaag agcaccatcg gcgtggagtt cgccacccgc   2760
agcatccagg tggacggcaa gaccatcaag gcgcagatct gggacaccgc tggccaggag   2820
cgctaccgcg ccatcacctc cgcgtactac cgtggtgcag tgggcgccct gctggtgtac   2880
gacatcgcca agcacctgac ctatgagaac gtggagcgct ggctgaagga gctgcgggac   2940
cacgcagaca gcaacatcgt catcatgctg gtgggcaaca agagtgacct gcgccacctg   3000
cgggctgtgc ccactgacga ggcccgcgcc ttcgcagaaa agaacaactt gtccttcatc   3060
```

-continued

```
gagacctcag ccttggattc cactaacgta gaggaagcat tcaagaacat cctcacagag   3120

atctaccgca tcgtgtcaca gaaacagatc gcagaccgtg ctgcccacga cgagtccccg   3180

gggaacaacg tggtggacat cagcgtgccg cccaccacgg acggacagaa gcccaacaag   3240

ctgcagtgct gccagaacct gtgacccctg cgcctccacc cagcgtgcgt gcacgtcctc   3300

cgcccgtccc cgccacggta tcctctggcc cctccctgct gtccctctgt ggccggctcg   3360

ttccagccct cccagtgagc tctgcacggc cgggccgggg cccaggaagg acaggagcca   3420

gtgctacccc gtcctgcccg gggaaaagct agaagccccg gtttgctgca cccatgaaac   3480

tcgggtcccc acagcgtctt ggcggggtgg ggagggcggc aggatggacg gggctggcca   3540

gaggcgagga ggacgggcgg acggcgccgc cttctcccct tttccttggc cgactctagg   3600

gagcgattgc ctccctccct ctgtgaccgg gtggcccagc cagcccgtcg tccccaccca   3660

gaaccgtgct ctgggccaaa gcccgaagaa ccaggcagcg ggggccgggg caggcggacc   3720

ccccgggctc tcagcgccca cccgctcctc cgcacacagc agctcgcaca ggcctcccac   3780

tctgcctgtc cccctnctnt gtctcgtctc cccatntggt ctggaacctg tttgcaagtg   3840

aagcaatatc tccgtgtttt gtagtataca accgctcttg tagcctttgg tttgtgttaa   3900

tgtagagaaa ctcagattct ttatacactt ttgtaa                             3936
```

```
<210> SEQ ID NO 50
<211> LENGTH: 1114
<212> TYPE: DNA
<213> ORGANISM: Homo sapiens
<220> FEATURE:
<221> NAME/KEY: misc_feature
<223> OTHER INFORMATION: Incyte ID No: 632664CB1

<400> SEQUENCE: 50

gccgcctctg ccgccgcgga cttcccgaac ctcttcagcc gcccggagcc gctcccggag     60

cccggccgta gaggctgcaa tcgcagccgg tgagcccgca gcccgcgccc cgagcccgcc    120

gccgcccttc gagggcgccc caggccgcgc catggtgaag gtgacgttca actccgctct    180

ggcccagaag gaggccaaga aggacgagcc caagagcggc gaggaggcgc tcatcatccc    240

ccccgacgcc gtcgcggtgg actgcaagga cccagatgat gtggtaccag ttggccaaag    300

aagagcctgg tgttggtgca tgtgctttgg actagcattt atgcttgcag gtgttattct    360

aggaggagca tacttgtaca aatattttgc acttcaacca gatgacgtgt actactgtgg    420

aataaagtac atcaaagatg atgtcatctt aaatgagccc tctgcagatg ccccagctgc    480

tctctaccag acaattgaag aaaatattaa aatctttgaa gaagaagaag ttgaatttat    540

cagtgtgcct gtcccagagt ttgcagatag tgatcctgcc aacattgttc atgactttaa    600

caagaaactt acagcctatt tagatcttaa cctggataag tgctatgtga tccctctgaa    660

cacttccatt gttatgccac ccagaaacct actggagtta cttattaaca tcaaggctgg    720

aacctatttg cctcagtcct atctgattca tgagcacatg gttattactg atcgcattga    780

aaacattgat cacctgggtt tctttattta tcgactgtgt catgacaagg aaacttacaa    840

actgcaacgc agagaaacta ttaaaggtat tcagaaacgt gaagccagca attgtttcgc    900

aattcggcat tttgaaaaca aatttgccgt ggaaacttta atttgttctt gaacagtcaa    960

gaaaaacatt attgaggaaa attaatatca cagcataacc ccacccttta cattttgtgc   1020

agtgattatt ttttaaagtc ttctttcatg taagtagcaa acagggcttt actatctttt   1080

catctcatta attcaattaa aaccattacc ttaa                               1114
```

```
<210> SEQ ID NO 51
<211> LENGTH: 266
<212> TYPE: PRT
<213> ORGANISM: Homo sapiens
<220> FEATURE:
<221> NAME/KEY: misc_feature
<223> OTHER INFORMATION: Incyte ID No: 632664CD1

<400> SEQUENCE: 51

Met Val Lys Val Thr Phe Asn Ser Ala Leu Ala Gln Lys Glu Ala
  1               5                  10                  15

Lys Lys Asp Glu Pro Lys Ser Gly Glu Glu Ala Leu Ile Ile Pro
                 20                  25                  30

Pro Asp Ala Val Ala Val Asp Cys Lys Asp Pro Asp Asp Val Val
                 35                  40                  45

Pro Val Gly Gln Arg Arg Ala Trp Cys Trp Cys Met Cys Phe Gly
                 50                  55                  60

Leu Ala Phe Met Leu Ala Gly Val Ile Leu Gly Gly Ala Tyr Leu
                 65                  70                  75

Tyr Lys Tyr Phe Ala Leu Gln Pro Asp Asp Val Tyr Tyr Cys Gly
                 80                  85                  90

Ile Lys Tyr Ile Lys Asp Asp Val Ile Leu Asn Glu Pro Ser Ala
                 95                 100                 105

Asp Ala Pro Ala Ala Leu Tyr Gln Thr Ile Glu Glu Asn Ile Lys
                110                 115                 120

Ile Phe Glu Glu Glu Glu Val Glu Phe Ile Ser Val Pro Val Pro
                125                 130                 135

Glu Phe Ala Asp Ser Asp Pro Ala Asn Ile Val His Asp Phe Asn
                140                 145                 150

Lys Lys Leu Thr Ala Tyr Leu Asp Leu Asn Leu Asp Lys Cys Tyr
                155                 160                 165

Val Ile Pro Leu Asn Thr Ser Ile Val Met Pro Pro Arg Asn Leu
                170                 175                 180

Leu Glu Leu Leu Ile Asn Ile Lys Ala Gly Thr Tyr Leu Pro Gln
                185                 190                 195

Ser Tyr Leu Ile His Glu His Met Val Ile Thr Asp Arg Ile Glu
                200                 205                 210

Asn Ile Asp His Leu Gly Phe Phe Ile Tyr Arg Leu Cys His Asp
                215                 220                 225

Lys Glu Thr Tyr Lys Leu Gln Arg Arg Glu Thr Ile Lys Gly Ile
                230                 235                 240

Gln Lys Arg Glu Ala Ser Asn Cys Phe Ala Ile Arg His Phe Glu
                245                 250                 255

Asn Lys Phe Ala Val Glu Thr Leu Ile Cys Ser
                260                 265


<210> SEQ ID NO 52
<211> LENGTH: 1189
<212> TYPE: DNA
<213> ORGANISM: Homo sapiens
<220> FEATURE:
<221> NAME/KEY: misc_feature
<223> OTHER INFORMATION: Incyte ID No: 457372.17

<400> SEQUENCE: 52

acaggtgtga gccaccacac ccagcagttt ttttaaggtc acaaaatgac aagactagga     60

tttggaccca gttctgttcg actcaaaata gagtgcccta cacttatgtg tcatgctgca    120
```

```
tttggcaagt cacgtcactt ctttgaatct ccttttccct ctgcaaaaca gtaaccttat    180

ctagcctgca gacttcaaag gtggttatgg agatcaaatg aagtaaaatg ttttaaaaat    240

tgtacaatat ataccaataa aagctattgg ggaggtatat gtatgaacag gtagttggtt    300

tttctaccct gccacctcat aaagagtttg cagtggcacg tagaagggtt tatcttatta    360

tcacaaagct acccatttgc tggccatact gatacttggc acattaaact atcagagaaa    420

tatatgtggc tcctttacaa ctgtgtctag aagggtacat ttccaatcag agttcccagg    480

ttctgacttt ctcccattac atatttgtaa ttagtcatct ttgatactga ttcaaatttt    540

tgattaacat taattatata tatttacaag aatcttataa aaattaagat tttatttcac    600

ctcattttgc cctgtgagat agatggaaat agactatatt ctacccaggt taaaagtaca    660

gataatgaga caaaatgtca atagaacctg aaaaaagatt tttttagttg cctctagtct    720

ctgtttactt ggtatagata gtatgctgct tttttttctt ttttttaaaa tgtaactgct    780

gggttgtttt ttttttcttg ttttttcttt ccctccagga tacaatgtct ctttgctata    840

tgaccttgaa aatcttccgg catccaagga ttccattgtg catcaagctg gcatgttgaa    900

gcgaaattgt tttgcctctg tctttgaaaa atacttccaa ttccaagaag agggcaagga    960

aggagagaac agggcagtta tccattatag ggatgatgag accatgtatg ttgagtctaa   1020

aaaggacaga gtcacagtag tcttcagcac agtgtttaag gatgacgacg atgtggtcat   1080

tggaaaggtg ttcatgcagg tatggagcag acatcttggg ggaaacccat gcatggcgac   1140

ttataccttt gcacccaaac ataccatgag cgtaggaaag agatctagc              1189
```

<210> SEQ ID NO 53
<211> LENGTH: 2539
<212> TYPE: DNA
<213> ORGANISM: Homo sapiens
<220> FEATURE:
<221> NAME/KEY: misc_feature
<223> OTHER INFORMATION: Incyte ID No: 2993696CB1

<400> SEQUENCE: 53

```
ctcgagccgc aagacagcac agacagattg acctattggg gtgtttcgcg agtgtgagag     60

ggaagcgccg cggcctgtat ttctagacct gcccttcgcc tggttcgtgg cgccttgtga    120

ccccgggccc ctgccgcctg caagtcggaa attgcgctgt gctcctgtgc tacggcctgt    180

ggctggactg cctgctgctg cccaactggc tggcaagatg aagctctccc tggtggccgc    240

gatgctgctg ctgctcagcg cggcgcgggc cgaggaggag gacaagaagg aggacgtggg    300

cacggtggtc ggcatcgacc tggggaccac ctactcctgc gtcggcgtgt tcaagaacgg    360

ccgcgtggag atcatcgcca acgatcaggg caaccgcatc acgccgtcct atgtcgcctt    420

cactcctgaa ggggaacgtc tgattggcga tgccgccaag aaccagctca cctccaaccc    480

cgagaacacg gtctttgacg ccaagcggct catcggccgc acgtggaatg acccgtctgt    540

gcagcaggac atcaagttct tgccgttcaa ggtggttgaa aagaaaacta aaccatacat    600

tcaagttgat attggaggtg ggcaaacaaa gacatttgct cctgaagaaa tttctgccat    660

ggttctcact aaaatgaaag aaaccgctga ggcttatttg ggaaagaagg ttacccatgc    720

agttgttact gtaccagcct attttaatga tgcccaacgc caagcaacca aagacgctgg    780

aactattgct ggcctaaatg ttatgaggat catcaacgag cctacggcag ctgctattgc    840

ttatggcctg gataagaggg agggggagaa gaacatcctg gtgtttgacc tgggtggcgg    900

aaccttcgat gtgtctcttc tcaccattga caatggtgtc ttcgaagttg tggccactaa    960
```

```
tggagatact catctgggtg gagaagactt tgaccagcgt gtcatggaac acttcatcaa   1020
actgtacaaa aagaagacgg gcaaagatgt caggaaagac aatagagctg tgcagaaact   1080
ccggcgcgag gtagaaaagg ccaaacgggc cctgtcttct cagcatcaag caagaattga   1140
aattgagtcc ttctatgaag gagaagactt ttctgagacc ctgactcggg ccaaatttga   1200
agagctcaac atggatctgt tccggtctac tatgaagccc gtccagaaag tgttggaaga   1260
ttctgatttg aagaagtctg atattgatga aattgttctt gttggtggct cgactcgaat   1320
tccaaagatt cagcaactgg ttaaagagtt cttcaatggc aaggaaccat cccgtggcat   1380
aaacccagat gaagctgtag cgtatggtgc tgctgtccag gctggtgtgc tctctggtga   1440
tcaagataca ggtgacctgg tactgcttga tgtatgtccc cttacacttg gtattgaaac   1500
tgtgggaggt gtcatgacca aactgattcc aaggaacaca gtggtgccta ccaagaagtc   1560
tcagatcttt tctacagctt ctgataatca accaactgtt acaatcaagg tctatgaagg   1620
tgaaagaccc ctgacaaaag acaatcatct tctgggtaca tttgatctga ctggaattcc   1680
tcctgctcct cgtggggtcc cacagattga agtcaccttt gagatagatg tgaatggtat   1740
tcttcgagtg acagctgaag acaagggtac agggaacaaa aataagatca caatcaccaa   1800
tgaccagaat cgcctgacac ctgaagaaat cgaaaggatg gttaatgatg ctgagaagtt   1860
tgctgaggaa gacaaaaagc tcaaggagcg cattgatact agaaatgagt tggaaagcta   1920
tgcctattct ctaaagaatc agattggaga taaagaaaag ctgggaggta aactttcctc   1980
tgaagataag gagaccatgg aaaaagctgt agaagaaaag attgaatggc tggaaagcca   2040
ccaagatgct gacattgaag acttcaaagc taagaagaag gaactggaag aaattgttca   2100
accaattatc agcaaactct atggaagtgc aggccctccc ccaactggtg aagaggatac   2160
agcagaaaaa gatgagttgt agacactgat ctgctagtgc tgtaatattg taaatactgg   2220
actcaggaac ttttgttagg aaaaaattga aagaacttaa gtctcgaatg taattggaat   2280
cttcacctca gagtggagtt gaaactgcta tagcctaagc ggctgtttac tgcttttcat   2340
tagcagttgc tcacatgtct ttgggtgggg gggagaagaa gaattggcca tcttaaaaag   2400
cgggtaaaaa acctgggtta gggtgtgtgt tcaccttcaa aatgttctat ttaacaactg   2460
ggtcatgtgc atctggtgta ggaagttttt tctaccataa gtgacaccaa taaatgtttg   2520
ttatttacac tggtaagcg                                                2539


<210> SEQ ID NO 54
<211> LENGTH: 654
<212> TYPE: PRT
<213> ORGANISM: Homo sapiens
<220> FEATURE:
<221> NAME/KEY: misc_feature
<223> OTHER INFORMATION: Incyte ID No: 2993696CD1

<400> SEQUENCE: 54

Met Lys Leu Ser Leu Val Ala Ala Met Leu Leu Leu Leu Ser Ala
  1               5                  10                  15

Ala Arg Ala Glu Glu Glu Asp Lys Lys Glu Asp Val Gly Thr Val
                 20                  25                  30

Val Gly Ile Asp Leu Gly Thr Thr Tyr Ser Cys Val Gly Val Phe
                 35                  40                  45

Lys Asn Gly Arg Val Glu Ile Ile Ala Asn Asp Gln Gly Asn Arg
                 50                  55                  60

Ile Thr Pro Ser Tyr Val Ala Phe Thr Pro Glu Gly Glu Arg Leu
```

-continued

```
                65                  70                  75

Ile Gly Asp Ala Ala Lys Asn Gln Leu Thr Ser Asn Pro Glu Asn
                80                  85                  90

Thr Val Phe Asp Ala Lys Arg Leu Ile Gly Arg Thr Trp Asn Asp
                95                  100                 105

Pro Ser Val Gln Gln Asp Ile Lys Phe Leu Pro Phe Lys Val Val
                110                 115                 120

Glu Lys Lys Thr Lys Pro Tyr Ile Gln Val Asp Ile Gly Gly Gly
                125                 130                 135

Gln Thr Lys Thr Phe Ala Pro Glu Glu Ile Ser Ala Met Val Leu
                140                 145                 150

Thr Lys Met Lys Glu Thr Ala Glu Ala Tyr Leu Gly Lys Lys Val
                155                 160                 165

Thr His Ala Val Val Thr Val Pro Ala Tyr Phe Asn Asp Ala Gln
                170                 175                 180

Arg Gln Ala Thr Lys Asp Ala Gly Thr Ile Ala Gly Leu Asn Val
                185                 190                 195

Met Arg Ile Ile Asn Glu Pro Thr Ala Ala Ala Ile Ala Tyr Gly
                200                 205                 210

Leu Asp Lys Arg Glu Gly Glu Lys Asn Ile Leu Val Phe Asp Leu
                215                 220                 225

Gly Gly Gly Thr Phe Asp Val Ser Leu Leu Thr Ile Asp Asn Gly
                230                 235                 240

Val Phe Glu Val Val Ala Thr Asn Gly Asp Thr His Leu Gly Gly
                245                 250                 255

Glu Asp Phe Asp Gln Arg Val Met Glu His Phe Ile Lys Leu Tyr
                260                 265                 270

Lys Lys Lys Thr Gly Lys Asp Val Arg Lys Asp Asn Arg Ala Val
                275                 280                 285

Gln Lys Leu Arg Arg Glu Val Glu Lys Ala Lys Arg Ala Leu Ser
                290                 295                 300

Ser Gln His Gln Ala Arg Ile Glu Ile Glu Ser Phe Tyr Glu Gly
                305                 310                 315

Glu Asp Phe Ser Glu Thr Leu Thr Arg Ala Lys Phe Glu Glu Leu
                320                 325                 330

Asn Met Asp Leu Phe Arg Ser Thr Met Lys Pro Val Gln Lys Val
                335                 340                 345

Leu Glu Asp Ser Asp Leu Lys Lys Ser Asp Ile Asp Glu Ile Val
                350                 355                 360

Leu Val Gly Gly Ser Thr Arg Ile Pro Lys Ile Gln Gln Leu Val
                365                 370                 375

Lys Glu Phe Phe Asn Gly Lys Glu Pro Ser Arg Gly Ile Asn Pro
                380                 385                 390

Asp Glu Ala Val Ala Tyr Gly Ala Ala Val Gln Ala Gly Val Leu
                395                 400                 405

Ser Gly Asp Gln Asp Thr Gly Asp Leu Val Leu Leu Asp Val Cys
                410                 415                 420

Pro Leu Thr Leu Gly Ile Glu Thr Val Gly Gly Val Met Thr Lys
                425                 430                 435

Leu Ile Pro Arg Asn Thr Val Val Pro Thr Lys Lys Ser Gln Ile
                440                 445                 450

Phe Ser Thr Ala Ser Asp Asn Gln Pro Thr Val Thr Ile Lys Val
                455                 460                 465
```

```
Tyr Glu Gly Glu Arg Pro Leu Thr Lys Asp Asn His Leu Leu Gly
                470                 475                 480

Thr Phe Asp Leu Thr Gly Ile Pro Pro Ala Pro Arg Gly Val Pro
                485                 490                 495

Gln Ile Glu Val Thr Phe Glu Ile Asp Val Asn Gly Ile Leu Arg
                500                 505                 510

Val Thr Ala Glu Asp Lys Gly Thr Gly Asn Lys Asn Lys Ile Thr
                515                 520                 525

Ile Thr Asn Asp Gln Asn Arg Leu Thr Pro Glu Glu Ile Glu Arg
                530                 535                 540

Met Val Asn Asp Ala Glu Lys Phe Ala Glu Glu Asp Lys Lys Leu
                545                 550                 555

Lys Glu Arg Ile Asp Thr Arg Asn Glu Leu Glu Ser Tyr Ala Tyr
                560                 565                 570

Ser Leu Lys Asn Gln Ile Gly Asp Lys Glu Lys Leu Gly Gly Lys
                575                 580                 585

Leu Ser Ser Glu Asp Lys Glu Thr Met Glu Lys Ala Val Glu Glu
                590                 595                 600

Lys Ile Glu Trp Leu Glu Ser His Gln Asp Ala Asp Ile Glu Asp
                605                 610                 615

Phe Lys Ala Lys Lys Lys Glu Leu Glu Glu Ile Val Gln Pro Ile
                620                 625                 630

Ile Ser Lys Leu Tyr Gly Ser Ala Gly Pro Pro Pro Thr Gly Glu
                635                 640                 645

Glu Asp Thr Ala Glu Lys Asp Glu Leu
                650

<210> SEQ ID NO 55
<211> LENGTH: 5762
<212> TYPE: DNA
<213> ORGANISM: Homo sapiens
<220> FEATURE:
<221> NAME/KEY: misc_feature
<223> OTHER INFORMATION: Incyte ID No: 331106.6

<400> SEQUENCE: 55

gcgcgaccgt cccgggggtg gggccgggcg cagcggcgag aggaggcgaa ggtggctgcg     60

gtagcagcag cgcggcagcc tcgtgaccca gcccggagcg cagggcggcc gctgcaggtc    120

cccgctcccc tccccgtgcg tccgcccatg gccgccgccg ggcagctgtg cttgctctac    180

ctgtcggcgg ggctcctgtc ccggctcggc gcagccttca acttggacac tcgggaggac    240

aacgtgatcc ggaaatatgg agaccccggg agcctcttcg gcttctcgct ggccatgcac    300

tggcaactgc agcccgagga caagcggctg ttgctcgtgg gggccccgcg ggcagaagcg    360

cttccactgc agagagccaa cagaacggga gggctgtaca gctgcgacat caccgcccgg    420

gggccatgca cgcggatcga gtttgataac gatgctgacc ccacgtcaga aagcaaggaa    480

gatcagtgga tgggggtcac cgtccagagc caaggtccag gggggcaaggt cgtgacatgt    540

gctcaccgat atgaaaaaag gcagcatgtt aatacgaagc aggaatcccg agacatcttt    600

gggcggtgtt atgtcctgag tcagaatctc aggattgaag acgatatgga tgggggagat    660

tggagctttt gtgatgggcg attgagaggc catgagaaat ttggctcttg ccagcaaggt    720

gtagcagcta cttttactaa agactttcat tacattgtat ttggagcccc gggtacttat    780

aactggaaag ggattgttcg tgtagagcaa aagaataaca cttttttga catgaacatc    840
```

-continued

```
tttgaagatg ggccttatga agttggtgga gagactgagc atgatgaaag tctcgttcct    900
gttcctgcta acagttactt aggtttttct ttggactcag ggaaaggtat tgtttctaaa    960
gatgagatca cttttgtatc tggtgctccc agagccaatc acagtggagc cgtggttttg   1020
ctgaagagag acatgaagtc tgcacatctc ctccctgagc acatattcga tggagaaggt   1080
ctggcctctt catttggcta tgatgtggcg gtggtggacc tcaacaagga tgggtggcaa   1140
gatatagtta ttggagcccc acagtatttt gatagagatg gagaagttgg aggtgcagtg   1200
tatgtctaca tgaaccagca aggcagatgg aataatgtga agccaattcg tcttaatgga   1260
accaaagatt ctatgtttgg cattgcagta aaaaatattg gagatattaa tcaagatggc   1320
tacccagata ttgcagttgg agctccgtat gatgacttgg gaaaggtttt tatctatcat   1380
ggatctgcaa atggaataaa taccaaacca acacaggttc tcaagggtat atcaccttat   1440
tttggatatt caattgctgg aaacatggac cttgatcgaa attcctaccc tgatgttgct   1500
gttggttccc tctcagattc agtaactatt ttcagatccc ggcctgtgat taatattcag   1560
aaaaccatca cagtaactcc taacagaatt gacctccgcc agaaaacagc gtgtggggcg   1620
cctagtggga tatgcctcca ggttaaatcc tgttttgaat atactgctaa ccccgctggt   1680
tataatcctt caatatcaat tgtgggcaca cttgaagctg aaaaagaaag aagaaaatct   1740
gggctatcct caagagttca gtttcgaaac caaggttctg agcccaaata tactcaagaa   1800
ctaactctga agaggcagaa acagaaagtg tgcatggagg aaaccctgtg gctacaggat   1860
aatatcagag ataaactgcg tcccattccc ataactgcct cagtggagat ccaagagcca   1920
agctctcgta ggcgagtgaa ttcacttcca gaagttcttc caattctgaa ttcagatgaa   1980
cccaagacag ctcatattga tgttcacttc ttaaaagagg gatgtggaga cgacaatgta   2040
tgtaacagca accttaaact agaatataaa ttttgcaccc gagaaggaaa tcaagacaaa   2100
ttttcttatt taccaattca aaaaggtgta ccagaactag ttctaaaaga tcagaaggat   2160
attgctttag aaataacagt gacaaacagc ccttccaacc caaggaatcc cacaaaagat   2220
ggcgatgacg cccatgaggc taaactgatt gcaacgtttc cagacacttt aacctattct   2280
gcatatagag aactgagggc tttccctgag aaacagttga gttgtgttgc caaccagaat   2340
ggctcgcaag ctgactgtga gctcggaaat ccttttaaaa gaaattcaaa tgtcactttt   2400
tatttggttt taagtacaac tgaagtcacc tttgacaccc cagatctgga tattaatctg   2460
aagttagaaa caacaagcaa tcaagataat ttggctccaa ttacagctaa agcaaaagtg   2520
gttattgaac tgcttttatc ggtctcggga gttgctaaac cttcccaggt gtattttgga   2580
ggtacagttg ttggcgagca agctatgaaa tctgaagatg aagtgggaag tttaatagag   2640
tatgaattca gggtaataaa cttaggtaaa cctcttacaa acctcggcac agcaaccttg   2700
aacattcagt ggccaaaaga aattagcaat gggaaatggt tgctttattt ggtgaaagta   2760
gaatccaaag gattggaaaa ggtaacttgt gagccacaaa aggagataaa ctccctgaac   2820
ctaacggagt ctcacaactc aagaaagaaa cgggaaatta ctgaaaaaca gatagatgat   2880
aacagaaaat tttctttatt tgctgaaaga aaataccaga ctcttaactg tagcgtgaac   2940
gtgaactgtg tgaacatcag atgcccgctg cgggggctgg acagcaaggc gtctcttatt   3000
ttgcgctcga ggttatggaa cagcacattt ctagaggaat attccaaact gaactacttg   3060
gacattctca tgcgagcctt cattgatgtg actgctgctg ccgaaaatat caggctgcca   3120
aatgcaggca ctcaggttcg agtgactgtg tttccctcaa agactgtagc tcagtattcg   3180
ggagtacctt ggtggatcat cctagtggct attctcgctg ggatcttgat gcttgcttta   3240
```

-continued

```
ttagtgttta tactatggaa gtgtggtttc ttcaagagaa ataagaaaga tcattatgat   3300
gccacatatc acaaggctga gatccatgct cagccatctg ataaagagag gcttacttct   3360
gatgcatagt attgatctac ttctgtaatt gtgtggattc tttaaacgct ctaggtacga   3420
tgacagtgtt ccccgatacc atgctgtaag gatccggaaa gaagagcgag agatcaaaga   3480
tgaaaagtat attgataacc ttgaaaaaaa acagtggatc acaaagtgga acagaaatga   3540
aagctactca tagcgggggc ctaaaaaaaa aaaaagcttc acagtaccca aactgctttt   3600
tccaactcag aaattcaatt tggatttaaa agcctgctca atccctgagg actgatttca   3660
gagtgactac acacagtacg aacctacagt tttaactgtg gatattgtta cgtagcctaa   3720
ggctcctgtt ttgcacagcc aaatttaaaa ctgttggaat ggatttttct ttaactgccg   3780
taatttaact ttctgggttg cctttgtttt tggcgtggct gacttacatc atgtgttggg   3840
gaagggcctg cccagttgca ctcaggtgac atcctccaga tagtgtagct gaggaggcac   3900
ctacactcac ctgcactaac agagtggccg tcctaacctc gggcctgctg cgcagacgtc   3960
catcacgtta gctgtcccac atcacaagac tatgccattg ggtagttgt gtttcaacgg   4020
aaagtgctgt cttaaactaa atgtgcaata gaaggtgatg ttgccatcct accgtctttt   4080
cctgtttcct agctgtgtga atacctgctc acgtcaaatg catacaagtt tcattctccc   4140
tttcactaaa aacacacagg tgcaacagac ttgaatgcta gttatactta tttgtatatg   4200
gtatttattt tttcttttct ttacaaacca ttttgttatt gactaacagg ccaaagagtc   4260
tccagtttac ccttcaggtt ggtttaatca atcagaatta gaattagagc atgggaggtc   4320
atcactttga cctaaattat ttactgcaaa aagaaaatct ttataaatgt accagagaga   4380
gttgttttaa taacttatct ataaactata acctctcctt catgacagcc tccaccccac   4440
aacccaaaag gtttaagaaa tagaattata actgtaaaga tgtttatttc aggcattgga   4500
tattttttac tttagaagcc tgcataatgt ttctggattt catactgtaa cattcaggaa   4560
ttcttggaga aaatgggttt attcactgaa ctctagtgcg gtttactcac tgctgcaaat   4620
actgtatatt caggacttga aagaaatggt gaatgcctat ggtggatcca aactgatcca   4680
gtataagact actgaatctg ctaccaaaac agttaatcag tgagtcgatg ttctattttt   4740
tgttttgttt cctcccctat ctgtattccc aaaaattact ttggggctaa tttaacaaga   4800
actttaaatt gtgttttaat tgtaaaaatg gcagggggtg gaattattac tctatacatt   4860
caacagagac tgaatagata tgaaagctga ttttttttaa ttaccatgct tcacaatgtt   4920
aagttatatg gggagcaaca gcaaacaggt gctaatttgt tttggatata gtataagcag   4980
tgtctgtgtt ttgaaagaat agaacacagt ttgtagtgcc actgttgttt tggggggct   5040
tttttctttt cggaaatctt aaaccttaag atactaagga cgttgttttg gttgtacttt   5100
ggaattctta gtcacaaaat atattttgtt tacaaaaatt tctgtaaaac aggttataac   5160
agtgtttaaa gtctcagttt cttgcttggg gaacttgtgt ccctaatgtg tttagattgc   5220
tagattgcta aggagctgat actttgacag tgtttttaga cctgtgttac taaaaaaaag   5280
atgaatgtcc tgaaaagggt gttgggaggg tggttcaaca aagaaacaaa gatgttatgg   5340
tgtttagatt tatggttgtt aaaaatgtca tctcaagtca agtcactggt ctgtttgcat   5400
ttgatacatt tttgtactaa ctagcattgt aaaattattt catgattaga aattacctgt   5460
ggatatttgt ataaaagtgt gaaataaatt ttttataaaa gtgttcattg tttcgtaaca   5520
cagcattgta tatgtgaagc aaactctaaa attataaatg acaacctgaa ttatctattt   5580
```

```
catcaaacca aagttcagtg tttttatttt tggtgtctca tgtaatctca gatcagccaa   5640

agatactagt gccaaagcaa tgggattcgg ggtttttttc tgttttcgct ctatgtaggt   5700

gatcctcaag tctttcattt tccttcttta tgattaaaag aaacctacag gtatttaaca   5760

ac                                                                   5762


<210> SEQ ID NO 56
<211> LENGTH: 2471
<212> TYPE: DNA
<213> ORGANISM: Homo sapiens
<220> FEATURE:
<221> NAME/KEY: misc_feature
<223> OTHER INFORMATION: Incyte ID No: 1256895CB1

<400> SEQUENCE: 56

ccgcgcgtcg cctgtcctcc gagccagtcg ctgacagccg cggcgccgcg agcttctcct     60

ctcctcacga ccgaggcaga gcagtcatta tggcgaacct tggctgctgg atgctggttc    120

tctttgtggc cacatggagt gacctgggcc tctgcaagaa gcgcccgaag cctggaggat    180

ggaacactgg gggcagccga tacccggggc agggcagccc tggaggcaac cgctacccac    240

ctcagggcgg tggtggctgg gggcagcctc atggtggtgg ctgggggcag cctcatggtg    300

gtggctgggg gcagccccat ggtggtggct ggggacagcc tcatggtggt ggctggggtc    360

aaggaggtgg cacccacagt cagtggaaca agccgagtaa gccaaaaacc aacatgaagc    420

acatggctgg tgctgcagca gctggggcag tggtgggggg ccttggcggc tacgtgctgg    480

gaagtgccat gagcaggccc atcatacatt tcggcagtga ctatgaggac cgttactatc    540

gtgaaaacat gcaccgttac cccaaccaag tgtactacag gcccatggat gagtacagca    600

accagaacaa ctttgtgcac gactgcgtca atatcacaat caagcagcac acggtcacca    660

caaccaccaa gggggagaac ttcaccgaga ccgacgttaa gatgatggag cgcgtggttg    720

agcagatgtg tatcacccag tacgagaggg aatctcaggc ctattaccag agaggatcga    780

gcatggtcct cttctcctct ccacctgtga tcctcctgat ctctttcctc atcttcctga    840

tagtgggatg aggaaggtct tcctgttttc accatctttc taatcttttt ccagcttgag    900

ggaggcggta tccacctgca gcccttttag tggtggtgtc tcactctttc ttctctcttt    960

gtcccggata ggctaatcaa tacccttggc actgatgggc actggaaaac atagagtaga   1020

cctgagatgc tggtcaagcc ccctttgatt gagttcatca tgagccgttg ctaatgccag   1080

gccagtaaaa gtataacagc aaataaccat tggttaatct ggacttattt ttggacttag   1140

tgcaacaggt tgaggctaaa acaaatctca gaacagtctg aaataccttt gcctggatac   1200

ctctggctcc ttcagcagct agagctcagt atactaatgc cctatcttag tagagatttc   1260

atagctattt agagatattt tccattttaa gaaaacccga caacatttct gccaggtttg   1320

ttaggaggcc acatgatact tattcaaaaa aatcctagag attcttagct cttgggatgc   1380

aggctcagcc cgctggagca tgagctctgt gtgtaccgag aactggggtg atgttttact   1440

tttcacagta tgggctacac agcagctgtt caacaagagt aaatattgtc acaacactga   1500

acctctggct agaggacata ttcacagtga acataactgt aacatatatg aaaggcttct   1560

gggacttgaa atcaaatgtt tgggaatggt gcccttggag gcaacctccc attttagatg   1620

tttaaaggac cctatatgtg gcattccttt ctttaaacta taggtaatta aggcagctga   1680

aaagtaaatt gccttctaga cactgaaggc aaatctcctt tgtccattta cctggaaacc   1740

agaatgattt tgacatacag gagagctgca gttgtgaaag caccatcatc atagaggatg   1800
```

-continued

```
atgtaattaa aaaatggtca gtgtgcaaag aaaagaactg cttgcatttc tttatttctg   1860

tctcataatt gtcaaaaacc agaattaggt caagttcata gtttctgtaa ttggcttttg   1920

aatcaaagaa tagggagaca atctaaaaaa tatcttaggt tggagatgac agaaatatga   1980

ttgatttgaa gtggaaaaag aaattctgtt aatgttaatt aaagtaaaat tattccctga   2040

attgtttgat attgtcacct agcagatatg tattactttt ctgcaatgtt attattggct   2100

tgcactttgt gagtattcta tgtaaaaata tatatgtata taaaatatat attgcatagg   2160

acagacttag gagttttgtt tagagcagtt aacatctgaa gtgtctaatg cattaacttt   2220

tgtaaggtac tgaatactta atatgtggga aacccttttg cgtggtcctt aggcttacaa   2280

tgtgcactga atcgtttcat gtaagaatcc aaagtggaca ccattaacag gtctttgaaa   2340

tatgcatgta ctttatattt tctatatttg taactttgca tgttcttgtt ttgttatata   2400

aaaaaattgt aaatgtttaa tatctgactg aaattaaacg agcgaagatg agcaccaaaa   2460

aaaaaaaaaa a                                                        2471
```

<210> SEQ ID NO 57
<211> LENGTH: 253
<212> TYPE: PRT
<213> ORGANISM: Homo sapiens
<220> FEATURE:
<221> NAME/KEY: misc_feature
<223> OTHER INFORMATION: Incyte ID No: 1256895CD1

<400> SEQUENCE: 57

```
Met Ala Asn Leu Gly Cys Trp Met Leu Val Leu Phe Val Ala Thr
  1               5                  10                  15

Trp Ser Asp Leu Gly Leu Cys Lys Lys Arg Pro Lys Pro Gly Gly
                 20                  25                  30

Trp Asn Thr Gly Gly Ser Arg Tyr Pro Gly Gln Gly Ser Pro Gly
                 35                  40                  45

Gly Asn Arg Tyr Pro Pro Gln Gly Gly Gly Gly Trp Gly Gln Pro
                 50                  55                  60

His Gly Gly Gly Trp Gly Gln Pro His Gly Gly Gly Trp Gly Gln
                 65                  70                  75

Pro His Gly Gly Gly Trp Gly Gln Pro His Gly Gly Gly Trp Gly
                 80                  85                  90

Gln Gly Gly Gly Thr His Ser Gln Trp Asn Lys Pro Ser Lys Pro
                 95                 100                 105

Lys Thr Asn Met Lys His Met Ala Gly Ala Ala Ala Ala Gly Ala
                110                 115                 120

Val Val Gly Gly Leu Gly Gly Tyr Val Leu Gly Ser Ala Met Ser
                125                 130                 135

Arg Pro Ile Ile His Phe Gly Ser Asp Tyr Glu Asp Arg Tyr Tyr
                140                 145                 150

Arg Glu Asn Met His Arg Tyr Pro Asn Gln Val Tyr Tyr Arg Pro
                155                 160                 165

Met Asp Glu Tyr Ser Asn Gln Asn Asn Phe Val His Asp Cys Val
                170                 175                 180

Asn Ile Thr Ile Lys Gln His Thr Val Thr Thr Thr Thr Lys Gly
                185                 190                 195

Glu Asn Phe Thr Glu Thr Asp Val Lys Met Met Glu Arg Val Val
                200                 205                 210

Glu Gln Met Cys Ile Thr Gln Tyr Glu Arg Glu Ser Gln Ala Tyr
                215                 220                 225
```

```
Tyr Gln Arg Gly Ser Ser Met Val Leu Phe Ser Ser Pro Pro Val
                230                 235                 240

Ile Leu Leu Ile Ser Phe Leu Ile Phe Leu Ile Val Gly
                245                 250


<210> SEQ ID NO 58
<211> LENGTH: 5681
<212> TYPE: DNA
<213> ORGANISM: Homo sapiens
<220> FEATURE:
<221> NAME/KEY: misc_feature
<223> OTHER INFORMATION: Incyte ID No: 474630.29

<400> SEQUENCE: 58

cccgcgcccg ccctcggaca gtccctgctc gcccgcgcgc tgcagcccca tctcctagcg     60

gcagcccagg cgcggaggga gcgagtccgc cccgaggtag gtccaggacg ggcgcacagc    120

agcagccgag gctggccggg agagggagga agaggatggc agggccacgc cccagcccat    180

gggccaggct gctcctggca gccttgatca gcgtcagcct ctctgggacc ttggcaaacc    240

gctgcaagaa ggccccagtg aagagctgca cggagtgtgt ccgtgtggat aaggactgcg    300

cctactgcac agacgagatg ttcagggacc ggcgctgcaa cacccaggcg gagctgctgg    360

ccgcgggctg ccagcgggag agcatcgtgg tcatggagag cagcttccaa atcacagagg    420

agacccagat tgacaccacc ctgcggcgca gccagatgtc cccccaaggc ctgcgggtcc    480

gtctgcggcc cggtgaggag cggcattttg agctggaggt gtttgagcca ctggagagcc    540

ccgtggacct gtacatcctc atggacttct ccaactccat gtccgatgat ctggacaacc    600

tcaagaagat ggggcagaac ctggctcggg tcctgagcca gctcaccagc gactacacta    660

ttggatttgg caagtttgtg gacaaagtca gcgtcccgca gacggacatg aggcctgaga    720

agctgaagga gccctggccc aacagtgacc ccccttctc cttcaagaac gtcatcagcc     780

tgacagaaga tgtggatgag ttccggaata aactgcaggg agagcggatc tcaggcaacc    840

tggatgctcc tgagggcggc ttcgatgcca tcctgcagac agctgtgtgc acgagggaca    900

ttggctggcg cccggacagc acccacctgc tggtcttctc caccgagtca gccttccact    960

atgaggctga tggcgccaac gtgctggctg gcatcatgag ccgcaacgat gaacggtgcc   1020

acctggacac cacgggcacc tacacccagt acaggacaca ggactacccg tcggtgccca   1080

ccctggtgcg cctgctcgcc aagcacaaca tcatccccat ctttgctgtc accaactact   1140

cctatagcta ctacgagaag cttcacacct atttccctgt ctcctcactg gggggtgctgc  1200

aggaggactc gtccaacatc gtggagctgc tggaggaggc cttcaatcgg atccgctcca   1260

acctggacat ccgggcccta gacagccccc gaggccttcg gacagaggtc acctccaaga   1320

tgttccagaa gacgaggact gggtcctttc acatccggcg gggggaagtg ggtatatacc   1380

aggtgcagct gcgggccctt gagcacgtgg atgggacgca cgtgtgccag ctgccggagg   1440

accagaaggg caacatccat ctgaaacctt ccttctccga cggcctcaag atggacgcgg   1500

gcatcatctg tgatgtgtgc acctgcgagc tgcaaaaaga ggtgcggtca gctcgctgca   1560

gcttcaacgg agacttcgtg tgcggacagt gtgtgtgcag cgagggctgg agtggccaga   1620

cctgcaactg ctccaccggc tctctgagtg acattcagcc ctgcctgcgg gagggcgagg   1680

acaagccgtg ctccggccgt ggggagtgcc agtgcgggca ctgtgtgtgc tacggcgaag   1740

gccgctacga gggtcagttc tgcgagtatg acaacttcca gtgtccccgc acttccgggt   1800

tcctctgcaa tgaccgagga cgctgctcca tgggccagtg tgtgtgtgag cctggttgga   1860
```

-continued

```
caggcccaag ctgtgactgt cccctcagca atgccacctg catcgacagc aatgggggca   1920
tctgtaatgg acgtggccac tgtgagtgtg gccgctgcca ctgccaccag cagtcgctct   1980
acacggacac catctgcgag atcaactact cggcgatcca cccgggcctc tgcgaggacc   2040
tacgctcctg cgtgcagtgc caggcgtggg gcaccggcga gaagaagggg cgcacgtgtg   2100
aggaatgcaa cttcaaggtc aagatggtgg acgagcttaa gagagccgag gaggtggtgg   2160
tgcgctgctc cttccgggac gaggatgacg actgcaccta cagctacacc atggaaggtg   2220
acggcgcccc tgggcccaac agcactgtcc tggtgcacaa gaagaaggac tgccctccgg   2280
gctccttctg gtggctcatc cccctgctcc tcctcctcct gccgctcctg gccctgctac   2340
tgctgctatg ctggaagtac tgtgcctgct gcaaggcctg cctggcactt ctcccgtgct   2400
gcaaccgagg tcacatggtg ggctttaagg aagaccacta catgctgcgg gagaacctga   2460
tggcctctga ccacttggac acgcccatgc tgcgcagcgg gaacctcaag ggccgtgacg   2520
tggtccgctg gaaggtcacc aacaacatgc agcggcctgg ctttgccact catgccgcca   2580
gcatcaaccc cacagagctg gtgccctacg ggctgtcctt gcgcctggcc cgcctttgca   2640
ccgagaacct gctgaagcct gacactcggg agtgcgccca gctgcgccag gaggtggagg   2700
agaacctgaa cgaggtctac aggcagatct ccggtgtaca caagctccag cagaccaagt   2760
tccggcagca gcccaatgcc gggaaaaagc aagaccacac cattgtggac acagtgctga   2820
tggcgccccg ctcggccaag ccggccctgc tgaagcttac agagaagcag gtggaacaga   2880
gggccttcca cgacctcaag gtggcccccg gctactacac cctcactgca gaccaggacg   2940
cccggggcat ggtggagttc caggagggcg tggagctggt ggacgtacgg gtgcccctct   3000
ttatccggcc tgaggatgac gacgagaagc agctgctggt ggaggccatc gacgtgcccg   3060
caggcactgc caccctcggc cgccgcctgg taaacatcac catcatcaag gagcaagcca   3120
gagacgtggt gtcctttgag cagcctgagt tctcggtcag ccgcggggac caggtggccc   3180
gcatccctgt catccggcgt gtcctggacg gcgggaagtc ccaggtctcc taccgcacac   3240
aggatggcac cgcgcagggc aaccgggact acatccccgt ggagggtgag ctgctgttcc   3300
agcctgggga ggcctggaaa gagctgcagg tgaagctcct ggagctgcaa gaagttgact   3360
ccctcctgcg gggccgccag gtccgccgtt tccacgtcca gctcagcaac cctaagtttg   3420
gggcccacct gggccagccc cactccacca ccatcatcat cagggaccca gatgaactgg   3480
accggagctt cacgagtcag atgttgtcat cacagccacc ccctcacggc gacctgggcg   3540
ccccgcagaa ccccaatgct aaggccgctg ggtccaggaa gatccatttc aactggctgc   3600
ccccttctgg caagccaatg ggtacagggg taaagtactg gattcagggt gactccgaat   3660
ccgaagccca cctgctcgac agcaaggtgc cctcagtgga gctcaccaac ctgtacccgt   3720
attgcgacta tgagatgaag gtgtgcgcct acggggctca gggcgaggga ccctacagct   3780
ccctggtgtc ctgccgcacc caccaggaag tgcccagcga gccagggcgt ctggccttca   3840
atgtcgtctc ctccacggtg acccagctga gctgggctga gccggctgag accaacggtg   3900
agatcacagc ctacgaggtc tgctatggcc tggtcaacga tgacaaccga cctattgggc   3960
ccatgaagaa agtgctggtt gacaacccta agaaccggat gctgcttatt gagaaccttc   4020
gggagtccca gccctaccgc tacacggtga aggcgcgcaa cggggccggc tgggggcctg   4080
agcgggaggc catcatcaac ctggccaccc agcccaagag gcccatgtcc atccccatca   4140
tccctgacat ccctatcgtg gacgcccaga gcggggagga ctacgacagc ttccttatgt   4200
```

-continued

```
acagcgatga cgttctacgc tctccatcgg gcagccagag gcccagcgtc tccgatgaca   4260

ctgagcacct ggtgaatggc cggatggact ttgccttccc gggcagcacc aactccctgc   4320

acaggatgac cacgaccagt gctgctgcct atggcaccca cctgagccca cacgtgcccc   4380

accgcgtgct aagcacatcc tccaccctca cacgggacta caactcactg acccgctcag   4440

aacactcaca ctcgaccaca ctgccgaggg actactccac cctcacctcc gtctcctccc   4500

acgactctcg cctgactgct ggtgtgcccg acacgcccac ccgcctggtg ttctctgccc   4560

tggggcccac atctctcaga gtgagctggc aggagccgcg gtgcgagcgg ccgctgcagg   4620

gctacagtgt ggagtaccag ctgctgaacg gcggtgagct gcatcggctc aacatcccca   4680

accctgccca gacctcggtg gtggtggaag acctcctgcc caaccactcc tacgtgttcc   4740

gcgtgcgggc ccagagccag gaaggctggg gccgagagcg tgagggtgtc atcaccattg   4800

aatcccaggt gcacccgcag agcccactgt gtcccctgcc aggctccgcc ttcactttga   4860

gcactcccag tgccccaggc ccgctggtgt tcactgccct gagcccagac tcgctgcagc   4920

tgagctggga gcggccacgg aggcccaatg gggatatcgt cggctacctg gtgacctgtg   4980

agatggccca aggaggaggg ccagccaccg cattccgggt ggatggagac agccccgaga   5040

gccggctgac cgtgccgggc ctcagcgaga acgtgcccta caagttcaag gtgcaggcca   5100

ggaccactga gggcttcggg ccagagcgcg agggcatcat caccatagag tcccaggatg   5160

gaggaccctt cccgcagctg ggcagccgtg ccgggctctt ccagcacccg ctgcaaagcg   5220

agtacagcag catcaccacc acccacacca gcgccaccga gcccttccta gtggatgggc   5280

tgaccctggg ggcccagcac ctggaggcag gcggctccct cacccggcat gtgacccagg   5340

agtttgtgag ccggacactg accaccagcg gaacccttag cacccacatg gaccaacagt   5400

tcttccaaac ttgaccgcac cctgccccac ccccgccatg tcccactagg cgtcctcccg   5460

actcctctcc cggagcctcc tcagctactc catccttgca cccctggggg cccagcccac   5520

ccgcatgcac agagcagggg ctaggtgtct cctgggaggc atgaaggggg caaggtccgt   5580

cctctgtggg cccaaaccta tttgtaacca aagagctggg agcagcacaa ggacccagcc   5640

tttgttctgc acttaataaa tggttttgct actgctaaaa a                       5681
```

```
<210> SEQ ID NO 59
<211> LENGTH: 1366
<212> TYPE: DNA
<213> ORGANISM: Homo sapiens
<220> FEATURE:
<221> NAME/KEY: misc_feature
<223> OTHER INFORMATION: Incyte ID No: 1256295.18

<400> SEQUENCE: 59

ctttgtcctc cagtggctgg taggcagtgg ctgggaggca gcggcccaat tagtgtcgtg     60

cggcccgtgg cgaggcgagg tccggggagc gagcgagcaa gcaaggcggg aggggtggcc    120

ggagctgcgg cggctggcac aggaggagga gcccgggcgg gcgaggggcg gccggagagc    180

gccagggcct gagctgccgg agcggcgcct gtgagtgagt gcagaaagca ggcgcccgcg    240

cgctagccgt ggcaggagca gcccgcacgc cgcgctctct ccctgggcga cctgcagttt    300

gcaatatgac tttggaggaa ttctcggctg gagagcagaa gaccgaaagg atggataagg    360

tgggggatgc cctggaggaa gtgctcagca aagccctgag tcagcgcacg atcactgtcg    420

gggtgtacga agcggccaag ctgctcaacg tcgaccccga taacgtggtg ttgtgcctgc    480

tggcggcgga cgaggacgac gacagagatg tggctctgca gatccacttc accctgatcc    540
```

-continued

```
aggcgttttg ctgcgagaac gacatcaaca tcctgcgcgt cagcaacccg ggccggctgg    600

cggagctcct gctcttggag accgacgctg gccccgcggc gagcgagggc gccgagcagc    660

ccccggacct gcactgcgtg ctggtgacga atccacattc atctcaatgg aaggatcctg    720

ccttaagtca acttatttgt ttttgccggg aaagtcgcta catggatcaa tgggttccag    780

tgattaatct ccctgaacgg tgatggcatc tgaatgaaaa taactgaacc aaattgcact    840

gaagtttttg aaataccttt gtagttactc aagcagttac tccctacact gatgcaagga    900

ttacagaaac tgatgccaag ggctgagtg agttcaacta catgttctgg gggcccggag    960

atagatgact ttgcagatgg aaagaggtga aaatgaagaa ggaagctgtg ttgaaacaga   1020

aaaataagtc aaaaggaaca aaaattacaa agaaccatgc aggaaggaaa actatgtatt   1080

aatttagaat ggttgagtta cattaaaata aaccaaatat gttaaagttt aagtgtgcag   1140

ccatagtttg ggtatttttg gtttatatgc cctcaagtaa aagaaaagcc gaaagggtta   1200

atcatatttg aaaaccatat tttattgtat tttgatgaga tattaaattc tcaaagtttt   1260

attataaatt ctactaagtt attttatgac atgaaaagtt atttatgcta taaatttttt   1320

gaaacacaat acctacaata aactggtatg aataattgca tcattt                  1366
```

<210> SEQ ID NO 60
<211> LENGTH: 1432
<212> TYPE: DNA
<213> ORGANISM: Homo sapiens
<220> FEATURE:
<221> NAME/KEY: misc_feature
<223> OTHER INFORMATION: Incyte ID No: 444096.1

<400> SEQUENCE: 60

```
gacccatcag ggcttctgta aggctgagtg ggtcccatgc ctgaaaggag agccaggctg     60

agcctggcct gagtctccca tgtgtaacag gtacgaggat gaaatcaaca agcacactgc    120

tgcagagaac gagtttgtgg tgctcaagaa ggatgtggat gcagcataca tgggccggat    180

ggatctgcat ggcaaagtgg gcaccttgac ccaggagatt gacttcctgc agcaactcta    240

tgaaatggag ctgagccaag tgcagaccca cgtgtctaac accaatgtgg tgctgtccat    300

ggacaacaac cgcaacctgg acctggacag catcatcgcc gaggtcaagg cccagtatga    360

gctgattgcc cagaggagcc gggctgaggc cgaggcctgg taccagacca agtatgagga    420

gctgcaggtg actgctggga agcatgggga caacctgcgg gacaccaaga acgagattgc    480

tgagctcacc cgcactatcc agaggctgca gggggaggct gatgcagcca agaagcagtg    540

tcagcagctg cagacggcca ttgcggaacg cggagcagcg tggggagctg gcactcaagg    600

atgctcagaa gaagcttggg gatctggatg tggccctgca ccaggccaag gaggacctga    660

cacggctgct gcgtgactac caggagctga tgaatgtcaa gctggccctg gacgtggaga    720

ttgccaccta ccgcaagctt ctggagagcg aggagagcag gatgtctgga gaatgtccca    780

gtgcagtcag catttctgtg actggcaact ccaccactgt gtgcggaggt ggcgcaccag    840

ctttggaggt ggcatctccc tgggtgggag tgggggggcc accaagggtg gattcagcac    900

aaatgtgggc tatagcaccg tcaagggagg gccagtctct gcgggcacct ccatcctgcg    960

gaagaccact acggtcaaga cgtccagcca gaggtattag ctgctgagcc ctgcaaggcc   1020

ccctgcaatc atgtccctgc cctcctcacc ccacctctgc tgtcctttcc agtcacttct   1080

caggagcagg aacagccagg ggacctcaga cccagggtat tttcatacca gactatttgc   1140

atcttgggaa gcgctcaaat ctactcaggt tttctccttg gtcctgcagt aggatgggag   1200
```

-continued

```
ggaaggttaa agttgccagc ttgagtgatg tgcttgggtg acttgggggt gaccttttga   1260

ccaccgagag gaggctgaat ttctcaagcc attaggagag agagaaattg ggagtggtcc   1320

ccaaagaccc ttcaacctcc ccagtccccc accagaccca ccctctccct gaatctaccc   1380

acatccccct tccctgtctg tgtctcaata aatggtgcaa ctgcaaaaaa aa           1432


<210> SEQ ID NO 61
<211> LENGTH: 4559
<212> TYPE: DNA
<213> ORGANISM: Homo sapiens
<220> FEATURE:
<221> NAME/KEY: misc_feature
<223> OTHER INFORMATION: Incyte ID No: 008942.10

<400> SEQUENCE: 61

agcgggcggc gcgcacactg ctcgctgggc cgcggctccc gggtgtccca ggcccggccg     60

gtgcgcagag catggcgggt gcgggcccga agcggcgcgc gctagcggcg ccggcggccg    120

aggagaagga agaggcgcgg gagaagatgc tggccgccaa gagcgcggac ggctcggcgc    180

cggcaggcga gggcgagggc gtgaccctgc agcggaacat cacgctgctc aacggcgtgg    240

ccatcatcgt ggggaccatt atcggctcgg gcatcttcgt gacgcccacg ggcgtgctca    300

aggaggcagg ctcgccgggg ctggcgctgg tggtgtgggc cgcgtgcggc gtcttctcca    360

tcgtgggcgc gctctgctac gcggagctcg gcaccaccat ctccaaatcg ggcggcgact    420

acgcctacat gctggaggtc tacggctcgc tgcccgcctt cctcaagctc tggatcgagc    480

tgctcatcat ccggccttca tcgcagtaca tcgtggccct ggtcttcgcc acctacctgc    540

tcaagccgct cttccccacc tgcccggtgc ccgaggaggc agccaagctc gtggcctgcc    600

tgtgcgtgct gctgctcacg gccgtgaact gctacagcgt gaaggccgcc acccgggtcc    660

aggatgcctt tgccgccgcc aagctcctgg ccctggccct gatcatcctg ctgggcttcg    720

tccagatcgg gaagggtgat gtgtccaatc tagatcccaa cttctcattt gaaggcacca    780

aactggatgt ggggaacatt gtgctggcat tatacagcgg cctctttgcc tatggaggat    840

ggaattactt gaatttcgtc acagaggaaa tgatcaaccc ctacagaaac ctgcccctgg    900

ccatcatcat ctccctgccc atcgtgacgc tggtgtacgt gctgaccaac ctggcctact    960

tcaccaccct gtccaccgag cagatgctgt cgtccgaggc cgtggccgtg gacttcggga   1020

actatcacct gggcgtcatg tcctggatca tccccgtctt cgtgggcctg tcctgctttg   1080

gctccgtcaa tgggtccctg ttcacatcct ccaggctctt cttcgtgggg tcccgggaag   1140

gccacctgcc ctccatcctc tccatgatcc acccacagct cctcaccccc gtgccgtccc   1200

tcgtgttcac gtgtgtgatg acgctgctct acgccttctc caaggacatc ttctccgtca   1260

tcaacttctt cagcttcttc aactggctct gcgtggccct ggccatcatc ggcatgatct   1320

ggctgcgcca cagaaagcct gagcttgagc ggcccatcaa ggtgaacctg gccctgcctg   1380

tgttcttcat cctggcctgc ctcttcctga tcgccgtctc cttctggaag acacccgtgg   1440

agtgtggcat cggcttcacc atcatcctca gcgggctgcc cgtctacttc ttcggggtct   1500

ggtggaaaaa caagcccaag tggctcctcc agggcatctt ctccacgacc gtcctgtgtc   1560

agaagctcat gcaggtggtc ccccaggaga catagccagg aggccgagtg gctgccggag   1620

gagcatgcgc agaggccagt taaagtagat cacctcctcg aacccactcc ggttccccgc   1680

aacccacagc tcagctgccc atcccagtcc ctcgccgtcc ctcccaggtc gggcagtgga   1740

ggctgctgtg aaaactctgg tacgaatctc atccctcaac tgagggccag ggacccaggt   1800
```

-continued

```
gtgcctgtgc tcctgcccag gagcagcttt tggtctcctt gggccctttt tcccttccct   1860
cctttgttta cttatatata tattttttt aaacttaaat tttgggtcaa cttgacacca   1920
ctaagatgat tttttaagga gctgggggaa ggcaggagcc ttcctttctc ctgccccaag   1980
ggcccagacc ctgggcaaac agagctactg agacttggaa cctcattgct accacagact   2040
tgcactgaag ccggacagct gcccagacac atgggcttgt gacattcgtg aaaaccaacc   2100
ctgtgggctt atgtctctgc cttagggttt gcagagtgga aactcagccg tagggtggca   2160
ctgggagggg gtgggggatc tgggcaaggt gggtgattcc tcccaggagg tgcttgaggc   2220
cccgatggac tcctgaccat aatcctagcc ccgagacacc atcctgagcc agggaacagc   2280
cccagggttg gggggtgccg gcatctcccc tagctcacca ggcctggcct ctgggcagtg   2340
tggcctcttg gctatttctg tgtccagttt tggaggctga gttctggttc atgcagacaa   2400
agccctgtcc ttcagtcttc tagaaacaga gacaagaaag gcagacacac cgcggccagg   2460
cacccatgtg ggcgcccacc ctgggctcca cacagcagtg tcccctgccc cagaggtcgc   2520
agctaccctc agcctccaat gcattggcct ctgtaccgcc cggcagcccc ttctggccgg   2580
tgctgggttc ccactcccgg cctaggcacc tccccgctct ccctgtcacg ctcatgtcct   2640
gtcctggtcc tgatgcccgt tgtctaggag acagagccaa gcactgctca cgtctctgcc   2700
gcctgcgttt ggaggcccct gggctctcac ccagtcccca cccgcctgca gagagggaac   2760
tagggcaccc cttgtttctg ttgttcccgt gaattttttt cgctatggga ggcagccgag   2820
gcctggccaa tgcggcccac tttcctgagc tgtcgctgcc tccatggcag cagccaagga   2880
cccccagaac aagaagaccc ccccgcagga tccctcctga gctcgggggg ctctgccttc   2940
tcagggcccc gggcttccct tctccccagc cagaggtgga gccaagtggt ccagcgtcac   3000
tccagtgctc agctgtggct ggaggagctg gcctgtggca cagccctgag tgtcccaagc   3060
cgggagccaa cgaagccgga cacggcttca ctgaccagcg gctgctcaag ccgcaagctc   3120
tcagcaagtg cccagtggag cctgccgccc ccacctgggc accgggaccc cctcaccatc   3180
cagtgggccc ggagaaacct gatgaacagt ttggggactc aggaccagat gtccgtctct   3240
cttgcttgag gaatgaagac ctttattcac ccctgccccg ttgcttcccg ctgcacatgg   3300
acagacttca cagcgtctgc tcataggacc tgcatccttc ctggggacga attccactcg   3360
tccaagggac agcccacggt ctggaggccg aggaccacca gcaggcaggt ggactgactg   3420
ttgggcaaga cctcttccct ctgggcctgt tctcttggct gcaaataagg acagcagctg   3480
gtgccccacc tgcctggtgc attgctgtgt gaatccagga ggcagtggac atcgtaggca   3540
gccacggccc cgggtccagg agaagtgctc cctggaggca cgcaccactg cttcccactg   3600
gggccggcgg ggcccacgca cgacgtcagc ctcttacctt cccgcctcgg ctaggggtcc   3660
tcgggatgcc gttctgttcc aacctcctgc tctgggacgt ggacatgcct caaggataca   3720
gggagccggc ggcctctcga cggcacgcac ttgcctgttg gctgctgcgg ctgtgggcga   3780
gcatgggggc tgccagcgtc tgttgtggaa agtagctgct agtgaaatgg ctggggccgc   3840
tggggtccgt cttcacactg cgcaggtctc ttctgggcgt ctgagctggg gtgggagctc   3900
ctccgcagaa ggttggtggg gggtccagtc tgtgatcctt ggtgctgtgt gccccactcc   3960
agcctgggga ccccacttca gaaggtaggg gccgtgtccc gcggtgctga ctgaggcctg   4020
cttccccctc cccctcctgc tgtgctggaa ttccacaggg accagggcca ccgcagggga   4080
ctgtctcaga agacttgatt tttccgtccc tttttctcca cactccactg acaaacgtcc   4140
ccagcggttt ccacttgtgg gcttcaggtg ttttcaagca caacccacca caacaagcaa   4200
```

```
gtgcattttc agtcgttgtg ctttttttgtt ttgtgctaac gtcttactaa tttaaagatg   4260

ctgtcggcac catgtttatt tatttccagt ggtcatgctc agccttgctg ctctgcgtgg   4320

cgcaggtgcc atgcctgctc cctgtctgtg tcccagccac gcagggccat ccactgtgac   4380

gtcggccgac caggctggac accctctgcc gagtaatgac gtgtgtggct gggaccttct   4440

ttattctgtg ttaatggcta acctgttaca ctgggctggg ttgggtaggg tgttctggct   4500

tttttgtggg gtttttattt ttaaagaaac actcaatcat cctaaaaaaa aattaaaaa    4559
```

```
<210> SEQ ID NO 62
<211> LENGTH: 1756
<212> TYPE: DNA
<213> ORGANISM: Homo sapiens
<220> FEATURE:
<221> NAME/KEY: misc_feature
<223> OTHER INFORMATION: Incyte ID No: 008942.9

<400> SEQUENCE: 62

agtccccaca ccgcctgcag agagggaact agggcaccac cttgtttcat gttgttcccg     60

tgaatttttt tcagctatgg gaggcaaccg aggcactggc caaatgcagg cccaacattt    120

cactgagcat gtcagcatgc acatcacaat ggcaagcagc cagggaccca ccaagaacaa    180

gaagacccca gcaggatccc tcactgagca tcgggggggca tctgcacttc atcaggcacc   240

ccagggcatt caccattcat cacaccaagc acagaggtgg agcacaagtg gtccagcgtc    300

acatccaagt gctcagctgt ggctggagga gctggcctgt ggcacagcca ctgagtgtcc    360

acaagccagg gagcacaacg atagccagga cacaggcttc actgaccagc aggctgcatc    420

aagccagcaa gcatctcagc aagtgcacca gtggagcact gccagcaccc cagcactggg    480

cacacaggga ccccacatca ccagtccagt gggccacgga gaaacactga tgcccgttgt    540

ctaggagaca gagcacaagc actgctcacg tctctgccgc ctgcgtttgg aggcccctgg    600

gctctcaccc agtccccacc cgcctgcaga gagggaacta gggcacccct tgtttctgtt    660

gttcccgtga attttttttcg ctatgggagg cagccgaggc ctggccaatg cggcccactt   720

tcctgagctg tcgctgcctc catggcagca gccagggacc cccagaacaa gaagaccccg    780

caggatccct cctgagctcg gggggctctg ccttctcagg ccccgggctt cccttctccc    840

cagccagagg tggagccaag tggtccagcg tcactccagt gctcagctgt ggctggagga    900

gctggcctgt ggcacagccc tgagtgtccc aagccgggag ccaacgaagc cggacacggc    960

ttcactgacc agcggctgct caagccgcaa gctctcagca agtgcccagt ggagcctgcc   1020

gcccccgcct gggcaccggg accccctcac catccagtgg gcccggagaa acctgatgaa   1080

cagtttgggg actcaggacc agatgtccgt ctctcttgct tgaggaatga agacctttat   1140

tcacccctgc cccgttgctt cccgctgcac atggacagac ttcacagcgt ctgctcatag   1200

gacctgcatc cttcctgggg acgaattcca ctcgtccaag ggacagccca cggtctggag   1260

gccgaggacc accagcaggc aggtggactg actgtgttgg gcaagacctc ttccctctgg   1320

gcctgttctc ttggctgcaa ataaggacag cagctggtgc ccccacctgcc tggtgcattg  1380

ctgtgtgaat ccaggaggca gtggacatcg taggcagcca cggccccggg tccaggagaa   1440

gtgctccctg gaggcacgca ccactgcttc ccactggggc cggcggggcc cacgcacgac   1500

gtcagcctct taccttcccg cctcggctag gggtcctcgg gatgccgttc tgttccaacc   1560

tcctgctctg ggacgtggac atgcctcaac tgagggccag ggacccaggt gtgcctgtgc   1620

tcctgcccag gagcagcttt tggtctcctt gggccctttt tcccttccct cctttgttta   1680
```

```
cttatatata tatttttttt aaacttaaat tttgggtcaa cttgacacca ctaagatgat   1740

ttttaaggag ctgggg                                                   1756
```

<210> SEQ ID NO 63
<211> LENGTH: 3304
<212> TYPE: DNA
<213> ORGANISM: Homo sapiens
<220> FEATURE:
<221> NAME/KEY: misc_feature
<223> OTHER INFORMATION: Incyte ID No: 1252415.1
<221> NAME/KEY: unsure
<222> LOCATION: 3267, 3276, 3289-3290, 3297, 3299
<223> OTHER INFORMATION: a, t, c, g, or other

<400> SEQUENCE: 63

```
gcggaactct gaggtgaggg tgtgcagctt ggtagggatt ggggtccctt ccggggccca     60

tcggcccctg gtggtgttaa tggcccttct ggcctacgcg cgtgtcatga accctggccg    120

agagggccgg ggctgaggcc ctcaggccga cccggactct tgggcgcggt ctcttgaggt    180

ggggccgggg tgagcagctg agtccgggtg ccccggggag gcccctctgg cccgatttcg    240

cagcgctgcc catcagcttc agcggaggcc tgattcctga ggtgctctga ctggaaggaa    300

cctccgagat cggagagtct tccctgtctc ctgttgatgc tcccattgca ctgataggta    360

aattgatccc tagagaagag gctagtctga gatatatagc gagtgaggaa aagaatcgga    420

atcatgatcc tggtgcctta gataaccagc cccagttctt cccgtgttgc tcggaacctc    480

tctaacttgg gatggtcttc cggtcggtgt tgccccgcag gctgctgcag cttaaaggcc    540

agcgctgcgt ggaacttttt tttttctctc ctcccaaatt gagccgtttg aaatgcctag    600

ggagttttta aaagaaaggc gggcacatcc ttgtatttac aggcagatat cctccctttc    660

ctcctcggct gctgctctta ctttgacaag ccaggctaac attgaaggtg gtccattatg    720

gctgacatgc aaaatctggt agaaagattg gagagggcag tgggccgcct ggaggcagta    780

tctcatacct ctgacatgca ccgtgggtat gcagacagtc cttcaaaagc aggagcagct    840

ccatatgtgc aggcatttga ctcgctgctt gctggtcctg tggcagagta cttgaagatc    900

agtaaagaga ttggggggaga cgtgcagaaa catgcggaga tggtccacac aggtttgaag    960

ttggagcgag ctctgttggt tacagcttct cagtgtcaac agccagcaga aaataagctt   1020

tccgatttgt tggcacccat ctcagagcag atcaaagaag tgataacctt tcgggagaag   1080

aaccgaggca gcaagttgtt taatcacctg tcagctgtca gcgaaagtat ccaggccctg   1140

ggctgggtgg ctatggctcc caagcctggc ccttatgtga aagaaatgaa tgatgccgcc   1200

atgttttata caaaccgagt cctcaaagag tacaaagatg tggataagaa gcatgtagac   1260

tgggtcaaag cttatttaag tatatggaca gagctgcagg cttacattaa ggagttccat   1320

accaccggac tggcctggag caaaacgggg cctgtggcaa aagaactgag cggactgcca   1380

tctggaccct ctgccggatc aggtcctcct ccccctccac caggcccccc tcctccccca   1440

gtctctacca gttcaggctc agatgagtct gcttcccgct cagcactgtt cgcgcagatt   1500

aatcaggggg agagcattac acatgccctg aaacatgtat ctgatgacat gaagactcac   1560

aagaaccctg ccctgaaggc tcagagtggt ccagtacgca gtggccccaa accattctct   1620

gcacctaaac cccaaaccag cccatccccc aaacgagcca caaagaagga gccagctgta   1680

cttgaactgg agggcaagaa gtggagagtg gaaaatcagg aaaatgtttc caacctggtg   1740

attgaggaca cagagctgaa acaggtggct tacatataca agtgtgtcaa cacgacattg   1800
```

```
caaatcaagg gcaaaattaa ctccattaca gtagataact gtaagaaact tggcctggta   1860

ttcgatgacg tggtgggcat tgtggagata atcaacagta aggatgtcaa agttcaggta   1920

atgggtaaag tgccaaccat atccatcaac aaaacagatg gctgccatgc ttacctgagc   1980

aagaattccc tggattgtga aatagtcagt gccaaatctt ccgagatgaa tgtcctcatt   2040

cctacagaag gcggtgactt taatgaattc ccagttcctg agcagttcaa gaccctatgg   2100

aacgggcaga agttggtcac cacagtgaca gaaattgctg gataagcgaa gtgccactgg   2160

gttctttgcc ctcccttcac accatgggat aaatctgtat caagacggtt cttttctaga   2220

tttcctctac ctttttgctc ttaaaactgc ttctctgctc tgagaagcac agctacctgc   2280

cttcactgaa atatacctca ggctgaaatt tggggtggga tagcaggtca gttgatcttc   2340

tgcaggaagg tgcagctttt ccatatcagc tcaaccacgc cgccagtcca ttcttaagga   2400

actgccgact aggactgatg atgcatttta gctttgagct tttgggggtt attctaccaa   2460

caaacagtcc attggaaaga aaacagtccc tggaattaac agatcagaat gttcacactg   2520

gttaatcttt ttttaacaat gagcatgaag gtagcagaag ctggtgtgtt tccagatggt   2580

tcttctaacc aaactaattt ttcactgttg acaagcgagg caagggttgc actggaccaa   2640

aggctgaggc ttggccatct agcattccat acaaaattgt ttcctataag cattcctttt   2700

attctctatt ctatcctggg tctgcctcaa ccgtgagata ggagagtctc tggtactagc   2760

tgctgtagca gtgcccttca tccagggcag ttaatggagt cttggaccct ttctttctct   2820

gggatccctg cccagcacct tcctatagag atgactttaa aaggaaaaaa aaaaaaaaaa   2880

caaacccaca tgatttcaag gagtctggca ttcctgaatc cttcttccct gccaggtgcc   2940

tgtcacctgt cttcactgcc tccttttccc tgtcatgctc atcagcttat ggcttctgtc   3000

taagcacctg aacagaggac tgaaacctcc actgcaggct ggttttaggt cttgaattat   3060

gtaagaatct tgcacagcac tgctaatgta aatttcagtt gtttttccct ctaggacaaa   3120

cacttaccaa aatatgcaac tttttttttgg tgggaagaga gattgtcctg tgatttctac   3180

ccatttcctg aggcctgtgg aaataaacct ttatgtactt aaagttatac agaaaataga   3240

ataaagttaa taccaaactt gaaaaanaaa aaaaangggg ggccgccgnn tagtgancnc   3300

gtcg                                                                3304
```

<210> SEQ ID NO 64
<211> LENGTH: 7231
<212> TYPE: DNA
<213> ORGANISM: Homo sapiens
<220> FEATURE:
<221> NAME/KEY: misc_feature
<223> OTHER INFORMATION: Incyte ID No: 1399366.20
<221> NAME/KEY: unsure
<222> LOCATION: 5601, 5609, 7107
<223> OTHER INFORMATION: a, t, c, g, or other

<400> SEQUENCE: 64

```
cccgagctgg cctgcgagtt cagggctcct gccgctctcc aggagcaacc tctactccgg     60

acgcacaggc attccccgcg cccctccagc cctcgccgcc ctcgccaccg ctcccggccg    120

ccgcgctccg gtacacacag gatccctgct gggcaccaac agctccacca tggggctggc    180

ctggggacta ggcgtcctgt tcctgatgca tgtgtgtggc accaaccgca ttccagagtc    240

tggcggagac aacagcgtgt ttgacatctt tgaactcacc ggggccgccc gcaaggggtc    300

tgggcgccga ctggtgaagg gccccgaccc ttccagccca gctttccgca tcgaggatgc    360

caacctgatc ccccctgtgc ctgatgacaa gttccaagac ctggtggatg ctgtgcgggc    420
```

-continued

```
agaaaagggt ttcctccttc tggcatccct gaggcagatg aagaagaccc ggggcacgct    480
gctggccctg gagcggaaag accactctgg ccaggtcttc agcgtggtgt ccaatggcaa    540
ggcgggcacc ctggacctca gcctgaccgt ccaaggaaag cagcacgtgg tgtctgtgga    600
agaagctctc ctggcaaccg gccagtggaa gagcatcacc ctgtttgtgc aggaagacag    660
ggcccagctg tacatcgact gtgaaaagat ggagaatgct gagttggacg tccccatcca    720
aagcgtcttc accagagacc tggccagcat cgccagactc cgcatcgcaa agggggggcgt    780
caatgacaat ttccaggggg tgctgcagaa tgtgaggttt gtctttggaa ccacaccaga    840
agacatcctc aggaacaaag gctgctccag ctctaccagt gtcctcctca cccttgacaa    900
caacgtggtg aatggttcca gccctgccat ccgcactaac tacattggcc acaagacaaa    960
ggacttgcaa gccatctgcg gcatctcctg tgatgagctg tccagcatgg tcctggaact   1020
caggggcctg cgcaccattg tgaccacgct gcaggacagc atccgcaaag tgactgaaga   1080
gaacaaagag ttggccaatg agctgaggcg gcctccccta tgctatcaca acggagttca   1140
gtacagaaat aacgaggaat ggactgttga tagctgcact gagtgtcact gtcagaactc   1200
agttaccatc tgcaaaaagg tgtcctgccc catcatgccc tgctccaatg ccacagttcc   1260
tgatggagaa tgctgtcctc gctgttggcc cagcgactct gcggacgatg gctggtctcc   1320
atggtccgag tggacctcct gttctacgag ctgtggcaat ggaattcagc agcgcggccg   1380
ctcctgcgat acgctcaaca accgatgtga gggctcctcg gtccagacac ggacctgcca   1440
cattcaggag tgtgacaaga gatttaaaca ggatggtggc tggagccact ggtccccgtg   1500
gtcatcttgt tctgtgacat gtggtgatgg tgtgatcaca aggatccggc tctgcaactc   1560
tcccagcccc cagatgaacg ggaaaccctg tgaaggcgaa gcgcgggaga ccaaagcctg   1620
caagaaagac gcctgcccca tcaatggagg ctggggtcct tggtcaccat gggacatctg   1680
ttctgtcacc tgtggaggag ggtacagaa acgtagtcgt ctctgcaaca accccacacc   1740
ccagtttgga ggcaaggact gcgttggtga tgtaacagaa aaccagatct gcaacaagca   1800
ggactgtcca attgatggat gcctgtccaa tccctgcttt gccggcgtga agtgtactag   1860
ctaccctgat ggcagctgga aatgtggtgc ttgtccccct ggttacagtg gaaatggcat   1920
ccagtgcaca gatgttgatg agtgcaaaga agtgcctgat gcctgcttca accacaatgg   1980
agagcaccgg tgtgagaaca cggaccccgg ctacaactgc ctgccctgcc ccccacgctt   2040
caccggctca cagcccttcg gccagggtgt cgaacatgcc acggccaaca aacaggtgtg   2100
caagccccgt aacccctgca cggatgggac ccacgactgc aacaagaacg ccaagtgcaa   2160
ctacctgggc cactatagcg accccatgta ccgctgcgag tgcaagcctg gctacgctgg   2220
caatggcatc atctgcgggg aggacacaga cctggatggc tggcccaatg agaacctggt   2280
gtgcgtggcc aatgcgactt accactgcaa aaaggataat tgccccaacc ttcccaactc   2340
agggcaggaa gactatgaca aggatggaat tggtgatgcc tgtgatgatg acgatgacaa   2400
tgataaaatt ccagatgaca gggacaactg tccattccat tacaacccag ctcagtatga   2460
ctatgacaga gatgatgtgg gagaccgctg tgacaactgt ccctacaacc acaacccaga   2520
tcaggcagac acagacaaca atggggaagg agacgcctgt gctgcagaca ttgatggaga   2580
cggtatcctc aatgaacggg acaactgcca gtacgtctac aatgtggacc agagagacac   2640
tgatatggat ggggttggag atcagtgtga caattgcccc ttggaacaca atccggatca   2700
gctggactct gactcagacc gcattggaga tacctgtgac aacaatcagg atattgatga   2760
```

-continued

```
agatggccac cagaacaatc tggacaactg tccctatgtg cccaatgcca accaggctga   2820
ccatgacaaa gatggcaagg gagatgcctg tgaccacgat gatgacaacg atggcattcc   2880
tgatgacaag gacaactgca gactcgtgcc caatcccgac cagaaggact ctgacggcga   2940
tggtcgaggt gatgcctgca aagatgattt tgaccatgac agtgtgccag acatcgatga   3000
catctgtcct gagaatgttg acatcagtga gaccgacttc cgccgattcc agatgattcc   3060
tctggacccc aaagggacat cccaaaatga ccctaactgg gttgtacgcc atcagggtaa   3120
agaactcgtc cagactgtca actgtgatcc tggactcgct gtaggttatg atgagtttaa   3180
tgctgtggac ttcagtggca ccttcttcat caacaccgaa agggacgatg actatgctgg   3240
atttgtcttt ggctaccagt ccagcagccg cttttatgtt gtgatgtgga agcaagtcac   3300
ccagtcctac tgggacacca accccacgag ggctcaggga tactcgggcc tttctgtgaa   3360
agttgtaaac tccaccacag ggcctggcga gcacctgcgg aacgccctgt ggcacacagg   3420
aaacacccct ggccaggtgc gcaccctgtg gcatgaccct cgtcacatag gctggaaaga   3480
tttcaccgcc tacagatggc gtctcagcca caggccaaag acgggtttca ttagagtggt   3540
gatgtatgaa gggaagaaaa tcatggctga ctcaggaccc atctatgata aaacctatgc   3600
tggtggtaga ctagggttgt ttgtcttctc tcaagaaatg gtgttcttct ctgacctgaa   3660
atacgaatgt agagatccct aatcatcaaa ttgttgattg aaagactgat cataaaccaa   3720
tgctggtatt gcaccttctg gaactatggg cttgagaaaa cccccaggat cacttctcct   3780
tggcttcctt cttttctgtg cttgcatcag tgtggactcc tagaacgtgc gacctgcctc   3840
aagaaaatgc agttttcaaa aacagactca gcattcagcc tccaatgaat aagacatctt   3900
ccaagcatat aaacaattgc tttggtttcc ttttgaaaaa gcatctactt gcttcagttg   3960
ggaaggtgcc cattccactc tgcctttgtc acagagcagg gtgctattgt gaggccatct   4020
ctgagcagtg gactcaaaag cattttcagg catgtcagag aagggaggac tcactagaat   4080
tagcaaacaa aaccaccctg acatcctcct tcaggaacac ggggagcaga ggccaaagca   4140
ctaaggggag ggcgcatacc cgagacgatt gtatgaagaa aatatggagg aactgttaca   4200
tgttcggtac taagtcattt tcaggggatt gaaagactat tgctggattt catgatgctg   4260
actggcgtta gctgattaac ccatgtaaat aggcacttaa atagaagcag gaaagggaga   4320
caaagactgg cttctggact tcctccctga tccccaccct tactcatcac ctgcagtggc   4380
cagaattagg gaatcagaat caaaccagtg taaggcagtg ctggctgcca ttgcctggtc   4440
acattgaaat tggtggcttc attctagatg tagcttgtgc agatgtagca ggaaaatagg   4500
aaaacctacc atctcagtga gcaccagctg cctcccaaag gaggggcagc cgtgcttata   4560
tttttatggt tacaatggca caaaattatt atcaacctaa ctaaaacatt ccttttctct   4620
tttttcctga attatcatgg agttttctaa ttctctcttt tggaatgtag attttttta    4680
aatgctttac gatgtaaaat atttattttt tacttattct ggaagatctg gctgaaggat   4740
tattcatgga acaggaagaa gcgtaaagac tatccatgtc atctttgttg agagtcttcg   4800
tgactgtaag attgtaaata cagattattt attaactctg ttctgcctgg aaatttaggc   4860
ttcatacgga aagtgtttga gagcaagtag ttgacattta tcagcaaatc tcttgcaaga   4920
acagcacaag gaaaatcagt ctaataagct gctctgcccc ttgtgctcag agtggatgtt   4980
atgggattct ttttttctct gttttatctt ttcaagtgga attagttggt tatccatttg   5040
caaatgtttt aaattgcaaa gaaagccatg aggtcttcaa tactgtttta ccccatccct   5100
tgtgcatatt tccagggaga aggaaagcat atacactttt ttctttcatt tttccaaaag   5160
```

-continued

```
agaaaaaaat gacaaaaggt gaaacttaca tacaaatatt acctcatttg ttgtgtgact   5220
gagtaaagaa tttttggatc aagcggaaag agtttaagtg tctaacaaac ttaaagctac   5280
tgtagtacct aaaaagtcag tgttgtacat agcataaaaa ctctgcagag aagtattccc   5340
aataaggaaa tagcattgaa atgttaaata caatttctga aagttatgtt ttttatctat   5400
catctggtat accattgctt tatttttata aattattttc tcattgccat tggaatagat   5460
atctcagatt gtgtagatat gctatttaaa taatttatca ggaaatactg cctgtagagt   5520
tagtatttct atttttatat aatgtttgca cactgaattg aagaattgtt ggtttttttct  5580
tttttttgtt ttgttttttt ntttttttnt ttttgctttt gacctcccat ttttactatt   5640
tgccaatacc tttttctagg aatgtgcttt tttttgtaca catttttatc cattttacat   5700
tctaaagcag tgtaagttgt atattactgt ttcttatgta caaggaacaa caataaatca   5760
tatggaaatt tatatttata cttactgtat ccatgcttat ttgttctcta ctggctttat   5820
gtcatgaagt atatgcgtaa ataccattca taaatcaata tagcatatac aaaaataaat   5880
tacagtaagt catagcaaca ttcacagttt gtatgtgatt gagaaagact gagttgctca   5940
ggcctaggct tagaatttgc tgcgtttgtg gaataaaaga acaaaatgat acattagcct   6000
gccatatcaa aaacatataa aagagaaatt atccctaagt caagggcccc cataagaata   6060
aaatttctta ttaaggtcat tagatgtcat tgaatccttt tcaaagtgca gtatgaaaac   6120
aaagggaaaa acactgaagc acacgcaact ctcacagcga cattttctga cccacgaatg   6180
atgccttggg tgggcaacac gattgcatgt tgtggagaca cttcggaagt aaatgtggat   6240
gagggaggag ctgtccttgc aatgttgagc caagcattac agatacctcc tcttgaagaa   6300
ggaataataa gtttaatcaa aaaagaagac taaaaaatgt aaaatttgga aggaatccat   6360
aaatgcgtgt gtgtctaaat acaaattatc atgtgaagaa aaggcccaag tgtaccaata   6420
agcagacctt gatttttgga tggctaatt atgaatgtgg aatactgacc agttaatttc   6480
cagttttaat gaaaacagat caaagaagaa attttatgag taggttaaag gtctggcttt   6540
gaggtctatt aaacactaga aaggactggc tgggtgagat aaaatcttcc ttgttgattt   6600
tcactctcat tctataaata ctcatctttc tgagtagcca tgatcacata caaatgtaaa   6660
ttgccaaatc attttatagt accaaggtga agaagcagga actagaaagt gttgataata   6720
gctgtggagt taggaaaact gatgtgaagg aaataattct ttgaaatggc aaagaattaa   6780
ataccatcat tcattatcag aagagttcaa cgtttgaagt gctgggagat aattctaatt   6840
cattcttgga tagtgaagca aaactgattg aaaataccaa gataagacag aaaaagtgac   6900
tggaaagagg agcttttctt ccaggcatgt tccagtttca ccctaagact gaccttcaaa   6960
taatcaggtt gtactgaaat aaaggacttg ttaaaaatta aaattatgtc atcgagatga   7020
tagctttttt cctcctccaa cagtttattg tgcatgtgtt gtgggagagc tcgagtgaag   7080
agcaataaac tccaggtctt ataagantgt acatacaata aaggtggtgc cagcagtttt   7140
tttttttcta aagagtcaca tgtagaaaag cctccagtat taagctcctg aattcattcc   7200
tataaataaa ttggctctct ctctcttcta t                                  7231
```

<210> SEQ ID NO 65
<211> LENGTH: 961
<212> TYPE: DNA
<213> ORGANISM: Homo sapiens
<220> FEATURE:
<221> NAME/KEY: misc_feature
<223> OTHER INFORMATION: Incyte ID No: 3732868CB1

-continued

<221> NAME/KEY: unsure
<222> LOCATION: 19
<223> OTHER INFORMATION: a, t, c, g, or other

<400> SEQUENCE: 65

```
ctggctctga ccgcgctgnc ctgggcccga gagcccagga ggcgtgtctc agagaaaaga     60
tataagcggc ccccggacgc taaagcggtg ccagcggcgg agtctccaac tgggagagct    120
gcagctgccg agaggaggag aacgctgagg tcggtcggac caacggacgc gctgaccgct    180
gccaactgca gctcgcgctg cctcctgctc gcgccgtgcc actaaggtca ctcccgcctc    240
cgagagccca gagccgagat ggaaacggtc caggagctga tccccctggc caaggagatg    300
atggcccaga agcgcaaggg gaagatggtg aagctgtacg tgctgggcag cgtgctggcc    360
ctcttcggcg tggtgctcgg cctgatggag actgtgtgca gccccttcac ggccgccaga    420
cgtctgcggg accaggaggc agccgtggcg gagctgcagg ccgccctgga gcgacaggct    480
ctccagaagc aagccctgca ggagaaaggc aagcagcagg acacggtcct cggcggccgg    540
gccctgtcca accggcagca cgcctcctag gaactgtggg agaccagcgg agtgggaggg    600
agacgcagta gacagagaca gaccgagaag gaagggagag acagaggggg cgcgcgcaca    660
ggagcctgac tccgctggga gagtgcagga gcacgtgctg ttttttattt ggacttaact    720
tcagagaaac cgctgacatc tagaactgac ctaccacaag catccaccaa aggagtttgg    780
gattgagttt tgctgctgtg cagcactgca ttgtcatgac atttccaaca ctgtgtgaat    840
tatctaaatg cgtctaccat tttgcactag ggaggaagga taaatgcttt ttatgttatt    900
attattaatt attacaatga ccaccatttt gcattttgaa ataaaaaact ttttatacca    960
t                                                                    961
```

<210> SEQ ID NO 66
<211> LENGTH: 103
<212> TYPE: PRT
<213> ORGANISM: Homo sapiens
<220> FEATURE:
<221> NAME/KEY: misc_feature
<223> OTHER INFORMATION: Incyte ID No: 3732868CD1

<400> SEQUENCE: 66

```
Met Glu Thr Val Gln Glu Leu Ile Pro Leu Ala Lys Glu Met Met
  1               5                  10                  15

Ala Gln Lys Arg Lys Gly Lys Met Val Lys Leu Tyr Val Leu Gly
                 20                  25                  30

Ser Val Leu Ala Leu Phe Gly Val Val Leu Gly Leu Met Glu Thr
                 35                  40                  45

Val Cys Ser Pro Phe Thr Ala Ala Arg Arg Leu Arg Asp Gln Glu
                 50                  55                  60

Ala Ala Val Ala Glu Leu Gln Ala Ala Leu Glu Arg Gln Ala Leu
                 65                  70                  75

Gln Lys Gln Ala Leu Gln Glu Lys Gly Lys Gln Gln Asp Thr Val
                 80                  85                  90

Leu Gly Gly Arg Ala Leu Ser Asn Arg Gln His Ala Ser
                 95                 100
```

<210> SEQ ID NO 67
<211> LENGTH: 2608
<212> TYPE: DNA
<213> ORGANISM: Homo sapiens
<220> FEATURE:
<221> NAME/KEY: misc_feature
<223> OTHER INFORMATION: Incyte ID No: 1137894.1

<400> SEQUENCE: 67

```
ttcagcgctc ccactctcgg ccgacacccc tgcatggcca accgttacac catggatctg     60
actgccatct acgaggtgag tccccgccgc acggcatccc cggtacctgc atgcctgagt    120
ccgagtcccc acctctctag cgccgcaaac tccagcccgg gacgcttgcc tcccttctcc    180
aactggggct ccctagcgcc gcgccctcca gcctggggcc cctgcctccc gctcagacca    240
gcttggtgat ttggaggtga aaatggaacc cgcgacaccc ggctcttcgc tcaaacatgg    300
gtggggcggc ccatgcaagt ggaaagtcgg agaacttttc tcagaccgag gctgcctgga    360
ggcggaagtg gcccccatac ctggctcacc cctagtcgtt gctgagggcg tggttttgcg    420
cggaggcgtc tctggggctg aagtctcagg gtggggggat ccgacttctg tctctccagt    480
ccctgaccgt agagacagag aaccctaaaa ccgaagcaat ccggacttcc aggtcaactt    540
tgcccggttt ctccagttgt gaaactggag atcccgacgc gtgggtcata tccggggagg    600
acaagagacc caaaattggg aaacagtggt gcgccctgac ttcggggtcc ccctcttggt    660
ccagccgggg aagccgggat tcctgggtcc ctcgggataa ggcctcggtg gtgggtaaac    720
tcagaacctc caactctggg ttcctggcat ccggaaccca ggggtttctg cgggcgggtg    780
gggctcaggc ggggagccca caaaccggcc tggcaagctc tagttccctg cagctggggt    840
ggggcgtcgc cctgcatttt caggtgcctt aaccgaccca tttccgcaga gcctcctgtc    900
gctgagccct gacgtgcccg tgccatccga ccatggaggg actgagtcca gcccaggctg    960
gggctcctcg ggaccctgga gcctgagccc ctccgactcc agcccgtctg ggtcacctc   1020
ccgcctgcct ggccgctcca ccagcctagt ggagggccgc agctgtggct gggtgccccc   1080
acccccctggc ttcgcaccgc tggctccccg cctgggccct gagctgtcac cctcacccac   1140
ttcgcccact gcaacctcca ccaccccctc gcgctacaag actgagctat gtcggacctt   1200
ctcagagagt gggcgctgcc gctacggggc caagtgccag tttgcccatg gcctgggcga   1260
gctgcgccag gccaatcgcc accccaaata caagacggaa ctctgtcaca agttctacct   1320
ccagggccgc tgcccctacg gctctcgctg ccacttcatc cacaacccta gcgaagacct   1380
ggcggccccg ggccaccctc ctgtgcttcg ccagagcatc agcttctccg gcctgccctc   1440
tggccgccgg acctcaccac caccaccagg cctggccggc ccttccctgt cctccagctc   1500
cttctcgccc tccagctccc caccaccacc tggggacctt ccactgtcac cctctgcctt   1560
ctctgctgcc cctggcaccc ccctggctcg aagagacccc accccagtct gttgcccctc   1620
ctgccgaagg gccactccta tcagcgtctg gggcccttg ggtggcctgg ttcggacccc   1680
ctctgtacag tccctgggat ccgaccctga tgaatatgcc agcagcggca gcagcctggg   1740
gggctctgac tctcccgtct tcgaggcggg agtttttgca ccaccccagc ccgtggcagc   1800
cccccggcga ctccccatct tcaatcgcat ctctgtttct gagtgacaaa gtgactgccc   1860
ggtcagatca gctggatctc agcggggagc cacgtctctt gcactgtggt ctctgcatgg   1920
accccagggc tgtggggact tgggggacag taatcaagta atcccctttt ccagaatgca   1980
ttaacccact cccctgacct cacgctgggg caggtcccca agtgtgcaag ctcagtattc   2040
atgatggtgg gggatggagt gtcttccgag gttcttgggg gaaaaaaaat tgtagcatat   2100
ttaagggagg caatgaaccc tctcccccac ctcttccctg cccaaatctg tctcctagaa   2160
tcttatgtgc tgtgaataat aggccttcac tgcccctcca gtttttatag acctgaggtt   2220
ccagtgtctc ctggtaactg gaacctctcc tgagggggaa tcctggtgct caaattaccc   2280
```

-continued

```
tccaaaagca agtagccaaa gccgttgcca aaccccaccc ataaatcaat gggcccttta   2340

tttatgacga ctttatttat tctaatatga ttttatagta tttatatata ttgggtcgtc   2400

tgcttccctt gtatttttct tccttttttt gtaatattga aaacgacgat ataattatta   2460

taagtagact ataatatatt tagtaatata tattattacc ttaaaagtct atttttgtgt   2520

tttgggcatt tttaaataaa caatctgagt gtgttcttcg tagaggaact cgattgagga   2580

ccagaggtcc tggacctcca aatacaac                                       2608


<210> SEQ ID NO 68
<211> LENGTH: 1527
<212> TYPE: DNA
<213> ORGANISM: Homo sapiens
<220> FEATURE:
<221> NAME/KEY: misc_feature
<223> OTHER INFORMATION: Incyte ID No: 1418671CB1

<400> SEQUENCE: 68

gcttcctggg cgccgtgggc gcggactgcg cgggctgcgc gggtgccgag gagcgcgagg     60

cgcggggaag gcgcacctgg ggtggccctg gcgtgcgggc ggcgacatgg aggacggcgt    120

gctcaaggag ggcttcctgg tcaagagggg ccacattgtc cacaactgga aggcgcgatg    180

gttcatcctt cggcagaaca cgctggtgta ctacaagctt gaggggggtc ggagagtgac    240

ccctcccaag ggccggatcc tcctggatgg ctgcaccatc acctgcccct gcctggagta    300

tgaaaaccga ccgctcctca ttaagctgaa gactcaaaca tccacggagt acttcctgga    360

ggcctgttct cgagaggagc gggatgcctg ggcctttgag atcaccgggg ctattcatgc    420

agggcagccg gggaaggtcc agcagctgca cagcctgaga aactccttca agctgccccc    480

gcacatcagc ctgcatcgca ttgtggacaa gatgcacgat agcaacaccg gaatccgttc    540

aagccccaac atggagcagg gaagcaccta taaaaagacc ttcctcggct cctccctggt    600

ggactggctc atctccaaca gcttcacggc cagccgtctg gaggcggtga ccctggcctc    660

catgctcatg gaggagaact tcctcaggcc tgtgggtgtc cgaagcatgg gagccattcg    720

ctctggggat ctggccgagc agttcctgga tgactccaca gccctgtaca cttttgctga    780

gagctacaaa aagaagataa gccccaagga agaaattagc ctgagcactg tggagttaag    840

tggcacggtg gtgaaacaag gctacctggc caagcaggga cacaagagga aaaactggaa    900

ggtgcgtcgc tttgttctaa ggaaggatcc agctttcctg cattactatg acccttccaa    960

agaagagaac aggccagtgg gtgggttttc tcttcgtggt tcactcgtgt ctgctctgga   1020

agataatggc gttcccactg ggggttaaagg gaatgtccag ggaaacctct tcaaagtgat   1080

tactaaggat gacacacact attacattca ggccagcagc aaggctgagc gagccgagtg   1140

gattgaagct atcaaaaagc taacatgaca aggacctgag ggaaccagga ttcctccctc   1200

ctaccagatg acacagacaa gagttcctgg agaatgggag tgttaagact tttgacttct   1260

ttgtaagttt tgtactgctt tggagagtga atgctgccaa gagttcctca gattacaaac   1320

agcagtggtg ccatttcctt ccccatcttc atgttacaaa cctggaaagg ctagaacagc   1380

cattaggcgt cagcatcttg acttttcccc agcatcacaa acagccattt cctcgggcac   1440

caaagtaggt tccctttgtt ggaacaatta cactggccat gccataatgt tgaataaaac   1500

tctcttctta tgaaaaaaaa aaaaaaa                                        1527


<210> SEQ ID NO 69
<211> LENGTH: 353
```

-continued

```
<212> TYPE: PRT
<213> ORGANISM: Homo sapiens
<220> FEATURE:
<221> NAME/KEY: misc_feature
<223> OTHER INFORMATION: Incyte ID No: 1418671CD1

<400> SEQUENCE: 69

Met Glu Asp Gly Val Leu Lys Glu Gly Phe Leu Val Lys Arg Gly
  1               5                  10                  15

His Ile Val His Asn Trp Lys Ala Arg Trp Phe Ile Leu Arg Gln
                 20                  25                  30

Asn Thr Leu Val Tyr Tyr Lys Leu Glu Gly Gly Arg Arg Val Thr
                 35                  40                  45

Pro Pro Lys Gly Arg Ile Leu Leu Asp Gly Cys Thr Ile Thr Cys
                 50                  55                  60

Pro Cys Leu Glu Tyr Glu Asn Arg Pro Leu Leu Ile Lys Leu Lys
                 65                  70                  75

Thr Gln Thr Ser Thr Glu Tyr Phe Leu Glu Ala Cys Ser Arg Glu
                 80                  85                  90

Glu Arg Asp Ala Trp Ala Phe Glu Ile Thr Gly Ala Ile His Ala
                 95                 100                 105

Gly Gln Pro Gly Lys Val Gln Gln Leu His Ser Leu Arg Asn Ser
                110                 115                 120

Phe Lys Leu Pro Pro His Ile Ser Leu His Arg Ile Val Asp Lys
                125                 130                 135

Met His Asp Ser Asn Thr Gly Ile Arg Ser Ser Pro Asn Met Glu
                140                 145                 150

Gln Gly Ser Thr Tyr Lys Lys Thr Phe Leu Gly Ser Ser Leu Val
                155                 160                 165

Asp Trp Leu Ile Ser Asn Ser Phe Thr Ala Ser Arg Leu Glu Ala
                170                 175                 180

Val Thr Leu Ala Ser Met Leu Met Glu Glu Asn Phe Leu Arg Pro
                185                 190                 195

Val Gly Val Arg Ser Met Gly Ala Ile Arg Ser Gly Asp Leu Ala
                200                 205                 210

Glu Gln Phe Leu Asp Asp Ser Thr Ala Leu Tyr Thr Phe Ala Glu
                215                 220                 225

Ser Tyr Lys Lys Lys Ile Ser Pro Lys Glu Glu Ile Ser Leu Ser
                230                 235                 240

Thr Val Glu Leu Ser Gly Thr Val Val Lys Gln Gly Tyr Leu Ala
                245                 250                 255

Lys Gln Gly His Lys Arg Lys Asn Trp Lys Val Arg Arg Phe Val
                260                 265                 270

Leu Arg Lys Asp Pro Ala Phe Leu His Tyr Tyr Asp Pro Ser Lys
                275                 280                 285

Glu Glu Asn Arg Pro Val Gly Gly Phe Ser Leu Arg Gly Ser Leu
                290                 295                 300

Val Ser Ala Leu Glu Asp Asn Gly Val Pro Thr Gly Val Lys Gly
                305                 310                 315

Asn Val Gln Gly Asn Leu Phe Lys Val Ile Thr Lys Asp Asp Thr
                320                 325                 330

His Tyr Tyr Ile Gln Ala Ser Ser Lys Ala Glu Arg Ala Glu Trp
                335                 340                 345

Ile Glu Ala Ile Lys Lys Leu Thr
                350
```

<210> SEQ ID NO 70
<211> LENGTH: 5648
<212> TYPE: DNA
<213> ORGANISM: Homo sapiens
<220> FEATURE:
<221> NAME/KEY: misc_feature
<223> OTHER INFORMATION: Incyte ID No: 464689.64

<400> SEQUENCE: 70

```
ggtgtggtgt cggtgtcggc agcatccccg gcgccctgct gcggtcgccg cgagcctcgg     60
cctctgtctc ctccccctcc cgcccttacc tccacgcggg accgcccgcg ccagtcaact    120
cctcgcactt tgcccctgct tggcagcgga taaaaggggg ctgaggaaat accggacacg    180
gtcacccgtt gccagctcta gcctttaaat tcccggctcg gggacctcca cgcaccgcgg    240
ctagcgccga caaccagcta gcgtgcaagg cgccgcggct cagcgcgtac cggcgggctt    300
cgaaaccgca gtcctccggc gaccccgaac tccgctccgg agcctcagcc ccctggaaag    360
tgatcccggc atcggagagc caagatgccg gcccacttgc tgcaggacga tatctctagc    420
tcctatacca ccaccaccac cattacagcg cctccctcca ggggtcctgc agaatggagg    480
agataagttg gagacgatgc ccctctactt ggaagacgac attcgccctg atataaaaga    540
tgatatatat gaccccacct acaaggataa ggaaggccca agccccaagg ttgaatatgt    600
ctggagaaac atcatcctta tgtctctgct acacttggga gccctgtatg ggatcacttt    660
gattcctacc tgcaagttct acacctggct ttggggggta ttctactatt ttgtcagtgc    720
cctgggcata acagcaggag ctcatcgtct gtggagccac cgctcttaca aagctcggct    780
gcccctacgg ctctttctga tcattgccaa cacaatggca ttccagaatg atgtctatga    840
atgggctcgt gaccaccgtg cccaccacaa gttttcagaa acacatgctg atcctcataa    900
ttcccgacgt ggctttttct tctctcacgt gggttggctg cttgtgcgca aacacccagc    960
tgtcaaagag aaggggagta cgctagactt gtctgaccta gaagctgaga aactggtgat   1020
gttccagagg aggtactaca aacctggctt gctgatgatg tgcttcatcc tgcccacgct   1080
tgtgccctgg tatttctggg gtgaaacttt tcaaaacagt gtgttcgttg ccactttctt   1140
gcgatatgct gtggtgctta atgccacctg gctggtgaac agtgctgccc acctcttcgg   1200
atatcgtcct tatgacaaga acattagccc ccgggagaat atcctggttt cacttggagc   1260
tgtgggtgag ggcttccaca actaccacca ctcctttccc tatgactact ctgccagtga   1320
gtaccgctgg cacatcaact tcaccacatt cttcattgat tgcatggccg ccctcggtct   1380
ggcctatgac cggaagaaag tctccaaggc cgccatcttg gccaggatta aaagaaccgg   1440
agatggaaac tacaagagtg gctgagtttg gggtccctca ggttcctttt tcaaaaacca   1500
gccaggcaga ggttttaatg tctgtttatt aactactgaa taatgctacc aggatgctaa   1560
agatgatgat gttaacccat tccagtacag tattctttta aaattcaaaa gtattgaaag   1620
ccaacaactc tgcctttatg atgctaagct gatattattt cttctcttat cctctctctc   1680
ttctaggccc attgtcctcc ttttcacttt attgctatcg ccctcctttc ccttattgcc   1740
tcccaggcaa gcagctggtc agtctttgct cagtgtccag cttccaaagc ctagacaacc   1800
tttctgtagc ctaaaacgaa tggtctttgc tccagataac tctctttcct tgagctgttg   1860
tgagctttga agtaggtggc ttgagctaga gataaaacag aatcttctgg gtagtcccct   1920
gttgattatc ttcagcccag gcttttgcta gatggaatgg aaaagcaact tcatttgaca   1980
caaagcttct aaagcaggta aattgtcggg ggagagagtt agcatgtatg aatgtaagga   2040
```

-continued

```
tgagggaagc gaagcaagag gaacctctcg ccatgatcag acatacagct gcctacctaa   2100
tgaggacttc aagccccacc acatagcatg cttcctttct ctcctggctc ggggtaaaaa   2160
gtggctgcgg tgtttggcaa tgctaattca atgccgcaac atatagttga ggccgaggat   2220
aaagaaagac attttaagtt tgtagtaaaa gtggtctctg ctggggaagg gtttcttttc   2280
ttttttcttt atcacaagga gatttcttag ttcatatatc aagaagtctt gaagttgggt   2340
gtttccagaa ttggtaaaaa cagcagctca tggaattttg agtattccat gagctgctca   2400
ttacagttct ttcctctttc tgctctgcca tcttcaggat attggttctt cccctcatag   2460
taataagatg gctgtggcat ttccaaacat ccaaaaaaag ggaaggattt aaggaggtga   2520
agtcgggtca aaaataaaat atatatacat atatacattg cttagaacgt taaactatta   2580
gagtatttcc cttccaaaga gggatgtttg gaaaaaactc tgaaggagag gaggaattag   2640
ttgggatgcc aatttcctct ccactgctgg acatgagatg gagaggctga gggacaggat   2700
ctataggcag cttctaagag cgaacttcac ataggaaggg atctgagaac acgttgccag   2760
gggcttgaga aggttactga gtgagttatt gggagtctta ataaaataaa ctagatatta   2820
ggtccattca ttaattagtt ccagtttctc cttgaaatga gtaaaaacta gaaggcttct   2880
ctccacagtg ttgtgcccct tcactcattt ttttttgagg agaaggggggt ctctgttaac   2940
atctagccta aagtatacaa ctgcctgggg ggcagggtta ggaatctctt cactaccctg   3000
attcttgatt cctggctcta ccctgtctgt cccttttctt tgaccagatc tttctcttcc   3060
ctgaacgttt tcttctttcc ctggacaggc agcctccttt gtgtgtattc agaggcagtg   3120
atgacttgct gtccaggcag ctccctcctg cacacagaat gctcagggtc actgaaccac   3180
tgcttctctt ttgaaagtag agctagctgc cactttcacg tggcctccgc agtgtctcca   3240
cctacacccc tgtgctcccc tgccacactg atggctcaag acaaggctgg caaaccctcc   3300
cagaaacatc tctggcccag aaagcctctc tctccctccc tctctcatga ggcacagcca   3360
agccaagcgc tcatgttgag ccagtgggcc agccacagag caaaagaggg tttattttca   3420
gtcccctctc tctgggtcag aaccagaggg catgctgaat gccccctgct tacttggtga   3480
gggtgccccg cctgagtcag tgctctcagc tggcagtgca atgcttgtag aagtaggagg   3540
aaacagttct cactgggaag aagcaagggc aagaacccaa gtgcctcacc tcgaaaggag   3600
gccctgttcc ctggagtcag ggtgaactgc aaagctttgg ctgagacctg ggatttgaga   3660
taccacaaac cctgctgaac acagtgtctg ttcagcaaac taaccagcat tccctacagc   3720
ctagggcaga caatagtata gaagtctgga aaaaaacaaa aacagaattt gagaaccttg   3780
gaccactcct tgtccctgta gctcagtcat caaagcagaa gtcctggctt tgctctataa   3840
agaattggaa atggtacact acccaaacac tcagttcact tgttgagccc cagtgcctgg   3900
aagggaggaa ggcctttctt ctgtgttaat tgccgtagag gctacagggg ttagccctgg   3960
actaaaggca tccttgtctt ttgagctatt cacctcagta gaaaaggatc taagggaaga   4020
tcactgtagt ttagttctgt tgaccttgtg cacctacccc ttggaaatgt ctgctggtat   4080
ttctaattcc acaggtcatc agatgcctgc ttgataatat ataaacaata aaaacaactt   4140
tcacttcttc ctattgtaat cgtgtgccat ggatctgatc tgtaccatga ccctacataa   4200
ggctggatgg cacctcaggc tgagggcccc aatgtatgtg tggctgtggg tgtgggtggg   4260
agtgtgtctg ctgagtaagg aacacgattt tcaagattct aaagctcaat tcaagtgaca   4320
cattaatgat aaactcagat ctgatcaaga gtccggattt ctaacagtcc ttgctttggg   4380
```

```
ggggtgtgct gacaacttag ctcaggtgcc ttacatcttt tctaatcaca gtgttgcata   4440

tgagcctgcc ctcactccct ctgcagaatc cctttgcacc tgagacccta ctgaagtggc   4500

tggtagaaaa aggggcctga gtggaggatt atcagtatca cgatttgcag gattcccttc   4560

tgggcttcat tctggaaact tttgttaggg ctgcttttct taagtgccca catttgatgg   4620

agggtggaaa taatttgaat gtatttgatt tataagtttt tttttttttt ttgggttaaa   4680

agatggttgt agcatttaaa atggaaaatt ttctccttgg tttgctagta tcttgggtgt   4740

attctctgta agtgtagctc aaataggtca tcatgaaagg ttaaaaaagc gaggtggcca   4800

tgttatgctg gtggttaagg ccagggcctc tccaaccact gtgccactga cttgctgtgt   4860

gacctctggg caagtcactt aacgtataag gtgcctcagt tttccttctg ttaaaatggg   4920

gataataata ctgacctacc tcaaagggca gttttgaggc atgactaatg ctttttagaa   4980

agcattttgg gatccttcag cacaggaatt ctcaagacct gagtattttt tataatagga   5040

atgtccacca tgaacttgat acgtccgtgt gtcccagatg ctgtcattag tctatatggt   5100

tctccaagaa actgaatgaa tccattggag aagcggtgga taactagcca gacaaaattt   5160

gagaatacat aaacaacgca ttgccacgga aacatacaga ggatgccttt tctgtgattg   5220

ggtgggattt ttttcccttt ttatgtggga tatagtagtt acttgtgaca agaataattt   5280

tggaataatt tctattaata tcaactctga agctaattgt actaatctga gattgtggtg   5340

agcagtgacg atgaggagtt gtccagggac agagacgtat atgtgactac ccatactccc   5400

agaaacgcca gggatgaggg cgctacaggc ctcaggccct caggtactgt cagttgtccc   5460

atctgcatgg actggatact cagaggtaag taaaccaagc tgtatcttcc aggcttctgg   5520

tttctaaact tcactgaaag aattggatga gacaggatct tccccctcgg tgggattgga   5580

cacccctact cacagtcatg cctgggccct cacttattgc agatctgcct gtgaggggag   5640

aatgtgcc                                                            5648
```

<210> SEQ ID NO 71
<211> LENGTH: 56
<212> TYPE: DNA
<213> ORGANISM: Homo sapiens
<220> FEATURE:
<221> NAME/KEY: misc_feature
<223> OTHER INFORMATION: Incyte ID No: 053959.1
<221> NAME/KEY: unsure
<222> LOCATION: 2, 13, 20, 32, 41, 47
<223> OTHER INFORMATION: a, t, c, g, or other

<400> SEQUENCE: 71

```
gngaggcaat ganccctctn ccccacctct tncctgccca natctgnctc ctagaa         56
```

<210> SEQ ID NO 72
<211> LENGTH: 580
<212> TYPE: DNA
<213> ORGANISM: Homo sapiens
<220> FEATURE:
<221> NAME/KEY: misc_feature
<223> OTHER INFORMATION: Incyte ID No: 1384594.1

<400> SEQUENCE: 72

```
cttgggtgat ggggcacgga agagggttac aggcaaaggg accagcgttt ctaaactctt     60

ggagacacag tgaagaaggt tcatacctgg agtgccaagg ttactgtgtc tccagaaaca    120

catatggacc tcacaaagga cgagtgggga cttcttgatg aggctcagag actcctgtac    180

cttgaagtga tgctggagaa ctttgccctt gtagcctcac tgggttgtgg ccatggaaca    240
```

-continued

```
gaggatgaag agacaccttc tgaccagaat gtttactcta ggagtgtcac agtcaaaagg    300

caggttcatc caaaacagga gactccagtc ctgtggaaag tgtgtccaag tcctaaagat    360

aattttggat ctagctgaat ctcctagggc aggaaacata cttgggttcg ggagatgtac    420

aaacctggca caaggacaag aaggcttaac agtgcaaaga aaaaccttga taaggggcaa    480

tggacagagc ctcaaaaatg tggaagtgag gaccctagca tgtaagtcga tggaagccct    540

ttcgggaatt gggagggttt ggaaagggac cctccagacc                          580


<210> SEQ ID NO 73
<211> LENGTH: 2572
<212> TYPE: DNA
<213> ORGANISM: Homo sapiens
<220> FEATURE:
<221> NAME/KEY: misc_feature
<223> OTHER INFORMATION: Incyte ID No: 021667CB1

<400> SEQUENCE: 73

gtgcgtaaca cacatcaaga cagaacctgt tgccattttc agccaccaga gtgaaacgac     60

tgcccctcct ccggccccga cccaggccct ccctgagttc accagtatat tcagctcaca    120

ccagaccgca gctccagagg tgaacaatat tttcatcaaa caagaacttc ctacaccaga    180

tcttcatctt tctgtcccta cccagcaggg ccacctgtac cagctactga atacaccgga    240

tctagatatg cccagttcta caaatcagac agcagcaatg gacactctta atgtttctat    300

gtcagctgcc atggcaggcc ttaacacaca cacctctgct gttccgcaga ctgcagtgaa    360

acaattccag ggcatgcccc cttgcacata cacaatgcca agtcagtttc ttccacaaca    420

ggccacttac tttcccccgt caccaccaag ctcagagcct ggaagtccag atagacaagc    480

agagatgctc cagaatttaa ccccacctcc atcctatgct gctacaattg cttctaaact    540

ggcaattcac aatccaaatt tacccaccac cctgccagtt aactcacaaa acatccaacc    600

tgtcagatac aatagaagga gtaaccccga tttggagaaa cgacgcatcc actactgcga    660

ttaccctggt tgcacaaaag tttataccaa gtcttctcat ttaaaagctc acctgaggac    720

tcacactggt gaaaagccat acaagtgtac ctgggaaggc tgcgactgga ggttcgcgcg    780

atcggatgag ctgacccgcc actaccggaa gcacacaggc gccaagccct tccagtgcgg    840

ggtgtgcaac cgcagcttct cgcgctctga ccacctggcc ctgcatatga agaggcacca    900

gaactgagca ctgcccgtgt gacccgttcc aggtcccctg ggctccctca aatgacagac    960

ctaactattc ctgtgtaaaa acaacaaaaa caaacaaaag caagaaaacc acaactaaaa   1020

ctggaaatgt atattttgta tatttgagaa aacagggaat acattgtatt aataccaaag   1080

tgtttggtca ttttaagaat ctggaatgct tgctgtaatg tatatggctt tactcaagca   1140

gatctcatct catgacaggc agccacgtct caacatgggt aaggggtggg ggtggagggg   1200

agtgtgtgca gcgtttttac ctaggcacca tcatttaatg tgacagtgtt cagtaaacaa   1260

atcagttggc aggcaccaga agaagaatgg attgtatgtc aagattttac ttggcattga   1320

gtagtttttt tcaatagtag gtaattcctt agagatacag tatacctggc aattcacaaa   1380

tagccattga acaaatgtgt gggtttttaa aaattatata catatatgag ttgcctatat   1440

ttgctattca aaattttgta aatatgcaaa tcagctttat aggtttatta caagtttttt   1500

aggattcttt tggggaagag tcataattct tttgaaaata accatgaata cacttacagt   1560

taggatttgt ggtaaggtac ctctcaacat taccaaaatc atttctttag agggaaggaa   1620

taatcattca aatgaacttt aaaaaagcaa atttcatgca ctgattaaaa taggattatt   1680
```

-continued

```
ttaaatacaa aaggcatttt atatgaatta taaactgaag agcttaaaga tagttacaaa   1740

atacaaaagt tcaacctctt acaataagct aaacgcaatg tcatttttaa aaagaaggac   1800

ttagggtgtc gttttcacat atgacaatgt tgcatttatg atgcagtttc aagtaccaaa   1860

acgttgaatt gatgatgcag ttttcatata tcgagatgtt cgctcgtgca gtactgttgg   1920

ttaaatgaca atttatgtgg attttgcatg taatacacag tgagacacag taattttatc   1980

taaattacag tgcagtttag ttaatctatt aatactgact cagtgtctgc ctttaaatat   2040

aaatgatatg ttgaaaactt aaggaagcaa atgctacata tatgcaatat aaaatagtaa   2100

tgtgatgctg atgctgttaa ccaaagggca gaataaataa gcaaaatgcc aaaaggggtc   2160

ttaattgaaa tgaaaattta attttgtttt taaaatattg tttatcttta tttattttgt   2220

ggtaatatag taagtttttt tagaagacaa ttttcataac ttgataaatt atagttttgt   2280

ttgttagaaa agttgctctt aaaagatgta aatagatgac aaacgatgta aataattttg   2340

taagaggctt caaaatgttt atacgtggaa acacacctac atgaaaagca gaaatcggtt   2400

gctgttttgc ttctttttcc ctcttatttt tgtattgtgg tcatttccta tgcaaataat   2460

ggagcaaaca gctgtatagt tgtagaattt tttgagagaa tgagatgttt atatattaac   2520

gacaattttt tttttggaaa ataaaaagtg cctaaaagac aaaaaaaaaa aa           2572
```

```
<210> SEQ ID NO 74
<211> LENGTH: 219
<212> TYPE: PRT
<213> ORGANISM: Homo sapiens
<220> FEATURE:
<221> NAME/KEY: misc_feature
<223> OTHER INFORMATION: Incyte ID No: 021667CD1

<400> SEQUENCE: 74

Met Pro Ser Ser Thr Asn Gln Thr Ala Ala Met Asp Thr Leu Asn
  1               5                  10                  15

Val Ser Met Ser Ala Ala Met Ala Gly Leu Asn Thr His Thr Ser
                 20                  25                  30

Ala Val Pro Gln Thr Ala Val Lys Gln Phe Gln Gly Met Pro Pro
                 35                  40                  45

Cys Thr Tyr Thr Met Pro Ser Gln Phe Leu Pro Gln Gln Ala Thr
                 50                  55                  60

Tyr Phe Pro Pro Ser Pro Pro Ser Ser Glu Pro Gly Ser Pro Asp
                 65                  70                  75

Arg Gln Ala Glu Met Leu Gln Asn Leu Thr Pro Pro Pro Ser Tyr
                 80                  85                  90

Ala Ala Thr Ile Ala Ser Lys Leu Ala Ile His Asn Pro Asn Leu
                 95                 100                 105

Pro Thr Thr Leu Pro Val Asn Ser Gln Asn Ile Gln Pro Val Arg
                110                 115                 120

Tyr Asn Arg Arg Ser Asn Pro Asp Leu Glu Lys Arg Arg Ile His
                125                 130                 135

Tyr Cys Asp Tyr Pro Gly Cys Thr Lys Val Tyr Thr Lys Ser Ser
                140                 145                 150

His Leu Lys Ala His Leu Arg Thr His Thr Gly Glu Lys Pro Tyr
                155                 160                 165

Lys Cys Thr Trp Glu Gly Cys Asp Trp Arg Phe Ala Arg Ser Asp
                170                 175                 180

Glu Leu Thr Arg His Tyr Arg Lys His Thr Gly Ala Lys Pro Phe
                185                 190                 195
```

-continued

```
Gln Cys Gly Val Cys Asn Arg Ser Phe Ser Arg Ser Asp His Leu
            200                 205                 210

Ala Leu His Met Lys Arg His Gln Asn
            215


<210> SEQ ID NO 75
<211> LENGTH: 5325
<212> TYPE: DNA
<213> ORGANISM: Homo sapiens
<220> FEATURE:
<221> NAME/KEY: misc_feature
<223> OTHER INFORMATION: Incyte ID No: 224855.4
<221> NAME/KEY: unsure
<222> LOCATION: 1500-1699
<223> OTHER INFORMATION: a, t, c, g, or other

<400> SEQUENCE: 75

acctcgcact ctcagtttca ccgctcgatc ttgggaccca ccgctgccct cagctccgag     60

tccagggcga gtgcagagca gagcgggcgg aggaccccgg gcgcgggcgc ggacggcacg    120

cggggcatga acctggaggg cggcggccga ggcggagagt tcggcatgag cgcggtgagc    180

tgcggcaacg ggaagctccg ccagtggctg atcgaccaga tcgacagcgg caagtacccc    240

gggctggtgt gggagaacga ggagaagagc atcttccgca tcccctggaa gcacgcgggc    300

aagcaggact acaaccgcga ggaggacgcc gcgctcttca aggcttgggc actgtttaaa    360

ggaaagttcc gagaaggcat cgacaagccg gaccctccca cctggaagac gcgcctgcgg    420

tgcgctttga acaagagcaa tgactttgag gaactggttg agcggagcca gctggacatc    480

tcagacccgt acaaagtgta caggattgtt cctgagggag ccaaaaaagg agccaagcag    540

ctcaccctgg aggacccgca gatgtccatg agccacccct acaccatgac aacgccttac    600

ccttcgctcc cagcccaggt tcacaactac atgatgccac ccctcgaccg aagctggagg    660

gactacgtcc cggatcagcc acacccggaa atcccgtacc aatgtcccat gacgtttgga    720

ccccgcggcc accactggca aggcccagct tgtgaaaatg gttgccaggt gacaggaacc    780

ttttatgctt gtgccccacc tgagtcccag gctcccggag tccccacaga gccaagcata    840

aggtctgccg aagccttggc gttctcagac tgccggctgc acatctgcct gtactaccgg    900

gaaatcctcg tgaaggagct gaccacgtcc agccccgagg gctgccggat ctcccatgga    960

catacgtatg acgccagcaa cctggaccag gtcctgttcc cctacccaga ggacaatggc   1020

cagaggaaaa acattgagaa gctgctgagc cacctggaga ggggcgtggt cctctggatg   1080

gcccccgacg ggctctatgc gaaaagactg tgccagagca ggatctactg ggacgggccc   1140

ctggcgctgt gcaacgaccg gcccaacaaa ctggagagag accagacctg caagctcttt   1200

gacacacagc agttcttgtc agagctgcaa gcgtttgctc accacggccg ctccctgcca   1260

agattccagg tgactctatg ctttggagag gagtttccag accctcagag gcaaagaaag   1320

ctcatcacag ctcacgtaga acctctgcta gccagacaac tatattattt tgctcaacaa   1380

aacagtggac atttcctgag ggctacgat ttaccagaac acatcagcaa tccagaagat   1440

taccacagat ctatccgcca ttcctctatt caagaatgaa aaatgtcaag atgagtgggn   1500

nnnnnnnnnn nnnnnnnnnn nnnnnnnnnn nnnnnnnnnn nnnnnnnnnn nnnnnnnnnn   1560

nnnnnnnnnn nnnnnnnnnn nnnnnnnnnn nnnnnnnnnn nnnnnnnnnn nnnnnnnnnn   1620

nnnnnnnnnn nnnnnnnnnn nnnnnnnnnn nnnnnnnnnn nnnnnnnnnn nnnnnnnnnn   1680

nnnnnnnnnn nnnnnnnnnc attgtaaata tttgacttta gtgaaagcgt ccaattgact   1740
```

-continued

```
gcgcctctta ctgttttgag gaactcagaa gtggagattt cagttcagcg gttgaggaga   1800
attgcggcga gacaagcatg gaaaatcagt gacatctgat tggcagatga gcttatttca   1860
aaaggaaggg tggctttgca ttttcttgtg ttctgtagac tgccatcatt gatgatcact   1920
gtgaaaattg accaagtgat gtgtttacat ttactgaaat gcgctcttta atttgttgta   1980
gattaggtct tgctggaaga cagagaaaac ttgcctttca gtattgacac tgactagagt   2040
gatgactgct tgtaggtatg tctgtgccat ttctcaggga agtaagatgt aaattgaaga   2100
agcctcacac gtaaaagaaa tgtattaatg tatgtaggag ctgcagttct tgtggaagac   2160
acttgctgag tgaaggaaat gaatctttga ctgaagccgt gcctgtagcc ttggggaggc   2220
ccatccccca cctgccagcg gtttcctggt gtgggtccct ctgccccacc ctccttccca   2280
ttggctttct ctccttggcc tttcctggaa gccagttagt aaacttccta ttttcttgag   2340
tcaaaaaaca tgagcgctac tcttggatgg gacatttttg tctgtcctac aatctagtaa   2400
tgtctaagta atggttaagt ttttcttgttt ctgcatcttt ttgaccctca ttctttagag   2460
atgctaaaat tcttcgcata aagaagaaga aattaaggaa cataaatctt aatacttgaa   2520
ctgttgccct tctgtccaag tacttaacta tctgttccct tcctctgtgc cacgctcctc   2580
tgtttgtttg gctgtccagc gatcagccat ggcgacacta aaggaggagg agccggggac   2640
tcccaggctg gagagcactg ccaggaccca ccactggaag caggatggag ctgactacgg   2700
aactgcacac tcagtgggct gtttctgctt atttcatctg ttctatgctt cctcgtgcca   2760
attatagttt gacagggcct taaaattact tggctttttc caaatgcttc tatttataga   2820
atcccaaaga cctccacttg cttaagtata cctatcactt acatttttgt ggttttgaga   2880
aagtacagca gtagactggg gcgtcacctc caggccgttt ctcatactac aggatattta   2940
ctattactcc caggatcagc agaagattgc gtagctctca aatgtgtgtt cctgcttttc   3000
taatggatat tttaaattca ttcaacaagc acctagtaag tgcctgctgt atccctacat   3060
tacacagttc agcctttatc aagcttagtg agcagtgagc actgaaacat tattttttaa   3120
tgtttaaaaa gtttctaata ttaaagtcag aatattaata caattaatat taatattaac   3180
tacagaaaag acaaacagta gagaacagca aaaaaataaa aaggatctcc tttttttccca   3240
gcccaaattc tcctctctaa aagtgtccac aagaaggggt gtttattctt ccaacacatt   3300
tcacttttct gtaaatatac ataaacttaa aaagaaaacc tcatggagtc atcttgcaca   3360
cactttcatg cagtgctctt tgtagctaac agtgaagatt tacctcgttc tgctcagagg   3420
ccttgctgtg gagctccact gccatgtacc cagtagggtt tgacatttca ttagccatgc   3480
aacatggata tgtattgggc agcagactgt gtttcgtgaa ctgcagtgat gtatacatct   3540
tatagatgca aagtattttg ggtatatta tcctaaggga agataaagat gatattaaga   3600
actgctgttt cacggggccc ttacctgtga ccctctttgc tgaagaatat ttaaccccac   3660
acagcacttt caaagaagct gtcttggaag tctgtctcag gagcaccctg tcttcttaat   3720
tctccaagcg gatgctccat ttcaattgct ttgtgacttc ttcttctttg ttttttttaaa   3780
tattatgctg ctttaacagt ggagctgaat tttctggaaa atgcttcttg gctggggcca   3840
ctacctcctt tcctatcttt acatctatgt gtatgttgac tttttaaaat tctgagtgat   3900
ccagggtatg acctagggaa tgaactagct atgaaatact cagggttagg aatcctagca   3960
cttgtctcag gactctgaaa aggaacggct tcctcattcc ttgtcttgat aaagtggaat   4020
tggcaaacta gaatttagtt tgtactcagt ggacagtgct gttgaagatt tgaggacttg   4080
ttaaagagca ctgggtcata tggaaaaaat gtatgtgtct cccaggtgca tttcttggtt   4140
```

```
tatgtcttgt tcttgagatt ttgtatattt aggaaaacct caagcagtaa ttaatatctc   4200
ctggaacact atagagaacc aagtgaccga ctcatttaca actgaaacct aggaagcccc   4260
tgagtcctga gcgaaaacag gagagttagt cgccctacag gaaacccagc tagactattg   4320
ggtatgaact aaaaagagac tgtgccatgg tgagaaaaat gtaaaatcct acagtggaat   4380
gagcagccct tacagtgttg ttaccaccaa gggcaggtag gtattagtgt ttgaaaaagc   4440
tggtctttga gcgagggcat aaatacagct agccccaggg gtggaacaac tctgggagtc   4500
ttgggtactc gcacctcttg gctttgttga tgctccgcca ggaaggccac ttgtgtgtgc   4560
gtgtcagtta ctttttttagt aacaattcag atccagtgta aacttccgtt cattgctctc   4620
cagtcacatg cccccacttc cccacaggtg aaagtttttc tgaaagtgtt gggattggtt   4680
aaggtcttta tttgtattac gtatctcccc aagtcctctg tggccagctg cgtctgtctg   4740
aatggtgcgt gaaggctctc agaccttaca caccattttg taagttatgt tttacatgcc   4800
ccgtttttga gactgatctc gatgcaggtg gatctccttg agatcctgat agcctgttac   4860
aggaatgaag taaaggtcag ttttttttgt attgattttc acagctttga ggaacatgca   4920
taagaaatgt agctgaagta gagggggcgt gagagaaggg ccaggccggc aggccaaccc   4980
tcctccaatg gaaattcccg tgttgcttca aactgagaca gatgggactt aacaggcaat   5040
ggggtccact tccccctctt cagcatcccc cgtaccccac tttctgctga aagaactgcc   5100
agcaggtagg accccagagg cccccaaatg aaagcttgaa tttcccctac tggctctgcg   5160
ttttgctgag atctgtagga aaggatgctt cacaaactga ggtagataat gctatgctgt   5220
cgttggtata catcatgaat ttttatgtaa attgctctgc aaagcaaatt gatatgtttg   5280
ataaatttat gtttttaggt aaataaaaac ttttaaaaag ttgtt                   5325
```

```
<210> SEQ ID NO 76
<211> LENGTH: 2278
<212> TYPE: DNA
<213> ORGANISM: Homo sapiens
<220> FEATURE:
<221> NAME/KEY: misc_feature
<223> OTHER INFORMATION: Incyte ID No: 1518310CB1

<400> SEQUENCE: 76
```

```
ggctcctctc cccgactcgg agcccctcgg cggcgcccgg cccaggaccc gcctaggagc     60
gcaggagccc cagcgcagag accccaacgc cgagaccccc gccccggccc cgccgcgctt    120
cctcccgacg cagagcaaac cgcccagagt agaagatgga ttggggcacg ctgcagacga    180
tcctgggggg tgtgaacaaa cactccacca gcattggaaa gatctggctc accgtcctct    240
tcatttttcg cattatgatc ctcgttgtgg ctgcaaagga ggtgtgggga gatgagcagg    300
ccgactttgt ctgcaacacc ctgcagccag gctgcaagaa cgtgtgctac gatcactact    360
tccccatctc ccacatccgg ctatgggccc tgcagctgat cttcgtgtcc acgccagcgc    420
tcctagtggc catgcacgtg gcctaccgga gacatgagaa gaagaggaag ttcatcaagg    480
gggagataaa gagtgaattt aaggacatcg aggagatcaa aacccagaag gtccgcatcg    540
aaggctccct gtggtggacc tacacaagca gcatcttctt ccgggtcatc ttcgaagccg    600
ccttcatgta cgtcttctat gtcatgtacg acggcttctc catgcagcgg ctggtgaagt    660
gcaacgcctg gccttgtccc aacactgtgg actgctttgt gtcccggccc acggagaaga    720
ctgtcttcac agtgttcatg attgcagtgt ctggaatttg catcctgctg aatgtcactg    780
aattgtgtta tttgctaatt agatattgtt ctgggaagtc aaaaaagcca gtttaacgca    840
```

```
ttgcccagtt gttagattaa gaaatagaca gcatgagagg gatgaggcaa cccgtgctca    900

gctgtcaagg ctcagtcgct agcatttccc aacacaaaga ttctgacctt aaatgcaacc    960

atttgaaacc cctgtaggcc tcaggtgaaa ctccagatgc cacaatggag ctctgctccc   1020

ctaaagcctc aaaacaaagg cctaattcta tgcctgtctt aattttcttt cacttaagtt   1080

agttccactg agaccccagg ctgttagggg ttattggtgt aaggtacttt catattttaa   1140

acagaggata tcggcatttg tttctttctc tgaggacaag agaaaaaagc caggttccac   1200

agaggacaca gagaaggttt gggtgtcctc ctggggttct ttttgccaac tttccccacg   1260

ttaaaggtga acattggttc tttcatttgc tttggaagtt ttaatctcta acagtggaca   1320

aagttaccag tgccttaaac tctgttacac tttttggaag tgaaaacttt gtagtatgat   1380

aggttatttt gatgtaaaga tgttctggat accattatat gttccccctg tttcagaggc   1440

tcagattgta atatgtaaat ggtatgtcat tcgctactat gatttaattt gaaatatggt   1500

cttttggtta tgaatacttt gcagcacagc tgagaggctg tctgttgtat tcattgtggt   1560

catagcacct aacaacattg tagcctcaat cgagtgagac agactagaag ttcctagtga   1620

tggcttatga tagcaaatgg cctcatgtca aatatttaga tgtaattttg tgtaagaaat   1680

acagactgga tgtaccacca actactacct gtaatgacag gcctgtccaa cacatctccc   1740

ttttccatga ctgtggtagc cagcatcgga aagaacgctg atttaaagag gtcgcttggg   1800

aattttattg acacagtacc atttaatggg gaggacaaaa tggggcaggg gagggagaag   1860

tttctgtcgt taaaaacaga tttggaaaga ctggactcta aattctgttg attaaagatg   1920

agctttgtct acttcaaaag tttgtttgct taccccttca gcctccaatt ttttaagtga   1980

aaatataact aataacatgt gaaaagaata gaagctaagg tttagataaa tattgagcag   2040

atctatagga agattgaacc tgaatattgc cattatgctt gacatggttt ccaaaaaatg   2100

gtactccaca tacttcagtg agggtaagta ttttcctgtt gtcaagaata gcattgtaaa   2160

agcattttgt aataataaag aatagcttta atgatatgct tgtaactaaa ataattttgt   2220

aatgtatcaa atacatttaa aacattaaaa tataatctct atagtaacga acagaaaa     2278
```

<210> SEQ ID NO 77
<211> LENGTH: 226
<212> TYPE: PRT
<213> ORGANISM: Homo sapiens
<220> FEATURE:
<221> NAME/KEY: misc_feature
<223> OTHER INFORMATION: Incyte ID No: 1518310CD1

<400> SEQUENCE: 77

```
Met Asp Trp Gly Thr Leu Gln Thr Ile Leu Gly Gly Val Asn Lys
  1               5                  10                  15

His Ser Thr Ser Ile Gly Lys Ile Trp Leu Thr Val Leu Phe Ile
                 20                  25                  30

Phe Arg Ile Met Ile Leu Val Val Ala Ala Lys Glu Val Trp Gly
                 35                  40                  45

Asp Glu Gln Ala Asp Phe Val Cys Asn Thr Leu Gln Pro Gly Cys
                 50                  55                  60

Lys Asn Val Cys Tyr Asp His Tyr Phe Pro Ile Ser His Ile Arg
                 65                  70                  75

Leu Trp Ala Leu Gln Leu Ile Phe Val Ser Thr Pro Ala Leu Leu
                 80                  85                  90

Val Ala Met His Val Ala Tyr Arg Arg His Glu Lys Lys Arg Lys
```

```
                95                  100                 105

Phe Ile Lys Gly Glu Ile Lys Ser Glu Phe Lys Asp Ile Glu Glu
                110                 115                 120

Ile Lys Thr Gln Lys Val Arg Ile Glu Gly Ser Leu Trp Trp Thr
                125                 130                 135

Tyr Thr Ser Ser Ile Phe Phe Arg Val Ile Phe Glu Ala Ala Phe
                140                 145                 150

Met Tyr Val Phe Tyr Val Met Tyr Asp Gly Phe Ser Met Gln Arg
                155                 160                 165

Leu Val Lys Cys Asn Ala Trp Pro Cys Pro Asn Thr Val Asp Cys
                170                 175                 180

Phe Val Ser Arg Pro Thr Glu Lys Thr Val Phe Thr Val Phe Met
                185                 190                 195

Ile Ala Val Ser Gly Ile Cys Ile Leu Leu Asn Val Thr Glu Leu
                200                 205                 210

Cys Tyr Leu Leu Ile Arg Tyr Cys Ser Gly Lys Ser Lys Lys Pro
                215                 220                 225

Val


<210> SEQ ID NO 78
<211> LENGTH: 445
<212> TYPE: DNA
<213> ORGANISM: Homo sapiens
<220> FEATURE:
<221> NAME/KEY: misc_feature
<223> OTHER INFORMATION: Incyte ID No: 098533.1
<221> NAME/KEY: unsure
<222> LOCATION: 406, 413
<223> OTHER INFORMATION: a, t, c, g, or other

<400> SEQUENCE: 78

ggcaaggcca gtggctccgc cgctgggtcc gctgcccttt actttcagtc agcctggggc     60

ggtgtcctct cctacagaag tcctgagcgg ccttccacgt ggccggccct cgagtccgtc    120

cgccccgacc cttcgtagtc ccgaaaccgc ccccctggct aaggtctctt tcccccaggc    180

tgcttccttt ctccttgctt ttttcccacc ttttttgtta ctgaccaagg tgaatccttt    240

ccttaacaaa tcggcttaaa gcaagctaac tcagttacaa tacagtagaa ctgtacttaa    300

aaaaaaaaga aacgtgaatc taaccgttac gtcagaaaaa aaaatcttaa attagacgaa    360

tttcaaacag tgcttaacac atcgcagagc atttgcagtt atttgnatca cgncttttga    420

aacaccttta tgctgtaaat agagc                                          445


<210> SEQ ID NO 79
<211> LENGTH: 5227
<212> TYPE: DNA
<213> ORGANISM: Homo sapiens
<220> FEATURE:
<221> NAME/KEY: misc_feature
<223> OTHER INFORMATION: Incyte ID No: 410785.1
<221> NAME/KEY: unsure
<222> LOCATION: 4928, 4934, 4939, 4944, 4973, 4992
<223> OTHER INFORMATION: a, t, c, g, or other

<400> SEQUENCE: 79

cacaagacct ggaattgaca ggactcccaa ctagtacaat gacagaagat aaggtcactg     60

ggaccctggt tttcactgtc atcactgctg tgctgggttc cttccagttt ggatatgaca    120

ttggtgtgat caatgcacct caacaggtaa taatatctca ctatagacat gttttgggtg    180

ttccactgga tgaccgaaaa gctatcaaca actatgttat caacagtaca gatgaactgc    240
```

-continued

```
ccacaatctc atactcaatg aacccaaaac caaccccttg ggctgaggaa gagactgtgg    300
cagctgctca actaatcacc atgctctggt ccctgtctgt atccagcttt gcagttggtg    360
gaatgactgc atcattcttt ggtgggtggc ttggggacac acttggaaga atcaaagcca    420
tgttagtagc aaacattctg tcattagttg gagctctctt gatggggttt tcaaaattgg    480
gaccatctca tatacttata attgctggaa gaagcatatc aggactatat tgtgggctaa    540
tttcaggcct ggttcctatg tatatcggtg aaattgctcc aaccgctctc aggggagcac    600
ttggcacttt tcatcagctg gccatcgtca cgggcattct tattagtcag attattggtc    660
ttgaatttat cttgggcaat tatgatctgt ggcacatctt gcttggcctg tctggtgtgc    720
gagccatcct tcagtctctg ctactctttt tctgtccaga aagccccaga tacctttaca    780
tcaagttaga tgaggaagtc aaagcaaaac aaagcttgaa aagactcaga ggatatgatg    840
atgtcaccaa agatattaat gaaatgagaa aagaaagaga agaagcatcg agtgagcaga    900
aagtctctat aattcagctc ttcaccaatt ccagctaccg acagcctatt ctagtggcac    960
tgatgctgca tgtggctcag caatttccg gaatcaatgg cattttttac tactcaacca   1020
gcatttttca gacggctggt atcagcaaac ctgtttatgc aaccattgga gttggcgctg   1080
taaacatggt tttcactgct gtctctgtat tccttgtgga gaaggcaggg cgacgttctc   1140
tctttctaat tggaatgagt gggatgtttg tttgtgccat cttcatgtca gtgggacttg   1200
tgctgctgaa taagttctct tggactgagt tactgtgagc atgatagcca tcttcctctt   1260
tgtcagcttc tttgaaattg ggccaggccc gatcccctgg ttcatggtgg ctgagttttt   1320
cagtcaagga ccacgtcctg ctgctttagc aatagctgca ttcagcaatt ggacctgcaa   1380
tttcattgta gctctgtgtt tccagtacat tgcggacttc tgtggacctt atgtgttttt   1440
cctctttgct ggagtgctcc tggcctttac cctgtttaca ttttttaaag ttccagaaac   1500
caaaggaaag tcttttgagg aaattgctgc agaattccaa aagaagagtg gctcagccca   1560
caggccaaaa gctgctgtag aaatgaaatt cctaggagct acagagactg tgtaaaaaaa   1620
aaaccctgct tttgacatg aacagaaaca ataagggaac cgtctgtttt taaatgatga   1680
ttccttgagc attttatatc cacatcttta agtattgttt tatttttatg tgctctcatc   1740
agaaatgtca tcaaatatta ccaaaaaagt attttttaa gttagagaat atatttttga    1800
tggtaagact gtaattaagt aaaccaaaaa ggctagttta ttttgttaaa ctaaagggca   1860
ggtggttcta atatttttag ctctgttctt tataacaagg ttcttctaaa attgaagaga   1920
tttcaacata tcattttttt aacacataac tagaaacctg aggatgcaac aaatatttat   1980
atatttgaat atcattaaat tggaattttc ttacccatat atcttatgtt aaaggagata   2040
tggctagtgg caataagttc catgttaaaa tagacaactc ttccatttat tgcactcagc   2100
tttttcttg agtactagaa tttgtatttt gcttaaaatt ttacttttgt tctgtatttt    2160
catgtggaat ggattataga gtatactaaa aaatgtctat agagaaaaac tttcattttt   2220
ggtaggctta tcaaaatctt tcagcactca gaaaagaaaa ccattttagt tcctttattt   2280
aatggccaaa tggtttttgc aagatttaac actaaaaagg tttcacctga tcatatagcg   2340
tgggttatca gttaacatta acatctatta taaaaccatg ttgattccct tctggtacaa   2400
tcctttgagt tatagtttgc tttgcttttt aattgaggac agcctggttt tcacatacac   2460
tcaaacatca tgagtcagac atttggtata ttacctcaat tcctaataag tttgatcaat   2520
ctaatgtaag aaaatttgaa gtaaaggatt gatcactttg ttaaaaatat tttctgaatt   2580
```

-continued

```
attatgtctc aaaataagtt gaaaaggtag ggtttgagga ttcctgagtg tgggcttctg   2640
aaacttcata aatgttcagc ttcagacttt tatcaaaatc cctatttaat tttcctggaa   2700
agactgattg ttttatggtg tgttcctaac ataaaataat cgtctccttt gacatttcct   2760
tctttgtctt agctgtatac agattctagc caaactattc tatggccatt actaacacgc   2820
attgtacact atctatctgc ctttacctac ataggcaaat tggaaataca cagatgatta   2880
aacagacttt agcttacagt caattttaca attatggaaa tatagttctg atgggtccca   2940
aaagcttagc agggtgctaa cgtatctcta ggctgttttc tccaccaact ggagcactga   3000
tcaatccttc ttatgtttgc tttaatgtgt attgaagaaa agcacttttt aaaaagtact   3060
ctttaagagt gaaataatta aaaaccactg aacatttgct ttgttttcta aagttgttca   3120
catatatgta atttagcagt ccaaagaaca agaaattgtt tcttttcagt gtgatttgtt   3180
tttcatttgg gccaatttgg gataaactat tttcacttgg gatttcagga tacagtcaaa   3240
ataagcttaa ataactcagg acatctttgt gctaaactgt gaactctgga caaaaataga   3300
gagtctctga atagggcagg agcaggaaaa tggctcctgg gtggctcttg tatgcttctt   3360
caggatgctg atggcctttg ggaagcccag tgtaaacaat gataaaggag cttaacactt   3420
ttataggtga tacatgtgat ttaatcaaat cactattcct gatctcattt actaacagaa   3480
taaagtggta aatatttaaa ttaaaaattc caaagaccac ttttaagtgc ttcttcacta   3540
ttttgactgg cccacaaaca ccagaaattc agaccctgaa gttttctgcc tcagagaaat   3600
ttaagtacct tatattgttc cccttctaca actttttcct tgcagagata catgtgagtt   3660
gacaagaaac attaaaggga aataagaaga agctgataaa gctttatagg aggaccaaag   3720
aactagctta ctataataaa aaaattttaa gtcttcaagg gtatacatca taataaaaaa   3780
taaaattgac agtaattaat taaatttaat cccagggaaa ttagatgtga atttgaacac   3840
ctaactttcc atgtactctc tcatttttgt ggaagtgttt ctatactcta atgcctttac   3900
aaatgtgatt tttctcttag ctcgtttgaa gtatgagaat tagagttttt ggtctcgcat   3960
tcacctgcta catctaggat tgcccactgt catgactccc agggaaaagg tcctatctta   4020
gcttcctcct ccctactttc ctctacatgg tcagcactgt aatgtagcta agatatagta   4080
aggcattgct ccctccccct acacttcaag gagttcacag tctaatgggg agttcaggaa   4140
ggccagagta ttaatatccc catctgtgtc ttttgccttc catgaacctg ggttttgagc   4200
cctctcttgt aaaatgggca cagtaatatt acctacctca gggagttgtg aggattaaac   4260
atgaagtgct aagcatagtg cctggtacaa agacagtact caataagtgc tacctaaaac   4320
tagtattcat agcaatactg ttaggataaa gaattatcat atatgagata gttccaaatt   4380
tttgtttttt taaaaaaaaa agagttttat aagttcaaga taatattttc ttacttcaaa   4440
gaaacaatct cacaacgagg gaatggtaag aatcaggaga gattactaac ctggcagagg   4500
agctatcaca atcacaaagg tggtttttcc agggcacggc tcatccatta cactccagat   4560
gtgctgaccc ctgccatttc cccaaatgtg ggaaacccaa ctgcacagtt tgtagtagtg   4620
ggtgactgtg ttcatgcgct cccctgaaaa caacaacaac aacaaagaat cagaagagat   4680
actaggctat ctaattccta aatccaaacc tgatatttct aagtaagatt ataagaattt   4740
ttattgcatt ttctgaattt gcttttgcat aagttatgtt atttttacag ggtctatatt   4800
actattattt cttagaataa tactaattat aaaacaaaat tctgtatatc acatttaaat   4860
gtaatttaat agaattataa tcacaagaca agaccaaact ttgtgtgata atcctcagta   4920
attgcganag gggnatatnc atgnaggcca gcatacatgc ataaactact tcntattgct   4980
```

aggctaattg tnccatatgt agcaaataca gcagttcagc aatatcttgt gcttacaggg 5040
tcctaagcag aggtgatgag tcaagtgtaa atatatatat atattttttt atttttcatg 5100
gcaattgtat attagtaacc tggggagaaa aggtttattg acaaccactc tgatccatct 5160
gctgctattt ttactgctaa tttggtgcac attaaaaaga atgatcatga aaagatatta 5220
ctttgag 5227

<210> SEQ ID NO 80
<211> LENGTH: 1199
<212> TYPE: DNA
<213> ORGANISM: Homo sapiens
<220> FEATURE:
<221> NAME/KEY: misc_feature
<223> OTHER INFORMATION: Incyte ID No: 1089210.1

<400> SEQUENCE: 80
aaggaaacag gatctgctta gtgaaagaag tggcaagcaa tggatcccaa atatcagcgt 60
gtagagctaa atgatggtca cttcatgccc gtattgggat ttggcaccta tgcacctcca 120
gaggttccga ggaacagagc tgtggaggtc accaaattag caatagaagc tggcttccgc 180
catattgatt ctgcttattt atacaataat gaggagcagg ttggactggc catccgaagc 240
aagattgcag atggcagtgt gaagagagaa gacatattct acacttcaaa gctttggtgc 300
actttctttc aaccacagat ggtccaacca gccttggaaa gctcactgaa aaaactttaa 360
ctggactatg ttgacctcta tcttcttcat ttcccaatgg ctctcaagcc aggtgagacg 420
ccactaccaa aagatgaaaa tggaaaagta atattcgaca cagtggatct ctctgccaca 480
tgggaggtca tggagaagtg taaggatgca ggattggcca agtccatcgg ggtgtcaaac 540
ttcaactgca ggcagctgga gatgatcctc aacaagccag gactcaagta caagcctgtc 600
tgcaaccagg tagaatgtca tccttacctc aaccagagca aactgctgga tttctgcaag 660
tcaaaagaca ttgttctggt tgcccacagt gctctgggaa cccaacgaca taaactatgg 720
gtggacccaa actccccagt tcttttggag gacccagttc tttgtgcctt agcaaagaaa 780
cacaaacgaa ccccagccct gattgccctg cgctaccagc tgcagcgtgg ggttgtggtc 840
ctggccaaga gctacaatga gcagcggatc agagagaaca tccaggtttt tgaattccag 900
ttgacatcag agggatatga aagttctaga tggtctaaac agaaattatc gatatgttgt 960
catggatttt cttatggacc atcctgatta tccattttca gatgaatatt agcatagagg 1020
gtgttgcacg acatctagca gaaggccctg tgtgtggatg gtgatgcaga ggatgtctct 1080
atgctggtga ctggacacac ggcctctggt taaatccctc ccctcctgct tggcaacttc 1140
agctagctag atatatccat ggtccagaaa gcaaacataa taaattttta tcttgaagt 1199

<210> SEQ ID NO 81
<211> LENGTH: 807
<212> TYPE: DNA
<213> ORGANISM: Homo sapiens
<220> FEATURE:
<221> NAME/KEY: misc_feature
<223> OTHER INFORMATION: Incyte ID No: 333453.6
<221> NAME/KEY: unsure
<222> LOCATION: 32, 35, 166
<223> OTHER INFORMATION: a, t, c, g, or other

<400> SEQUENCE: 81
gaacaagact ccgtcaaaaa aaaaaaaatt gnttnggaac ctggttctgg aatcggcttg 60
aatcattcca gcctttcata cttatagctg tgtggccttg ggcaacttac ttaactttat 120

```
ctataaaatg gggacaatag cttctcttcc tcatagcatg gttgtnagga ttagatgaag    180

ttctcagtgg gcattcctgt aagctctagg gagatgttag ctgttactaa tgtttggcac    240

catgacaaat gattagatgg aactttggag caattaataa tacaaattaa aataagggga    300

caaagccagc caaggagaaa agtaaaagat ccaagaatag gggcatataa tggctttatt    360

tttccttgag tctagtgtga ttctaacacc tgagtccaac cattcattat gtaggtccgt    420

atcctctcct gttcttttcc tctcatcctg ggtaccagac agaaggaaaa actgaaacaa    480

atgatgagtc ggctcccttt ctttccttcc atggtggcta tttaggtggc tgatttatga    540

agaacctgga tttcagggtg ttcctttcat cctggaacct ggtgaatacc ctgacttgtc    600

cttctgggat acagaagcag cgtacattgg atccatgcgg cctctgaaaa tggtaaaaat    660

gaaatccaaa tgtccttgtg gtgattcttt gtcagcttga cgtggtaatt cacagggtgt    720

gactttgaag caataaagct gacttttaag acacaaattt gtagtagatt ggacctattg    780

ctcaatacaa atcatggaaa gcataac                                        807
```

<210> SEQ ID NO 82
<211> LENGTH: 764
<212> TYPE: DNA
<213> ORGANISM: Homo sapiens
<220> FEATURE:
<221> NAME/KEY: misc_feature
<223> OTHER INFORMATION: Incyte ID No: 365070.1

<400> SEQUENCE: 82

```
acgaagcagc tgactgtgca tcacgcagtc acaatattgt ttttagggtg agggtggagg     60

actgtgtgtc cgtggattac tcctcctgct ggtggattgc agatgcatta ttaggtcata    120

ctggctagaa tgcagctttt ctcccaccat aacatgaaaa cagtgtaaga acatagggtg    180

ctttgtgcat agcccttctc tatgtaagca gccatggcag tcattaaaga gaaaggagta    240

gctttgacat taagctcccc agatccctgc tgctcatact tctggcaagg ggttcccctc    300

tctcatgcat gaacaggggc atccaaaata agaagctctc cattctgtgg tggggaaagc    360

ggagagggga gtgggtgaag ctgggaaagt aaaggcagca cgttacagaa ggaagaaagg    420

aagccagtaa ctgagggccc actgcctgcc cggccctggg ccaggccctc aacagaagcc    480

atctcattta agccctgcaa ccaatgagat gcacgtcatc attggctctt acagacaaga    540

aaactagact cagaggggct gagtccacat cccagacagc tcactgcaga cacaggtgga    600

gtggttccta caagacatcc agttttaaca acaaaagagt tattgaaatg catgggtaga    660

aattgaacca ggaaaatcag taaagtgatt gtaaaaaaga aggactagct tgcctggaga    720

tgatgtttct tgcttttgga aaaaaaaaaa aggtctctga aatt                     764
```

<210> SEQ ID NO 83
<211> LENGTH: 1325
<212> TYPE: DNA
<213> ORGANISM: Homo sapiens
<220> FEATURE:
<221> NAME/KEY: misc_feature
<223> OTHER INFORMATION: Incyte ID No: 365070.3
<221> NAME/KEY: unsure
<222> LOCATION: 1242
<223> OTHER INFORMATION: a, t, c, g, or other

<400> SEQUENCE: 83

```
gcgctgctgg cggccccggc ggccgggcgt gctgcctgca agatgtccgt gcgccgcggc     60

cggcggccgg cgcggccggg gacccgcctc tcctggctgc tgtgctgcag cgccctgctg    120
```

```
tccccggccg cgggctacgt gatcgtgagc tccgtgtctt gggccgtcac caacgaggtg    180
gacgaggagc tggacagcgc ctccactgag gaggctatgc ccgcgctgct agaggattcg    240
ggcagcatct ggcagcaaag cttccccgcc tctgcccaca aggaggacgc gcacctgcgg    300
ccccgggcgg gcgccgcccg ggccaggccg ccccccgcgc cacccgggat gttctcctac    360
cggcgcgagg gcggccagac ggccagtgcg cccccgggcc ctagactgcg cgccgccacc    420
gcccgctccc tggcccatgc cagcgtctgg ggctgcctgg ccaccgtgtc cacccacaag    480
aagatccaag gactgccatt tgggaactgc ctgcccgtca gtgatggccc cttcaacaat    540
agcactggga ttcctttctt ctacatgaca gccaaggacc ccgtggtggc tgatctgatg    600
aagaacccca tggcctcgct gatgctgcca gaatcagaag gggagttctg cagaaaaaac    660
atcgttgatc cggaagatcc ccgatgtgtc cagttaacgc tcactggcca gatgatcgca    720
gtgtctccag aagaagtaga atttgccaag caagccatgt tttcaaggca cccagggatg    780
aggaagtggc ctcgtcaata tgaatggttc tttatgaaga tgaggataga acatatctgg    840
cttcagaaat ggtatggagg cgcatccagt atttcaaggg aggaatattt caaagcagtt    900
cccagaaagg cctgatggag tgagaagaaa gtccttggtg tttgcactta aataaaaacc    960
ttttcagtga tgcagccaga cagctattga ccactgtctc tttgttgaag ggttcatagc   1020
agccctgcca tccctgcagc agaatgagag agggtgaaca gggaactcta tgctagattt   1080
gagattaaag tggtcatttg cagatctcca actcacacag atacttcacg tagatagtct   1140
ttattccatt gtattcaatc cagactcatc gattcagaaa tcatataata gctggtggtc   1200
aaaatgacat gttgagatca ttgttgtttc attgtttaag gnaaaaaaaa aatgcctgta   1260
cctacaatgt gattgctttg tattgtgaga gtatcttgtt gcttgctctg ccaaatgcag   1320
tcttg                                                               1325
```

<210> SEQ ID NO 84
<211> LENGTH: 3663
<212> TYPE: DNA
<213> ORGANISM: Homo sapiens
<220> FEATURE:
<221> NAME/KEY: misc_feature
<223> OTHER INFORMATION: Incyte ID No: 413921.2

<400> SEQUENCE: 84

```
gtgcgctagg ctccggactc cgcggcgcag actggcacct cgcagtctcc ccaggtccgc     60
ccagcagccg cgcttcagcc agaatactgg gatcttcagt ggcaggagga gtaatcagaa    120
gacggagatg aattttaaca ctattttgga ggagattctt attaaaaggt cacagcagaa    180
aaagaagaca tcgcccttaa actacaaaga gagacttttt gtacttacaa agtccatgct    240
aacctactat gagggtcgag cagagaagaa atacagaaag gggtttattg atgtttcaaa    300
aatcaagtgt gtggaaatag tgaagaatga tgatggtgtc attccctgtc aaaataagta    360
tccatttcag gttgttcatg atgctaacac actttacatt tttgcaccta gtccacaaag    420
cagggacctg tgggtgaaga agttaaaaga agaaataaag aacaacaata atattatgat    480
taaatatcat cctaaattct ggacagatgg aagttatcag tgttgtagac aaactgaaaa    540
attagcaccc ggatgtgaaa aatacaatct ttttgagagc agtataagaa aagcactacc    600
tccagcacca gaaacaaaga agcgaaggcc tcccccacca attccactag aagaagaaga    660
taatagtgaa gaaatcgttg tagccatgta tgatttccaa gcagcagaag gacatgatct    720
cagattagag agaggccaag agtatctcat tttagaaaag aatgatgtgc attggtggag    780
```

-continued

```
agcaagagat aaatatggga atgaaggata tatcccaagt aattacgtaa cgggaaagaa     840
atcaaacaac ttagatcaat atgaatggta ttgcagaaat atgaatagaa gcaaggcaga     900
gcaactcctc cgcagtgaag ataaagaagg tggttttatg gtaagggatt ccagtcaacc     960
aggcttgtac acagtctccc tttataccaa gtttggagga gaaggttcat cgggttttag    1020
gcattatcat ataaaggaaa caacaacatc tccaaagaag tattacctag ctgaaaaaca    1080
tgcttttggc tccattcctg agattattga atatcataag cacaatgcag caggacttgt    1140
caccaggctt cggtacccag ttagtgtgaa agggaagaat gcacccacca ctgcaggatt    1200
cagctatgag aaatgggaga ttaacccttc agaactgacc tttatgaggg aattgggaag    1260
tggactgttt ggagtggtga ggcttggcaa atggcgagcc cagtacaaag tcgcaatcaa    1320
agctattcgg gaaggtgcaa tgtgcgagga ggactttata gaagaagcta aagtgatgat    1380
gaagctgaca cacccgaagt tagtgcagct ttatggtgtg tgcacccagc agaaaccaat    1440
atacattgtt actgagttca tggaaagggg ctgccttctg aatttcctcc gacagagaca    1500
aggtcatttc agtagagacg tactgctgag catgtgtcag gatgtgtgtg aagggatgga    1560
gtatctggag agaaacagct tcatccacag agatctggct gccagaaatt gtctagtaag    1620
tgaggcggga gttgtaaaag tatctgattt tggaatggcc aggtatgttc tggatgatca    1680
gtacacaagt tcttctggtg ctaagtttcc tgtgaagtgg tgtccacctg aagtgtttaa    1740
ttacagccgc ttcagcagca aatcagatgt ctggtcattt ggtgttttaa tgtgggaagt    1800
attcacggaa ggcagaatgc cttttgaaaa atacaccaat tatgaagtgg taaccatggt    1860
tactcgaggc caccgactct accagccgaa gttggcgtcc aactatgtgt atgaggtgat    1920
gctgagatgt tggcaggaga aaccagaggg aaggccttct ttcgaagatc tgctgcgcac    1980
aatagatgaa ctagttgaat gtgaagaaac ttttggaaga taagtgatgt gtgaccagtg    2040
gctcccagat tcccaagcac aaggaaggat gggcattttg tggcttttaa tttattgagc    2100
acttggacat gtagatcatt ttacttatac agtggaaaca cataaataat ttgcttctag    2160
accagcctct gtctagactt gcttctagac agaatctccc agagtgtgga aatgttgcct    2220
tagaaatggt gattaaaatc actcatttct attcattcct caggcacttg agtgacagtt    2280
gtttaccagg cactgtgtgt agccccaggg tttggccatt caggggtgca cacatgggac    2340
catgttagct gatgccagtt gaaggccagg gtatttggga aggggaaggg tattagagtc    2400
atgaccaagc aacccttctt tttccctttg acttctacag aaatctgggc ctgagacatt    2460
gtctacaatt gggttctaga tacatcagga acccatcttg gataaataaa tacctatctt    2520
ttgttttgaa aacatctcag ttttcaagac tgctcttagt attacatgaa caatatttgt    2580
atgctgtata tattgtaaat atatataata tataaagtta tatatttatg agaaacacga    2640
attgtctttt aattgaaact tttaatcctg tagtatagga gttcaccttc ttaggactag    2700
agactgtgcc ttatagctgt taattcattt ccccctgaac atcaaatatg cctgaagaga    2760
agaaagtcta gattcttcta tgagtaacgc cccctcctca ctcaggtaaa tgtgtctggg    2820
gatgcctgtc cagcttaacc acgtgcattt ggcctatgta atcctgccca tggtggccgc    2880
agctaatcag aatcagatgg aaaattaaac cgggtaatct acttctaagc cttaagaata    2940
ttccctggga cacagacact ataattggaa gtgctgagct ctggggcaga aggatcaggt    3000
gaccttcgca acaaagtttg cccccacctc acataggacc cggaagcagc ctgagctgtg    3060
gcggaggatc caggaagcta cggagagaag cagccagcat ggtgttccgt gcctcccgga    3120
```

-continued

```
cgtttttcag gaggcctggt tggacttggg ttcctggatg gtgggattgt tgtacagcct   3180

ctcaggagac cctgctgtca agactgtgtg tgtggatttc tcacccttag aagctctact   3240

aagacatcaa cggaattagg gccttccttt ttgccttgtg agcgccaagg aaaagaaact   3300

atctcggtca cgtgagcgcc agcgaaaaga aactgtatca gtcatccaga gaccgtttat   3360

tgcccaacac gttattcttg ctgttggtgg ggtaactagc cgaggaagac acagcgcctt   3420

cccttcagga gttgcgtctc ctctgcaggc cacgatggtc tgctctggag cattgggtga   3480

acacacaggc tggctgctct gggcagcgcc ttcactctga ccctggagaa ccatttcatt   3540

tcatcctggt cagtctagag tctgtgcacc aggcagtcca tccactgaag gctgtgttta   3600

ttcttttcct gtgcccctca taaatggaag aaagtaaact gcttatcccg agccttaaaa   3660

aaa                                                                 3663
```

<210> SEQ ID NO 85
<211> LENGTH: 1344
<212> TYPE: DNA
<213> ORGANISM: Homo sapiens
<220> FEATURE:
<221> NAME/KEY: misc_feature
<223> OTHER INFORMATION: Incyte ID No: 336615.1

<400> SEQUENCE: 85

```
ggaggaggag gcagctacgg tgataaagaa gagcaatcaa aagggcaaag ccaaaggaaa     60

aggcaaaaag aaagcgaagg aggagagggc cccgtctccc cccgtggagg tggacgaacc    120

ccgggagttt gtgctccggc ctgcccccca gggccgcacg gtgcgctgcc ggctgacccg    180

ggacaaaaag ggcatggatc gaggcatgta tccctcctac ttcctgcacc tggacacgga    240

gaagaaggtg ttcctcttgg ctggcaggaa acgaaaacgg agcaagacag ccaattacct    300

catctccatc gaccctacca atctgtcccg aggaggggag aatttcatcg ggaagctgag    360

gtccaacctc ctggggaacc gcttcacggt ctttgacaac gggcagaacc cacagcgtgg    420

gtacagcact aatgtggcaa gccttcggca ggagctggca gctgtgatct atgaaaccaa    480

cgtgctgggc ttccgtggcc cccggcgcat gaccgtcatc attcctggca tgagtgcgga    540

gaacgagagg gtccccatcc ggccccgaaa tgctagtgac ggcctgctgg tgcgctggca    600

gaacaagacg ctggagagcc tcatagaact gcacaacaag ccacctgtct ggaacgatga    660

cagtggctcc tacaccctca acttccaagg ccgggtcacc caggcctcag tcaagaactt    720

ccagattgtc cacgctgatg accccgacta tatcgtgctg cagttcggcc gcgtggcgga    780

ggacgccttc accctagact accggtaccc gctgtgcgcc ctgcaggcct tcgccatcgc    840

cctctccagt ttcgacggga agctggcctg cgagtgaccc cagcagcccc tcagcgcccc    900

cagagcccgt cagcgtgggg gaaaggattc agtggaggct ggcagggtcc ctccagcaaa    960

gctcccgcgg aaaactgctc ctgtgtcggg gctgacctct cactgcctct cggtgacctc   1020

cgtcctctcc ccagcctggc acaggccgag gcaggaggag cccggacggc gggtaggacg   1080

gagatgaaga acatctggag ttggagccgc acatctggtc tcggagctcg cctgcgccgc   1140

tgtgcccccc tcctccccgc gccccagtca cttcctgtcc gggagcagta gtcattgttg   1200

ttttaacctc ccctctcccc gggaccgcgc tagggctccg aggagctggg gcgggctagg   1260

aggagggggt aggtgatggg ggacgagggc caggcaccca catccccaat aaagccgcgt   1320

ccttgtgcaa aaaaaaaaaa aagg                                          1344
```

<210> SEQ ID NO 86

-continued

<211> LENGTH: 3156
<212> TYPE: DNA
<213> ORGANISM: Homo sapiens
<220> FEATURE:
<221> NAME/KEY: misc_feature
<223> OTHER INFORMATION: Incyte ID No: 2733282CB1

<400> SEQUENCE: 86
gttcaggaag aaaccatctg catccatatt gaaaacctga cacaatgtat gcagcaggct 60
cagtgtgagt gaactggagg cttctctaca acatgaccca aaggagcatt gcaggtccta 120
tttgcaacct gaagtttgtg actctcctgg ttgccttaag ttcagaactc ccattcctgg 180
gagctggagt acagcttcaa gacaatgggt ataatggatt gctcattgca attaatcctc 240
aggtacctga gaatcagaac ctcatctcaa acattaagga aatgataact gaagcttcat 300
tttacctatt taatgctacc aagagaagag tatttttcag aaatataaag attttaatac 360
ctgccacatg gaaagctaat aataacagca aaataaaaca agaatcatat gaaaaggcaa 420
atgtcatagt gactgactgg tatggggcac atggagatga tccatacacc ctacaataca 480
gagggtgtgg aaaagaggga aaatacattc atttcacacc taatttccta ctgaatgata 540
acttaacagc tggctacgga tcacgaggcc gagtgtttgt ccatgaatgg gcccacctcc 600
gttggggtgt gttcgatgag tataacaatg acaaaccttt ctacataaat gggcaaaatc 660
aaattaaagt gacaaggtgt tcatctgaca tcacaggcat ttttgtgtgt gaaaaaggtc 720
cttgccccca agaaaactgt attattagta agctttttaa agaaggatgc acctttatct 780
acaatagcac ccaaaatgca actgcatcaa taatgttcat gcaaagttat ctctgtggtg 840
aaatttgtaa tgccagtacc cacaaccaag aagcaccaaa cctacagaac cagatgtgca 900
gcctcagaag tgcatgggat gtaatcacag actctgctga ctttcaccac agctttccca 960
tgaacgggac tgagcttcca cctcctccca cattctcgct tgtagaggct ggtgacaaag 1020
tggtctgttt agtgctggat gtgtccagca agatggcaga ggctgacaga ctccttcaac 1080
tacaacaagc cgcagaattt tatttgatgc agattgttga aattcatacc ttcgtgggca 1140
ttgccagttt cgacagcaaa ggagagatca gagcccagct acaccaaatt aacagcaatg 1200
atgatcgaaa gttgctggtt tcatatctgc ccaccactgt atcagctaaa acagacatca 1260
gcatttgttc agggcttaag aaaggatttg aggtggttga aaaactgaat ggaaaagctt 1320
atggctctgt gatgatatta gtgaccagcg gagatgataa gcttcttggc aattgcttac 1380
ccactgtgct cagcagtggt tcaacaattc actccattgc cctgggttca tctgcagccc 1440
caaatctgga ggaattatca cgtcttacag gaggtttaaa gttctttgtt ccagatatat 1500
caaactccaa tagcatgatt gatgctttca gtagaatttc ctctggaact ggagacattt 1560
tccagcaaca tattcagctt gaaagtacag gtgaaaatgt caaacctcac catcaattga 1620
aaaacacagt gactgtggat aatactgtgg gcaacgacac tatgtttcta gttacgtggc 1680
aggccagtgg tcctcctgag attatattat ttgatcctga tggacgaaaa tactacacaa 1740
ataattttat caccaatcta acttttcgga cagctagtct ttggattcca ggaacagcta 1800
agcctgggca ctggacttac accctgaaca atacccatca ttctctgcaa gccctgaaag 1860
tgacagtgac ctctcgcgcc tccaactcag ctgtgccccc agccactgtg gaagcctttg 1920
tggaaagaga cagcctccat tttcctcatc ctgtgatgat ttatgccaat gtgaaacagg 1980
gattttatcc cattcttaat gccactgtca ctgccacagt tgagccagag actggagatc 2040
ctgttacgct gagactcctt gatgatggag caggtgctga tgttataaaa aatgatggaa 2100

-continued

```
tttactcgag gtattttttc tcctttgctg caaatggtag atatagcttg aaagtgcatg   2160

tcaatcactc tcccagcata agcaccccag cccactctat tccagggagt catgctatgt   2220

atgtaccagg ttacacagca aacggtaata ttcagatgaa tgctccaagg aaatcagtag   2280

gcagaaatga ggaggagcga aagtggggct ttagccgagt cagctcagga ggctcctttt   2340

cagtgctggg agttccagct ggcccccacc ctgatgtgtt tccaccatgc aaaattattg   2400

acctggaagc tgtaaaagta gaagaggaat tgaccctatc ttggacagca cctggagaag   2460

actttgatca gggccaggct acaagctatg aaataagaat gagtaaaagt ctacagaata   2520

tccaagatga ctttaacaat gctattttag taaatacatc aaagcgaaat cctcagcaag   2580

ctggcatcag ggagatattt acgttctcac cccaaatttc cacgaatgga cctgaacatc   2640

agccaaatgg agaaacacat gaaagccaca gaatttatgt tgcaatacga gcaatggata   2700

ggaactcctt acagtctgct gtatctaaca ttgcccaggc gcctctgttt attcccccca   2760

attctgatcc tgtacctgcc agagattatc ttatattgaa aggagtttta acagcaatgg   2820

gtttgatagg aatcatttgc cttattatag ttgtgacaca tcatacttta agcaggaaaa   2880

agagagcaga caagaaagag aatggaacaa aattattata aataaatatc caaagtgtct   2940

tccttcttag atataagacc catggccttc gactacaaaa acatactaac aaagtcaaat   3000

taacatcaaa actgtattaa aatgcattga gtttttgtac aatacagata agatttttac   3060

atggtagatc aacaaattct tttgggggt agattagaaa acccttacac tttggctatg   3120

aacaaataat aaaaattatt ctttaaaaaa aaaaaa                             3156
```

```
<210> SEQ ID NO 87
<211> LENGTH: 942
<212> TYPE: PRT
<213> ORGANISM: Homo sapiens
<220> FEATURE:
<221> NAME/KEY: misc_feature
<223> OTHER INFORMATION: Incyte ID No: 2733282CD1

<400> SEQUENCE: 87

Met Thr Gln Arg Ser Ile Ala Gly Pro Ile Cys Asn Leu Lys Phe
  1               5                  10                  15

Val Thr Leu Leu Val Ala Leu Ser Ser Glu Leu Pro Phe Leu Gly
                 20                  25                  30

Ala Gly Val Gln Leu Gln Asp Asn Gly Tyr Asn Gly Leu Leu Ile
                 35                  40                  45

Ala Ile Asn Pro Gln Val Pro Glu Asn Gln Asn Leu Ile Ser Asn
                 50                  55                  60

Ile Lys Glu Met Ile Thr Glu Ala Ser Phe Tyr Leu Phe Asn Ala
                 65                  70                  75

Thr Lys Arg Arg Val Phe Phe Arg Asn Ile Lys Ile Leu Ile Pro
                 80                  85                  90

Ala Thr Trp Lys Ala Asn Asn Asn Ser Lys Ile Lys Gln Glu Ser
                 95                 100                 105

Tyr Glu Lys Ala Asn Val Ile Val Thr Asp Trp Tyr Gly Ala His
                110                 115                 120

Gly Asp Asp Pro Tyr Thr Leu Gln Tyr Arg Gly Cys Gly Lys Glu
                125                 130                 135

Gly Lys Tyr Ile His Phe Thr Pro Asn Phe Leu Leu Asn Asp Asn
                140                 145                 150

Leu Thr Ala Gly Tyr Gly Ser Arg Gly Arg Val Phe Val His Glu
                155                 160                 165
```

-continued

```
Trp Ala His Leu Arg Trp Gly Val Phe Asp Glu Tyr Asn Asn Asp
                170                 175                 180

Lys Pro Phe Tyr Ile Asn Gly Gln Asn Gln Ile Lys Val Thr Arg
                185                 190                 195

Cys Ser Ser Asp Ile Thr Gly Ile Phe Val Cys Glu Lys Gly Pro
                200                 205                 210

Cys Pro Gln Glu Asn Cys Ile Ile Ser Lys Leu Phe Lys Glu Gly
                215                 220                 225

Cys Thr Phe Ile Tyr Asn Ser Thr Gln Asn Ala Thr Ala Ser Ile
                230                 235                 240

Met Phe Met Gln Ser Tyr Leu Cys Gly Glu Ile Cys Asn Ala Ser
                245                 250                 255

Thr His Asn Gln Glu Ala Pro Asn Leu Gln Asn Gln Met Cys Ser
                260                 265                 270

Leu Arg Ser Ala Trp Asp Val Ile Thr Asp Ser Ala Asp Phe His
                275                 280                 285

His Ser Phe Pro Met Asn Gly Thr Glu Leu Pro Pro Pro Pro Thr
                290                 295                 300

Phe Ser Leu Val Glu Ala Gly Asp Lys Val Val Cys Leu Val Leu
                305                 310                 315

Asp Val Ser Ser Lys Met Ala Glu Ala Asp Arg Leu Leu Gln Leu
                320                 325                 330

Gln Gln Ala Ala Glu Phe Tyr Leu Met Gln Ile Val Glu Ile His
                335                 340                 345

Thr Phe Val Gly Ile Ala Ser Phe Asp Ser Lys Gly Glu Ile Arg
                350                 355                 360

Ala Gln Leu His Gln Ile Asn Ser Asn Asp Asp Arg Lys Leu Leu
                365                 370                 375

Val Ser Tyr Leu Pro Thr Thr Val Ser Ala Lys Thr Asp Ile Ser
                380                 385                 390

Ile Cys Ser Gly Leu Lys Lys Gly Phe Glu Val Val Glu Lys Leu
                395                 400                 405

Asn Gly Lys Ala Tyr Gly Ser Val Met Ile Leu Val Thr Ser Gly
                410                 415                 420

Asp Asp Lys Leu Leu Gly Asn Cys Leu Pro Thr Val Leu Ser Ser
                425                 430                 435

Gly Ser Thr Ile His Ser Ile Ala Leu Gly Ser Ser Ala Ala Pro
                440                 445                 450

Asn Leu Glu Glu Leu Ser Arg Leu Thr Gly Gly Leu Lys Phe Phe
                455                 460                 465

Val Pro Asp Ile Ser Asn Ser Asn Ser Met Ile Asp Ala Phe Ser
                470                 475                 480

Arg Ile Ser Ser Gly Thr Gly Asp Ile Phe Gln Gln His Ile Gln
                485                 490                 495

Leu Glu Ser Thr Gly Glu Asn Val Lys Pro His His Gln Leu Lys
                500                 505                 510

Asn Thr Val Thr Val Asp Asn Thr Val Gly Asn Asp Thr Met Phe
                515                 520                 525

Leu Val Thr Trp Gln Ala Ser Gly Pro Pro Glu Ile Ile Leu Phe
                530                 535                 540

Asp Pro Asp Gly Arg Lys Tyr Tyr Thr Asn Asn Phe Ile Thr Asn
                545                 550                 555
```

-continued

```
Leu Thr Phe Arg Thr Ala Ser Leu Trp Ile Pro Gly Thr Ala Lys
                560                 565                 570

Pro Gly His Trp Thr Tyr Thr Leu Asn Asn Thr His His Ser Leu
                575                 580                 585

Gln Ala Leu Lys Val Thr Val Thr Ser Arg Ala Ser Asn Ser Ala
                590                 595                 600

Val Pro Pro Ala Thr Val Glu Ala Phe Val Glu Arg Asp Ser Leu
                605                 610                 615

His Phe Pro His Pro Val Met Ile Tyr Ala Asn Val Lys Gln Gly
                620                 625                 630

Phe Tyr Pro Ile Leu Asn Ala Thr Val Thr Ala Thr Val Glu Pro
                635                 640                 645

Glu Thr Gly Asp Pro Val Thr Leu Arg Leu Leu Asp Asp Gly Ala
                650                 655                 660

Gly Ala Asp Val Ile Lys Asn Asp Gly Ile Tyr Ser Arg Tyr Phe
                665                 670                 675

Phe Ser Phe Ala Ala Asn Gly Arg Tyr Ser Leu Lys Val His Val
                680                 685                 690

Asn His Ser Pro Ser Ile Ser Thr Pro Ala His Ser Ile Pro Gly
                695                 700                 705

Ser His Ala Met Tyr Val Pro Gly Tyr Thr Ala Asn Gly Asn Ile
                710                 715                 720

Gln Met Asn Ala Pro Arg Lys Ser Val Gly Arg Asn Glu Glu Glu
                725                 730                 735

Arg Lys Trp Gly Phe Ser Arg Val Ser Ser Gly Gly Ser Phe Ser
                740                 745                 750

Val Leu Gly Val Pro Ala Gly Pro His Pro Asp Val Phe Pro Pro
                755                 760                 765

Cys Lys Ile Ile Asp Leu Glu Ala Val Lys Val Glu Glu Glu Leu
                770                 775                 780

Thr Leu Ser Trp Thr Ala Pro Gly Glu Asp Phe Asp Gln Gly Gln
                785                 790                 795

Ala Thr Ser Tyr Glu Ile Arg Met Ser Lys Ser Leu Gln Asn Ile
                800                 805                 810

Gln Asp Asp Phe Asn Asn Ala Ile Leu Val Asn Thr Ser Lys Arg
                815                 820                 825

Asn Pro Gln Gln Ala Gly Ile Arg Glu Ile Phe Thr Phe Ser Pro
                830                 835                 840

Gln Ile Ser Thr Asn Gly Pro Glu His Gln Pro Asn Gly Glu Thr
                845                 850                 855

His Glu Ser His Arg Ile Tyr Val Ala Ile Arg Ala Met Asp Arg
                860                 865                 870

Asn Ser Leu Gln Ser Ala Val Ser Asn Ile Ala Gln Ala Pro Leu
                875                 880                 885

Phe Ile Pro Pro Asn Ser Asp Pro Val Pro Ala Arg Asp Tyr Leu
                890                 895                 900

Ile Leu Lys Gly Val Leu Thr Ala Met Gly Leu Ile Gly Ile Ile
                905                 910                 915

Cys Leu Ile Ile Val Val Thr His His Thr Leu Ser Arg Lys Lys
                920                 925                 930

Arg Ala Asp Lys Lys Glu Asn Gly Thr Lys Leu Leu
                935                 940
```

<210> SEQ ID NO 88
<211> LENGTH: 1121
<212> TYPE: DNA
<213> ORGANISM: Homo sapiens
<220> FEATURE:
<221> NAME/KEY: misc_feature
<223> OTHER INFORMATION: Incyte ID No: 399161.1
<221> NAME/KEY: unsure
<222> LOCATION: 1070
<223> OTHER INFORMATION: a, t, c, g, or other

<400> SEQUENCE: 88
caggcgggag caccgtgcct ggcccagatg gatttttaaa tatcacctgt tcatattgtt 60
taaaatagat acaactaaaa cagctttgag gcatacagga actctacaga taaggaggac 120
catttcataa tgataaaggg cttatctcac caagaaggca gtcacactta cgtttttatg 180
tatttgttga agagtcccaa tgtatttaaa gcaaaaataa gcaactacaa agagaaagat 240
acaaatccat gatcaaagtg aggaattttc acacacatcg tagtaactga tggaatgagt 300
caatgaaaaa ttagtgagga aatagaagat ttggacagca caacaaatgg cctaggagaa 360
catttagaat gttgccttcg atgcttaaga atacatattc ttttcaaaag aaaacccaga 420
acagcctggc aggagagata ccatcatcat gaaggtgatt ttcccagagc tgggcttatc 480
cattgcattc tggatgtgct gacgcctgtg gttttcccaa atgtgggaaa ctggactgca 540
taatttgtgg tagtggggga ctatgttcgt gttctctcct ggtgtttaaa attaaaaaaa 600
aaaaaacttt attaaaggca cagaacatta ataaaaattg acaataaact gggctattaa 660
gtaaattgca acaatttcca gaggtttgaa atgatacaga gtatgttttc tgaccacagt 720
acagttaaac taggaatata acaaaaagat aactagggat atgtgtggat attgcatacc 780
tctaagtaac ccttgggatg agaaagaaat tacaatggaa attagaaaat atcttgaata 840
atgaaaatac aatatatgta agcttgtaga attcagctta ttaaatgcat attttagaaa 900
gaaggaaagg ctgaaaatca gtgagcaaag ccttccatct caagaaatag aaaaagaata 960
tagaaggaag gaattaatat ttttaaagaa gcactaattt acaagaataa ttaaatagaa 1020
aagaagttgt cattaggaag gatcaataaa gctagaagct tgttatttgn aaagacttgt 1080
aaatgtggta aatcacaagt aacgtacgta gatgaaaagg g 1121

<210> SEQ ID NO 89
<211> LENGTH: 721
<212> TYPE: DNA
<213> ORGANISM: Homo sapiens
<220> FEATURE:
<221> NAME/KEY: misc_feature
<223> OTHER INFORMATION: Incyte ID No: 339638.1
<221> NAME/KEY: unsure
<222> LOCATION: 266
<223> OTHER INFORMATION: a, t, c, g, or other

<400> SEQUENCE: 89
gtggcccaca gcgaactaga gaaacaaaag gagagtcttt tacccoctgg agttatcgcc 60 atcagcaaac tgagagctgc ctctcttcct ctccctgccc tgtgtctgtc tccacctcct 120
tccctctcat ccttgctctt tcccttttct ctttatcccc cgcccccttt ctttctcttc 180
ctcctttctc ctcccaggga ccaaagggag aagggagagc cgagaaagtg gccctgccat 240
cccctactgg aataaccgcc gccgcngccc catcactggt ggccacatcc cttctaattt 300
gtagtggtgg gtttctttcc ttgaagagca gggtactttt aaacagatag aggtaatggg 360
aggattaata ttcataggta agtccaaacg gaaaatgttt agcttcctta caccaaaggt 420

-continued

```
ctgctgtgtc tgagattaca ctaagttcaa gcaacatcat gtcagtgaag aagccattag    480

ctgcaggaac acactgagaa gtgagggagc ctgtctacca gaaggaaatg gagctaggat    540

ctttgcaaac tgctgagtag agaggagagg acgagtaaat gagacagacg gaaaagagct    600

ggaagagaga gactccttta tggcacattt ttatcctgag atttccaagc attttatata    660

tattgcatgg taaagaggaa ttgaaatagc caaaagaaat gaactaaaat gaaaagggag    720

g                                                                    721
```

```
<210> SEQ ID NO 90
<211> LENGTH: 538
<212> TYPE: DNA
<213> ORGANISM: Homo sapiens
<220> FEATURE:
<221> NAME/KEY: misc_feature
<223> OTHER INFORMATION: Incyte ID No: 697785CB1

<400> SEQUENCE: 90

cccacgcgtc cggtggagtc ttctgacagc tggtgcgcct gcccgggaac atcctcctgg     60

actcaatcat ggcttgtggt ctggtcgcca gcaacctgaa tctcaaacct ggagagtgcc    120

ttcgagtgcg aggcgaggtg gctcctgacg ctaagagctt cgtgctgaac ctgggcaaag    180

acagcaacaa cctgtgcctg cacttcaacc ctcgcttcaa cgcccacggc gacgccaaca    240

ccatcgtgtg caacagcaag gacggcgggg cctgggggac cgagcagcgg gaggctgtct    300

ttcccttcca gcctggaagt gttgcagagg tgtgcatcac cttcgaccag gccaacctga    360

ccgtcaagct gccagatgga tacgaattca agttccccaa ccgcctcaac ctggaggcca    420

tcaactacat ggcagctgac ggtgacttca agatcaaatg tgtggccttt gactgaaatc    480

agccagccca tggcccccaa taaaggcagc tgcctctgct ccctctgaaa aaaaaaaa      538
```

```
<210> SEQ ID NO 91
<211> LENGTH: 135
<212> TYPE: PRT
<213> ORGANISM: Homo sapiens
<220> FEATURE:
<221> NAME/KEY: misc_feature
<223> OTHER INFORMATION: Incyte ID No: 697785CD1

<400> SEQUENCE: 91

Met Ala Cys Gly Leu Val Ala Ser Asn Leu Asn Leu Lys Pro Gly
  1               5                  10                  15

Glu Cys Leu Arg Val Arg Gly Glu Val Ala Pro Asp Ala Lys Ser
                 20                  25                  30

Phe Val Leu Asn Leu Gly Lys Asp Ser Asn Asn Leu Cys Leu His
                 35                  40                  45

Phe Asn Pro Arg Phe Asn Ala His Gly Asp Ala Asn Thr Ile Val
                 50                  55                  60

Cys Asn Ser Lys Asp Gly Gly Ala Trp Gly Thr Glu Gln Arg Glu
                 65                  70                  75

Ala Val Phe Pro Phe Gln Pro Gly Ser Val Ala Glu Val Cys Ile
                 80                  85                  90

Thr Phe Asp Gln Ala Asn Leu Thr Val Lys Leu Pro Asp Gly Tyr
                 95                 100                 105

Glu Phe Lys Phe Pro Asn Arg Leu Asn Leu Glu Ala Ile Asn Tyr
                110                 115                 120

Met Ala Ala Asp Gly Asp Phe Lys Ile Lys Cys Val Ala Phe Asp
                125                 130                 135
```

<210> SEQ ID NO 92
<211> LENGTH: 866
<212> TYPE: DNA
<213> ORGANISM: Homo sapiens
<220> FEATURE:
<221> NAME/KEY: misc_feature
<223> OTHER INFORMATION: Incyte ID No: 399785.1
<221> NAME/KEY: unsure
<222> LOCATION: 18
<223> OTHER INFORMATION: a, t, c, g, or other

<400> SEQUENCE: 92

```
acgagacgag cacccgtngg gggctggagc accccgcgcg ctcccctggc gagagggagg     60

gtcgtggctc ggcccctgct cagacaaagg ctgggaggcg ggagacatgc acttcccctt    120

ccttttcagc caggcgcgcg ctgataccag gcccacgtca gctatttttg gagcctttta    180

cacgacagct ggaggagcgt ccttttttaat tttcccttt tgtttggccg cccccacccc    240

cacccccttcg ccttcatcgc tgcacttgag gctccatcct ggggcctctc cttgacttga    300

cctgccttgg caggcacatg ccctccctgc ctggctcact cgccgcagag acctggcagc    360

ccgcgcaaaa tgtcactttg cggaatcgtt cccacggctt ctgggtaccc ttagttccct    420

gcttagggag ggaagacagt agtcgggtcg taataagcaa gacttagccc gagcctccgt    480

tgccaacgca ggctgccttg cttggcgtgt gggcatcggc ctgcccccctc accctggcta    540

cccaacacag ctacaaaagg cagggaacaa tgtaggtccc ttggccctgc ctaatgcctg    600

ttgccatgga aacccctatc ctaatctggc caggagcccc ttgcagtgag ccaggagagt    660

gaggaagagg ggatggggcc cgctggcctg aacctggcca gaggaggtaa tggttaaccg    720

gattgtggga gcagctgact agagccgggg gggtagggag gcttgggccc cagtcctacc    780

ttccctgcca aggagaaagg ggcatgtctg cttttgtacc tctgggaatc tacctcaggg    840

atctgcccaa caactcccag gttcca                                         866
```

<210> SEQ ID NO 93
<211> LENGTH: 1274
<212> TYPE: DNA
<213> ORGANISM: Homo sapiens
<220> FEATURE:
<221> NAME/KEY: misc_feature
<223> OTHER INFORMATION: Incyte ID No: 002455.1

<400> SEQUENCE: 93

```
gcggccgcca gcttgcaaag ccgaagtctg gccgcgctct tcgactcgct gcgccacgtc     60

cccgggggtg ccgagccggc ggggggtgag tggtctgcgc cggcggccgc gctaggaggt    120

gcgggcactt gggggcgccg ggaaggggaa cttggcagcc ccgcgggggc cacgggcgat    180

cccaggggcc aggaaggtcc cgctgcgggc acgcaatctg cctccgtcct tcttcacgga    240

gccgtcccgg gcaggcggcg gcgggtgtgg cccgtcgggg ccggacgtga gcttgggcga    300

cctggagaag ggcgcggagg ccgtggagtt ctttgagctg ctggggcccg actacggcgc    360

cggcacggag gcggcagtct tgcttgccgc cgagcctctc gacgtgttcc ccgccggagc    420

ctccgtactg cggggacccc cggagctgga gcccggcctc tttgagccgc cgccggcagt    480

ggtgggaaac ctactgtacc ccgagccctg gagcgtcccg ggctgctccc cgaccaaaaa    540

gagcccccctg actgcccccc gcggcggctt gaccttgaac gagcccttga gccccctgta    600

ccccgccgct gcggattctc ccggcgggga ggacgggcgg ggccatttgg cctctttcgc    660

ccccttcttt ccagactgcg ccctgccccc gacgccgccg ccccatcagg tgtcctacga    720
```

-continued

```
ttacagcgcg ggctacagcc gcaccgccta ttccagcctt tggagatccg acggggtttg    780

ggaaggggcg ccgggggagg agggggcgca ccgggactga cttcgaggca cgcttccctt    840

cattagagac ggctgtggag agcgccgcgc ctccgtgggt ttctcctaaa tctgaagaac    900

gatgggaaaa tgcacgtgga gatgaaacca gatttttaaa aattcaatta ataaaagcaa    960

ycttcagaaaa aagagatgaa gacgagttgg ggattgttta atcacaacct caagtgttaa  1020

aacaaaaaca aacaaacacg tttgtaggtt cttactggac cagaggagtc aagaaaccaa   1080

gatggtttgg ggtatggggt ggggacggca aaaggggtaa gagctggctt ctgtagccac   1140

ctgtcccttc tatttttcag cgaaggtcag tgtatttagt gtaattaccc cttctaaaca   1200

gtgtcctagt ccctcccttc cctctccttg agtgcatttt gaattaaagc ctatattgaa   1260

aaaaaaaaaa aagg                                                    1274


<210> SEQ ID NO 94
<211> LENGTH: 924
<212> TYPE: DNA
<213> ORGANISM: Homo sapiens
<220> FEATURE:
<221> NAME/KEY: misc_feature
<223> OTHER INFORMATION: Incyte ID No: 1382920.38

<400> SEQUENCE: 94

atctagaact accgagagtc gtcggggttt cctgcttcaa cagtgcttgg acggaacccg     60

gcgctcgttc cccaccccgg ccggccgccc atagccagcc ctccgtcacc tcttcaccgc    120

accctcggac tgccccaagg cccccgccgc cgctccagcg ccgcgcagcc accgccgccg    180

ccgcctcctt tccttagtcg ccgccatgac gaccgcgtcc acctgcgcag gtgccgccag    240

aactaccacc aggactcaga ggccgccatc aaccgccaga tcaacctgga gctctacgcc    300

tcctacgttt acctgtccat gtcttactac tttgaccgcg atgatgtggc tttgaagaac    360

tttgccaaat actttcttca ccaatctcat gaggagaggg aacatgctga gaaactgatg    420

aagctgcaga accaacgagg tggccgaatc ttccttcagg atatcaagaa accagactgt    480

gatgactggg agagcgggct gaatgcaatg gagtgtgcat tacatttgga aaaaaatgtg    540

aatcagtcac tactggaact gcacaaactg gccactgaca aaaatgaccc ccatttgtgt    600

gacttcattg agacacatta cctgaatgag caggtgaaag ccatcaaaga attgggtgac    660

cacgtgacca acttgcgcaa gatgggagcg cccgaatctg gcttggcgga atatctcttt    720

gacaagcaca ccctgggaga cagtgataat gaaagctaag cctcgggcta atttccccat    780

agccgtgggg tgactttcct ggtcaccaag gcagtgcatg catgttgggg tttcctttac    840

cttttctata agttgtacca aaacatccac ttaagttctt tgatttgtac cattccttca    900

aataaagaaa tttggtaccc aaaa                                           924


<210> SEQ ID NO 95
<211> LENGTH: 634
<212> TYPE: DNA
<213> ORGANISM: Homo sapiens
<220> FEATURE:
<221> NAME/KEY: misc_feature
<223> OTHER INFORMATION: Incyte ID No: 334749.1

<400> SEQUENCE: 95

gacgcccatc aatgaacaaa caagattccc actgtcccat ctcctatcca gtgaaacaca     60

gccaacttga taatttgtgc agggaaagac tctgtttagc ttataccttg aacctaaggg    120

aaattaaatt gcacattttc tgttcctggc taatcttctg aataatgtac tgaacacagt    180
```

```
aggagttaag aattaaaaat acctgtctgc agtttcagaa acaatcacac acaaaatatt    240

tgtttatttc cagactgatg aaagactgaa tttttggtct catgtattta ctgtattgtt    300

tcatatattt atctatatgc tttggctgta ttaacttgtt gaaatagttt gtggttcttt    360

atatttagct tttataaata attgaaaatc taatgaatgc ttacttaata accaatctaa    420

actggggact tcaaacatag ggagtcaagt aatctggttg tgtaataaat aagcaagttg    480

ttatctttca ggctgagggc atatcaacca agctaaaaga cgtgtgtgta ttaaaaaaaa    540

aaaaaagtct accaaaccac catatgatat ccaaggttaa ctatatagga ggtctaataa    600

cattcagaag gtgctagatg aatataccaa aaac                                634
```

<210> SEQ ID NO 96
<211> LENGTH: 579
<212> TYPE: DNA
<213> ORGANISM: Homo sapiens
<220> FEATURE:
<221> NAME/KEY: misc_feature
<223> OTHER INFORMATION: Incyte ID No: 041764.1

<400> SEQUENCE: 96

```
gaaaaaccat ataatggagg aaggccttgc cccaaactgg accatgtcaa ccaggcacag     60

gtgtatgagg ttgtcccatg ccacagtgac tgcaaccagt acctatgggt cacagagccc    120

tggagcatct gcaaggtgac ctttgtgaat atgcgggaga actgtggaga gggcgtgcaa    180

acccgaaaag tgagatgcat gcagaataca gcagatggcc cttctgaaca tgtagaggat    240

tacctctgtg acccagaaga gatgcccctg ggctctagag tgtgcaaatt accatgccct    300

gaggactgtg tgatatctga atggggtcca tggacccaat gtgttttgcc ttgcaatcaa    360

agcagtttcc ggcaaaggtc agctgatccc atcagacaac cagctgatga aggaagatct    420

tgccctaatg ctgttgagaa agaaccctgt aacctgaaca aaaactgcta ccactatgat    480

tataatgtaa cagactggag tacatgtcag ctgagtgaga aggcagtttg tggaaatgga    540

ataaaaaacaa ggatgttgga ttgtgttcga agtgatggc                          579
```

<210> SEQ ID NO 97
<211> LENGTH: 10432
<212> TYPE: DNA
<213> ORGANISM: Homo sapiens
<220> FEATURE:
<221> NAME/KEY: misc_feature
<223> OTHER INFORMATION: Incyte ID No: 2700132CB1

<400> SEQUENCE: 97

```
tggttcgaca agtggccttg cgggccggat cgtcccagtg gaagagttgt aaatttgctt     60

ctggccttcc cctacggatt atacctggcc ttcccctacg gattatactc aacttactgt    120

ttagaaaatg tggcccacga gacgcctggt tactatcaaa aggagcgggg tcgacggtcc    180

ccactttccc ctgagcctca gcacctgctt gtttggaagg ggtattgaat gtgacatccg    240

tatccagctt cctgttgtgt caaaacaaca ttgcaaaatt gaaatccatg agcaggaggc    300

aatattacat aatttcagtt ccacaaatcc aacacaagta aatgggtctg ttattgatga    360

gcctgtacgg ctaaaacatg gagatgtaat aactattatt gatcgttcct tcaggtatga    420

aaatgaaagt cttcagagtg gaaggaagtc aactgaattt ccaagaaaaa tacgtgaaca    480

ggagccagca cgtcgtgtct caagatctag cttctcttct gaccctgatg agaaagctca    540

agattccaag gcctattcaa aaatcactga aggaaaagtt tcaggaaatc ctcaggtaca    600
```

-continued

```
tatcaagaat gtcaaagaag acagtaccgc agatgactca aaagacagtg ttgctcaggg    660
aacaactaat gttcattcct cagaacatgc tggacgtaat ggcagaaatg cagctgatcc    720
catttctggg gattttaaag aaatttccag cgttaaatta gtgagccgtt atggagaatt    780
gaagtctgtt cccactacac aatgtcttga caatagcaaa aaaaatgaat ctcccttttg    840
gaagctttat gagtcagtga agaaagagtt ggatgtaaaa tcacaaaaag aaaatgtcct    900
acagtattgt agaaaatctg gattacaaac tgattacgca acagagaaag aaagtgctga    960
ytggtttacag ggggagaccc aactgttggt ctcgcgtaag tcaagaccaa aatctggtgg   1020
gagcggccac gctgtggcag agcctgcttc acctgaacaa gagcttgacc agaacaaggg   1080
gaagggaaga gacgtggagt ctgttcagac tcccagcaag gctgtgggcg ccagctttcc   1140
tctctatgag ccggctaaaa tgaagacccc tgtacaatat tcacagcaac aaaattctcc   1200
acaaaaacat aagaacaaag acctgtatac tactggtaga agagaatctg tgaatctggg   1260
taaaagtgaa ggcttcaagg ctggtgataa aactcttact cccaggaagc tttcaactag   1320
aaatcgaaca ccagctaaag ttgaagatgc agctgactct gccactaagc cagaaaatct   1380
ctcttccaaa accagaggaa gtattcctac agatgtggaa gttctgccta cggaaactga   1440
aattcacaat gagccatttt taactctgtg gctcactcaa gttgagagga agatccaaaa   1500
ggattccctc agcaagcctg agaaattggg cactacagct ggacagatgt gctctgggtt   1560
acctggtctt agttcagttg atatcaacaa ctttggtgat tccattaatg agagtgaggg   1620
aatacctttg aaaagaaggc gtgtgtcctt tggtgggcac ctaagacctg aactatttga   1680
tgaaaacttg cctcctaata cgcctctcaa aaggggagaa gccccaacca aaagaaagtc   1740
tctggtaatg cacactccac ctgtcctgaa gaaaatcatc aaggaacagc ctcaaccatc   1800
aggaaaacaa gagtcaggtt cagaaatcca tgtggaagtg aaggcacaaa gcttggttat   1860
aagccctcca gctcctagtc ctaggaaaac tccagttgcc agtgatcaac gccgtaggtc   1920
ctgcaaaaca gcccctgctt ccagcagcaa atctcagaca gaggttccta agagaggagg   1980
agaaagagtg gcaacctgcc ttcaaaagag agtgtctatc agccgaagtc aacatgatat   2040
tttacagatg atatgttcca aaagaagaag tggtgcttcg gaagcaaatc tgattgttgc   2100
aaaatcatgg gcagatgtag taaaacttgg tgcaaaacaa acacaaacta aagtcataaa   2160
acatggtcct caaaggtcaa tgaacaaaag gcaaagaaga cctgctactc caaagaagcc   2220
tgtgggcgaa gttcacagtc aatttagtac aggccacgca aactctcctt gtaccataat   2280
aatagggaaa gctcatactg aaaaagtaca tgtgcctgct cgaccctaca gagtgctcaa   2340
caacttcatt tccaaccaaa aaatggactt taaggaagat ctttcaggaa tagctgaaat   2400
gttcaagacc ccagtgaagg agcaaccgca gttgacaagc acatgtcaca tcgctatttc   2460
aaattcagag aatttgcttg gaaaacagtt tcaaggaact gattcaggag aagaacctct   2520
gctccccacc tcagagagtt ttggaggaaa tgtgttcttc agtgcacaga atgcagcaaa   2580
acagccatct gataaatgct ctgcaagccc tcccttaaga cggcagtgta ttagagaaaa   2640
tggaaacgta gcaaaaacgc ccaggaacac ctacaaaatg acttctctgg agacaaaaac   2700
ttcagatact gagacagagc cttcaaaaac agtatccact gtaaacaggt caggaaggtc   2760
tacagagttc aggaatatac agaagctacc tgtggaaagt aagagtgaag aaacaaatac   2820
agaaattgtt gagtgcatcc taaaaagagg tcagaaggca acactactac aacaaaggag   2880
agaaggagag atgaaggaaa tagaaagacc ttttgagaca tataaggaaa atattgaatt   2940
aaaagaaaac gatgaaaaga tgaaagcaat gaagagatca agaacttggg ggcagaaatg   3000
```

-continued

```
tgcaccaatg tctgacctga cagacctcaa gagcttgcct gatacagaac tcatgaaaga   3060
cacggcacgt ggccagaatc tcctccaaac ccaagatcat gccaaggcac caaagagtga   3120
gaaaggcaaa atcactaaaa tgccctgcca gtcattacaa ccagaaccaa taaacacccc   3180
aacacacaca aaacaacagt tgaaggcatc cctggggaaa gtaggtgtga aagaagagct   3240
cctagcagtc ggcaagttca cacggacgtc aggggagacc acgcacacgc acagagagcc   3300
agcaggagat ggcaagagca tcagaacgtt taaggagtct ccaaagcaga tcctggaccc   3360
agcagcccgt gtaactggaa tgaagaagtg gccaagaacg cctaaggaag aggcccagtc   3420
actagaagac ctggctggct tcaaagagct cttccagaca ccaggtccct ctgaggaatc   3480
aatgactgat gagaaaacta ccaaaatagc ctgcaaatct ccaccaccag aatcagtgga   3540
cactccaaca agcacaaagc aatggcctaa gagaagtctc aggaaagcag atgtagagga   3600
agaattctta gcactcagga aactaacacc atcagcaggg aaagccatgc ttacgcccaa   3660
accagcagga ggtgatgaga aagacattaa agcatttatg ggaactccag tgcagaaact   3720
ggacctggca ggaactttac ctggcagcaa aagacagcta cagactccta aggaaaaggc   3780
ccaggctcta gaagacctgg ctggctttaa agagctcttc cagactcctg gtcacaccga   3840
ggaattagtg gctgctggta aaaccactaa aataccctgc gactctccac agtcagaccc   3900
agtggacacc ccaacaagca caaagcaacg acccaagaga agtatcagga aagcagatgt   3960
agagggagaa ctcttagcgt gcaggaatct aatgccatca gcaggcaaag ccatgcacac   4020
gcctaaacca tcagtaggtg aagagaaaga catcatcata tttgtgggaa ctccagtgca   4080
gaaactggac ctgacagaga acttaaccgg cagcaagaga cggccacaaa ctcctaagga   4140
agaggcccag gctctggaag acctgactgg ctttaaagag ctcttccaga cccctggtca   4200
tactgaagaa gcagtggctg ctggcaaaac tactaaaatg ccctgcgaat cttctccacc   4260
agaatcagca gacaccccaa caagcacaag aaggcagccc aagacacctt tggagaaaag   4320
ggacgtacag aaggagctct cagccctgaa gaagctcaca cagacatcag gggaaaccac   4380
acacacagat aaagtaccag gaggtgagga taaaagcatc aacgcgttta gggaaactgc   4440
aaaacagaaa ctggacccag cagcaagtgt aactggtagc aagaggcacc caaaaactaa   4500
ggaaaaggcc caacccctag aagacctggc tggctggaaa gagctcttcc agacaccagt   4560
atgcactgac aagcccacga ctcacgagaa aactaccaaa atagcctgca gatcacaacc   4620
agacccagtg gacacaccaa caagctccaa gccacagtcc aagagaagtc tcaggaaagt   4680
ggacgtagaa gaagaattct tcgcactcag gaaacgaaca ccatcagcag gcaaagccat   4740
gcacacaccc aaaccagcag taagtggtga gaaaaacatc tacgcattta tgggaactcc   4800
agtgcagaaa ctggacctga cagagaactt aactggcagc aagagacggc tacaaactcc   4860
taaggaaaag gcccaggctc tagaagacct ggctggcttt aaagagctct tccagacacg   4920
aggtcacact gaggaatcaa tgactaacga taaaactgcc aaagtagcct gcaaatcttc   4980
acaaccagac ctagacaaaa acccagcaag ctccaagcga cggctcaaga catccctggg   5040
gaaagtgggc gtgaaagaag agctcctagc agttggcaag ctcacacaga catcaggaga   5100
gactacacac acacacacag agccaacagg agatggtaag agcatgaaag catttatgga   5160
gtctccaaag cagatcttag actcagcagc aagtctaact ggcagcaaga ggcagctgag   5220
aactcctaag ggaaagtctg aagtccctga agacctggcc ggcttcatcg agctcttcca   5280
gacaccaagt cacactaagg aatcaatgac taatgaaaaa actaccaaag tatcctacag   5340
```

-continued

```
agcttcacag ccagacctag tggacacccc aacaagctcc aagccacagc ccaagagaag   5400
tctcaggaaa gcagacactg aagaagaatt tttagcattt aggaaacaaa cgccatcagc   5460
aggcaaagcc atgcacacac ccaaaccagc agtaggtgaa gagaaagaca tcaacacgtt   5520
tttgggaact ccagtgcaga aactggacca gccaggaaat ttacctggca gcaatagacg   5580
gctacaaact cgtaaggaaa aggcccaggc tctagaagaa ctgactggct tcagagagct   5640
tttccagaca ccatgcactg ataaccccac gactgatgag aaaactacca aaaaaatact   5700
ctgcaaatct ccgcaatcag acccagcgga caccccaaca aacacaaagc aacggcccaa   5760
gagaagcctc aagaaagcag acgtagagga agaattttta gcattcagga aactaacacc   5820
atcagcaggc aaagccatgc acacgcctaa agcagcagta ggtgaagaga aagacatcaa   5880
cacatttgtg ggactccag tggagaaact ggacctgcta ggaaatttac ctggcagcaa   5940
gagacggcca caaactccta aagaaaaggc caaggctcta gaagatctgg ctggcttcaa   6000
agagctcttc cagacaccag gtcacactga ggaatcaatg accgatgaca aaatcacaga   6060
agtatcctgc aaatctccac aaccagaccc agtcaaaacc ccaacaagct ccaagcaacg   6120
actcaagata tccttgggga aagtaggtgt gaaagaagag gtcctaccag tcggcaagct   6180
cacacagacg tcagggaaga ccacacagac acacagagag acagcaggag atggaaagag   6240
catcaaagcg tttaaggaat ctgcaaagca gatgctggac ccagcaaact atggaactgg   6300
gatggagagg tggccaagaa cacctaagga agaggcccaa tcactagaag acctggccgg   6360
cttcaaagag ctcttccaga caccagacca cactgaggaa tcaacaactg atgacaaaac   6420
taccaaaata gcctgcaaat ctccaccacc agaatcaatg gacactccaa caagcacaag   6480
gaggcggccc aaaacacctt tggggaaaag ggatatagtg gaagagctct cagccctgaa   6540
gcagctcaca cagaccacac acacagacaa agtaccagga gatgaggata aaggcatcaa   6600
cgtgttcagg gaaactgcaa aacagaaact ggacccagca gcaagtgtaa ctggtagcaa   6660
gaggcagcca agaactccta agggaaaagc ccaaccccta gaagacttgg ctggcttgaa   6720
agagctcttc cagacaccaa tatgcactga caagcccacg actcatgaga aaactaccaa   6780
aatagcctgc agatctccac aaccagaccc agtgggtacc ccaacaatct tcaagccaca   6840
gtccaagaga agtctcagga aagcagacgt agaggaagaa tccttagcac tcaggaaacg   6900
aacaccatca gtagggaaag ctatggacac acccaaacca gcaggaggtg atgagaaaga   6960
catgaaagca tttatgggaa ctccagtgca gaaattggac ctgccaggaa atttacctgg   7020
cagcaaaaga tggccacaaa ctcctaagga aaaggcccag gctctagaag acctggctgg   7080
cttcaaagag ctcttccaga caccaggcac tgacaagccc acgactgatg agaaaactac   7140
caaaatagcc tgcaaatctc cacaaccaga cccagtggac accccagcaa gcacaaagca   7200
acggcccaag agaaacctca ggaaagcaga cgtagaggaa gaatttttag cactcaggaa   7260
acgaacacca tcagcaggca aagccatgga cacaccaaaa ccagcagtaa gtgatgagaa   7320
aaatatcaac acatttgtgg aaactccagt gcagaaactg gacctgctag gaaatttacc   7380
tggcagcaag agacagccac agactcctaa ggaaaaggct gaggctctag aggacctggt   7440
tggcttcaaa gaactcttcc agacaccagg tcacactgag gaatcaatga ctgatgacaa   7500
aatcacagaa gtatcctgta aatctccaca gccagagtca ttcaaaacct caagaagctc   7560
caagcaaagg ctcaagatac ccctggtgaa agtggacatg aaagaagagc ccctagcagt   7620
cagcaagctc acacggacat caggggagac tacgcaaaca cacacagagc caacaggaga   7680
tagtaagagc atcaaagcgt ttaaggagtc tccaaagcag atcctggacc cagcagcaag   7740
```

-continued

```
tgtaactggt agcaggaggc agctgagaac tcgtaaggaa aaggcccgtg ctctagaaga   7800
cctggttgac ttcaaagagc tcttctcagc accaggtcac actgaagagt caatgactat   7860
tgacaaaaac acaaaaattc cctgcaaatc tcccccacca gaactaacag acactgccac   7920
gagcacaaag agatgcccca agacacgtct caggaaagaa gtaaaagagg agctctcagc   7980
agttgagagg ctcacgcaaa catcagggca aagcacacac acacacaaag aaccagcaag   8040
cggtgatgag ggcatcaaag tattgaagca acgtgcaaag aagaaaccaa acccagtaga   8100
agaggaaccc agcaggagaa ggccaagagc acctaaggaa aaggcccaac ccctggaaga   8160
cctggccggc ttcacagagc tctctgaaac atcaggtcac actcaggaat cactgactgc   8220
tggcaaagcc actaaaatac cctgcgaatc tcccccacta gaagtggtag acaccacagc   8280
aagcacaaag aggcatctca ggacacgtgt gcagaaggta caagtaaaag aagagccttc   8340
agcagtcaag ttcacacaaa catcagggga aaccacggat gcagacaaag aaccagcagg   8400
tgaagataaa ggcatcaaag cattgaagga atctgcaaaa cagacaccgg ctccagcagc   8460
aagtgtaact ggcagcagga gacggccaag agcacccagg gaaagtgccc aagccataga   8520
agacctagct ggcttcaaag acccagcagc aggtcacact gaagaatcaa tgactgatga   8580
caaaaccact aaaataccct gcaaatcatc accagaacta gaagacaccg caacaagctc   8640
aaagagacgg cccaggacac gtgcccagaa agtagaagtg aaggaggagc tgttagcagt   8700
tggcaagctc acacaaacct caggggagac cacgcacacc gacaaagagc cggtaggtga   8760
gggcaaaggc acgaaagcat ttaagcaacc tgcaaagcgg aagctggacg cagaagatgt   8820
aattggcagc aggagacagc caagagcacc taaggaaaag gcccaacccc tggaagatct   8880
ggccagcttc caagagctct ctcaaacacc aggccacact gaggaactgg caaatggtgc   8940
tgctgatagc tttacaagcg ctccaaagca aacacctgac agtggaaaac ctctaaaaat   9000
atccagaaga gttcttcggg cccctaaagt agaacccgtg ggagacgtgg taagcaccag   9060
agaccctgta aaatcacaaa gcaaaagcaa cacttccctg cccccactgc ccttcaagag   9120
gggaggtggc aaagatggaa gcgtcacggg aaccaagagg ctgcgctgca tgccagcacc   9180
agaggaaatt gtggaggagc tgccagccag caagaagcag agggttgctc ccagggcaag   9240
aggcaaatca tccgaacccg tggtcatcat gaagagaagt ttgaggactt ctgcaaaaag   9300
aattgaacct gcggaagagc tgaacagcaa cgacatgaaa accaacaaag aggaacacaa   9360
attacaagac tcagtccctg aaaataaggg aatatccctg cgctccagac gccaaaataa   9420
gactgaggca gaacagcaaa taactgaggt ctttgtatta gcagaaagaa tagaaataaa   9480
cagaaatgaa aagaagccca tgaagacctc cccagagatg gacattcaga atccagatga   9540
tggagcccgg aaacccatac ctagagacaa agtcactgag aacaaaaggt gcttgaggtc   9600
tgctagacag aatgagagct cccagcctaa ggtggcagag gagagcggag ggcagaagag   9660
tgcgaaggtt ctcatgcaga atcagaaagg gaaaggagaa gcaggaaatt cagactccat   9720
gtgcctgaga tcaagaaaga caaaaagcca gcctgcagca agcactttgg agagcaaatc   9780
tgtgcagaga gtaacgcgga gtgtcaagag gtgtgcagaa aatccaaaga aggctgagga   9840
caatgtgtgt gtcaagaaaa taagaaccag aagtcatagg gacagtgaag atatttgaca   9900
gaaaaatcga actgggaaaa atataataaa gttagttttg tgataagttc tagtgcagtt   9960
tttgtcataa attacaagtg aattctgtaa gtaaggctgt cagtctgctt aagggaagaa  10020
aactttggat ttgctgggtc tgaatcggct tcataaactc cactgggagc actgctgggc  10080
```

-continued

```
tcctggactg agaatagttg aacaccgggg gctttgtgaa ggagtctggg ccaaggtttg  10140

ccctcagctt tgcagaatga agccttgagg tctgtcacca cccacagcca ccctacagca  10200

gccttaactg tgacacttgc cacactgtgt cgtcgtttgt ttgcctatgt cctccagggc  10260

acggtggcag gaacaactat cctcgtctgt cccaacactg agcaggcact cggtaaacac  10320

gaatgaatgg atgagcgcac ggatgaatgg agcttacaga tctgtctttc caatggccgg  10380

ggggatttgg tccccaaatt aaggctattg gacatctgca caggacagtc ta          10432
```

```
<210> SEQ ID NO 98
<211> LENGTH: 3256
<212> TYPE: PRT
<213> ORGANISM: Homo sapiens
<220> FEATURE:
<221> NAME/KEY: misc_feature
<223> OTHER INFORMATION: Incyte ID No: 2700132CD1

<400> SEQUENCE: 98

Met Trp Pro Thr Arg Arg Leu Val Thr Ile Lys Arg Ser Gly Val
  1               5                  10                  15

Asp Gly Pro His Phe Pro Leu Ser Leu Ser Thr Cys Leu Phe Gly
                 20                  25                  30

Arg Gly Ile Glu Cys Asp Ile Arg Ile Gln Leu Pro Val Val Ser
                 35                  40                  45

Lys Gln His Cys Lys Ile Glu Ile His Glu Gln Glu Ala Ile Leu
                 50                  55                  60

His Asn Phe Ser Ser Thr Asn Pro Thr Gln Val Asn Gly Ser Val
                 65                  70                  75

Ile Asp Glu Pro Val Arg Leu Lys His Gly Asp Val Ile Thr Ile
                 80                  85                  90

Ile Asp Arg Ser Phe Arg Tyr Glu Asn Glu Ser Leu Gln Ser Gly
                 95                 100                 105

Arg Lys Ser Thr Glu Phe Pro Arg Lys Ile Arg Glu Gln Glu Pro
                110                 115                 120

Ala Arg Arg Val Ser Arg Ser Ser Phe Ser Ser Asp Pro Asp Glu
                125                 130                 135

Lys Ala Gln Asp Ser Lys Ala Tyr Ser Lys Ile Thr Glu Gly Lys
                140                 145                 150

Val Ser Gly Asn Pro Gln Val His Ile Lys Asn Val Lys Glu Asp
                155                 160                 165

Ser Thr Ala Asp Asp Ser Lys Asp Ser Val Ala Gln Gly Thr Thr
                170                 175                 180

Asn Val His Ser Ser Glu His Ala Gly Arg Asn Gly Arg Asn Ala
                185                 190                 195

Ala Asp Pro Ile Ser Gly Asp Phe Lys Glu Ile Ser Ser Val Lys
                200                 205                 210

Leu Val Ser Arg Tyr Gly Glu Leu Lys Ser Val Pro Thr Thr Gln
                215                 220                 225

Cys Leu Asp Asn Ser Lys Lys Asn Glu Ser Pro Phe Trp Lys Leu
                230                 235                 240

Tyr Glu Ser Val Lys Lys Glu Leu Asp Val Lys Ser Gln Lys Glu
                245                 250                 255

Asn Val Leu Gln Tyr Cys Arg Lys Ser Gly Leu Gln Thr Asp Tyr
                260                 265                 270

Ala Thr Glu Lys Glu Ser Ala Asp Gly Leu Gln Gly Glu Thr Gln
                275                 280                 285
```

-continued

```
Leu Leu Val Ser Arg Lys Ser Arg Pro Lys Ser Gly Gly Ser Gly
                290                 295                 300

His Ala Val Ala Glu Pro Ala Ser Pro Glu Gln Glu Leu Asp Gln
                305                 310                 315

Asn Lys Gly Lys Gly Arg Asp Val Glu Ser Val Gln Thr Pro Ser
                320                 325                 330

Lys Ala Val Gly Ala Ser Phe Pro Leu Tyr Glu Pro Ala Lys Met
                335                 340                 345

Lys Thr Pro Val Gln Tyr Ser Gln Gln Gln Asn Ser Pro Gln Lys
                350                 355                 360

His Lys Asn Lys Asp Leu Tyr Thr Thr Gly Arg Arg Glu Ser Val
                365                 370                 375

Asn Leu Gly Lys Ser Glu Gly Phe Lys Ala Gly Asp Lys Thr Leu
                380                 385                 390

Thr Pro Arg Lys Leu Ser Thr Arg Asn Arg Thr Pro Ala Lys Val
                395                 400                 405

Glu Asp Ala Ala Asp Ser Ala Thr Lys Pro Glu Asn Leu Ser Ser
                410                 415                 420

Lys Thr Arg Gly Ser Ile Pro Thr Asp Val Glu Val Leu Pro Thr
                425                 430                 435

Glu Thr Glu Ile His Asn Glu Pro Phe Leu Thr Leu Trp Leu Thr
                440                 445                 450

Gln Val Glu Arg Lys Ile Gln Lys Asp Ser Leu Ser Lys Pro Glu
                455                 460                 465

Lys Leu Gly Thr Thr Ala Gly Gln Met Cys Ser Gly Leu Pro Gly
                470                 475                 480

Leu Ser Ser Val Asp Ile Asn Asn Phe Gly Asp Ser Ile Asn Glu
                485                 490                 495

Ser Glu Gly Ile Pro Leu Lys Arg Arg Arg Val Ser Phe Gly Gly
                500                 505                 510

His Leu Arg Pro Glu Leu Phe Asp Glu Asn Leu Pro Pro Asn Thr
                515                 520                 525

Pro Leu Lys Arg Gly Glu Ala Pro Thr Lys Arg Lys Ser Leu Val
                530                 535                 540

Met His Thr Pro Pro Val Leu Lys Lys Ile Ile Lys Glu Gln Pro
                545                 550                 555

Gln Pro Ser Gly Lys Gln Glu Ser Gly Ser Glu Ile His Val Glu
                560                 565                 570

Val Lys Ala Gln Ser Leu Val Ile Ser Pro Pro Ala Pro Ser Pro
                575                 580                 585

Arg Lys Thr Pro Val Ala Ser Asp Gln Arg Arg Arg Ser Cys Lys
                590                 595                 600

Thr Ala Pro Ala Ser Ser Ser Lys Ser Gln Thr Glu Val Pro Lys
                605                 610                 615

Arg Gly Gly Glu Arg Val Ala Thr Cys Leu Gln Lys Arg Val Ser
                620                 625                 630

Ile Ser Arg Ser Gln His Asp Ile Leu Gln Met Ile Cys Ser Lys
                635                 640                 645

Arg Arg Ser Gly Ala Ser Glu Ala Asn Leu Ile Val Ala Lys Ser
                650                 655                 660

Trp Ala Asp Val Val Lys Leu Gly Ala Lys Gln Thr Gln Thr Lys
                665                 670                 675
```

-continued

```
Val Ile Lys His Gly Pro Gln Arg Ser Met Asn Lys Arg Gln Arg
                680                 685                 690

Arg Pro Ala Thr Pro Lys Lys Pro Val Gly Glu Val His Ser Gln
                695                 700                 705

Phe Ser Thr Gly His Ala Asn Ser Pro Cys Thr Ile Ile Ile Gly
                710                 715                 720

Lys Ala His Thr Glu Lys Val His Val Pro Ala Arg Pro Tyr Arg
                725                 730                 735

Val Leu Asn Asn Phe Ile Ser Asn Gln Lys Met Asp Phe Lys Glu
                740                 745                 750

Asp Leu Ser Gly Ile Ala Glu Met Phe Lys Thr Pro Val Lys Glu
                755                 760                 765

Gln Pro Gln Leu Thr Ser Thr Cys His Ile Ala Ile Ser Asn Ser
                770                 775                 780

Glu Asn Leu Leu Gly Lys Gln Phe Gln Gly Thr Asp Ser Gly Glu
                785                 790                 795

Glu Pro Leu Leu Pro Thr Ser Glu Ser Phe Gly Gly Asn Val Phe
                800                 805                 810

Phe Ser Ala Gln Asn Ala Ala Lys Gln Pro Ser Asp Lys Cys Ser
                815                 820                 825

Ala Ser Pro Pro Leu Arg Arg Gln Cys Ile Arg Glu Asn Gly Asn
                830                 835                 840

Val Ala Lys Thr Pro Arg Asn Thr Tyr Lys Met Thr Ser Leu Glu
                845                 850                 855

Thr Lys Thr Ser Asp Thr Glu Thr Glu Pro Ser Lys Thr Val Ser
                860                 865                 870

Thr Val Asn Arg Ser Gly Arg Ser Thr Glu Phe Arg Asn Ile Gln
                875                 880                 885

Lys Leu Pro Val Glu Ser Lys Ser Glu Glu Thr Asn Thr Glu Ile
                890                 895                 900

Val Glu Cys Ile Leu Lys Arg Gly Gln Lys Ala Thr Leu Leu Gln
                905                 910                 915

Gln Arg Arg Glu Gly Glu Met Lys Glu Ile Glu Arg Pro Phe Glu
                920                 925                 930

Thr Tyr Lys Glu Asn Ile Glu Leu Lys Glu Asn Asp Glu Lys Met
                935                 940                 945

Lys Ala Met Lys Arg Ser Arg Thr Trp Gly Gln Lys Cys Ala Pro
                950                 955                 960

Met Ser Asp Leu Thr Asp Leu Lys Ser Leu Pro Asp Thr Glu Leu
                965                 970                 975

Met Lys Asp Thr Ala Arg Gly Gln Asn Leu Leu Gln Thr Gln Asp
                980                 985                 990

His Ala Lys Ala Pro Lys Ser Glu Lys Gly Lys Ile Thr Lys Met
                995                1000                1005

Pro Cys Gln Ser Leu Gln Pro Glu Pro Ile Asn Thr Pro Thr His
               1010                1015                1020

Thr Lys Gln Gln Leu Lys Ala Ser Leu Gly Lys Val Gly Val Lys
               1025                1030                1035

Glu Glu Leu Leu Ala Val Gly Lys Phe Thr Arg Thr Ser Gly Glu
               1040                1045                1050

Thr Thr His Thr His Arg Glu Pro Ala Gly Asp Gly Lys Ser Ile
               1055                1060                1065

Arg Thr Phe Lys Glu Ser Pro Lys Gln Ile Leu Asp Pro Ala Ala
```

-continued

```
                1070                1075                1080

Arg Val Thr Gly Met Lys Lys Trp Pro Arg Thr Pro Lys Glu Glu
                1085                1090                1095

Ala Gln Ser Leu Glu Asp Leu Ala Gly Phe Lys Glu Leu Phe Gln
                1100                1105                1110

Thr Pro Gly Pro Ser Glu Glu Ser Met Thr Asp Glu Lys Thr Thr
                1115                1120                1125

Lys Ile Ala Cys Lys Ser Pro Pro Pro Glu Ser Val Asp Thr Pro
                1130                1135                1140

Thr Ser Thr Lys Gln Trp Pro Lys Arg Ser Leu Arg Lys Ala Asp
                1145                1150                1155

Val Glu Glu Glu Phe Leu Ala Leu Arg Lys Leu Thr Pro Ser Ala
                1160                1165                1170

Gly Lys Ala Met Leu Thr Pro Lys Pro Ala Gly Gly Asp Glu Lys
                1175                1180                1185

Asp Ile Lys Ala Phe Met Gly Thr Pro Val Gln Lys Leu Asp Leu
                1190                1195                1200

Ala Gly Thr Leu Pro Gly Ser Lys Arg Gln Leu Gln Thr Pro Lys
                1205                1210                1215

Glu Lys Ala Gln Ala Leu Glu Asp Leu Ala Gly Phe Lys Glu Leu
                1220                1225                1230

Phe Gln Thr Pro Gly His Thr Glu Glu Leu Val Ala Ala Gly Lys
                1235                1240                1245

Thr Thr Lys Ile Pro Cys Asp Ser Pro Gln Ser Asp Pro Val Asp
                1250                1255                1260

Thr Pro Thr Ser Thr Lys Gln Arg Pro Lys Arg Ser Ile Arg Lys
                1265                1270                1275

Ala Asp Val Glu Gly Glu Leu Leu Ala Cys Arg Asn Leu Met Pro
                1280                1285                1290

Ser Ala Gly Lys Ala Met His Thr Pro Lys Pro Ser Val Gly Glu
                1295                1300                1305

Glu Lys Asp Ile Ile Ile Phe Val Gly Thr Pro Val Gln Lys Leu
                1310                1315                1320

Asp Leu Thr Glu Asn Leu Thr Gly Ser Lys Arg Arg Pro Gln Thr
                1325                1330                1335

Pro Lys Glu Glu Ala Gln Ala Leu Glu Asp Leu Thr Gly Phe Lys
                1340                1345                1350

Glu Leu Phe Gln Thr Pro Gly His Thr Glu Glu Ala Val Ala Ala
                1355                1360                1365

Gly Lys Thr Thr Lys Met Pro Cys Glu Ser Ser Pro Pro Glu Ser
                1370                1375                1380

Ala Asp Thr Pro Thr Ser Thr Arg Arg Gln Pro Lys Thr Pro Leu
                1385                1390                1395

Glu Lys Arg Asp Val Gln Lys Glu Leu Ser Ala Leu Lys Lys Leu
                1400                1405                1410

Thr Gln Thr Ser Gly Glu Thr Thr His Thr Asp Lys Val Pro Gly
                1415                1420                1425

Gly Glu Asp Lys Ser Ile Asn Ala Phe Arg Glu Thr Ala Lys Gln
                1430                1435                1440

Lys Leu Asp Pro Ala Ala Ser Val Thr Gly Ser Lys Arg His Pro
                1445                1450                1455

Lys Thr Lys Glu Lys Ala Gln Pro Leu Glu Asp Leu Ala Gly Trp
                1460                1465                1470
```

-continued

```
Lys Glu Leu Phe Gln Thr Pro Val Cys Thr Asp Lys Pro Thr Thr
            1475                1480                1485

His Glu Lys Thr Thr Lys Ile Ala Cys Arg Ser Gln Pro Asp Pro
            1490                1495                1500

Val Asp Thr Pro Thr Ser Ser Lys Pro Gln Ser Lys Arg Ser Leu
            1505                1510                1515

Arg Lys Val Asp Val Glu Glu Glu Phe Phe Ala Leu Arg Lys Arg
            1520                1525                1530

Thr Pro Ser Ala Gly Lys Ala Met His Thr Pro Lys Pro Ala Val
            1535                1540                1545

Ser Gly Glu Lys Asn Ile Tyr Ala Phe Met Gly Thr Pro Val Gln
            1550                1555                1560

Lys Leu Asp Leu Thr Glu Asn Leu Thr Gly Ser Lys Arg Arg Leu
            1565                1570                1575

Gln Thr Pro Lys Glu Lys Ala Gln Ala Leu Glu Asp Leu Ala Gly
            1580                1585                1590

Phe Lys Glu Leu Phe Gln Thr Arg Gly His Thr Glu Glu Ser Met
            1595                1600                1605

Thr Asn Asp Lys Thr Ala Lys Val Ala Cys Lys Ser Ser Gln Pro
            1610                1615                1620

Asp Leu Asp Lys Asn Pro Ala Ser Ser Lys Arg Arg Leu Lys Thr
            1625                1630                1635

Ser Leu Gly Lys Val Gly Val Lys Glu Glu Leu Leu Ala Val Gly
            1640                1645                1650

Lys Leu Thr Gln Thr Ser Gly Glu Thr Thr His Thr His Thr Glu
            1655                1660                1665

Pro Thr Gly Asp Gly Lys Ser Met Lys Ala Phe Met Glu Ser Pro
            1670                1675                1680

Lys Gln Ile Leu Asp Ser Ala Ala Ser Leu Thr Gly Ser Lys Arg
            1685                1690                1695

Gln Leu Arg Thr Pro Lys Gly Lys Ser Glu Val Pro Glu Asp Leu
            1700                1705                1710

Ala Gly Phe Ile Glu Leu Phe Gln Thr Pro Ser His Thr Lys Glu
            1715                1720                1725

Ser Met Thr Asn Glu Lys Thr Thr Lys Val Ser Tyr Arg Ala Ser
            1730                1735                1740

Gln Pro Asp Leu Val Asp Thr Pro Thr Ser Ser Lys Pro Gln Pro
            1745                1750                1755

Lys Arg Ser Leu Arg Lys Ala Asp Thr Glu Glu Glu Phe Leu Ala
            1760                1765                1770

Phe Arg Lys Gln Thr Pro Ser Ala Gly Lys Ala Met His Thr Pro
            1775                1780                1785

Lys Pro Ala Val Gly Glu Glu Lys Asp Ile Asn Thr Phe Leu Gly
            1790                1795                1800

Thr Pro Val Gln Lys Leu Asp Gln Pro Gly Asn Leu Pro Gly Ser
            1805                1810                1815

Asn Arg Arg Leu Gln Thr Arg Lys Glu Lys Ala Gln Ala Leu Glu
            1820                1825                1830

Glu Leu Thr Gly Phe Arg Glu Leu Phe Gln Thr Pro Cys Thr Asp
            1835                1840                1845

Asn Pro Thr Thr Asp Glu Lys Thr Thr Lys Lys Ile Leu Cys Lys
            1850                1855                1860
```

-continued

```
Ser Pro Gln Ser Asp Pro Ala Asp Thr Pro Thr Asn Thr Lys Gln
                1865                1870                1875

Arg Pro Lys Arg Ser Leu Lys Lys Ala Asp Val Glu Glu Glu Phe
                1880                1885                1890

Leu Ala Phe Arg Lys Leu Thr Pro Ser Ala Gly Lys Ala Met His
                1895                1900                1905

Thr Pro Lys Ala Ala Val Gly Glu Glu Lys Asp Ile Asn Thr Phe
                1910                1915                1920

Val Gly Thr Pro Val Glu Lys Leu Asp Leu Leu Gly Asn Leu Pro
                1925                1930                1935

Gly Ser Lys Arg Arg Pro Gln Thr Pro Lys Glu Lys Ala Lys Ala
                1940                1945                1950

Leu Glu Asp Leu Ala Gly Phe Lys Glu Leu Phe Gln Thr Pro Gly
                1955                1960                1965

His Thr Glu Glu Ser Met Thr Asp Asp Lys Ile Thr Glu Val Ser
                1970                1975                1980

Cys Lys Ser Pro Gln Pro Asp Pro Val Lys Thr Pro Thr Ser Ser
                1985                1990                1995

Lys Gln Arg Leu Lys Ile Ser Leu Gly Lys Val Gly Val Lys Glu
                2000                2005                2010

Glu Val Leu Pro Val Gly Lys Leu Thr Gln Thr Ser Gly Lys Thr
                2015                2020                2025

Thr Gln Thr His Arg Glu Thr Ala Gly Asp Gly Lys Ser Ile Lys
                2030                2035                2040

Ala Phe Lys Glu Ser Ala Lys Gln Met Leu Asp Pro Ala Asn Tyr
                2045                2050                2055

Gly Thr Gly Met Glu Arg Trp Pro Arg Thr Pro Lys Glu Glu Ala
                2060                2065                2070

Gln Ser Leu Glu Asp Leu Ala Gly Phe Lys Glu Leu Phe Gln Thr
                2075                2080                2085

Pro Asp His Thr Glu Glu Ser Thr Thr Asp Asp Lys Thr Thr Lys
                2090                2095                2100

Ile Ala Cys Lys Ser Pro Pro Pro Glu Ser Met Asp Thr Pro Thr
                2105                2110                2115

Ser Thr Arg Arg Arg Pro Lys Thr Pro Leu Gly Lys Arg Asp Ile
                2120                2125                2130

Val Glu Glu Leu Ser Ala Leu Lys Gln Leu Thr Gln Thr Thr His
                2135                2140                2145

Thr Asp Lys Val Pro Gly Asp Glu Asp Lys Gly Ile Asn Val Phe
                2150                2155                2160

Arg Glu Thr Ala Lys Gln Lys Leu Asp Pro Ala Ala Ser Val Thr
                2165                2170                2175

Gly Ser Lys Arg Gln Pro Arg Thr Pro Lys Gly Lys Ala Gln Pro
                2180                2185                2190

Leu Glu Asp Leu Ala Gly Leu Lys Glu Leu Phe Gln Thr Pro Ile
                2195                2200                2205

Cys Thr Asp Lys Pro Thr Thr His Glu Lys Thr Thr Lys Ile Ala
                2210                2215                2220

Cys Arg Ser Pro Gln Pro Asp Pro Val Gly Thr Pro Thr Ile Phe
                2225                2230                2235

Lys Pro Gln Ser Lys Arg Ser Leu Arg Lys Ala Asp Val Glu Glu
                2240                2245                2250

Glu Ser Leu Ala Leu Arg Lys Arg Thr Pro Ser Val Gly Lys Ala
```

-continued

```
            2255                2260                2265

Met Asp Thr Pro Lys Pro Ala Gly Gly Asp Glu Lys Asp Met Lys
            2270                2275                2280

Ala Phe Met Gly Thr Pro Val Gln Lys Leu Asp Leu Pro Gly Asn
            2285                2290                2295

Leu Pro Gly Ser Lys Arg Trp Pro Gln Thr Pro Lys Glu Lys Ala
            2300                2305                2310

Gln Ala Leu Glu Asp Leu Ala Gly Phe Lys Glu Leu Phe Gln Thr
            2315                2320                2325

Pro Gly Thr Asp Lys Pro Thr Thr Asp Glu Lys Thr Thr Lys Ile
            2330                2335                2340

Ala Cys Lys Ser Pro Gln Pro Asp Pro Val Asp Thr Pro Ala Ser
            2345                2350                2355

Thr Lys Gln Arg Pro Lys Arg Asn Leu Arg Lys Ala Asp Val Glu
            2360                2365                2370

Glu Glu Phe Leu Ala Leu Arg Lys Arg Thr Pro Ser Ala Gly Lys
            2375                2380                2385

Ala Met Asp Thr Pro Lys Pro Ala Val Ser Asp Glu Lys Asn Ile
            2390                2395                2400

Asn Thr Phe Val Glu Thr Pro Val Gln Lys Leu Asp Leu Leu Gly
            2405                2410                2415

Asn Leu Pro Gly Ser Lys Arg Gln Pro Gln Thr Pro Lys Glu Lys
            2420                2425                2430

Ala Glu Ala Leu Glu Asp Leu Val Gly Phe Lys Glu Leu Phe Gln
            2435                2440                2445

Thr Pro Gly His Thr Glu Glu Ser Met Thr Asp Asp Lys Ile Thr
            2450                2455                2460

Glu Val Ser Cys Lys Ser Pro Gln Pro Glu Ser Phe Lys Thr Ser
            2465                2470                2475

Arg Ser Ser Lys Gln Arg Leu Lys Ile Pro Leu Val Lys Val Asp
            2480                2485                2490

Met Lys Glu Glu Pro Leu Ala Val Ser Lys Leu Thr Arg Thr Ser
            2495                2500                2505

Gly Glu Thr Thr Gln Thr His Thr Glu Pro Thr Gly Asp Ser Lys
            2510                2515                2520

Ser Ile Lys Ala Phe Lys Glu Ser Pro Lys Gln Ile Leu Asp Pro
            2525                2530                2535

Ala Ala Ser Val Thr Gly Ser Arg Arg Gln Leu Arg Thr Arg Lys
            2540                2545                2550

Glu Lys Ala Arg Ala Leu Glu Asp Leu Val Asp Phe Lys Glu Leu
            2555                2560                2565

Phe Ser Ala Pro Gly His Thr Glu Glu Ser Met Thr Ile Asp Lys
            2570                2575                2580

Asn Thr Lys Ile Pro Cys Lys Ser Pro Pro Pro Glu Leu Thr Asp
            2585                2590                2595

Thr Ala Thr Ser Thr Lys Arg Cys Pro Lys Thr Arg Leu Arg Lys
            2600                2605                2610

Glu Val Lys Glu Glu Leu Ser Ala Val Glu Arg Leu Thr Gln Thr
            2615                2620                2625

Ser Gly Gln Ser Thr His Thr His Lys Glu Pro Ala Ser Gly Asp
            2630                2635                2640

Glu Gly Ile Lys Val Leu Lys Gln Arg Ala Lys Lys Lys Pro Asn
            2645                2650                2655
```

-continued

```
Pro Val Glu Glu Glu Pro Ser Arg Arg Arg Pro Arg Ala Pro Lys
            2660                2665                2670

Glu Lys Ala Gln Pro Leu Glu Asp Leu Ala Gly Phe Thr Glu Leu
            2675                2680                2685

Ser Glu Thr Ser Gly His Thr Gln Glu Ser Leu Thr Ala Gly Lys
            2690                2695                2700

Ala Thr Lys Ile Pro Cys Glu Ser Pro Pro Leu Glu Val Val Asp
            2705                2710                2715

Thr Thr Ala Ser Thr Lys Arg His Leu Arg Thr Arg Val Gln Lys
            2720                2725                2730

Val Gln Val Lys Glu Glu Pro Ser Ala Val Lys Phe Thr Gln Thr
            2735                2740                2745

Ser Gly Glu Thr Thr Asp Ala Asp Lys Glu Pro Ala Gly Glu Asp
            2750                2755                2760

Lys Gly Ile Lys Ala Leu Lys Glu Ser Ala Lys Gln Thr Pro Ala
            2765                2770                2775

Pro Ala Ala Ser Val Thr Gly Ser Arg Arg Arg Pro Arg Ala Pro
            2780                2785                2790

Arg Glu Ser Ala Gln Ala Ile Glu Asp Leu Ala Gly Phe Lys Asp
            2795                2800                2805

Pro Ala Ala Gly His Thr Glu Glu Ser Met Thr Asp Asp Lys Thr
            2810                2815                2820

Thr Lys Ile Pro Cys Lys Ser Ser Pro Glu Leu Glu Asp Thr Ala
            2825                2830                2835

Thr Ser Ser Lys Arg Arg Pro Arg Thr Arg Ala Gln Lys Val Glu
            2840                2845                2850

Val Lys Glu Glu Leu Leu Ala Val Gly Lys Leu Thr Gln Thr Ser
            2855                2860                2865

Gly Glu Thr Thr His Thr Asp Lys Glu Pro Val Gly Glu Gly Lys
            2870                2875                2880

Gly Thr Lys Ala Phe Lys Gln Pro Ala Lys Arg Lys Leu Asp Ala
            2885                2890                2895

Glu Asp Val Ile Gly Ser Arg Arg Gln Pro Arg Ala Pro Lys Glu
            2900                2905                2910

Lys Ala Gln Pro Leu Glu Asp Leu Ala Ser Phe Gln Glu Leu Ser
            2915                2920                2925

Gln Thr Pro Gly His Thr Glu Glu Leu Ala Asn Gly Ala Ala Asp
            2930                2935                2940

Ser Phe Thr Ser Ala Pro Lys Gln Thr Pro Asp Ser Gly Lys Pro
            2945                2950                2955

Leu Lys Ile Ser Arg Arg Val Leu Arg Ala Pro Lys Val Glu Pro
            2960                2965                2970

Val Gly Asp Val Val Ser Thr Arg Asp Pro Val Lys Ser Gln Ser
            2975                2980                2985

Lys Ser Asn Thr Ser Leu Pro Pro Leu Pro Phe Lys Arg Gly Gly
            2990                2995                3000

Gly Lys Asp Gly Ser Val Thr Gly Thr Lys Arg Leu Arg Cys Met
            3005                3010                3015

Pro Ala Pro Glu Glu Ile Val Glu Glu Leu Pro Ala Ser Lys Lys
            3020                3025                3030

Gln Arg Val Ala Pro Arg Ala Arg Gly Lys Ser Ser Glu Pro Val
            3035                3040                3045
```

-continued

```
Val Ile Met Lys Arg Ser Leu Arg Thr Ser Ala Lys Arg Ile Glu
                3050                3055                3060

Pro Ala Glu Glu Leu Asn Ser Asn Asp Met Lys Thr Asn Lys Glu
                3065                3070                3075

Glu His Lys Leu Gln Asp Ser Val Pro Glu Asn Lys Gly Ile Ser
                3080                3085                3090

Leu Arg Ser Arg Arg Gln Asn Lys Thr Glu Ala Glu Gln Gln Ile
                3095                3100                3105

Thr Glu Val Phe Val Leu Ala Glu Arg Ile Glu Ile Asn Arg Asn
                3110                3115                3120

Glu Lys Lys Pro Met Lys Thr Ser Pro Glu Met Asp Ile Gln Asn
                3125                3130                3135

Pro Asp Asp Gly Ala Arg Lys Pro Ile Pro Arg Asp Lys Val Thr
                3140                3145                3150

Glu Asn Lys Arg Cys Leu Arg Ser Ala Arg Gln Asn Glu Ser Ser
                3155                3160                3165

Gln Pro Lys Val Ala Glu Glu Ser Gly Gly Gln Lys Ser Ala Lys
                3170                3175                3180

Val Leu Met Gln Asn Gln Lys Gly Lys Gly Glu Ala Gly Asn Ser
                3185                3190                3195

Asp Ser Met Cys Leu Arg Ser Arg Lys Thr Lys Ser Gln Pro Ala
                3200                3205                3210

Ala Ser Thr Leu Glu Ser Lys Ser Val Gln Arg Val Thr Arg Ser
                3215                3220                3225

Val Lys Arg Cys Ala Glu Asn Pro Lys Lys Ala Glu Asp Asn Val
                3230                3235                3240

Cys Val Lys Lys Ile Arg Thr Arg Ser His Arg Asp Ser Glu Asp
                3245                3250                3255

Ile


<210> SEQ ID NO 99
<211> LENGTH: 826
<212> TYPE: DNA
<213> ORGANISM: Homo sapiens
<220> FEATURE:
<221> NAME/KEY: misc_feature
<223> OTHER INFORMATION: Incyte ID No: 211881.1

<400> SEQUENCE: 99

cttaaaacct gacatccttc atgttagcta acctttataa tctctttgga tgtagtaaat     60

ttttagtatt ttttagattg aatttgtatc atatttgcta gcaaattgag tataaagagt    120

agcatatttt tactacagat gtattatttt aactaacaaa ggcatattat acattttttt    180

catatataaa ctttggaata ggattttaca gtaacttaag ttttttattt ctacccatgt    240

gtcaaagttt tatgctaaat tctgaataga atagttgtaa ctcccactct gggtatttta    300

tttattttaa acagttctag tattgtttcc tgtgaatttt ttccagggat tgctactttc    360

tgcactattc attagaccaa gagcatttca ccaaatactt aaaacttaaa aatttttaaa    420

cttttccaaa tttgattaaa aggataacat attctaaagg tattcaatat ttttacttat    480

ctctgaaaaa cttaatcaca taaaagcata catttacac atacagctct ctccatcttc    540

cacaatagat taagacataa aacataacca gtatttttga aaagccccct taactggcat    600

gcttcttact gaaattatca taaaaggttc gtatgagaaa ggattccaga atatccctta    660

attgtgttgt agcttatgca tttctattta ttttatacat tatttaattc atgtgagtta    720
```

-continued

```
cttacctggc agggaagata tgatcaccaa ggtgcctttc acattcattg cactctggat    780

gtgctgaccc ctgcaatttc cccaaatggg ggaagctcaa ctgcat                   826
```

<210> SEQ ID NO 100
<211> LENGTH: 1498
<212> TYPE: DNA
<213> ORGANISM: Homo sapiens
<220> FEATURE:
<221> NAME/KEY: misc_feature
<223> OTHER INFORMATION: Incyte ID No: 409895.2

<400> SEQUENCE: 100

```
agctaatgtg ttacattaga atcacctcgg ggaggccctg ggtgcccttc tcagccctcc     60

ctccggaggc tgctgaagcc cagcaaagcc ggagtcagag aacaatgtcc gcctgagggc    120

agggctgggc tgggctggcc ttctggccct atctgctccg tgcccaaccc agcgccccgc    180

acagtcggag ctttgtaaat acgaggtgac tgtctgccta caaactttgt aaacatcact    240

tgaaatggcc gcagggtatt gcgacatggc cataccacta tttgtttgct attgaatttg    300

tacttccctg ccttactttt gctattgcaa accatgctgt cactaaggtc ttcatgcaca    360

cagttgtgtc ttggtcagat gatatgtttc taccaatttt aattgtgttt ctttccacct    420

gggacacaca gctctctggg ccccagggct gggtcatcag cacaccctgc tgctgctgtt    480

cagatctgca tcctggtccc gcttggtccc acagtgagaa cgctttgcta tcacatgggc    540

aggctctgag agccctgccg gcctggcctt ctcaaagaag acctgagagc ttgggaccca    600

agcagagagg aagaacaggg ctcagggtgc ttgctccatg ctcgctccac acctggggct    660

caaccctggc tttccccggc tccctgtgtg acttcagggc aggtcccttg ggccctctgg    720

gccttatcat cttcatctgt aacagggcga tgcctctgcc gtgtctggtg gtgttgagga    780

gttcctgttt gtgtaagcag ctagttcagt gccagcacga gatgggaggc ccatgaagtt    840

agcagtgcac aaaaaataga gcaaagactg gatgcatttc ctgagaacaa ccatcactgt    900

aaagcacttt acaaatccaa agacaacccc cggcaaaaac tcaaaatgaa actccctctc    960

gcagagcaca attccaattc gctctaaaaa cattacaagt tagttcatgt catgccagat   1020

agctgaaggc agctcacaag ttcttaaggc caggaatgcc atgtgtctgc tatgcacagc   1080

tggccctggc cctgagcctg aatgacagca aaggtgacgc agatgtgggt gccctgctcc   1140

tgcccagcag cagtgcttgg tggaggctga ggccctgcac aggcaccctc actgctgacc   1200

ttgagcctct ctctcctcta gagtggaaaa gacaaggatg ccgtggataa attgctcaag   1260

gacctggacg ccaatggaga tgcccaggtg gacttcagtg agttcatcgt gttcgtggct   1320

gcaatcacgt ctgcctgtca caagtacttt gagaaggcag gactcaaatg atgccctgga   1380

gatgtcacag attcctggca gagccatggt cccaggcttc ccaaaagtgt ttgttggcaa   1440

ttattcccct aggctgagcc tgctcatgta cctctgatta ataaatgctt atgaaatg     1498
```

<210> SEQ ID NO 101
<211> LENGTH: 860
<212> TYPE: DNA
<213> ORGANISM: Homo sapiens
<220> FEATURE:
<221> NAME/KEY: misc_feature
<223> OTHER INFORMATION: Incyte ID No: 1422432CB1
<221> NAME/KEY: unsure
<222> LOCATION: 205
<223> OTHER INFORMATION: a, t, c, g, or other

<400> SEQUENCE: 101

-continued

```
agagcaaaga ctggatgcat ttcctgagaa caaccatcac tgtaaagcac tttacaaatc     60

caaagacaac ccccggcaaa aactcaaaat gaaactccct ctcgcagagc acaattccaa    120

ttcgctctaa aaacattaca agttagttca tgtcatgcca gatagctgaa ggcagctcac    180

aagttcttaa ggccaggaat gccangtgtc tgctatgcac agctggccct ggccctgagc    240

ctgaatgaca gcaaaggtga cgcagatgtg ggtgccctgc tcctgcccag cagcagtgct    300

tggtggaggc tgaggccctg cacaggcacc ctcactgctg accttgagcc tctctctcct    360

ctcaagaggc tgccagtggg acattttctc ggccctgcca gcccccagga ggaaggtggg    420

tctgaatcta gcaccatgac ggaactagag acagccatgg gcatgatcat agacgtcttt    480

tcccgatatt cgggcagcga gggcagcacg cagaccctga ccaaggggga gctcaaggtg    540

ctgatggaga aggagctacc aggcttcctg cagagtggaa aagacaagga tgccgtggat    600

aaattgctca aggacctgga cgccaatgga gatgcccagg tggacttcag tgagttcatc    660

gtgttcgtgg ctgcaatcac gtctgcctgt cacaagtact ttgagaaggc aggactcaaa    720

tgatgccctg gagatgtcac agattcctgg cagagccatg gtcccaggct tcccaaaagt    780

gtttgttggc aattattccc ctaggctgag cctgctcatg tacctctgat taataaatgc    840

ttatgaaatg aaaaaaaaaa                                                860


<210> SEQ ID NO 102
<211> LENGTH: 95
<212> TYPE: PRT
<213> ORGANISM: Homo sapiens
<220> FEATURE:
<221> NAME/KEY: misc_feature
<223> OTHER INFORMATION: Incyte ID No: 1422432CD1

<400> SEQUENCE: 102

Met Thr Glu Leu Glu Thr Ala Met Gly Met Ile Ile Asp Val Phe
  1               5                  10                  15

Ser Arg Tyr Ser Gly Ser Glu Gly Ser Thr Gln Thr Leu Thr Lys
                 20                  25                  30

Gly Glu Leu Lys Val Leu Met Glu Lys Glu Leu Pro Gly Phe Leu
                 35                  40                  45

Gln Ser Gly Lys Asp Lys Asp Ala Val Asp Lys Leu Leu Lys Asp
                 50                  55                  60

Leu Asp Ala Asn Gly Asp Ala Gln Val Asp Phe Ser Glu Phe Ile
                 65                  70                  75

Val Phe Val Ala Ala Ile Thr Ser Ala Cys His Lys Tyr Phe Glu
                 80                  85                  90

Lys Ala Gly Leu Lys
                 95
```

PROSTATE CANCER MARKERS

This application claims the benefit of Provisional Application No. 60/222,469, filed Jul. 28, 2000.

FIELD OF THE INVENTION

The present invention relates to a composition comprising a plurality of cDNAs which are differentially expressed in prostate cancer and which may be used entirely or in part to diagnose, to stage, to treat, or to monitor the progression or treatment of prostate cancer.

BACKGROUND OF THE INVENTION

Array technology can provide a simple way to explore the expression of a single polymorphic gene or the expression profile of a large number of related or unrelated genes. When the expression of a single gene is examined, arrays are employed to detect the expression of a specific gene or its variants. When an expression profile is examined, arrays provide a platform for examining which genes are tissue specific, carrying out housekeeping functions, parts of a signaling cascade, or specifically related to a particular genetic predisposition, condition, disease, or disorder.

The potential application of gene expression profiling is particularly relevant to improving diagnosis, prognosis, and treatment of disease. For example, both the levels and sequences expressed in tissues from subjects with prostate cancer may be compared with the levels and sequences expressed in normal tissue.

Prostate cancer is a common malignancy in men over the age of 50, and the incidence increases with age. In the U.S., there are approximately 132,000 newly diagnosed cases of prostate cancer and more than 33,000 deaths from the disorder each year.

Once cancer cells arise in the prostate, they are stimulated by testosterone to a more rapid growth. Thus, removal of the testes can indirectly reduce both rapid growth and metastasis of the cancer. Over 95 percent of prostatic cancers are adenocarcinomas which originate in the prostatic acini. The remaining 5 percent are divided between squamous cell and transitional cell carcinomas, both of which arise in the prostatic ducts or other parts of the prostate gland.

As with most cancers, prostate cancer develops through a multistage progression ultimately resulting in an aggressive, metastatic phenotype. The initial step in tumor progression involves the hyperproliferation of normal luminal and/or basal epithelial cells that become hyperplastic and evolve into early-stage tumors. The early-stage tumors are localized in the prostate but eventually may metastasize, particularly to the bone, brain or lung. About 80% of these tumors remain responsive to androgen treatment, an important hormone controlling the growth of prostate epithelial cells. However, in its most advanced state, cancer growth becomes androgen-independent and there is currently no known treatment for this condition.

A primary diagnostic marker for prostate cancer is prostate specific antigen (PSA). PSA is a tissue-specific serine protease almost exclusively produced by prostatic epithelial cells. The quantity of PSA correlates with the number and volume of the prostatic epithelial cells, and consequently, the levels of PSA are an excellent indicator of abnormal prostate growth. Men with prostate cancer exhibit an early linear increase in PSA levels followed by an exponential increase prior to diagnosis. However, since PSA levels are also influenced by factors such as inflammation, androgen and other growth factors, some scientists maintain that changes in PSA levels are not useful in detecting individual cases of prostate cancer.

Current areas of cancer research provide additional prospects for markers as well as potential therapeutic targets for prostate cancer. Several growth factors have been shown to play a critical role in tumor development, growth, and progression. The growth factors Epidermal Growth Factor (EGF), Fibroblast Growth Factor (FGF), and Tumor Growth Factor alpha (TGF$\alpha$) are important in the growth of normal as well as hyperproliferative prostate epithelial cells, particularly at early stages of tumor development and progression, and affect signaling pathways in these cells in various ways (Lin J et al. (1999) Cancer Res. 59:2891–2897; Putz T et al. (1999) Cancer Res 59:227–233). The TGF-$\beta$ family of growth factors are generally expressed at increased levels in human cancers and the high expression levels in many cases correlates with advanced stages of malignancy and poor survival (Gold L I (1999) Crit Rev Oncog 10:303–360). Finally, there are human cell lines representing both the androgen-dependent stage of prostate cancer (LNCap) as well as the androgen-independent, hormone refractory stage of the disease PC3 and DU-145) that have proved useful in studying gene expression patterns associated with the progression of prostate cancer, and the effects of cell treatments on these expressed genes (Chung T D (1999) Prostate 15:199–207).

The present invention provides for a composition comprising a plurality of cDNAs for use in detecting changes in expression of genes encoding proteins that are associated with prostate cancer. Such a composition can be employed for the diagnosis, prognosis or treatment of prostate cancer and related disorders correlated with differential gene expression. The present invention satisfies a need in the art in that it provides a set of differentially expressed genes which may be used entirely or in part to diagnose, to stage, to treat, or to monitor the progression or treatment of a subject with prostate cancer.

SUMMARY

The present invention provides a composition comprising a plurality of cDNAs and their complements which are differentially expressed in prostate adenocarcinomas and which are selected from SEQ ID NOs:1–1–3, 5, 6, 8, 10–15, 17–19, 21, 23–28, 30, 32, 34–36, 38, 40, 42–45, 47–50, 52, 53, 55, 56, 58–65, 67, 68, 70–73, 75, 76, 78–86, 88–90, 92–97, 99–101 as presented in the Sequence Listing. In one embodiment, each cDNA is differentially regulated in metastatic versus non-metastatic tissue samples, SEQ ID NOs:1–3, 5, 6, 8, 10–15, 17–19, 21, 23–28, 30, 32, 34–36, 38, 40, 42–45, 47–50, 52, 53, 55, 56, 58–65, 67, 68, 70–73, 75; in another embodiment, each cDNA is differentially regulated at all stages of the disease, SEQ ID NOs:76, 78–86, 88–90, 92–97, 99–101. In one aspect, the composition is immobilized on a substrate. In another aspect, the composition is used to diagnose the presence and stage of prostate cancer in a subject. The invention also provides proteins encoded by the cDNAs and which are selected from SEQ ID NOs:4, 7, 9, 16, 20, 22, 29, 31, 33, 37, 39, 41, 46, 51, 54, 57, 66, 69, 74, 77, 87, 91, 98 as presented in the Sequence Listing.

The invention also provides a high throughput method to detect differential expression of one or more of the cDNAs of the composition. The method comprises hybridizing the substrate comprising the composition with the nucleic acids of a sample, thereby forming one or more hybridization complexes, detecting the hybridization complexes, and comparing the hybridization complexes with those of a standard, wherein differences in the size and signal intensity of each hybridization complex indicates differential expression of nucleic acids in the sample. In one aspect, the sample is from a subject with prostate cancer and differential expression determines an early, mid, and late stage of the disorder.

The invention further provides a high throughput method of screening a library or a plurality of molecules or compounds to identify a ligand. The method comprises combining the substrate comprising the composition with a library or a plurality of molecules or compounds under conditions to allow specific binding and detecting specific binding, thereby identifying a ligand. The library or a plurality of molecules or compounds are selected from DNA molecules, RNA molecules, peptide nucleic acid molecules, mimetics, peptides, transcription factors, repressors, and other regulatory proteins.

The invention still further provides an isolated cDNA encoding the protein comprising the amino acid sequence of SEQ ID NO:37. The invention also provides an isolated cDNA comprising SEQ ID NO:36 as presented in the Sequence Listing. The invention also provides a vector comprising the cDNA, a host cell comprising the vector, and a method for producing a protein comprising culturing the host cell under conditions for the expression of a protein and recovering the protein from the host cell culture. The invention additionally provides a method for purifying a ligand, the method comprising combining a cDNA of the invention with a sample under conditions which allow specific binding, recovering the bound cDNA, and separating the cDNA from the ligand, thereby obtaining purified ligand.

The present invention provides a purified protein encoded and produced by a cDNA of the invention. The invention also provides a high-throughput method for using a protein to screen a library or a plurality of molecules or compounds to identify a ligand. The method comprises combining the protein or a portion thereof with the library or a plurality of molecules or compounds under conditions to allow specific binding and detecting specific binding, thereby identifying a ligand which specifically binds the protein. A library or a plurality of molecules or compounds are selected from DNA molecules, RNA molecules, peptide nucleic acid molecules, mimetics, peptides, proteins, agonists, antagonists, antibodies or their fragments, immunoglobulins, inhibitors, drug compounds, and pharmaceutical agents. The invention further provides for using a protein to purify a ligand. The method comprises combining the protein or a portion thereof with a sample under conditions to allow specific binding, recovering the bound protein, and separating the protein from the ligand, thereby obtaining purified ligand. The invention still further provides a pharmaceutical composition comprising the protein. The invention yet still further provides a method for using the protein to produce an antibody. The method comprises immunizing an animal with the protein or an antigenically-effective epitope under conditions to elicit an antibody response, isolating animal antibodies, and screening the isolated antibodies with the protein to identify an antibody which specifically binds the protein. The invention yet still further provides a method for using the protein to purify antibodies which bind specifically to the protein.

DESCRIPTION OF THE SEQUENCE LISTING AND TABLES

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

The Sequence Listing is a compilation of cDNAs obtained by sequencing and extension of clone inserts. Each sequence is identified by a sequence identification number (SEQ ID NO) and by the template number (TEMPLATE ID) from which it was obtained.

Table 1 shows the differential expression of cDNAs of the present invention in metastatic versus non-metastatic prostate adenocarcinoma. Column 1 shows the Clone ID of each sequence represented on a microarray. Columns 2–6 show differential expression in adenocarcinomas derived from prostate tissue relative to primary prostate epithelium. Differential expression values are presented as log 2 (normal tissue/adenocarcinoma). Negative values represent an increase in expression. Column 7 shows the t-test statistic used to evaluate markers specific to metastatic versus non-metastatic prostate adenocarcinoma.

Table 2 shows the differential expression of cDNAs of the present invention in prostate adenocarcinoma versus normal prostate. Column 1 shows the Clone ID of each sequence represented on a microarray. Columns 2–6 show differential expression in adenocarcinomas derived from prostate tissue relative to primary prostate epithelium. Differential expression values are presented as log 2 (normal tissue/adenocarcinoma). Negative values represent an increase in expression.

Table 3 shows the region within a gene template of each cDNA encompassed by a clone identified in Tables 1 and 2. Columns 1 and 2 show the SEQ ID NO: and Template ID, respectively. Column 3 shows the Clone ID and columns 4 and 5 show the first residue (Start) and last residue (Stop) encompassed by the clone on the template.

Table 4 lists the functional annotation of the cDNAs of the present invention. Columns 1 and 2 show the SEQ ID NO and Template ID, respectively. Columns 3, 4, and 5 show the GenBank hit (GI Number), probability score (E-value), and functional annotation, respectivly, as determined by BLAST analysis (version 1.4 using default parameters; Altschul (1993) J Mol Evol 36: 290–300; Altschul et al. (1990) J Mol Biol 215:403–410) of the cDNA against GenBank (release 117; National Center for Biotechnology Information (NCBI), Bethesda Md.).

Table 5 shows Pfam annotations of the cDNAs of the present invention. Columns 1 and 2 show the SEQ ID NO and Template ID, respectively. Columns 3, 4, and 5 show the first residue (Start), last residue (Stop), and reading frame, respectively, for the segment of the cDNA identified by Pfam analysis. Columns 6, 7, and 8 show the PFAM Hit, PFAM Annotation, and E-value, respectively, corresponding to the polypeptide domain of the protein or encoded by the cDNA segment.

Table 6 shows signal peptide and transmembrane regions predicted within the cDNAs of the present invention. Columns 1 and 2 show the SEQ ID NO and Template ID, respectively. Columns 3, 4, and 5 show the first residue (Start), last residue (Stop), and reading frame, respectively, for a segment of the cDNA, and column 6 identifies the polypeptide encoded by the segment as either a signal peptide (SP) or transmembrane (TM) domain.

DESCRIPTION OF THE INVENTION

Definitions

"Array" refers to an ordered arrangement of at least two cDNAs on a substrate. At least one of the cDNAs represents a control or standard sequence, and the other, a cDNA of diagnostic interest. The arrangement of from about two to about 40,000 cDNAs on the substrate assures that the size and signal intensity of each labeled hybridization complex formed between a cDNA and a sample nucleic acid is individually distinguishable.

The "complement" of a nucleic acid molecule of the Sequence Listing refers to a cDNA which is completely complementary over the full length of the sequence and which will hybridize to the nucleic acid molecule under conditions of high stringency.

A "composition" comprises at least two sequences selected from the Sequence Listing. "cDNA" refers to a chain of nucleotides, an isolated polynucleotide, nucleic acid molecule, or any fragment or complement thereof. It may have originated recombinantly or synthetically, be double-stranded or single-stranded, coding and/or noncoding, an exon with or without an intron from a genomic DNA molecule, and purified or combined with carbohydrate, lipids, protein or inorganic elements or substances. Preferably, the cDNA is from about 4000 to about 5000 nucleotides.

The phrase "cDNA encoding a protein" refers to a nucleic acid sequence that closely aligns with sequences which encode conserved regions, motifs or domains that were identified by employing analyses well known in the art. These analyses include BLAST (Basic Local Alignment Search Tool; Altschul (1993) J Mol Evol 36: 290–300; Altschul et al. (1990) J Mol Biol 215:403–410) which provides identity within the conserved region. Brenner et al. (1998; Proc Natl Acad Sci 95:6073–6078) who analyzed BLAST for its ability to identify structural homologs by sequence identity found 30% identity is a reliable threshold for sequence alignments of at least 150 residues and 40% is a reasonable threshold for alignments of at least 70 residues (Brenner et al., page 6076, column 2).

"Derivative" refers to a cDNA or a protein that has been subjected to a chemical modification. Derivatization of a cDNA can involve substitution of a nontraditional base such as queosine or of an analog such as hypoxanthine. These substitutions are well known in the art. Derivatization of a protein involves the replacement of a hydrogen by an acetyl, acyl, alkyl, amino, formyl, or morpholino group. Derivative molecules retain the biological activities of the naturally occurring molecules but may confer advantages such as longer lifespan or enhanced activity.

"Differential expression" refers to an increased, upregulated or present, or decreased, downregulated or absent, gene expression as detected by the absence, presence, or at least two-fold changes in the amount of transcribed messenger RNA or translated protein in a sample.

"Disorder" refers to conditions, diseases or syndromes associated with prostate cancer.

"Fragment" refers to a chain of consecutive nucleotides from about 200 to about 700 base pairs in length. Fragments may be used in PCR or hybridization technologies to identify related nucleic acid molecules and in binding assays to screen for a ligand. Nucleic acids and their ligands identified in this manner are useful as therapeutics to regulate replication, transcription or translation.

A "hybridization complex" is formed between a cDNA and a nucleic acid of a sample when the purines of one molecule hydrogen bond with the pyrimidines of the complementary molecule, e.g., 5'-A-G-T-C-3' base pairs with 3'-T-C-A-G-5'. The degree of complementarity and the use of nucleotide analogs affect the efficiency and stringency of hybridization reactions.

"Ligand" refers to any agent, molecule, or compound which will bind specifically to a complementary site on a cDNA molecule or polynucleotide, or to an epitope or a protein. Such ligands stabilize or modulate the activity of polynucleotides or proteins and may be composed of inorganic or organic substances including nucleic acids, proteins, carbohydrates, fats, and lipids.

"Oligonucleotide" refers a single stranded molecule from about 18 to about 60 nucleotides in length which may be used in hybridization or amplification technologies or in regulation of replication, transcription or translation. Substantially equivalent terms are amplimer, primer, and oligomer.

"Portion" refers to any part of a protein used for any purpose; but especially, to an epitope for the screening of ligands or for the production of antibodies.

"Post-translational modification" of a protein can involve lipidation, glycosylation, phosphorylation, acetylation, racemization, proteolytic cleavage, and the like. These processes may occur synthetically or biochemically. Biochemical modifications will vary by cellular location, cell type, pH, enzymatic milieu, and the like.

"Probe" refers to a cDNA that hybridizes to at least one nucleic acid molecule in a sample. Where targets are single stranded, probes are complementary single strands. Probes can be labeled with reporter molecules for use in hybridization reactions including Southern, northern, in situ, dot blot, array, and like technologies or in screening assays.

"Protein" refers to a polypeptide or any portion thereof. A "portion" of a protein retains at least one biological or antigenic characteristic of a native protein. An "oligopeptide" is an amino acid sequence from about five residues to about 15 residues that is used as part of a fusion protein to produce an antibody.

"Purified" refers to any molecule or compound that is separated from its natural environment and is from about 60% free to about 90% free from other components with which it is naturally associated.

"Sample" is used in its broadest sense as containing nucleic acids, proteins, antibodies, and the like. A sample may comprise a bodily fluid; the soluble fraction of a cell preparation, or an aliquot of media in which cells were grown; a chromosome, an organelle, or membrane isolated or extracted from a cell; genomic DNA, RNA, or cDNA in solution or bound to a substrate; a cell; a tissue; a tissue print; a fingerprint, buccal cells, skin, or hair; and the like.

"Specific binding" refers to a special and precise interaction between two molecules which is dependent upon their structure, particularly their molecular side groups. For example, the intercalation of a regulatory protein into the major groove of a DNA molecule, the hydrogen bonding along the backbone between two single stranded nucleic acids, or the binding between an epitope of a protein and an agonist, antagonist, or antibody.

"Similarity" as applied to sequences, refers to the quantification (usually percentage) of nucleotide or residue matches between at least two sequences aligned using a standardized algorithm such as Smith-Waterman alignment (Smith and Waterman (1981) J Mol Biol 147:195–197) or BLAST2 (Altschul et al. (1997) Nucleic Acids Res 25:3389–3402). BLAST2 may be used in a standardized and reproducible way to insert gaps in one of the sequences in order to optimize alignment and to achieve a more meaningful comparison between them.

"Substrate" refers to any rigid or semi-rigid support to which cDNAs or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

"Variant" refers to molecules that are recognized variations of a cDNA or a protein encoded by the cDNA. Splice variants may be determined by BLAST score, wherein the score is at least 100, and most preferably at least 400. Allelic variants have a high percent identity to the cDNAs and may differ by about three bases per hundred bases. "Single nucleotide polymorphism" (SNP) refers to a change in a single base as a result of a substitution, insertion or deletion. The change may be conservative (purine for purine) or non-conservative (purine to pyrimidine) and may or may not result in a change in an encoded amino acid.

The Invention

The present invention provides for a composition comprising a plurality of cDNAs or their complements, SEQ ID NOs:1–3, 5, 6, 8, 10–15, 17–19, 21, 23–28, 30, 32, 34–36, 38, 40, 42–45, 47–50, 52, 53, 55, 56, 58–65, 67, 68, 70–73, 75, 76, 78–86, 88–90, 92–97, 99–101, which may be used on a substrate to diagnose, to stage, to treat or to monitor the progression or treatment of prostate cancer. These cDNAs represent known and novel genes differentially expressed in cells from non-metastatic and metastatic prostate tumors. The composition may be used in its entirety or in part, as subsets of cDNAs differentially regulated between non-metastatic and metastatic prostate cancer, SEQ ID NOs:1–3, 5, 6, 8, 10–15, 17–19, 21, 23–28, 30, 32, 34–36, 38, 40, 42–45, 47–50, 52, 53, 55, 56, 58–65, 67, 68, 70–73, 75, or of cDNAs differentially regulated at all stages of prostate cancer, SEQ ID NOs:76, 78–86, 88–90, 92–97, 99–101. SEQ ID NOs:24, 36, 47, 60, 82, 88, 89, 92, 93, and 95 represent novel cDNAs associated with prostate cancer. Since the novel cDNAs were identified solely by their differential expression, it is not essential to know a priori the name, structure, or function of the gene or it's encoded protein. The usefulness of the novel cDNAs exist in their immediate value as diagnostics for prostate cancer.

Table 1 shows the differential expression of cDNAs of the present invention in metastatic versus non-metastatic prostate adenocarcinoma. Column 1 shows the Clone ID of each sequence represented on a microarray. Columns 2–6 show the differential expression in adenocarcinomas derived from prostate tissue relative to primary prostate epithelium. Differential expression values are presented as log 2 of the absolute expression in normal prostate tissue÷the absolute expression in prostate adenocarcinoma. Negative values represent an increase in expression. Column 7 shows the t-test statistic used to evaluate markers specific to metastatic versus non-metastatic prostate adenocarcinoma. All of the cDNAs in Table 1 show significant differential regulation in metastatic cancer relative to non-metastatic cancer. Further, expression profiles between the metastatic cancer lines show a high degree of correlation (>0.48), as do the expression profiles between the non-metastatic lines (0.64). However, the expression profiles between the metastatic and non-metastatic lines show significantly less correlation (<0.3).

Table 2 shows the differential expression of cDNAs of the present invention in prostate adenocarcinoma versus normal prostate. Column 1 shows the Clone ID of each sequence represented on a microarray. Columns 2–6 show differential expression in adenocarcinomas derived from prostate tissue relative to primary prostate epithelium. Differential expression values are presented as log 2 (normal tissue÷adenocarcinoma). Negative values represent an increase in expression. The expression profile for the cDNAs identified in Table 2 show high correlation between all tumor lines (>0.5).

SEQ ID NO:36 is a novel sequence differentially regulated between metastatic and non-metastatic prostate tumors. SEQ ID NO:36 encodes SEQ ID NO:37 which is 193 amino acids in length.

The cDNAs of the invention define a differential expression pattern against which to compare the expression pattern of biopsied and/or in vitro treated tissues. Experimentally, differential expression of the cDNAs can be evaluated by methods including, but not limited to, differential display by spatial immobilization or by gel electrophoresis, genome mismatch scanning, representational discriminate analysis, clustering, transcript imaging and array technologies. These methods may be used alone or in combination.

The composition may be arranged on a substrate and hybridized with tumor tissues from subjects to identify those sequences which are differentially expressed in both prostate cancer and tumors derived from other tissues. This allows identification of those sequences of highest diagnostic and potential therapeutic value. In one embodiment, an additional set of cDNAs, such as cDNAs encoding signaling molecules, are arranged on the substrate with the composition. Such combinations may be useful in the elucidation of pathways which are affected in a particular cancer or to identify new, coexpressed, candidate, therapeutic molecules.

In another embodiment, the composition can be used for large scale genetic or gene expression analysis of a large number of novel, nucleic acid molecules. These samples are prepared by methods well known in the art and are from mammalian cells or tissues which are in a certain stage of development; have been treated with a known molecule or compound, such as a cytokine, growth factor, a drug, and the like; or have been extracted or biopsied from a mammal with a known or unknown condition, disorder, or disease before or after treatment. The sample nucleic acid molecules are hybridized to the composition for the purpose of defining a novel gene profile associated with that developmental stage, treatment, or disorder.

cDNAs and Their Uses cDNAs can be prepared by a variety of synthetic or enzymatic methods well known in the art. cDNAs can be synthesized, in whole or in part, using chemical methods well known in the art (Caruthers et al. (1980) Nucleic Acids Symp. Ser. (7):215–233). Alternatively, cDNAs can be produced enzymatically or recombinantly, by in vitro or in vivo transcription.

Nucleotide analogs can be incorporated into cDNAs by methods well known in the art. The only requirement is that the incorporated analog must base pair with native purines or pyrimidines. For example, 2,6-diaminopurine can substitute for adenine and form stronger bonds with thymidine than those between adenine and thymidine. A weaker pair is formed when hypoxanthine is substituted for guanine and base pairs with cytosine. Additionally, cDNAs can include nucleotides that have been derivatized chemically or enzymatically.

cDNAs can be synthesized on a substrate. Synthesis on the surface of a substrate may be accomplished using a chemical coupling procedure and a piezoelectric printing apparatus as described by Baldeschweiler et al. (PCT publication WO95/251116). Alternatively, the cDNAs can be synthesized on a substrate surface using a self-addressable electronic device that controls when reagents are added as described by Heller et al. (U.S. Pat. No. 5,605,662). cDNAs can be synthesized directly on a substrate by sequentially dispensing reagents for their synthesis on the substrate surface or by dispensing preformed DNA fragments to the substrate surface. Typical dispensers include a micropipette delivering solution to the substrate with a robotic system to control the position of the micropipette with respect to the substrate. There can be a multiplicity of dispensers so that reagents can be delivered to the reaction regions efficiently.

cDNAs can be immobilized on a substrate by covalent means such as by chemical bonding procedures or UV irradiation. In one method, a cDNA is bound to a glass surface which has been modified to contain epoxide or aldehyde groups. In another method, a cDNA is placed on a polylysine coated surface and UV cross-linked to it as described by Shalon et al. (WO95/35505). In yet another method, a cDNA is actively transported from a solution to a given position on a substrate by electrical means (Heller, supra). cDNAs do not have to be directly bound to the substrate, but rather can be bound to the substrate through a linker group. The linker groups are typically about 6 to 50 atoms long to provide exposure of the attached cDNA. Preferred linker groups include ethylene glycol oligomers, diamines, diacids and the like. Reactive groups on the substrate surface react with a terminal group of the linker to bind the linker to the substrate. The other terminus of the linker is then bound to the cDNA. Alternatively, polynucleotides, plasmids or cells can be arranged on a filter. In the latter case, cells are lysed, proteins and cellular components degraded, and the DNA is coupled to the filter by UV cross-linking.

The cDNAs may be used for a variety of purposes. For example, the composition of the invention may be used on an array. The array, in turn, can be used in high-throughput methods for detecting a related polynucleotide in a sample, screening a plurality of molecules or compounds to identify a ligand, diagnosing prostate cancer, or inhibiting or inactivating a therapeutically relevant gene related to the cDNA.

When the cDNAs of the invention are employed on a microarray, the cDNAs are arranged in an ordered fashion so that each cDNA is present at a specified location. Because the cDNAs are at specified locations on the substrate, the hybridization patterns and intensities, which together create a unique expression profile, can be interpreted in terms of expression levels of particular genes and can be correlated with a particular metabolic process, condition, disorder, disease, stage of disease, or treatment.

Hybridization

The cDNAs or fragments or complements thereof may be used in various hybridization technologies. The cDNAs may be labeled using a variety of reporter molecules by either PCR, recombinant, or enzymatic techniques. For example, a commercially available vector containing the cDNA is transcribed in the presence of an appropriate polymerase, such as T7 or SP6 polymerase, and at least one labeled nucleotide. Commercial kits are available for labeling and cleanup of such cDNAs. Radioactive (Amersham Pharmacia Biotech (APB), Piscataway N.J.), fluorescent (Operon Technologies, Alameda Calif.), and chemiluminescent labeling (Promega, Madison Wis.) are well known in the art.

A cDNA may represent the complete coding region of an mRNA or be designed or derived from unique regions of the mRNA or genomic molecule, an intron, a 3' untranslated region, or from a conserved motif. The cDNA is at least 18 contiguous nucleotides in length and is usually single stranded. Such a cDNA may be used under hybridization conditions that allow binding only to an identical sequence, a naturally occurring molecule encoding the same protein, or an allelic variant. Discovery of related human and mammalian sequences may also be accomplished using a pool of degenerate cDNAs and appropriate hybridization conditions. Generally, a cDNA for use in Southern or northern hybridizations may be from about 400 to about 6000 nucleotides long. Such cDNAs have high binding specificity in solution-based or substrate-based hybridizations. An oligonucleotide, a fragment of the cDNA, may be used to detect a polynucleotide in a sample using PCR.

The stringency of hybridization is determined by G+C content of the cDNA, salt concentration, and temperature. In particular, stringency is increased by reducing the concentration of salt or raising the hybridization temperature. In solutions used for some membrane based hybridizations, addition of an organic solvent such as formamide allows the reaction to occur at a lower temperature. Hybridization may be performed with buffers, such as 5×saline sodium citrate (SSC) with 1% sodium dodecyl sulfate (SDS) at 60° C., that permit the formation of a hybridization complex between nucleic acid sequences that contain some mismatches. Subsequent washes are performed with buffers such as 0.2×SSC with 0.1% SDS at either 45° C. (medium stringency) or 65°–68° C. (high stringency). At high stringency, hybridization complexes will remain stable only where the nucleic acid molecules are completely complementary. In some membrane-based hybridizations, preferably 35% or most preferably 50%, formamide may be added to the hybridization solution to reduce the temperature at which hybridization is performed. Background signals may be reduced by the use of detergents such as Sarkosyl or Triton X-100 (Sigma Aldrich, St. Louis Mo.) and a blocking agent such as denatured salmon sperm DNA. Selection of components and conditions for hybridization are well known to those skilled in the art and are reviewed in Ausubel et al. (1997, *Short Protocols in Molecular Biology,* John Wiley & Sons, New York N.Y., Units 2.8–2.11, 3.18–3.19 and 4–64.9).

Dot-blot, slot-blot, low density and high density arrays are prepared and analyzed using methods known in the art. cDNAs from about 18 consecutive nucleotides to about 5000 consecutive nucleotides in length are contemplated by the invention and used in array technologies. The preferred number of cDNAs on an array is at least about 100,000, a more preferred number is at least about 40,000, an even more preferred number is at least about 10,000, and a most preferred number is at least about 600 to about 800. The array may be used to monitor the expression level of large numbers of genes simultaneously and to identify genetic variants, mutations, and SNPs. Such information may be used to determine gene function; to understand the genetic basis of a disorder; to diagnose a disorder; and to develop and monitor the activities of therapeutic agents being used to control or cure a disorder. (See, e.g., U.S. Pat. No. 5,474,796; WO95/11995; WO95/35505; U.S. Pat. No. 5,605,662; and U.S. Pat. No. 5,958,342.)

Screening and Purification Assays

A cDNA may be used to screen a library or a plurality of molecules or compounds for a ligand which specifically binds the cDNA. Ligands may be DNA molecules, RNA molecules, peptide nucleic acid molecules, peptides, proteins such as transcription factors, promoters, enhancers, repressors, and other proteins that regulate replication, transcription, or translation of the polynucleotide in the biological system. The assay involves combining the cDNA or a fragment thereof with the molecules or compounds under conditions that allow specific binding and detecting the bound cDNA to identify at least one ligand that specifically binds the cDNA.

In one embodiment, the cDNA may be incubated with a library of isolated and purified molecules or compounds and binding activity determined by methods such as a gel-retardation assay (U.S. Pat. No. 6,010,849) or a reticulocyte lysate transcriptional assay. In another embodiment, the cDNA may be incubated with nuclear extracts from biopsied and/or cultured cells and tissues. Specific binding between the cDNA and a molecule or compound in the nuclear extract is initially determined by gel shift assay. Protein binding may be confirmed by raising antibodies against the protein and adding the antibodies to the gel-retardation assay where specific binding will cause a supershift in the assay.

In another embodiment, the cDNA may be used to purify a molecule or compound using affinity chromatography methods well known in the art. In one embodiment, the cDNA is chemically reacted with cyanogen bromide groups on a polymeric resin or gel. Then a sample is passed over and reacts with or binds to the cDNA. The molecule or compound which is bound to the cDNA may be released from the cDNA by increasing the salt concentration of the flow-through medium and collected.

The cDNA may be used to purify a ligand from a sample. A method for using a cDNA to purify a ligand would involve combining the cDNA or a fragment thereof with a sample under conditions to allow specific binding, recovering the bound cDNA, and using an appropriate agent to separate the cDNA from the purified ligand.

Protein Production and Uses

The full length cDNAs or fragment thereof may be used to produce purified proteins using recombinant DNA technologies described herein and taught in Ausubel et al. (supra; Units 16.1–16.62). One of the advantages of producing proteins by these procedures is the ability to obtain highly-enriched sources of the proteins thereby simplifying purification procedures.

The proteins may contain amino acid substitutions, deletions or insertions made on the basis of similarity in polarity, charge, solubility, hydrophobicity, hydrophilicity, and/or the amphipathic nature of the residues involved. Such substitutions may be conservative in nature when the substituted residue has structural or chemical properties similar to the original residue (e.g., replacement of leucine with isoleucine or valine) or they may be nonconservative when the replacement residue is radically different (e.g., a glycine replaced by a tryptophan). Computer programs included in LASERGENE software (DNASTAR, Madison Wis.), MACVECTOR software (Genetics Computer Group, Madison Wis.) and RasMol software (www.umass.edu/microbio/rasmol) may be used to help determine which and how many amino acid residues in a particular portion of the protein may be substituted, inserted, or deleted without abolishing biological or immunological activity.

Expression of Encoded Proteins

Expression of a particular cDNA may be accomplished by cloning the cDNA into a vector and transforming this vector into a host cell, The cloning vector used for the construction of cDNA libraries in the LIFESEQ databases may also be used for expression. Such vectors usually contain a promoter and a polylinker useful for cloning, priming, and transcription. An exemplary vector may also contain the promoter for β-galactosidase, an amino-terminal methionine and the subsequent seven amino acid residues of β-galactosidase. The vector may be transformed into competent *E. coli* cells. Induction of the isolated bacterial strain with isopropylthiogalactoside (IPTG) using standard methods will produce a fusion protein that contains an N terminal methionine, the first seven residues of β-galactosidase, about 15 residues of linker, and the protein encoded by the cDNA.

The cDNA may be shuttled into other vectors known to be useful for expression of protein in specific hosts. Oligonucleotides containing cloning sites and fragments of DNA sufficient to hybridize to stretches at both ends of the cDNA may be chemically synthesized by standard methods. These primers may then be used to amplify the desired fragments by PCR. The fragments may be digested with appropriate restriction enzymes under standard conditions and isolated using gel electrophoresis. Alternatively, similar fragments are produced by digestion of the cDNA with appropriate restriction enzymes and filled in with chemically synthesized oligonucleotides. Fragments of the coding sequence from more than one gene may be ligated together and expressed.

Signal sequences that dictate secretion of soluble proteins are particularly desirable as component parts of a recombinant sequence. For example, a chimeric protein may be expressed that includes one or more additional purification-facilitating domains. Such domains include, but are not limited to, metal-chelating domains that allow purification on immobilized metals, protein A domains that allow purification on immobilized immunoglobulin, and the domain utilized in the FLAGS extension/affinity purification system (Immunex, Seattle Wash.). The inclusion of a cleavable-linker sequence such as ENTEROKINASEMAX (Invitrogen, San Diego Calif.) between the protein and the purification domain may also be used to recover the protein.

Suitable host cells may include, but are not limited to, mammalian cells such as Chinese Hamster Ovary (CHO) and human 293 cells, insect cells such as Sf9 cells, plant cells such as *Nicotiana tabacum,* yeast cells such as *Saccharomyces cerevisiae,* and bacteria such as *E. coli.* For each of these cell systems, a useful vector may also include an origin of replication and one or two selectable markers to allow selection in bacteria as well as in a transformed eukaryotic host. Vectors for use in eukaryotic host cells may require the addition of 3' poly(A) tail if the cDNA lacks poly(A).

Additionally, the vector may contain promoters or enhancers that increase gene expression. Many promoters are known and used in the art. Most promoters are host specific and exemplary promoters includes SV40 promoters for CHO cells; T7 promoters for bacterial hosts; viral promoters and enhancers for plant cells; and PGH promoters for yeast. Adenoviral vectors with the rous sarcoma virus enhancer or retroviral vectors with long terminal repeat promoters may be used to drive protein expression in mammalian cell lines. Once homogeneous cultures of recombinant cells are obtained, large quantities of secreted soluble protein may be recovered from the conditioned medium and analyzed using chromatographic methods well known in the art. An alternative method for the production of large amounts of secreted protein involves the transformation of mammalian embryos and the recovery of the recombinant protein from milk produced by transgenic cows, goats, sheep, and the like.

In addition to recombinant production, proteins or portions thereof may be produced manually, using solid-phase techniques (Stewart et al. (1969) *Solid-Phase Peptide Synthesis,* W H Freeman, San Francisco Calif.; Merrifield (1963) J Am Chem Soc 5:2149–2154), or using machines such as the ABI 431A peptide synthesizer (Applied Biosystems, Foster City Calif.). Proteins produced by any of the above methods may be used as pharmaceutical compositions to treat disorders associated with null or inadequate expression of the genomic sequence.

Screening and Purification Assays

A protein or a portion thereof encoded by the cDNA may be used to screen a library or a plurality of molecules or compounds for a ligand with specific binding affinity or to purify a molecule or compound from a sample. The protein or portion thereof employed in such screening may be free in solution, affixed to an abiotic or biotic substrate, or located intracellularly. For example, viable or fixed prokaryotic host cells that are stably transformed with recombinant nucleic acids that have expressed and positioned a protein on their cell surface can be used in screening assays. The cells are screened against a library or a plurality of ligands and the specificity of binding or formation of complexes between the expressed protein and the ligand may be measured. The ligands may be DNA, RNA, or PNA molecules, agonists, antagonists, antibodies, immunoglobulins, inhibitors, peptides, pharmaceutical agents, proteins, drugs, or any other test molecule or compound that specifically binds the protein. An exemplary assay involves combining the mammalian protein or a portion thereof with the molecules or compounds under conditions that allow specific binding and detecting the bound protein to identify at least one ligand that specifically binds the protein.

This invention also contemplates the use of competitive drug screening assays in which neutralizing antibodies capable of binding the protein specifically compete with a test compound capable of binding to the protein or oligopeptide or fragment thereof. One method for high throughput screening using very small assay volumes and very small amounts of test compound is described in U.S. Pat. No. 5,876,946. Molecules or compounds identified by screening may be used in a model system to evaluate their toxicity, diagnostic, or therapeutic potential.

The protein may be used to purify a ligand from a sample. A method for using a protein to purify a ligand would involve combining the protein or a portion thereof with a sample under conditions to allow specific binding, recovering the bound protein, and using an appropriate chaotropic agent to separate the protein from the purified ligand.

Production of Antibodies

A protein encoded by a cDNA of the invention may be used to produce specific antibodies. Antibodies may be produced using an oligopeptide or a portion of the protein with inherent immunological activity. Methods for producing antibodies include: 1) injecting an animal, usually goats, rabbits, or mice, with the protein, or an antigenically-effective portion or an oligopeptide thereof, to induce an immune response; 2) engineering hybridomas to produce monoclonal antibodies; 3) inducing in vivo production in the lymphocyte population; or 4) screening libraries of recombinant immunoglobulins. Recombinant immunoglobulins may be produced as taught in U.S. Pat. No. 4,816,567.

Antibodies produced using the proteins of the invention are useful for the diagnosis of prepathologic disorders as well as the diagnosis of chronic or acute diseases characterized by abnormalities in the expression, amount, or distribution of the protein. A variety of protocols for competitive binding or immunoradiometric assays using either polyclonal or monoclonal antibodies specific for proteins are well known in the art. Immunoassays typically involve the formation of complexes between a protein and its specific binding molecule or compound and the measurement of complex formation. Immunoassays may employ a two-site, monoclonal-based assay that utilizes monoclonal antibodies reactive to two noninterfering epitopes on a specific protein or a competitive binding assay (Pound (1998) *Immunochemical Protocols,* Humana Press, Totowa N.J.).

Immunoassay procedures may be used to quantify expression of the protein in cell cultures, in subjects with a particular disorder or in model animal systems under various conditions. Increased or decreased production of proteins as monitored by immunoassay may contribute to knowledge of the cellular activities associated with developmental pathways, engineered conditions or diseases, or treatment efficacy. The quantity of a given protein in a given tissue may be determined by performing immunoassays on freeze-thawed detergent extracts of biological samples and comparing the slope of the binding curves to binding curves generated by purified protein.

Labeling of Molecules for Assay

A wide variety of reporter molecules and conjugation techniques are known by those skilled in the art and may be used in various cDNA, polynucleotide, protein, peptide or antibody assays. Synthesis of labeled molecules may be achieved using commercial kits for incorporation of a labeled nucleotide such as $^{32}$P-dCTP, Cy3-dCTP or Cy5-dCTP or amino acid such as $^{35}$S-methionine. Polynucleotides, cDNAs, proteins, or antibodies may be directly labeled with a reporter molecule by chemical conjugation to amines, thiols and other groups present in the molecules using reagents such as BIODIPY or FITC (Molecular Probes, Eugene Oreg.).

The proteins and antibodies may be labeled for purposes of assay by joining them, either covalently or noncovalently, with a reporter molecule that provides for a detectable signal. A wide variety of labels and conjugation techniques are known and have been reported in the scientific and patent literature including, but not limited to U.S. Pat. Nos. 3,817,837; 3,850,752; 3,939,350; 3,996,345; 4,277,437; 4,275,149; and 4,366,241.

Diagnostics

The cDNAs, or fragments thereof, may be used to detect and quantify differential gene expression; absence, presence, or excess expression of mRNAs; or to monitor mRNA levels during therapeutic intervention in subjects with prostate-related disorders including prostate cancer. These cDNAs can also be utilized as markers of treatment efficacy against prostate cancer over a period ranging from several days to months. The diagnostic assay may use hybridization or amplification technology to compare gene expression in a biological sample from a patient to standard samples in order to detect altered gene expression. Qualitative or quantitative methods for this comparison are well known in the art.

For example, the cDNA may be labeled by standard methods and added to a biological sample from a patient under conditions for hybridization complex formation. After an incubation period, the sample is washed and the amount of label (or signal) associated with hybridization complexes is quantified and compared with a standard value. If the amount of label in the patient sample is significantly altered in comparison to the standard value, then the presence of the associated condition, disease or disorder is indicated.

In order to provide a basis for the diagnosis of a condition, disease or disorder associated with gene expression, a normal or standard expression profile is established. This may be accomplished by combining a biological sample taken from normal subjects, either animal or human, with a probe under conditions for hybridization or amplification. Standard hybridization may be quantified by comparing the values obtained using normal subjects with values from an experiment in which a known amount of a substantially purified target sequence is used. Standard values obtained in this manner may be compared with values obtained from samples from patients who are symptomatic for a particular condition, disease, or disorder. Deviation from standard values toward those associated with a particular condition is used to diagnose that condition.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to months.

Gene Expression Profiles

A gene expression profile comprises a plurality of cDNAs and a plurality of detectable hybridization complexes, wherein each complex is formed by hybridization of one or more probes to one or more complementary sequences in a sample. The cDNA composition of the invention is used as elements on a microarray to analyze gene expression profiles. In one embodiment, the microarray is used to monitor the progression of prostate cancer. Researchers can assess and catalog the differences in gene expression between healthy and diseased tissues or cells. By analyzing changes in patterns of gene expression, prostate cancer can be diagnosed at earlier stages before the patient is symptomatic. The invention can be used to formulate a prognosis and to design a treatment regimen. The invention can also be used to monitor the efficacy of treatment. For treatments with known side effects, the microarray is employed to improve the treatment regimen. A dosage is established that causes a change in genetic expression patterns indicative of successful treatment. Expression patterns associated with the onset of undesirable side effects are avoided. This approach may be more sensitive and rapid than waiting for the patient to show inadequate improvement, or to manifest side effects, before altering the course of treatment.

In another embodiment, animal models which mimic a human disease can be used to characterize expression profiles associated with a particular condition, disorder or disease; or treatment of the condition, disorder or disease. Novel treatment regimens may be tested in these animal models using microarrays to establish and then follow expression profiles over time. In addition, microarrays may be used with cell cultures or tissues removed from animal models to rapidly screen large numbers of candidate drug molecules, looking for ones that produce an expression profile similar to those of known therapeutic drugs, with the expectation that molecules with the same expression profile will likely have similar therapeutic effects. Thus, the invention provides the means to rapidly determine the molecular mode of action of a drug.

Assays Using Antibodies

Antibodies directed against epitopes on a protein encoded by a cDNA of the invention may be used in assays to quantify the amount of protein found in a particular human cell. Such assays include methods utilizing the antibody and a label to detect expression level under normal or disease conditions. The antibodies may be used with or without modification, and labeled by joining them, either covalently or noncovalently, with a labeling moiety.

Protocols for detecting and measuring protein expression using either polyclonal or monoclonal antibodies are well known in the art. Examples include ELISA, RIA, and fluorescent activated cell sorting (FACS). Such immunoassays typically involve the formation of complexes between the protein and its specific antibody and the measurement of such complexes. These and other assays are described in Pound (supra). The method may employ a two-site, monoclonal-based immunoassay utilizing monoclonal antibodies reactive to two non-interfering epitopes, or a competitive binding assay. (See, e.g., Coligan et al. (1997) *Current Protocols in Immunology,* Wiley-Interscience, New York N.Y.; Pound, supra)

Therapeutics

The cDNAs and fragments thereof can be used in gene therapy. cDNAs can be delivered ex vivo to target cells, such as cells of bone marrow. Once stable integration and transcription and or translation are confirmed, the bone marrow may be reintroduced into the subject. Expression of the protein encoded by the cDNA may correct a cancer associated with mutation of a normal sequence, reduction or loss of an endogenous target protein, or overepression of an endogenous or mutant protein. Alternatively, cDNAs may be delivered in vivo using vectors such as retrovirus, adenovirus, adeno-associated virus, herpes simplex virus, and bacterial plasmids. Non-viral methods of gene delivery include cationic liposomes, polylysine conjugates, artificial viral envelopes, and direct injection of DNA (Anderson (1998) Nature 392:25–30; Dachs et al. (1997) Oncol Res 9:313–325; Chu et al. (1998) J Mol Med 76(34):184–192; Weiss et al. (1999) Cell Mol Life Sci 55(3):334–358; Agrawal (1996) *Antisense Therapeutics,* Humana Press, Totowa N.J.; and August et al. (1997) *Gene Therapy* (*Advances in Pharmacology, Vol.* 40), Academic Press, San Diego Calif.).

In addition, expression of a particular protein can be regulated through the specific binding of a fragment of a cDNA to a genomic sequence or an mRNA which encodes the protein or directs its transcription or translation. The cDNA can be modified or derivatized to any RNA-like or DNA-like material including peptide nucleic acids, branched nucleic acids, and the like. These sequences can be produced biologically by transforming an appropriate host cell with a vector containing the sequence of interest.

Molecules which regulate the activity of the cDNA or encoded protein are useful as therapeutics for prostate cancer. Such molecules include agonists which increase the expression or activity of the polynucleotide or encoded protein, respectively; or antagonists which decrease expression or activity of the polynucleotide or encoded protein, respectively. In one aspect, an antibody which specifically binds the protein may be used directly as an antagonist or indirectly as a delivery mechanism for bringing a pharmaceutical agent to cells or tissues which express the protein.

Additionally, any of the proteins, or their ligands, or complementary nucleic acid sequences may be administered as pharmaceutical compositions or in combination with other appropriate therapeutic agents. Selection of the appropriate agents for use in combination therapy may be made by one of ordinary skill in the art, according to conventional pharmaceutical principles. The combination of therapeutic agents may act synergistically to affect the treatment or prevention of the conditions and disorders associated with an immune response. Using this approach, one may be able to achieve therapeutic efficacy with lower dosages of each agent, thus reducing the potential for adverse side effects. Further, the therapeutic agents may be combined with pharmaceutically-acceptable carriers including excipients and auxiliaries which facilitate processing of the active compounds into preparations which can be used pharmaceutically. Further details on techniques for formulation and administration used by doctors and pharmacists may be found in the latest edition of *Remington's Pharmaceutical Sciences* (Maack Publishing, Easton Pa.).

Model Systems

Animal models may be used as bioassays where they exhibit a phenotypic response similar to that of humans and where exposure conditions are relevant to human exposures. Mammals are the most common models, and most infectious agent, cancer, drug, and toxicity studies are performed on rodents such as rats or mice because of low cost, availability, lifespan, reproductive potential, and abundant reference literature. Inbred and outbred rodent strains provide a convenient model for investigation of the physiological consequences of underexpression or overexpression of genes of interest and for the development of methods for diagnosis and treatment of diseases. A mammal inbred to overexpress a particular gene (for example, secreted in milk) may also serve as a convenient source of the protein expressed by that gene.

Transgenic Animal Models

Transgenic rodents that overexpress or underexpress a gene of interest may be inbred and used to model human diseases or to test therapeutic or toxic agents. (See, e.g., U.S. Pat. No. 5,175,383 and U.S. Pat. No. 5,767,337.) In some cases, the introduced gene may be activated at a specific time in a specific tissue type during fetal or postnatal development. Expression of the transgene is monitored by analysis of phenotype, of tissue-specific mRNA expression, or of serum and tissue protein levels in transgenic animals before, during, and after challenge with experimental drug therapies.

Embryonic Stem Cells

Embryonic (ES) stem cells isolated from rodent embryos retain the potential to form embryonic tissues. When ES cells such as the mouse 129/SvJ cell line are placed in a blastocyst from the C57BL/6 mouse strain, they resume normal development and contribute to tissues of the live-born animal. ES cells are preferred for use in the creation of experimental knockout and knockin animals. The method for this process is well known in the art and the steps are: the cDNA is introduced into a vector, the vector is transformed into ES cells, transformed cells are identified and microinjected into mouse cell blastocysts, blastocysts are surgically transferred to pseudopregnant dams. The resulting chimeric progeny are genotyped and bred to produce heterozygous or homozygous strains.

Knockout Analysis

In gene knockout analysis, a region of a gene is enzymatically modified to include a non-natural intervening sequence such as the neomycin phosphotransferase gene (neo; Capecchi (1989) Science 244:1288–1292). The modified gene is transformed into cultured ES cells and integrates into the endogenous genome by homologous recombination. The inserted sequence disrupts transcription and translation of the endogenous gene.

Knockin Analysis

ES cells can be used to create knockin humanized animals or transgenic animal models of human diseases. With knockin technology, a region of a human gene is injected into animal ES cells, and the human sequence integrates into the animal cell genome. Transgenic progeny or inbred lines are studied and treated with potential pharmaceutical agents to obtain information on the progression and treatment of the analogous human condition.

As described herein, the uses of the cDNAs, provided in the Sequence Listing of this application, and their encoded proteins are exemplary of known techniques and are not intended to reflect any limitation on their use in any technique that would be known to the person of average skill in the art. Furthermore, the cDNAs provided in this application may be used in molecular biology techniques that have not yet been developed, provided the new techniques rely on properties of nucleotide sequences that are currently known to the person of ordinary skill in the art, e.g., the triplet genetic code, specific base pair interactions, and the like. Likewise, reference to a method may include combining more than one method for obtaining or assembling full length cDNA sequences that will be known to those skilled in the art. It is also to be understood that this invention is not limited to the particular methodology, protocols, and reagents described, as these may vary. It is also understood that the terminology used herein is for the purpose of describing particular embodiments only, and is not intended to limit the scope of the present invention which will be limited only by the appended claims. The examples below are provided to illustrate the subject invention and are not included for the purpose of limiting the invention.

EXAMPLES

I Construction of cDNA Libraries

RNA was purchased from Clontech Laboratories (Palo Alto Calif.) or isolated from various tissues. Some tissues were homogenized and lysed in guanidinium isothiocyanate, while others were homogenized and lysed in phenol or in a suitable mixture of denaturants, such as TRIZOL reagent (Life Technologies, Rockville Md.). The resulting lysates were centrifuged over CsCl cushions or extracted with chloroform. RNA was precipitated with either isopropanol or ethanol and sodium acetate, or by other routine methods.

Phenol extraction and precipitation of RNA were repeated as necessary to increase RNA purity. In most cases, RNA was treated with DNase. For most libraries, poly(A) RNA was isolated using oligo d(T)-coupled paramagnetic particles (Promega), OLIGOTEX latex particles (Qiagen, Valencia Calif.), or an OLIGOTEX mRNA purification kit (Qiagen). Alternatively, poly(A) RNA was isolated directly from tissue lysates using other kits, including the POLY(A) PURE mRNA purification kit (Ambion, Austin Tex.).

In some cases, Stratagene (La Jolla Calif.) was provided with RNA and constructed the corresponding cDNA libraries. Otherwise, cDNA was synthesized and cDNA libraries were constructed with the UNIZAP vector system (Stratagene) or SUPERSCRIPT plasmid system (Life Technologies) using the recommended procedures or similar methods known in the art. (See Ausubel, supra, Units 5.1 through 6.6.) Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected (300–1000 bp) using SEPHACRYL S1000, SEPHAROSE CL2B, or SEPHAROSE CL4B column chromatography (APB) or preparative agarose gel electrophoresis. cDNAs were ligated into compatible restriction enzyme sites of the polylinker of the PBLUESCRIPT phagemid (Stratagene), PSPORT1 plasmid (Life Technologies), or PINCY plasmid (Incyte Pharmaceuticals). Recombinant plasmids were transformed into XL1-BLUE, XL1-BLUEMRF, or SOLR competent *E. coli* cells (Stratagene) or DH5α, DH10B, or ELECTROMAX DH10B competent *E. coli* cells (Life Technologies).

In some cases, libraries were superinfected with a 5×excess of the helper phage, M13K07, according to the method of Vieira et al. (1987, Methods Enzymol. 153:3–11) and normalized or subtracted using a methodology adapted from Soares (1994, Proc Natl Acad Sci 91:9228–9232), Swaroop et al. (1991, Nucl Acids Res 19:1954), and Bonaldo et al. (1996, Genome Research 6:791–806). The modified Soares normalization procedure was utilized to reduce the repetitive cloning of highly expressed high abundance cDNAs while maintaining the overall sequence complexity of the library. Modification included significantly longer hybridization times which allowed for increased gene discovery rates by biasing the normalized libraries toward those infrequently expressed low-abundance cDNAs which are poorly represented in a standard transcript image (Soares et al., supra).

II Isolation and Sequencing of cDNA Clones

Plasmids were recovered from host cells by in vivo excision using the UNIZAP vector system (Stratagene) or by cell lysis. Plasmids were purified using one of the following: the Magic or WIZARD MINIPREPS DNA purification system (Promega); the AGTC MINIPREP purification kit (Edge BioSystems, Gaithersburg Md.); the QIAWELL 8, QIAWELL 8 Plus, or QIAWELL 8 Ultra plasmid purification systems, or the REAL PREP 96 plasmid purification kit (QIAGEN, Valencia Calif.). Following precipitation, plasmids were resuspended in 0.1 ml of distilled water and stored, with or without lyophilization, at 4° C.

Alternatively, plasmid DNA was amplified from host cell lysates using direct link PCR in a high-throughput format (Rao (1994) Anal Biochem 216:1–14). Host cell lysis and thermal cycling steps were carried out in a single reaction mixture. Samples were processed and stored in 384-well plates, and the concentration of amplified plasmid DNA was quantified fluorometrically using PICOGREEN dye (Molecular Probes) and a FLUOROSKAN II fluorescence scanner (Labsystems Oy, Helsinki, Finland).

cDNA sequencing reactions were processed using standard methods or high-throughput instrumentation such as the ABI CATALYST 800 thermal cycler (Applied Biosystems) or the DNA ENGINE thermal cycler (MJ Research, Watertown Mass.) in conjunction with the HYDRA microdispenser (Robbins Scientific, Sunnyvale Calif.) or the MICROLAB 2200 system (Hamilton, Reno Nev.). cDNA sequencing reactions were prepared using reagents provided by APB or supplied in ABI sequencing kits such as the ABI PRISM BIGDYE cycle sequencing kit (Applied Biosystems). Electrophoretic separation of cDNA sequencing reactions and detection of labeled cDNAs were carried out using the MEGABACE 1000 DNA sequencing system (APB); the ABI PRISM 373 or 377 sequencing systems (Applied Biosystems) in conjunction with standard ABI protocols and base calling software; or other sequence analysis systems known in the art. Reading frames within the cDNA sequences were identified using standard methods (reviewed in Ausubel, supra, Unit 7.7).

III Extension of cDNA Sequences

Nucleic acid sequences were extended using the cDNA clones and oligonucleotide primers. One primer was synthesized to initiate 5' extension of the known fragment, and the other, to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed. Preferred libraries are ones that have been size-selected to include larger cDNAs. Also, random primed libraries are preferred because they will contain more sequences with the 5' and upstream regions of genes. A randomly primed library is particularly useful if an oligo d(T) library does not yield a full-length cDNA.

High fidelity amplification was obtained by PCR using methods well known in the art. PCR was performed in 96-well plates using the DNA ENGINE thermal cycler (MJ Research). The reaction mix contained DNA template, 200 nmol of each primer, reaction buffer containing $Mg^{2+}$, $(NH_4)_2SO_4$, and β-mercaptoethanol, Taq DNA polymerase (APB), ELONGASE enzyme (Life Technologies), and Pfu DNA polymerase (Stratagene), with the following parameters for primer pair PCI A and PCI B (Incyte Pharmaceuticals): Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ (Stratagene) were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 μl PICOGREEN reagent (0.25% reagent in 1×TE, v/v; Molecular Probes) and 0.5 μl of undiluted PCR product into each well of an opaque fluorimeter plate (Corning Costar, Acton Mass.) and allowing the DNA to bind to the reagent. The plate was scanned in a FLUOROSKAN II (Labsystems Oy) to measure the fluorescence of the sample and to quantify the concentration of DNA. A 5 μl to 10 μl aliquot of the reaction mixture was analyzed by electrophoresis on a 1% agarose mini-gel to determine which reactions were successful in extending the sequence.

The extended nucleic acids were desalted and concentrated, transferred to 384-well plates, digested with CviJI cholera virus endonuclease (Molecular Biology Research, Madison Wis.), and sonicated or sheared prior to religation into pUC18 vector (APB). For shotgun sequencing, the digested nucleic acids were separated on low concentration (0.6 to 0.8%) agarose gels, fragments were excised, and agar digested with AGARACE enzyme (Promega). Extended clones were religated using T4 DNA ligase (New England Biolabs, Beverly Mass.) into pUC18 vector (APB), treated with Pfu DNA polymerase (Stratagene) to fill-in restriction site overhangs, and transformed into competent *E. coli* cells. Transformed cells were selected on antibiotic-containing media, and individual colonies were picked and cultured overnight at 37° C. in 384-well plates in LB/2×carbenicillin liquid media.

The cells were lysed, and DNA was amplified by PCR using Taq DNA polymerase (APB) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified using PICOGREEN reagent (Molecular Probes) as described above. Samples with low DNA recoveries were reamplified using the same conditions described above. Samples were diluted with 20% dimethylsulfoxide (DMSO; 1:2, v/v), and sequenced using DYENAMIC energy transfer sequencing primers and the DYENAMIC DIRECT cycle sequencing kit (APB) or the ABI PRISM BIGDYE terminator cycle sequencing kit (Applied Biosystems).

IV Assembly and Analysis of Sequences

Component nucleotide sequences from chromatograms were subjected to PHRED analysis (Phil Green, University of Washington, Seattle Wash.) and assigned a quality score. The sequences having at least a required quality score were subject to various pre-processing algorithms to eliminate low quality 3' ends, vector and linker sequences, polyA tails, Alu repeats, mitochondrial and ribosomal sequences, bacterial contamination sequences, and sequences smaller than 50 base pairs. Sequences were screened using the BLOCK 2 program (Incyte Genomics), a motif analysis program based on sequence information contained in the SWISS-PROT and PROSITE databases (Bairoch et al. (1997) Nucleic Acids Res 25:217–221; Attwood et al. (1997) J Chem Inf Comput Sci 37:417–424).

Processed sequences were subjected to assembly procedures in which the sequences were assigned to bins, one sequence per bin. Sequences in each bin were assembled to produce consensus sequences, templates. Subsequent new sequences were added to existing bins using BLAST (Altschul (supra); Altschul et al. (supra); Karlin et al. (1988) Proc Natl Acad Sci 85:841–845), BLASTn (vers.1.4, WashU), and CROSSMATCH software (Phil Green, supra). Candidate pairs were identified as all BLAST hits having a quality score greater than or equal to 150. Alignments of at least 82% local identity were accepted into the bin. The component sequences from each bin were assembled using PHRAP (Phil Green, supra). Bins with several overlapping component sequences were assembled using DEEP PHRAP (Phil Green, supra).

Bins were compared against each other, and those having local similarity of at least 82% were combined and reassembled. Reassembled bins having templates of insufficient overlap (less than 95% local identity) were re-split. Assembled templates were also subjected to analysis by STITCHER/EXON MAPPER algorithms which analyzed the probabilities of the presence of splice variants, alternatively spliced exons, splice junctions, differential expression of alternative spliced genes across tissue types, disease states, and the like. These resulting bins were subjected to several rounds of the above assembly procedures to generate the template sequences found in the LIFESEQ GOLD database (Incyte Genomics).

The assembled templates were annotated using the following procedure. Template sequences were analyzed using BLASTn (vers. 2.0, NCBI) versus GBpri (GenBank vers. 116). "Hits" were defined as an exact match having from 95% local identity over 200 base pairs through 100% local identity over 100 base pairs, or a homolog match having an E-value equal to or greater than $1\times10^{-8}$. (The "E-value" quantifies the statistical probability that a match between two sequences occurred by chance). The hits were subjected to frameshift FASTx versus GENPEPT (GenBank version 109). In this analysis, a homolog match was defined as having an E-value of $1\times10^{-8}$. The assembly method used above was described in U.S. Ser. No. 09/276,534, filed Mar. 25, 1999, and the LIFESEQ GOLD user manual (Incyte Genomics).

Following assembly, template sequences were subjected to motif, BLAST, Hidden Markov Model (HMM; Pearson and Lipman (1988) Proc Natl Acad Sci 85:2444–2448; Smith and Waterman (1981) J Mol Biol 147:195–197), and functional analyses, and categorized in protein hierarchies using methods described in U.S. Ser. No. 08/812,290, filed Mar. 6, 1997; U.S. Ser. No. 08/947,845, filed Oct. 9, 1997; U.S. Pat. No. 5,953,727; and U.S. Ser. No. 09/034,807, filed Mar. 4, 1998. Template sequences may be further queried against public databases such as the GenBank rodent, mammalian, vertebrate, eukaryote, prokaryote, and human EST databases.

V Selection of Sequences, Microarray Preparation and Use

Incyte clones represent template sequences derived from the LIFESEQ GOLD assembled human sequence database (Incyte Genomics). In cases where more than one clone was available for a particular template, the 5'-most clone in the template was used on the microarray. The HUMAN GENOME GEM series 1–3 microarrays (Incyte Pharmaceuticals) contain 28,626 array elements which represent 10,068 annotated clusters and 18,558 unannotated clusters. Tables 1 and 2 show the GenBank annotations for SEQ ID NOs:1-x of this invention as produced by BLAST analysis.

To construct microarrays, cDNAs were amplified from bacterial cells using primers complementary to vector sequences flanking the cDNA insert. Thirty cycles of PCR increased the initial quantity of cDNAs from 1–2 ng to a final quantity greater than 5 $\mu$g. Amplified cDNAs were then purified using SEPHACRYL-400 columns (APB). Purified cDNAs were immobilized on polymer-coated glass slides. Glass microscope slides (Corning, Corning N.Y.) were cleaned by ultrasound in 0.1% SDS and acetone, with extensive distilled water washes between and after treatments. Glass slides were etched in 4% hydrofluoric acid (VWR Scientific Products, West Chester Pa.), washed thoroughly in distilled water, and coated with 0.05% aminopropyl silane (Sigma Aldrich) in 95% ethanol. Coated slides were cured in a 110° C. oven. cDNAs were applied to the coated glass substrate using a procedure described in U.S. Pat. No. 5,807,522. One microliter of the cDNA at an average concentration of 100 ng/ul was loaded into the open capillary printing element by a high-speed robotic apparatus which then deposited about 5 nl of cDNA per slide.

Microarrays were UV-crosslinked using a STRATALINKER UV-crosslinker (Stratagene), and then washed at room temperature once in 0.2% SDS and three times in distilled water. Non-specific binding sites were blocked by incubation of microarrays in 0.2% casein in phosphate buffered saline (Tropix, Bedford Mass.) for 30 minutes at 60° C. followed by washes in 0.2% SDS and distilled water as before.

VI Preparation of Samples

The following cell lines were obtained from American Type Culture Collection (Manassus Va.) and cultured in media according to the manufacturer's protocols: PZ-HPV-7 was derived from epithelial cells cultured from normal tissue from the peripheral zone of the prostate. CA-HPV-10 was derived from cells from a prostatic adenocarcinoma of Gleason Grade 4/4. Both PZ cells were transformed by transfection with human papillomavirus (HPV)-18, and express keratins 5 and 8 and the early region 6 oncoprotein of HPV. PZ-HPV-7 and CA-HPV-10 are negative for prostate specific antigen (PSA). DU-145 is a prostate carcinoma cell line isolated from a 69 year-old man with widespread metastatic disease. DU-145 was isolated from a brain metastasis and has no detectable hormone sensitivity. Further, DU-145 is negative for PSA: PC-3 is a prostate adenocarcinoma cell line isolated from a 62 year-old male with grade IV prostate adenocarcinoma metastasized to the bone. PC-3 cells exhibit low acid phosphatase and testosterone-5-alpha reductase activities; LNCaP is a prostate carcinoma cell line isolated from a lymph node biopsy of a 50 year-old male with metastatic prostate carcinoma. LNCaP cells are responsive to 5-alpha-dihydrotestosterone and express androgen receptors.

PrEC, a primary prostate epithelial cell line isolated from a normal donor, was obtained from Cambrex Bioscience Inc.

(Walkersville Md.) and cultured in media according to the manufacturer's protocols.

All cultures were maintained at 37° C. and 5% $CO_2$ for 3–5 passages.

Isolation and Labeling of Sample cDNAs

Cells were harvested when cultures were approximately 70% confluent and lysed in 1 ml of TRIZOL reagent ($5\times10^6$ cells/ml; Life Technologies). The lysates were vortexed thoroughly and incubated at room temperature for 2–3 minutes and extracted with 0.5 ml chloroform. The extract was mixed, incubated at room temperature for 5 minutes, and centrifuged at 15,000 rpm for 15 minutes at 4° C. The aqueous layer was collected and an equal volume of isopropanol was added. Samples were mixed, incubated at room temperature for 10 minutes, and centrifuged at 15,000 rpm for 20 minutes at 4° C. The supernatant was removed and the RNA pellet was washed with 1 ml of 70% ethanol, centrifuged at 15,000 rpm at 4° C., and resuspended in RNase-free water. The concentration of the RNA was determined by measuring the optical density at 260 nm.

Poly(A) RNA was prepared using an OLIGOTEX mRNA kit (QIAGEN) with the following modifications: OLIGOTEX beads were washed in tubes instead of on spin columns, resuspended in elution buffer, and then loaded onto spin columns to recover mRNA. To obtain maximum yield, the mRNA was eluted twice.

Each poly(A) RNA sample was reverse transcribed using MMLV reverse-transcriptase, 0.05 pg/$\mu$l oligo-d(T) primer (21 mer), 1×first strand buffer, 0.03 units/ul RNase inhibitor, 500 uM dATP, 500 uM dGTP, 500 uM dTTP, 40 uM dCTP, and 40 uM either dCTP-Cy3 or dCTP-Cy5 (APB). The reverse transcription reaction was performed in a 25 ml volume containing 200 ng poly(A) RNA using the GEMBRIGHT kit (Incyte Pharmaceuticals). Specific control poly (A) RNAs (YCFR06, YCFR45, YCFR67, YCFR85, YCFR43, YCFR22, YCFR23, YCFR25, YCFR44, YCFR26) were synthesized by in vitro transcription from non-coding yeast genomic DNA (W. Lei, unpublished). As quantitative controls, control mRNAs (YCFR06, YCFR45, YCFR67, and YCFR85) at 0.002 ng, 0.02 ng, 0.2 ng, and 2 ng were diluted into reverse transcription reaction at ratios of 1:100,000, 1:10,000, 1:1000, 1:100 (w/w) to sample mRNA, respectively. To sample differential expression patterns, control mRNAs (YCFR43, YCFR22, YCFR23, YCFR25, YCFR44, YCFR26) were diluted into reverse transcription reaction at ratios of 1:3, 3:1, 1:10, 10:1, 1:25, 25:1 (w/w) to sample mRNA. Reactions were incubated at 37° C. for 2 hr, treated with 2.5 ml of 0.5M sodium hydroxide, and incubated for 20 minutes at 85° C. to the stop the reaction and degrade the RNA.

cDNAs were purified using two successive CHROMA SPIN 30 gel filtration spin columns (Clontech). Cy3- and Cy5-labeled reaction samples were combined as follows: Aliquots of Cy3-labeled PrEC cDNA were individually mixed with Cy5 labeled cDNA from PZ-HPV-7, CA-HPV-10, DU-145, PC-3, and LNCaP cells. The mixtures were ethanol precipitated using 1 ml of glycogen (1 mg/ml), 60 ml sodium acetate, and 300 ml of 100% ethanol, dried to completion using a SpeedVAC system (Savant Instruments, Holbrook N.Y.), and resuspended in 14 $\mu$l 5×SSC/0.2% SDS.

VII Hybridization and Detection

Hybridization reactions contained 9 $\mu$l of sample mixture containing 0.2 $\mu$g each of Cy3 and Cy5 labeled cDNA synthesis products in 5×SSC, 0.2% SDS hybridization buffer. The mixture was heated to 65° C. for 5 minutes and was aliquoted onto the microarray surface and covered with an 1.8 $cm^2$ coverslip. The microarrays were transferred to a waterproof chamber having a cavity just slightly larger than a microscope slide. The chamber was kept at 100% humidity internally by the addition of 140 $\mu$l of 5×SSC in a corner of the chamber. The chamber containing the microarrays was incubated for about 6.5 hours at 60° C. The microarrays were washed for 10 min at 45° C. in low stringency wash buffer (1×SSC, 0.1% SDS), three times for 10 minutes each at 45° C. in high stringency wash buffer (0.1×SSC), and dried.

Reporter-labeled hybridization complexes were detected with a microscope equipped with an Innova 70 mixed gas 10 W laser (Coherent, Santa Clara Calif.) capable of generating spectral lines at 488 nm for excitation of Cy3 and at 632 nm for excitation of Cy5. The excitation laser light was focused on the microarray using a 20×microscope objective (Nikon, Melville N.Y.). The slide containing the microarray was placed on a computer-controlled X-Y stage on the microscope and raster-scanned past the objective. The 1.8 cm×1.8 cm microarray used in the present example was scanned with a resolution of 20 micrometers.

In two separate scans, the mixed gas multiline laser excited the two fluorophores sequentially. Emitted light was split, based on wavelength, into two photomultiplier tube detectors (PMT R1477; Hamamatsu Photonics Systems, Bridgewater N.J.) corresponding to the two fluorophores. Appropriate filters positioned between the microarray and the photomultiplier tubes were used to filter the signals. The emission maxima of the fluorophores used were 565 nm for Cy3 and 650 nm for Cy5. Each microarray was typically scanned twice, one scan per fluorophore using the appropriate filters at the laser source, although the apparatus was capable of recording the spectra from both fluorophores simultaneously.

The sensitivity of the scans was calibrated using the signal intensity generated by a cDNA control species. Samples of the calibrating cDNA were separately labeled with the two fluorophores and identical amounts of each were added to the hybridization mixture. A specific location on the microarray contained a complementary DNA sequence, allowing the intensity of the signal at that location to be correlated with a weight ratio of hybridizing species of 1:100,000.

The output of the photomultiplier tube was digitized using a 12-bit RTI-835H analog-to-digital (A/D) conversion board (Analog Devices, Norwood, Mass.) installed in an IBM-compatible PC computer. The digitized data were displayed as an image where the signal intensity was mapped using a linear 20-color transformation to a pseudocolor scale ranging from blue (low signal) to red (high signal). The data was also analyzed quantitatively. Where two different fluorophores were excited and measured simultaneously, the data were first corrected for optical crosstalk (due to overlapping emission spectra) between the fluorophores using each fluorophore's emission spectrum.

A grid was superimposed over the fluorescence signal image such that the signal from each spot was centered in each element of the grid. The fluorescence signal within each element was then integrated to obtain a numerical value corresponding to the average intensity of the signal. The software used for signal analysis was the GEMTOOLS gene expression analysis program (Incyte Pharmaceuticals). Significance was defined as signal to background ratio exceeding 2× and area hybridization exceeding 40%.

VIII Data Analysis and Results

Array elements that exhibited at least 2.5-fold change in expression at one or more time points, a signal intensity over 250 units, a signal-to-background ratio of at least 2.5, and an element spot size of at least 40% were identified as differentially expressed using the GEMTOOLS program (Incyte Genomics). Differential expression values were converted to log base 2 scale. Differential expression values were then compared between the cell lines to identify genes which discriminated between normal and cancerous and between non-metastatic and metastatic cancer. The student's t-test and Pearson correlation statistics were used to distinguish significant differences between the groups. The resulting cDNAs are shown in Tables 1 and 2. The cDNAs are identified by their Clone ID. Table 3 shows the sequence overlap between the clones identified in Tables 1 and 2 and gene templates. Columns 1–3 show the SEQ ID NO:, Template ID, and Clone ID, respectively. Columns 4 and 5 show the start and stop nucleotides for the clone on the template. Table 4 shows a GenBank homolog and description associated with at least a fragment of each Template ID. The descriptions were obtained using the sequences of the Sequence Listing and BLAST analysis. SEQ ID NOs:1–3, 5, 6, 8, 10–15, 17–19, 21, 23–28, 30, 32, 34–36, 38, 40, 42–45, 47–50, 52, 53, 55, 56, 58–65, 67, 68, 70–73, 75 are highly correlated with metastatic prostate cancer cells PC-3, LNCaP, and DU-145, and SEQ ID NOs:76, 78–86, 88–90, 92–97, 99–101 are differentially expressed at significant levels in all of the prostate cancer cell lines.

IX Other Hybridization Technologies and Analyses

Other hybridization technologies utilize a variety of substrates such as nylon membranes, capillary tubes, etc. Arranging cDNAs on polymer coated slides is described in Example V; sample cDNA preparation and hybridization and analysis using polymer coated slides is described in examples VI and VII, respectively.

cDNAs are applied to a membrane substrate by one of the following methods. A mixture of cDNAs is fractionated by gel electrophoresis and transferred to a nylon membrane by capillary transfer. Alternatively, the cDNAs are individually ligated to a vector and inserted into bacterial host cells to form a library. The cDNAs are then arranged on a substrate by one of the following methods. In the first method, bacterial cells containing individual clones are robotically picked and arranged on a nylon membrane. The membrane is placed on LB agar containing selective agent (carbenicillin, kanamycin, ampicillin, or chloramphenicol depending on the vector used) and incubated at 37° C. for 16 hr. The membrane is removed from the agar and consecutively placed colony side up in 10% SDS, denaturing solution (1.5 M NaCl, 0.5 M NaOH ), neutralizing solution (1.5 M NaCl, 1 M Tris, pH 8.0), and twice in 2×SSC for 10 min each. The membrane is then UV irradiated in a STRATALINKER UV-crosslinker (Stratagene).

In the second method, cDNAs are amplified from bacterial vectors by thirty cycles of PCR using primers complementary to vector sequences flanking the insert. PCR amplification increases a starting concentration of 1–2 ng nucleic acid to a final quantity greater than 5 $\mu$g. Amplified nucleic acids from about 400 bp to about 5000 bp in length are purified using SEPHACRYL400 beads (APB). Purified nucleic acids are arranged on a nylon membrane manually or using a dot/slot blotting manifold and suction device and are immobilized by denaturation, neutralization, and UV irradiation as described above.

Hybridization probes derived from cDNAs of the Sequence Listing are employed for screening cDNAs, mRNAs, or genomic DNA in membrane-based hybridizations. Probes are prepared by diluting the cDNAs to a concentration of 40–50 ng in 45 $\mu$l TE buffer, denaturing by heating to 100° C. for five min and briefly centrifuging. The denatured cDNA is then added to a REDIPRIME tube (APB), gently mixed until blue color is evenly distributed, and briefly centrifuged. Five microliters of [$^{32}$P]dCTP is added to the tube, and the contents are incubated at 37° C. for 10 min. The labeling reaction is stopped by adding 5 $\mu$l of 0.2M EDTA, and probe is purified from unincorporated nucleotides using a PROBEQUANT G-50 microcolumn (APB). The purified probe is heated to 100° C. for five min and then snap cooled for two min on ice.

Membranes are pre-hybridized in hybridization solution containing 1% Sarkosyl and 1×high phosphate buffer (0.5 M NaCl, 0.1 M $Na_2HPO_4$, 5 mM EDTA, pH 7) at 55° C. for two hr. The probe, diluted in 15 ml fresh hybridization solution, is then added to the membrane. The membrane is hybridized with the probe at 55° C. for 16 hr. Following hybridization, the membrane is washed for 15 min at 25° C. in 1 mM Tris (pH 8.0), 1% Sarkosyl, and four times for 15 min each at 25° C. in 1 mM Tris (pH 8.0). To detect hybridization complexes, XOMAT-AR film (Eastman Kodak, Rochester N.Y.) is exposed to the membrane overnight at −70° C., developed, and examined.

X Further Characterization of Differentially Expressed cDNAs and Proteins

Clones were blasted against the LIFESEQ Gold 5.1 database (Incyte Genomics) and an Incyte template and its sequence variants were chosen for each clone. The template and variant sequences were blasted against GenBank database to acquire annotation. The nucleotide sequences were translated into amino acid sequence which was blasted against the GenPept and other protein databases to acquire annotation and characterization, i.e., structural motifs.

Percent sequence identity can be determined electronically for two or more amino acid or nucleic acid sequences using the MEGALIGN program (DNASTAR). The percent identity between two amino acid sequences is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage identity.

Sequences with conserved protein motifs may be searched using the BLOCKS search program. This program analyses sequence information contained in the Swiss-Prot and PROSITE databases and is useful for determining the classification of uncharacterized proteins translated from genomic or cDNA sequences (Bairoch et al.(supra); Attwood et al. (supra). PROSITE database is a useful source for identifying functional or structural domains that are not detected using motifs due to extreme sequence divergence. Using weight matrices, these domains are calibrated against the SWISS-PROT database to obtain a measure of the chance distribution of the matches.

The PRINTS database can be searched using the BLIMPS search program to obtain protein family "fingerprints". The PRINTS database complements the PROSITE database by exploiting groups of conserved motifs within sequence alignments to build characteristic signatures of different protein families. For both BLOCKS and PRINTS analyses, the cutoff scores for local similarity were: >1300=strong, 1000–1300=suggestive; for global similarity were: p<exp-3; and for strength (degree of correlation) were: >1300=strong, 1000–1300=weak.

X Expression of the Encoded Protein

Expression and purification of a protein encoded by a cDNA of the invention is achieved using bacterial or virus-based expression systems. For expression in bacteria, cDNA is subcloned into a vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into bacterial hosts, such as BL21(DE3). Antibiotic resistant bacteria express the protein upon induction with IPTG. Expression in eukaryotic cells is achieved by infecting *Spodoptera frugiperda* (Sf9) insect cells with recombinant baculovirus, *Autographica californica* nuclear polyhedrosis virus. The polyhedrin gene of baculovirus is replaced with the cDNA by either homologous recombination or bacterial-mediated transposition involving transfer plasmid intermediates. Viral infectivity is maintained and the strong polyhedrin promoter drives high levels of transcription.

For ease of purification, the protein is synthesized as a fusion protein with glutathione-S-transferase (GST; APB) or a similar alternative such as FLAG. The fusion protein is purified on immobilized glutathione under conditions that maintain protein activity and antigenicity. After purification, the GST moiety is proteolytically cleaved from the protein with thrombin. A fusion protein with FLAG, an 8-amino acid peptide, is purified using commercially available monoclonal and polyclonal anti-FLAG antibodies (Eastman Kodak, Rochester N.Y.).

XI Production of Specific Antibodies

A denatured protein from a reverse phase HPLC separation is obtained in quantities up to 75 mg. This denatured protein is used to immunize mice or rabbits following standard protocols. About 100 μg is used to immunize a mouse, while up to 1 mg is used to immunize a rabbit. The denatured protein is radioiodinated and incubated with murine B-cell hybridomas to screen for monoclonal antibodies. About 20 mg of protein is sufficient for labeling and screening several thousand clones.

In another approach, the amino acid sequence translated from a cDNA of the invention is analyzed using PROTEAN software (DNASTAR) to determine regions of high antigenicity, essentially antigenically-effective epitopes of the protein. The optimal sequences for immunization are usually at the C-terminus, the N-terminus, and those intervening, hydrophilic regions of the protein that are likely to be exposed to the external environment when the protein is in its natural conformation. Typically, oligopeptides about 15 residues in length are synthesized using an ABI 431 peptide synthesizer (Applied Biosystems) using Fmoc-chemistry and then coupled to keyhole limpet hemocyanin (KLH; Sigma Aldrich) by reaction with M-maleimidobenzoyl-N-hydroxysuccinimide ester. If necessary, a cysteine may be introduced at the N-terminus of the peptide to permit coupling to KLH. Rabbits are immunized with the oligopeptide-KLH complex in complete Freund's adjuvant. The resulting antisera are tested for antipeptide activity by binding the peptide to plastic, blocking with 1% BSA, reacting with rabbit antisera, washing, and reacting with radioiodinated goat anti-rabbit IgG.

Hybridomas are prepared and screened using standard techniques. Hybridomas of interest are detected by screening with radioiodinated protein to identify those fusions producing a monoclonal antibody specific for the protein. In a typical protocol, wells of 96 well plates (FAST, Becton-Dickinson, Palo Alto Calif.) are coated with affinity-purified, specific rabbit-anti-mouse (or suitable anti-species Ig) antibodies at 10 mg/ml. The coated wells are blocked with 1% BSA and washed and exposed to supernatants from hybridomas. After incubation, the wells are exposed to radiolabeled protein at 1 mg/ml. Clones producing antibodies bind a quantity of labeled protein that is detectable above background.

Such clones are expanded and subjected to 2 cycles of cloning at 1 cell/3 wells. Cloned hybridomas are injected into pristane-treated mice to produce ascites, and monoclonal antibody is purified from the ascitic fluid by affinity chromatography on protein A (APB). Monoclonal antibodies with affinities of at least $10^8$ $M^{-1}$, preferably $10^9$ to $10^{10}$ $M^{-1}$ or stronger, are made by procedures well known in the art.

XII Purification of Naturally Occurring Protein Using Specific Antibodies

Naturally occurring or recombinant protein is substantially purified by immunoaffinity chromatography using antibodies specific for the protein. An immunoaffinity column is constructed by covalently coupling the antibody to CNBr-activated SEPHAROSE resin (APB). Media containing the protein is passed over the immunoaffinity column, and the column is washed using high ionic strength buffers in the presence of detergent to allow preferential absorbance of the protein. After coupling, the protein is eluted from the column using a buffer of pH 2–3 or a high concentration of urea or thiocyanate ion to disrupt antibody/protein binding, and the protein is collected.

XIII Screening Molecules for Specific Binding with the cDNA or Protein

The cDNA or fragments thereof and the protein or portions thereof are labeled with $^{32}$P-dCTP, Cy3-dCTP, Cy5-dCTP (APB), or BIODIPY or FITC (Molecular Probes), respectively. Candidate molecules or compounds previously arranged on a substrate are incubated in the presence of labeled nucleic or amino acid. After incubation under conditions for either a cDNA or a protein, the substrate is washed, and any position on the substrate retaining label, which indicates specific binding or complex formation, is assayed. The binding molecule is identified by its arrayed position on the substrate. Data obtained using different concentrations of the nucleic acid or protein are used to calculate affinity between the labeled nucleic acid or protein and the bound molecule. High throughput screening using very small assay volumes and very small amounts of test compound is fully described in Burbaum et al. U.S. Pat. No. 5,876,946.

All patents and publications mentioned in the specification are incorporated herein by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of molecular biology or related fields are intended to be within the scope of the following claims.

TABLE 1

| Clone ID | PrEC, Untx/CA-HPV-10 | PrEC, Untx/PZ-HPV-7 | PrEC, Untx/DU145 | PrEC, Untx/LNCaP | PrEC, Untx/PC3 | t-test |
|---|---|---|---|---|---|---|
| 3184882 | −0.26 | −0.41 | −3.37 | −3.80 | −3.28 | 0.0007 |
| 3973887 | −0.45 | −0.47 | −1.47 | −1.59 | −1.59 | 0.0010 |

TABLE 1-continued

| Clone ID | PrEC, Untx/CA-HPV-10 | PrEC, Untx/PZ-HPV-7 | PrEC, Untx/DU145 | PrEC, Untx/LNCaP | PrEC, Untx/PC3 | t-test |
|---|---|---|---|---|---|---|
| 557538 | 0.15 | 0.41 | −3.61 | −3.88 | −3.73 | 0.0029 |
| 793403 | −0.57 | −0.58 | −2.84 | −2.73 | −2.45 | 0.0031 |
| 423513 | −0.61 | −0.67 | −1.72 | −1.81 | −1.52 | 0.0036 |
| 5497369 | −0.53 | −0.24 | −2.15 | −2.62 | −1.91 | 0.0054 |
| 3432534 | −0.50 | −0.61 | −2.76 | −3.45 | −2.72 | 0.0072 |
| 1955573 | 0.12 | −0.07 | −1.27 | −0.84 | −1.32 | 0.0076 |
| 4029118 | 0.14 | 0.12 | −1.32 | −1.43 | −1.00 | 0.0082 |
| 2723829 | −0.58 | −0.41 | −1.45 | −1.30 | −1.17 | 0.0087 |
| 1628341 | −0.39 | −0.01 | −2.07 | −2.42 | −1.68 | 0.0087 |
| 4513549 | 0.04 | −0.19 | −1.34 | −1.78 | −1.14 | 0.0091 |
| 1967556 | −0.27 | −0.39 | −1.27 | −1.80 | −1.67 | 0.0095 |
| 2729629 | −0.22 | 0.09 | −1.32 | −1.92 | −1.27 | 0.0118 |
| 2701607 | −0.62 | −0.59 | −2.23 | −2.49 | −1.88 | 0.0119 |
| 4933404 | 0.28 | 0.22 | −1.05 | −1.50 | −0.95 | 0.0119 |
| 3616296 | −0.59 | −0.45 | −1.23 | −1.33 | −0.97 | 0.0136 |
| 154371 | 0.08 | 0.40 | −2.54 | −2.91 | −1.54 | 0.0154 |
| 3774181 | −0.59 | −0.55 | −2.25 | −3.28 | −2.83 | 0.0172 |
| 1709387 | −0.44 | −0.74 | −2.22 | −2.42 | −2.12 | 0.0184 |
| 351981 | −0.21 | −0.22 | −1.08 | −0.98 | −1.41 | 0.0186 |
| 2057510 | −0.68 | −0.23 | −3.49 | −3.82 | −3.77 | 0.0192 |
| 1324789 | −0.38 | −0.42 | −1.67 | −2.32 | −1.66 | 0.0199 |
| 3120070 | −1.03 | −0.70 | −2.60 | −2.71 | −2.40 | 0.0203 |
| 2833609 | −0.19 | 0.07 | −0.98 | −1.90 | −1.55 | 0.0221 |
| 3431481 | −0.30 | −0.21 | −1.65 | −2.39 | −1.57 | 0.0222 |
| 4557506 | −0.40 | −0.08 | −1.20 | −1.81 | −1.14 | 0.0233 |
| 1597810 | −0.30 | −0.55 | −1.59 | −2.31 | −1.46 | 0.0237 |
| 2962788 | −1.09 | −1.13 | −3.13 | −4.19 | −3.04 | 0.0240 |
| 3120209 | −0.79 | −0.60 | | −1.52 | −1.74 | 0.0247 |
| 1800609 | −0.33 | −0.61 | −1.68 | −1.31 | −1.47 | 0.0247 |
| 3384548 | 0.02 | −0.07 | −0.89 | −1.42 | −0.85 | 0.0250 |
| 2056584 | −0.18 | −0.21 | −1.23 | −1.81 | −1.17 | 0.0268 |
| 3096030 | −0.66 | −0.85 | | −2.07 | −1.79 | 0.0291 |
| 2505801 | −0.01 | 0.11 | −1.21 | −1.88 | −0.98 | 0.0300 |
| 3658143 | 0.07 | −0.35 | −1.64 | −1.56 | −0.98 | 0.0306 |
| 3384076 | −0.25 | −0.26 | −1.43 | −2.13 | −1.32 | 0.0327 |
| 2058209 | −0.34 | −0.01 | −1.46 | −1.24 | −0.80 | 0.0329 |
| 509758 | −0.31 | −0.39 | −2.19 | −2.24 | −1.30 | 0.0341 |
| 1723319 | −0.57 | −0.71 | −2.41 | −3.45 | −2.12 | 0.0343 |
| 2198951 | −0.24 | −0.26 | −0.86 | −1.32 | −0.88 | 0.0359 |
| 4365223 | −0.20 | −0.15 | −1.10 | −1.97 | −1.35 | 0.0372 |
| 1437565 | −0.40 | −0.31 | −1.19 | −1.93 | −1.26 | 0.0381 |
| 3837686 | 0.01 | 0.27 | −0.68 | −1.36 | −0.57 | 0.0387 |
| 36406 | −0.78 | −0.05 | −2.26 | −3.01 | −1.93 | 0.0403 |
| 1217764 | −0.49 | 0.18 | −2.16 | −2.48 | −1.21 | 0.0412 |
| 2059420 | −0.29 | −0.41 | −0.80 | −1.31 | −1.45 | 0.0425 |
| 1805911 | −0.22 | −0.16 | −1.52 | −2.32 | −1.23 | 0.0429 |
| 461367 | 0.19 | 0.18 | −1.00 | −1.66 | −0.71 | 0.0429 |
| 4089868 | 0.27 | 0.28 | −0.46 | −0.92 | −1.35 | 0.0437 |
| 1549141 | −0.48 | −0.80 | −1.18 | −1.65 | −1.58 | 0.0456 |
| 4571104 | −0.88 | −0.57 | −1.69 | −1.22 | −2.00 | 0.0464 |
| 552594 | −0.21 | −0.49 | −1.27 | −1.84 | −0.94 | 0.0475 |
| 2834343 | −0.11 | 0.02 | −0.94 | −2.02 | −1.21 | 0.0493 |

TABLE 2

| Clone ID | PrEC, Untx/CA-HPV-10 | PrEC, Untx/PZ-HPV-7 | PrEC, Untx/DU145 | PrEC, Untx/LNCaP | PrEC, Untx/PC3 |
|---|---|---|---|---|---|
| 1518310 | −1.74 | −1.27 | −2.60 | −2.97 | −2.50 |
| 2823767 | −1.70 | −1.92 | −1.72 | −1.54 | −1.34 |
| 2241825 | −1.66 | −1.49 | −1.98 | −1.55 | −1.44 |
| 5033671 | −1.33 | −1.44 | −1.53 | −2.59 | −1.62 |
| 44913 | −1.30 | −1.30 | −1.11 | −2.21 | −2.29 |
| 4549259 | −1.29 | −1.36 | −1.35 | −1.68 | −1.12 |
| 319075 | −1.29 | −1.37 | −1.08 | −2.26 | −2.15 |
| 2520894 | −1.27 | −1.43 | −1.50 | −1.15 | −1.04 |
| 4107861 | −1.27 | −2.03 | −2.20 | −2.67 | −2.13 |
| 3172265 | −1.67 | −1.48 | | −1.74 | −1.86 |
| 4402555 | −1.43 | −1.24 | | −1.52 | −1.11 |
| 2495131 | −1.40 | −1.01 | −1.26 | −3.32 | −0.95 |
| 3158828 | −1.37 | −1.19 | | −1.59 | −1.31 |

TABLE 2-continued

| Clone ID | PrEC, Untx/CA-HPV-10 | PrEC, Untx/PZ-HPV-7 | PrEC, Untx/DU145 | PrEC, Untx/LNCaP | PrEC, Untx/PC3 |
|---|---|---|---|---|---|
| 5266015 | −1.25 | −1.31 | | −1.56 | −1.26 |
| 4978708 | −1.24 | −1.42 | −1.20 | −1.63 | −0.54 |
| 3069190 | −1.21 | −1.33 | | −1.67 | −1.37 |
| 64073 | −1.15 | −1.09 | −0.91 | −2.04 | −2.18 |
| 172023 | 1.01 | 1.29 | 2.11 | 0.98 | 1.59 |
| 3068978 | −1.32 | −1.13 | | 0.00 | −1.94 |
| 2060823 | −1.08 | −1.35 | −1.38 | −0.93 | −0.95 |
| 2060823 | −1.08 | −1.35 | −1.38 | −0.93 | −0.95 |

TABLE 3

| SEQ ID NO: | Template ID | Clone ID | Start | Stop |
|---|---|---|---|---|
| 1 | 1382961.3 | 3184882 | 1080 | 1401 |
| 2 | 1382961.5 | 3184882 | 1 | 518 |
| 3 | 2852561CB1 | 3973887 | 1 | 1934 |
| 5 | 335942.2 | 557538 | −4 | 354 |
| 6 | 2483854CB1 | 557538 | 21 | 1677 |
| 8 | 1454852CB1 | 793403 | 54 | 1564 |
| 10 | 353005.1 | 423513 | 1 | 309 |
| 11 | 378497.1 | 5497369 | 1 | 176 |
| 12 | 994684.9 | 3432534 | 2312 | 2868 |
| 13 | 995610.1 | 1955573 | 2345 | 2804 |
| 14 | 417119.1 | 4029118 | 1 | 427 |
| 15 | 3615080CB1 | 2723829 | 563 | 4670 |
| 17 | 331749.3 | 1628341 | 264 | 748 |
| 18 | 979243.1 | 4513549 | 299 | 1245 |
| 19 | 3189059CB1 | 1967556 | 192 | 1981 |
| 21 | 1650519CB1 | 2729629 | 5 | 1448 |
| 23 | 474630.4 | 2701607 | 1610 | 2083 |
| 24 | 093496.1 | 4933404 | 319 | 455 |
| 25 | 1231633.4 | 3616296 | 7 | 58 |
| 26 | 988891.1 | 154371 | 987 | 1538 |
| 27 | 988891.15 | 154371 | 1 | 363 |
| 28 | 3774181CB1 | 3774181 | 37 | 7081 |
| 30 | 1709387CB1 | 1709387 | 34 | 1742 |
| 32 | 1709118CB1 | 351981 | 45 | 1437 |
| 34 | 008513.49 | 2057510 | 1721 | 2258 |
| 35 | 047568.1 | 1324789 | 1 | 493 |
| 36 | 3120070CB1 | 3120070 | 43 | 2028 |
| 38 | 1303785CB1 | 2833609 | 3251 | 4766 |
| 40 | 1798379CB1 | 3431481 | 3 | 2711 |
| 42 | 350650.1 | 4557506 | 1 | 663 |
| 43 | 474630.24 | 1597810 | 443 | 809 |
| 44 | 108089.1 | 2962788 | 1 | 295 |
| 45 | 3346307CB1 | 3120209 | 13 | 1756 |
| 47 | 200143.25 | 1800609 | 234 | 679 |
| 48 | 001929.1 | 3384548 | 12 | 432 |
| 48 | 001929.1 | 3384076 | 797 | 1744 |
| 49 | 1088524.8 | 2056584 | 1218 | 1900 |
| 50 | 632664CB1 | 3096030 | 67 | 1181 |
| 52 | 457372.17 | 2505801 | 527 | 824 |
| 53 | 2993696CB1 | 3658143 | 17 | 2556 |
| 55 | 331106.6 | 2058209 | 4948 | 5465 |
| 56 | 1256895CB1 | 509758 | 530 | 3000 |
| 58 | 474630.29 | 1723319 | 3978 | 4495 |
| 59 | 1256295.18 | 2198951 | 497 | 1314 |
| 60 | 444096.1 | 4365223 | 632 | 1383 |
| 60 | 444096.1 | 1805911 | 1 | 1387 |
| 61 | 008942.10 | 1437565 | 4357 | 4498 |
| 62 | 008942.9 | 1437565 | 1320 | 1602 |
| 63 | 1252415.1 | 3837686 | 2794 | 2872 |
| 64 | 1399366.20 | 36406 | 5046 | 5265 |
| 65 | 3732868CB1 | 1217764 | 1 | 961 |
| 67 | 1137894.1 | 2059420 | 1947 | 2552 |
| 68 | 1418671CB1 | 461367 | 1 | 1529 |
| 70 | 464689.64 | 4089868 | 4741 | 5350 |
| 71 | 053959.1 | 1549141 | 1 | 56 |
| 72 | 1384594.1 | 4571104 | 1 | 580 |
| 73 | 021667CB1 | 552594 | 778 | 3348 |
| 75 | 224855.4 | 2834343 | 3902 | 5287 |
| 76 | 1518310CB1 | 1518310 | 45 | 2323 |

TABLE 3-continued

| SEQ ID NO: | Template ID | Clone ID | Start | Stop |
|---|---|---|---|---|
| 78 | 098533.1 | 2823767 | 1 | 445 |
| 79 | 410785.1 | 2241825 | 4507 | 4882 |
| 80 | 1089210.1 | 5033671 | 34 | 1152 |
| 81 | 333453.6 | 44913 | 1 | 202 |
| 82 | 365070.1 | 4549259 | 123 | 698 |
| 83 | 365070.3 | 4549259 | 393 | 841 |
| 84 | 413921.2 | 319075 | 3140 | 3637 |
| 85 | 336615.1 | 2520894 | 1088 | 1325 |
| 86 | 2733282CB1 | 4107861 | 1 | 3156 |
| 88 | 399161.1 | 3172265 | 473 | 1121 |
| 89 | 339638.1 | 4402555 | 1 | 687 |
| 90 | 697785CB1 | 2495131 | 233 | 770 |
| 92 | 399785.1 | 3158828 | 199 | 627 |
| 93 | 002455.1 | 5266015 | 668 | 1133 |
| 94 | 1382920.38 | 4978708 | 49 | 565 |
| 95 | 334749.1 | 3069190 | 74 | 634 |
| 96 | 041764.1 | 64073 | 319 | 579 |
| 97 | 2700132CB1 | 172023 | 208 | 10640 |
| 99 | 211881.1 | 3068978 | 1 | 548 |
| 100 | 409895.2 | 2060823 | 1224 | 1458 |
| 101 | 1422432CB1 | 2060823 | 1 | 860 |

TABLE 4

| SEQ ID NO: | Template ID | GB Number | E-value | Annotation |
|---|---|---|---|---|
| 1 | 1382961.3 | g186704 | 0 | Human 50 kDa type I epidermal keratin gene, complete cds. |
| 2 | 1382961.5 | g186704 | 2.00E − 86 | Human 50 kDa type I epidermal keratin gene, complete cds. |
| 3 | 2852561CB1 | g5926733 | 0 | Human mRNA for 4F2 heavy chain, complete cds. |
| 4 | 2852561CD1 | g5926733 | 0 | Human mRNA for 4F2 heavy chain, complete cds. |
| 5 | 335942.2 | g33794 | 0 | Human mRNA for interleukin-1 precursor (pre IL-1). |
| 6 | 2483854CB1 | g33794 | 0 | Human mRNA for interleukin-1 precursor (pre IL-1). |
| 7 | 2483854CD1 | g33794 | 0 | Human mRNA for interleukin-1 precursor (pre IL-1). |
| 8 | 1454852CB1 | g34074 | 0 | Human mRNA for keratin-related protein. |
| 9 | 1454852CD1 | g34074 | 0 | Human mRNA for keratin-related protein. |
| 10 | 353005.1 | g183063 | 0 | Human glia-derived nexin (GDN) mRNA, 5' end. |
| 11 | 378497.1 | g2627428 | 7.00E − 36 | Human laminin alpha 3b chain mRNA, partial cds. |
| 12 | 994684.9 | g186697 | 0 | Human keratin type II (58 kD) mRNA, complete cds. |
| 13 | 995610.1 | g34815 | 0 | Human mRNA encoding the c-myc oncogene. |
| 14 | 417119.1 | g33788 | 0 | Human gene for prointerleukin 1 beta. |
| 15 | 3615080CB1 | g2429078 | 0 | Human mRNA for Laminin-5 beta3 chain, complete cds. |
| 16 | 3615080CD1 | g2429078 | 0 | Human mRNA for Laminin-5 beta3 chain, complete cds. |
| 17 | 331749.3 | g453368 | 0 | Human maspin mRNA, complete cds. |
| 18 | 979243.1 | g212752 | 4.00E − 61 | tensin |
| 19 | 3189059CB1 | g3242792 | 0 | Human herpesvirus entry protein C (HVEC) mRNA, complete cds. |
| 20 | 3189059CD1 | g3242792 | 0 | Human herpesvirus entry protein C (HVEC) mRNA, complete cds. |
| 21 | 1650519CB1 | g3483777 | 0 | Human full length insert cDNA clone ZD79H11. |
| 22 | 1650519CD1 | g3483777 | 0 | Human full length insert cDNA clone ZD79H11. |
| 23 | 474630.4 | g33956 | 0 | Human mRNA for integrin beta-4 subunit. |
| 24 | 093496.1 | g338320 | 4.00E − 12 | Human osyeonectin gene, exon 7. |
| 25 | 1231633.4 | g189265 | 5.00F-87 | Human novel gene mRNA, complete cds. |
| 26 | 988891.1 | g186268 | 0 | Human monocyte interleukin I (IL-1) mRNA, complete cds. |
| 27 | 988891.15 | g186268 | 0 | Human monocyte interleukin I (IL-1) mRNA, complete cds. |
| 28 | 3774181CB1 | g179522 | 0 | Human bullous pemphigoid antigen (BPAG1) mRNA, complete cds. |
| 29 | 3774181CD1 | g179522 | 0 | Human bullous pemphigoid antigen (BPAG1) mRNA, complete cds. |
| 30 | 1709387CB1 | g34070 | 0 | Human mRNA for cytokeratin 15. |
| 31 | 1709387CD1 | g34070 | 0 | Human mRNA for cytokeratin 15. |
| 32 | 1709118CB1 | g178037 | 0 | Human alpha-cardiac actin gene, exon 6 and 3' flank. |
| 33 | 1709118CD1 | g178037 | 0 | Human alpha-cardiac actin gene, exon 6 and 3' flank. |
| 34 | 008513.49 | g908802 | 0 | Human keratin 6 isoform K6e (KRT6E) mRNA, complete cds. |
| 35 | 047568.1 | g184056 | 0 | Human histatin 3 (HIS2) gene exons 3–5, complete cds. |
| 36 | 3120070CB1 | g7582391 | 1.00F-60 | p53 apoptosis-associated target |
| 37 | 3120070CD1 | g7582391 | 1.00F-60 | p53 apoptosis-associated target |
| 38 | 1303785CB1 | g34387 | 0 | Human mRNA for lipocortin. |
| 39 | 1303785CD1 | g34387 | 0 | Human mRNA for lipocortin. |
| 40 | 1798379CB1 | g181401 | 0 | Human epidermal cytokeratin 2 mRNA, complete cds. |
| 41 | 1798379CD1 | g181401 | 0 | Human epidermal cytokeratin 2 mRNA, complete cds. |
| 42 | 350650.1 | g7020235 | 0 | Human cDNA FLJ20261 fis, clone COLF7630. |
| 43 | 474630.24 | g2270919 | 0 | Human beta4-integrin (ITGB4) gene, exons 31, 32, 33 and 34 |
| 44 | 108089.1 | g747615 | 7.00E − 68 | Human laminin S B3 chain (LAMB3) gene, exons 2–3. |

TABLE 4-continued

| SEQ ID NO: | Template ID | GB Number | E-value | Annotation |
|---|---|---|---|---|
| 45 | 3346307CB1 | g7020644 | 0 | Human cDNA FLJ20500 fis, clone KAT09159. |
| 46 | 3346307CD1 | g7020644 | 0 | Human cDNA FLJ20500 fis, clone KAT09159. |
| 47 | 200143.25 | g897916 | 1.00E − 47 | Human 11kd protein mRNA, complete cds. |
| 48 | 001929.1 | g908779 | 0 | keratin type II |
| 49 | 1088524.8 | g7453533 | 0 | Human hepatic angiopoietin-related protein (ANGPTL2) mRNA, complete cds. |
| 50 | 632664CB1 | g7658294 | 0 | Human transmembrane protein BRI mRNA, complete cds. |
| 51 | 632664CD1 | g7658294 | 0 | Human transmembrane protein BRI mRNA, complete cds. |
| 52 | 457372.17 | g7959902 | 0 | Human PRO2446 mRNA, complete cds. |
| 53 | 2993696CB1 | g1143491 | 0 | Human mRNA for BiP protein. |
| 54 | 2993696CD1 | g1143491 | 0 | Human mRNA for BiP protein. |
| 55 | 331106.6 | g33943 | 0 | Human mRNA for integrin alpha 6. |
| 56 | 1256895CB1 | g2618612 | 0 | Human mRNA for prion protein, complete cds. |
| 57 | 1256895CD1 | g2618612 | 0 | Human mRNA for prion protein, complete cds. |
| 58 | 474630.29 | g33910 | 0 | Human mRNA for integrin beta(4) subunit. |
| 59 | 1256295.18 | g182939 | 0 | Human growth arrest and DNA-damage-inducible protein (gadd45) mRNA, complete cds. |
| 60 | 444096.1 | g34073 | 1.00E − 85 | cytokeratin 4 (408 AA) |
| 61 | 008942.10 | g4426639 | 0 | Human L-type amino acid transporter subunit LAT1 mRNA, complete cds. |
| 62 | 008942.9 | g5926731 | 0 | Human mRNA for L-type amino acid transporter 1, complete cds. |
| 63 | 1252415.1 | g178083 | 0 | Human adenylyl cyclase-associated protein (CAP) mRNA, complete cds. |
| 64 | 1399366.20 | g37464 | 0 | Human mRNA for thrombospondin. |
| 65 | 3732868CB1 | g182852 | 0 | Human GOS2 gene, 5' flank and cds. |
| 66 | 3732868CD1 | g182852 | 0 | Human GOS2 gene, 5' flank and cds. |
| 67 | 1137894.1 | g2072389 | 0 | Human zinc finger transcriptional regulator (COS24) gene, complete cds. |
| 68 | 1418671CB1 | g6984179 | 0 | Human pleckstrin 2 mRNA, complete cds. |
| 69 | 1418671CD1 | g6984179 | 0 | Human pleckstrin 2 mRNA, complete cds. |
| 70 | 464689.64 | g7415720 | 0 | Human Sed mRNA for stearoyl-CoA desaturase, complete cds. |
| 71 | 053959.1 | g340012 | 3.00E − 13 | Human tristetraproline (TTP) mRNA, complete cds. |
| 72 | 1384594.1 | g7020744 | 7.00E − 14 | Human cDNA FLJ20557 fis, clone KAT11869. |
| 73 | 021667CB1 | g6580834 | 0 | Human colon Kruppel-like factor (CKLF) mRNA, complete cds. |
| 74 | 021667CD1 | g6580834 | 0 | Human colon Kruppel-like factor (CKLF) mRNA, complete cds. |
| 75 | 224855.4 | g1378108 | 0 | Human lymphocyte specific interferon regulatory factor/ interferon regulatory factor 4 (LSIRF/IRF4) mRNA |
| 76 | 1518310CB1 | g4481752 | 0 | Human connexin 26 (GJB2) mRNA, complete cds. |
| 77 | 1518310CD1 | g4481752 | 0 | Human connexin 26 (GJB2) mRNA, complete cds. |
| 78 | 098533.1 | g2898163 | 4.00E − 52 | Human microtubule-associated protein tau (tau) gene, exon 0. |
| 79 | 410785.1 | g187133 | 0 | Human liver glucose transporter-like protein (GLUT2), complete cds. |
| 80 | 1089210.1 | g544761 | 0 | chlordecone reductase {clone HAKRa} [Human liver, mRNA, 1167 nt]. |
| 81 | 333453.6 | g2072424 | 5.00E − 65 | Human non-lens beta gamma-crystallin like protein (AIM1) mRNA, partial cds. |
| 82 | 365070.1 | | | Incyte Unique |
| 83 | 365070.3 | g3550345 | 4.00E − 34 | cellular repressor of E1A-stimulated genes CREG |
| 84 | 413921.2 | g474303 | 0 | Human mRNA for Tec protein-tyrosine kinase, complete cds. |
| 85 | 336615.1 | g2072161 | 0 | Human tubby related protein 1 (TULP1) mRNA, complete cds. |
| 86 | 2733282CB1 | g4887600 | 0 | Human mRNA for chloride channel protein, complete cds. |
| 87 | 2733282CD1 | g4887600 | 0 | Human mRNA for chloride channel protein, complete cds. |
| 88 | 399161.1 | g337708 | 2.00E − 37 | Human U1 small nuclear RNA gene, clone HSD4, complete cds. |
| 89 | 339638.1 | | | Incyte Unique |
| 90 | 697785CB1 | g187109 | 0 | Human 14 kd lectin mRNA, complete cds. |
| 91 | 697785CD1 | g187109 | 0 | Human 14 kd lectin mRNA, complete cds. |
| 92 | 399785.1 | | | Incyte Unique |
| 93 | 002455.1 | g2708709 | 2.00E − 13 | Wiskott-Aldrich Syndrome protein homolog |
| 94 | 1382920.38 | g31347 | 0 | Human pseudogene for apoferritin H (clone 133) |
| 95 | 334749.1 | | | Incyte Unique |
| 96 | 041764.1 | g4589563 | 0 | Human mRNA for KIAA0960 protein, partial cds. |
| 97 | 2700132CB1 | g415818 | 0 | Human mki67a mRNA (long type) for antigen of monoclonal anti-body Ki-67. |

TABLE 4-continued

| SEQ ID NO: | Template ID | GB Number | E-value | Annotation |
|---|---|---|---|---|
| 98 | 2700132CD1 | g415818 | 0 | Human mki67a mRNA (long type) for antigen of monoclonal antibody Ki-67. |
| 99 | 211881.1 | g340088 | 7.00E − 15 | Human small nuclear rna pseudogene (clone pul-1) and flanks. |
| 100 | 409895.2 | g36177 | 0 | Human mRNA for calcium-binding protein S100P. |
| 101 | 1422432CB1 | g36177 | 0 | Human mRNA for calcium-binding protein S100P. |
| 102 | 1422432CD1 | g36177 | 0 | Human mRNA for calcium-binding protein S100P. |

TABLE 5

| SEQ ID NO: | Template ID | Start | Stop | Frame | PFAM Hit | PFAM Annotaion | E-value |
|---|---|---|---|---|---|---|---|
| 1 | 1382961.3 | 413 | 1348 | forward 2 | filament | Intermediate filament proteins | 2.30E − 184 |
| 2 | 1382961.5 | 266 | 1036 | forward 2 | filament | Intermediate filament proteins | 1.40E − 114 |
| 4 | 2852561CD1 | 112 | 491 | | alpha-amylase | Alpha amylase | 1.70E − 04 |
| 7 | 2483854CD1 | 136 | 270 | | interleukin-1 | Interleukin-1 | 5.60E − 68 |
| 9 | 1454852CD1 | 83 | 394 | | filament | Intermediate filament proteins | 2.50E − 175 |
| 10 | 353005.1 | 87 | 242 | forward 3 | serpin | Serpins (serine protease inhibitors) | 2.50E − 14 |
| 12 | 994684.9 | 1870 | 2601 | forward 1 | filament | Intermediate filament proteins | 1.60E − 128 |
| 12 | 994684.9 | 2628 | 2729 | forward 3 | filament | Intermediate filament proteins | 4.50E − 20 |
| 12 | 994684.9 | 2534 | 2644 | forward 2 | filament | Intermediate filament proteins | 2.10E − 07 |
| 13 | 995610.1 | 2235 | 2393 | forward 3 | HLH | Helix-loop-helix DNA-binding domain | 2.40E − 24 |
| 13 | 995610.1 | 1260 | 2207 | forward 3 | Myc__N__term | Myc amino-terminal region | 2.90E − 166 |
| 16 | 3615080CD1 | 379 | 428 | | laminin__EGF | Laminin EGF-like (Domains III and V) | 9.50E − 18 |
| 16 | 3615080CD1 | 26 | 248 | | laminin__Nterm | Laminin N-terminal (Domain VI) | 1.50E − 38 |
| 20 | 3189059CD1 | 263 | 319 | | ig | Immunoglobulin domain | 2.50E − 06 |
| 22 | 1650519CD1 | 59 | 314 | | 7tm__1 | 7 transmembrane receptor (rhodopsin family) | 6.90E − 42 |
| 23 | 474630.4 | 4737 | 4991 | forward 3 | fn3 | Fibronectin type III domain | 1.80E − 25 |
| 23 | 474630.4 | 329 | 1192 | forward 2 | integrin__B | Integrins, beta chain | 1.10E − 231 |
| 23 | 474630.4 | 1179 | 1571 | forward 3 | integrin__B | Integrins, beta chain | 2.80E − 75 |
| 25 | 1231633.4 | 25 | 267 | forward 1 | Ribosomal__L10e | Ribosomal L10 | 7.40E − 24 |
| 26 | 988891.1 | 538 | 966 | forward 1 | interleukin-1 | Interleukin-1 | 2.60E − 86 |
| 27 | 988891.15 | 133 | 300 | forward 1 | interleukin-1 | Interleukin-1 | 2.50E − 25 |
| 29 | 3774181CD1 | 1953 | 1997 | | Plectin__repeat | Plectin repeat | 1.10E − 19 |
| 31 | 1709387CD1 | 104 | 416 | | filament | Intermediate filament proteins | 8.90E − 178 |
| 33 | 1709118CD1 | 3 | 377 | | actin | Actin | 3.90E − 282 |
| 34 | 008513.49 | 542 | 1483 | forward 2 | filament | Intermediate filament proteins | 7.00E − 170 |
| 39 | 1303785CD1 | 275 | 342 | | annexin | Annexin | 1.20E − 40 |
| 41 | 1798379CD1 | 183 | 496 | | filament | Intermediate filament proteins | 8.20E − 159 |
| 42 | 350650.1 | 5 | 232 | forward 2 | filament | Intermediate filament proteins | 1.10E − 27 |
| 48 | 001929.1 | 373 | 1314 | forward 1 | filament | Intermediate filament proteins | 1.60E − 119 |
| 49 | 1088524.8 | 775 | 1023 | forward 1 | fibrinogen__C | Fibrinogen beta and gamma chains, C-terminal globular domain | 1.80E − 41 |
| 49 | 1088524.8 | 1175 | 1399 | forward 2 | fibrinogen__C | Fibrinogen beta and gamma chains, C-terminal globular domain | 2.70E − 19 |
| 49 | 1088524.8 | 2596 | 3213 | forward 1 | ras | Ras family | 6.50E − 107 |
| 54 | 2993696CD1 | 30 | 636 | | HSP70 | Hsp70 protein | 0.00E + 00 |
| 55 | 331106.6 | 1084 | 1266 | forward 1 | FG-GAP | FG-GAP repeat | 3.50E − 17 |
| 55 | 331106.6 | 3259 | 3303 | forward 1 | integrin__A | Integrin alpha cytoplasmic region | 2.90E − 04 |
| 57 | 1256895CD1 | 23 | 253 | | prion | Prion protein | 6.30E − 203 |
| 58 | 474630.29 | 4527 | 4781 | forward 3 | fn3 | Fibronectin type III domain | 1.80E − 25 |
| 58 | 474630.29 | 264 | 1520 | forward 3 | integrin__B | Integrins, beta chain | 6.3e − 317 |
| 60 | 444096.1 | 83 | 565 | forward 2 | filament | Intermediate filament proteins | 2.20E − 61 |
| 60 | 444096.1 | 546 | 746 | forward 3 | filament | Intermediate filament proteins | 2.40E − 29 |
| 61 | 008942.10 | 207 | 1514 | forward 3 | aa__permeases | Amino acid permease | 2.30E − 06 |
| 63 | 1252415.1 | 682 | 2094 | forward 1 | CAP | CAP protein | 0.00E + 00 |
| 64 | 1399366.20 | 2117 | 2236 | forward 2 | EGF | EGF-like domain | 3.00E − 06 |
| 64 | 1399366.20 | 1484 | 1636 | forward 2 | tsp__1 | Thrombospondin type 1 domain | 1.60E − 24 |
| 64 | 1399366.20 | 1121 | 1285 | forward 2 | vwc | von Willebrand factor type C domain | 2.50E − 23 |
| 67 | 1137894.1 | 1145 | 1234 | forward 2 | zf-CCCH | Zinc finger C-x8-C-x5-C-x3-H type (and similar) | 3.80E − 16 |
| 69 | 1418671CD1 | 139 | 225 | | DEP | Domain found in Dishevelled, Egl-10, and Pleckstrin | 2.00E − 10 |
| 69 | 1418671CD1 | 248 | 353 | | PH | PH domain | 1.70E − 18 |
| 70 | 464689.64 | 608 | 1342 | forward 2 | Desaturase | Fatty acid desaturase | 1.20E − 163 |
| 72 | 1384594.1 | 121 | 264 | forward 1 | KRAB | KRAB box | 4.20E − 04 |
| 74 | 021667CD1 | 165 | 189 | | zf-C2H2 | Zinc finger, C2H2 type | 1.60E − 06 |
| 75 | 224855.4 | 175 | 516 | forward 1 | IRF | Interferon regulatory factor transcription factor | 2.60E − 76 |
| 77 | 1518310CD1 | 1 | 213 | | connexin | Connexin | 5.80E − 163 |
| 79 | 410785.1 | 72 | 1451 | forward 3 | sugar__tr | Sugar (and other) transporter | 8.10E − 124 |
| 79 | 410785.1 | 410 | 1480 | forward 2 | sugar__tr | Sugar (and other) transporter | 2.30E − 05 |
| 80 | 1089210.1 | 61 | 903 | forward 1 | aldo__ket__red | Aldo/keto reductase family | 2.60E − 192 |

TABLE 5-continued

| SEQ ID NO: | Template ID | Start | Stop | Frame | PFAM Hit | PFAM Annotaion | E-value |
|---|---|---|---|---|---|---|---|
| 84 | 413921.2 | 464 | 574 | forward 2 | BTK | BTK motif | 4.30E − 23 |
| 84 | 413921.2 | 140 | 460 | forward 2 | PH | PH domain | 2.70E − 16 |
| 84 | 413921.2 | 1235 | 1975 | forward 2 | pkinase | Eukaryotic protein kinase domain | 8.80E − 72 |
| 84 | 413921.2 | 866 | 1117 | forward 2 | SH2 | Src homology domain 2 | 2.30E − 35 |
| 84 | 413921.2 | 671 | 838 | forward 2 | SH3 | SH3 domain | 1.30E − 19 |
| 85 | 336615.1 | 86 | 874 | forward 2 | Tub | Tub family | 3.00E − 195 |
| 91 | 697785CD1 | 22 | 126 | | Gal-bind__lectin | Vertebrate galactoside-binding lectins | 2.90E − 65 |
| 94 | 1382920.38 | 253 | 723 | forward 1 | ferritin | Ferritins | 9.80E − 116 |
| 98 | 2700132CD1 | 27 | 91 | | FHA | FHA domain | 4.30E − 21 |
| 100 | 409895.2 | 1198 | 1284 | forward 1 | efhand | EF hand | 1.80E − 04 |
| 102 | 1422432CD1 | 53 | 81 | | efhand | EF hand | 1.80E − 04 |
| 102 | 1422432CD1 | 4 | 47 | | S__100 | S-100/ICaBP type calcium binding domain | 2.70E − 21 |

TABLE 6

| SEQ ID NO: | Template ID | Start | Stop | Frame | Domain |
|---|---|---|---|---|---|
| 1 | 1382961.3 | 336 | 422 | forward 3 | SP |
| 4 | 2852561CD1 | 79 | 106 | | SP |
| 5 | 335942.2 | 127 | 213 | forward 1 | TM |
| 10 | 353005.1 | 14 | 100 | forward 2 | SP |
| 12 | 994684.9 | 101 | 190 | forward 2 | SP |
| 12 | 994684.9 | 2354 | 2446 | forward 2 | SP |
| 13 | 995610.1 | 40 | 117 | forward 1 | SP |
| 20 | 3189059CD1 | 1 | 30 | | SP |
| 22 | 1650519CD1 | 43 | 70 | | TM |
| 23 | 474630.4 | 53 | 133 | forward 2 | SP |
| 26 | 988891.1 | 1300 | 1377 | forward 1 | TM |
| 34 | 008513.49 | 243 | 335 | forward 3 | SP |
| 37 | 3120070CD1 | 79 | 105 | | TM |
| 37 | 3120070CD1 | 1 | 31 | | SP |
| 49 | 1088524.8 | 1884 | 2000 | forward 3 | SP |
| 49 | 1088524.8 | 232 | 321 | forward 1 | SP |
| 49 | 1088524.8 | 1938 | 2015 | forward 3 | TM |
| 55 | 331106.6 | 857 | 943 | forward 2 | SP |

TABLE 6-continued

| SEQ ID NO: | Template ID | Start | Stop | Frame | Domain |
|---|---|---|---|---|---|
| 58 | 474630.29 | 2277 | 2369 | forward 3 | SP |
| 58 | 474630.29 | 156 | 236 | forward 3 | SP |
| 59 | 1256295.18 | 1242 | 1328 | forward 3 | TM |
| 64 | 1399366.20 | 210 | 299 | forward 3 | SP |
| 64 | 1399366.20 | 3746 | 3826 | forward 2 | SP |
| 67 | 1137894.1 | 1459 | 1536 | forward 1 | SP |
| 75 | 224855.4 | 2804 | 2890 | forward 2 | SP |
| 75 | 224855.4 | 3845 | 3922 | forward 2 | TM |
| 79 | 410785.1 | 1057 | 1143 | forward 1 | SP |
| 79 | 410785.1 | 1385 | 1471 | forward 2 | TM |
| 79 | 410785.1 | 2099 | 2185 | forward 2 | TM |
| 79 | 410785.1 | 4757 | 4840 | forward 2 | TM |
| 79 | 410785.1 | 4710 | 4787 | forward 3 | TM |
| 83 | 365070.3 | 43 | 135 | forward 1 | SP |
| 87 | 2733282CD1 | 900 | 926 | | TM |
| 99 | 211881.1 | 651 | 731 | forward 3 | TM |

What is claimed is:

1. A combination comprising a plurality of cDNAs that are differentially expressed in prostate cancer, wherein the plurality of cDNAs consist of SEQ ID NOs:1–3, 5, 6, 8, 10–15, 17–19, 21, 23–28, 30, 32, 34–36, 38, 40, 42–45, 47–50, 52, 53, 55, 56, 58–65, 67, 68, 70–73, 75, 76, 78–86, 88–90, 92–97, 99–101 or a plurality of cDNAs consisting of the complements thereof.

2. The combination of claim 1, wherein each of the cDNAs is differentially regulated between non-metastatic and metastatic prostate cancer, consisting of SEQ ID NOs:1–3, 5, 6, 8, 10–15, 17–19, 21, 23–28, 30, 32, 34–36, 38, 40, 42–45, 47–50, 52, 53, 55, 56, 58–65, 67, 68, 70–73, 75.

3. The combination of claim 1, wherein each of the cDNAs is differentially regulated between prostate cancer and normal prostate, consisting of SEQ ID NOs:76, 78–86, 88–90, 92–97, 99–101.

4. The combination of claim 1, wherein the cDNAs are immobilized on a substrate.

5. A high throughput method for detecting differential expression of one or more cDNAs in a sample containing nucleic acids, the method comprising:

(a) hybridizing the substrate of claim 4 with nucleic acids of the sample, thereby forming one or more hybridization complexes;

(b) detecting the hybridization complexes; and (c) comparing the hybridization complexes with those of a standard, wherein differences between the standard and sample hybridization complexes indicate differential expression of cDNAs in the sample.

6. The method of claim 5, wherein the nucleic acids of the sample are amplified prior to hybridization.

7. The method of claim 5, wherein the sample is from a subject with prostate cancer and comparison with a standard defines an early, mid, or late stage of that disease.

8. A high throughput method of screening a plurality of molecules or compounds to identify a ligand which specifically binds a cDNA, the method comprising:

(a) combining the composition of claim 1 with the plurality of molecules or compounds under conditions to allow specific binding; and (b) detecting specific binding between each cDNA and at least one molecule or compound, thereby identifying a ligand that specifically binds to each cDNA.

9. The method of claim 8 wherein the plurality of molecules or compounds are selected from DNA molecules, RNA molecules, peptide nucleic acid molecules, mimetics, peptides, transcription factors, repressors, and regulatory proteins.

* * * * *